(12) United States Patent
Kubota et al.

(10) Patent No.: US 7,781,443 B2
(45) Date of Patent: Aug. 24, 2010

(54) TETRAHYDRONAPHTHYRIDINE DERIVATIVES AND A PROCESS FOR PREPARING THE SAME

(75) Inventors: Hitoshi Kubota, Osaka (JP); Yoshinori Nakamura, Osaka (JP); Takanori Higashijima, Osaka (JP); Yasuo Yamamoto, Osaka (JP); Kozo Oka, Osaka (JP); Shigeki Igarashi, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 876 days.

(21) Appl. No.: 11/527,556

(22) Filed: Sep. 27, 2006

(65) Prior Publication Data

US 2007/0032485 A1    Feb. 8, 2007

Related U.S. Application Data

(63) Continuation-in-part of application No. PCT/JP2005/006895, filed on Apr. 1, 2005.

(60) Provisional application No. 60/720,447, filed on Sep. 27, 2005.

(30) Foreign Application Priority Data

Apr. 2, 2004 (JP) .............................. 2004-109551

(51) Int. Cl.
*A61K 31/506* (2006.01)
*C07D 403/14* (2006.01)

(52) U.S. Cl. ................ 514/275; 544/297; 544/122; 546/122; 514/234.5; 514/300

(58) Field of Classification Search ................ 514/275, 514/234.5, 300; 546/122; 544/297, 122
See application file for complete search history.

(56) References Cited

FOREIGN PATENT DOCUMENTS

| WO | WO-00/17164 | 3/2000 |
|----|-------------|--------|
| WO | WO-00/17165 | 3/2000 |
| WO | WO-00/17166 | 3/2000 |
| WO | WO-03/063868 | 8/2003 |
| WO | WO-2005/097806 | 10/2005 |

*Primary Examiner*—Charanjit S Aulakh
(74) *Attorney, Agent, or Firm*—Birch, Stewart, Kolasch & Birch, LLP

(57) ABSTRACT

A novel compound of the formula (I):

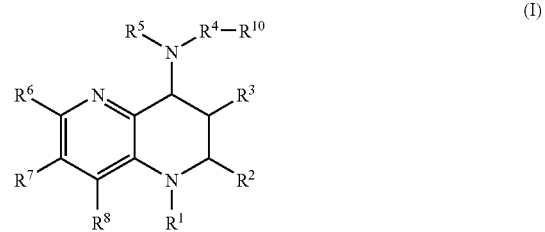

wherein $R^1$ is alkoxycarbonyl or the like, $R^2$ is alkyl or the like; $R^3$ is hydrogen or the like; $R^4$ is alkylene or the like; $R^5$ is optionally substituted heterocyclic group; $R^6$, $R^7$, and $R^8$ are independently hydrogen; alkyl, alkoxy, or the like; $R^{10}$ is optionally substituted aromatic ring, or the like; or a pharmaceutically acceptable salt thereof, which has an inhibitory activity against cholesteryl ester transfer protein (CETP).

16 Claims, No Drawings

TETRAHYDRONAPHTHYRIDINE DERIVATIVES AND A PROCESS FOR PREPARING THE SAME

This application is a Continuation-In-Part application based on PCT International Application No. PCT/JP2005/006895 filed on Apr. 1, 2005 and Provisional Application No. 60/720447 filed on Sep. 27, 2005, the entire contents of which are herein incorporated by reference.

TECHNICAL FIELD

The present invention relates to a novel tetrahydronaphthyridine derivative having an inhibitory activity against cholesteryl ester transfer protein (CETP).

BACKGROUND ART

Hypercholesterolemia, especially high serum level of low-density lipoprotein (LDL) cholesterol, has been revealed to be a risk factor of arteriosclerotic diseases by a number of epidemiological surveys. Actually, drugs capable of decreasing LDL cholesterol level such as 3-hydroxy-3-methylglutaryl-CoA (HMG-CoA) reductase inhibitors have been used with the aim of preventing coronary artery diseases, and demonstrated to have some benefits in many large scale clinical tests. However, their preventive effect on coronary diseases is limited to some extent, and is not satisfactory enough yet.

Recently, low serum level of high density lipoprotein (HDL) cholesterol has been revealed to be a potent risk factor of arteriosclerotic diseases by a number of epidemiological surveys and large scale clinical tests. HDL is known to have various antiarteriosclerotic effects and attention is focused on the potentiality of drugs increasing HDL cholesterol level as a means for prevention or treatment of arteriosclerotic diseases. However, there are no drugs that can be used in a satisfactory manner for this purpose. Fibrates and HMG-CoA reductase inhibitors have only low activity of increasing HDL cholesterol; nicotinic acid derivatives can significantly increase HDL, but have serious toleration issues. Accordingly, there has been a demand for a well-tolerated agent which can significantly elevate HDL cholesterol levels, thereby preventing or reversing the progression of atherosclerosis.

It is known that many proteins are involved in the regulation mechanism for catabolism of various lipoproteins. Among them, the role of cholesteryl ester transfer protein (CETP) became to draw attention. CETP is a protein responsible for transfer of cholesteryl ester (CE) and triglyceride between lipoproteins, and mediate the transfer of CE from HDL to LDL or to very low density lipoprotein (VLDL). Accordingly, CETP activity affects greatly the lipid composition in lipoprotein particles. For example, it is known that administration of a neutralizing monoclonal antibody to CETP to rabbit or hamster elevates HDL cholesterol levels and lower LDL cholesterol levels. Furthermore, human being having decreased or eliminated CETP activity due to gene mutation shows raised blood HDL cholesterol level and lowered blood LDL cholesterol level. On the other hand, it is known that transgenic mice and rats made to express CETP show lowered HDL cholesterol level and raised LDL cholesterol level. Thus, it is considered that CETP greatly contribute to the regulation of serum lipids, and thereby affecting the change of serum lipid profile such as decrease of HDL cholesterol level and increase of LDL cholesterol. Accordingly, it is assumed that a high value of CETP activity would induce arteriosclerosis such as atherosclerosis.

In fact, CETP activity varies depending on animal species. It is known that, arteriosclerotic lesions are readily formed by cholesterol loading in animals with high CETP activity such as rabbits, whereas such lesions hardly occur in animals with low CETP activity such as rats. Furthermore, it is confirmed that continuous suppression of CETP activity by administration of antisense oligodeoxynucleotide resulted in effects such as increase of blood HDL cholesterol level and reduction in arteriosclerotic lesions in cholesterol-fed rabbits.

The above findings indicate that CETP activity is in negative correlation with HDL cholesterol, and that inhibition of CETP activity would decrease the degree of risk for arteriosclerotic diseases. It is therefore expected that compounds capable of inhibiting CETP activity can block the transfer of cholesterol from HDL to LDL, and thereby increasing HDL cholesterol that tends to prevent arteriosclerosis such as atherosclerosis while lowering LDL cholesterol that tends to promote arteriosclerosis such as atherosclerosis. In this way, such compounds can serve as a useful preventive or therapeutic agent for arteriosclerotic diseases, hyperlipidemia or dyslipidemia and provide effective medical treatment for the first time.

Examples of compounds having CETP inhibitory activity include tetrahydronaphthyridine derivatives. See, WO00/17164, WO00/17165, WO00/17166.

However, these compounds have defects. That is, they are poorly soluble in water and cannot be absorbed enough in vivo, a sufficient blood level for taking medicinal effect can hardly be achieved even when administered as an ordinary formulation for oral administration. See, WO03/63868.

Accordingly, novel compounds in which the above-mentioned defects have been solved are highly demanded.

DISCLOSURE OF INVENTION

The present invention provides novel tetrahydronaphthyridine derivatives having an excellent CETP inhibitory activity wherein defects of existing CETP inhibitory compounds are rectified.

Thus, the present invention provides a compound of the formula (I):

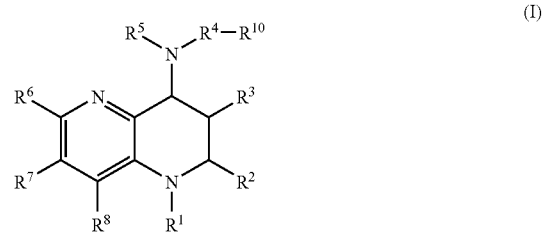

wherein $R^1$ is a hydrogen atom, an optionally substituted alkoxycarbonyl group, an optionally substituted carbamoyl group, an optionally substituted alkyl group, an optionally substituted alkanoyl group, a saturated or unsaturated monocyclic or bicyclic heterocyclic group containing 1 to 4 heteroatoms selected independently from oxygen, sulfur and nitrogen atoms (the heterocyclic group is optionally substituted), or a saturated or unsaturated monocyclic or bicyclic heterocyclic carbonyl group containing 1 to 4 heteroatoms selected independently from oxygen, sulfur and nitrogen atoms (the heterocyclic group is optionally substituted);

$R^2$ is a hydrogen atom or an optionally substituted alkyl group;

$R^3$ is a hydrogen atom or an optionally substituted alkyl group;

$R^4$ is an optionally substituted alkylene group;

$R^5$ is a saturated or unsaturated monocyclic or bicyclic heterocyclic group containing 1 to 4 heteroatoms selected independently from oxygen, sulfur and nitrogen atoms, said heterocyclic group being optionally substituted, $R^6$, $R^7$ and $R^8$ are independently a hydrogen atom, a halogen atom, a hydroxy group, a nitro group, a cyano group, an optionally substituted alkyl group, an optionally substituted alkoxy group, an optionally substituted alkylsulfonyloxy group, an optionally substituted mono- or di-alkylcarbamoyl group or an optionally substituted amino group; or $R^6$ and $R^7$, or $R^7$ and $R^8$ may combine at the ends to form an alkylene group which alkylene group optionally contains 1 to 3 heteroatoms selected independently from nitrogen, sulfur and oxygen atoms, and may have a substituent(s); and $R^{10}$ is an aromatic ring optionally containing 1 to 3 heteroatoms selected independently from oxygen, sulfur and nitrogen atoms (the aromatic ring is optionally substituted), or a pharmaceutically acceptable salt thereof.

The compound (I) of the present invention encompasses a mixture of stereoisomers, respective stereoisomers in a purified or substantially purified form. For example, the compounds of the formula (I) may have one or more asymmetric carbon atoms and therefore may occur as individual enantiomers or diastereomers, or a mixture thereof. The present compounds include respective isomers and a mixture thereof. In addition, when the compound (I) has a double bond, geometric isomers may occur (cis- and trans-forms), and when the compound (I) has a group containing an unsaturated bond such as carbonyl, tautomeric forms may occur, and the present compounds include respective isomers and a mixture thereof.

Further, the pharmaceutically acceptable salts of compound (I) of the present invention include an intramolecular salt, a hydrate, solvate or the like.

As used herein, the term "aromatic ring optionally containing 1 to 3 heteroatoms selected independently from oxygen, sulfur and nitrogen atoms" refers to preferably a "5- to 7-membered monocyclic aromatic ring optionally containing 1 to 3 heteroatoms selected independently from oxygen, sulfur and nitrogen atoms" including specifically phenyl, furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, azepinyl, oxepinyl and thiepinyl groups, and the like.

The term "saturated or unsaturated monocyclic or bicyclic heterocyclic group containing 1 to 4 heteroatoms selected independently from oxygen, sulfur and nitrogen atoms" refers to preferably a "saturated or unsaturated 5- to 8-membered heterocyclic group containing 1 to 4 heteroatoms selected independently from oxygen, sulfur and nitrogen atoms" including specifically the following groups. Examples of 5-membered heterocyclic group include 2H-pyrrolyl, 3H-pyrrolyl, 2-pyrrolyl, 3-pyrrolyl, pyrrolidinyl, 1,3-dioxolanyl, oxazolyl, oxazolinyl, oxazolidinyl, thiazolyl, imidazolyl, imidazolinyl, imidazolidinyl, pyrazolyl, 2-pyrazolinyl, pyrazolidinyl, isoxazolyl, isothiazolyl, tetrazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl groups, and the like.

Examples of 6-membered heterocyclic group include 2H-pyranyl, 4H-pyranyl, pyridyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-ozathiazinyl, 1,2,6-oxathiazinyl, 1,4,2-oxadiazinyl and 1,3,5,2-oxadiazinyl groups, and the like.

Examples of 7-membered heterocyclic group include azepinyl, oxepinyl and thiepinyl groups, and the like.

Examples of 8-membered heterocyclic group include azocinyl, oxocinyl and thiocinyl groups, and the like.

As used herein, the heterocyclic moiety of the "saturated or unsaturated monocyclic or bicyclic heterocyclic oxy group containing 1 to 4 heteroatoms selected independently from oxygen, sulfur and nitrogen atoms", "saturated or unsaturated monocyclic or bicyclic heterocyclic carbonyl group containing 1 to 4 heteroatoms selected independently from oxygen, sulfur and nitrogen atoms", and "a saturated or unsaturated monocyclic or bicyclic heterocyclic carbonylamino group containing 1 to 4 heteroatoms selected independently from oxygen, sulfur and nitrogen atoms" refers to the aforementioned "saturated or unsaturated monocyclic or bicyclic heterocyclic group containing 1 to 4 heteroatoms selected independently from oxygen, sulfur and nitrogen atoms".

In such cases where the binding position for these aromatic ring, heterocyclic group, and the like is not specifically defined, the definition is meant to encompass all the possible binding positions. For example, the term "pyridyl group" means 2-, 3- or 4-pyridyl group, and the term "thienyl group" means 2- or 3-thienyl group. The same is applied to other aromatic rings and heterocyclic groups.

When the saturated or unsaturated monocyclic or bicyclic heterocyclic group, heterocyclic oxy group, heterocyclic carbonyl group and heterocyclic carbonylamino group each containing 1 to 4 heteroatoms selected independently from oxygen, sulfur and nitrogen atoms have a substituent(s), the substitution includes oxidation of heteroatom(s) in the heterocycle in the respective groups. Specifically, compounds having a heteroatom(s) in the heterocycle of said groups as N-oxide, S-oxide (SO) or S,S-dioxide ($SO_2$) also fall within the scope of the present invention.

The term "halogen" refers to fluorine, chlorine, bromine or iodine.

The term "alkyl group" or "alkyl" means a straight or branched saturated hydrocarbon chain having 1 to 10 carbon atoms and a cyclic saturated hydrocarbon chain having 3 to 10 carbon atoms. As a straight or branched hydrocarbon chain, those having 2 to 10 carbon atoms are preferred and those having 2 to 6 carbons are more preferred. Other preferred examples are straight chain alkyl groups having 1 to 6 carbon atoms, especially those having 1 to 4 carbon atoms. Examples of alkyl group include methyl, ethyl, propyl, isopropyl, butyl, sec-butyl, tert-butyl, pentyl, isopentyl, neopentyl, tert-pentyl, 1-methylbutyl, 2-methylbutyl, 3-methylbutyl, hexyl and isohexyl groups, and the like.

The term "alkoxy group" or "alkoxy" means a straight or branched alkyloxy group having 1 to 10 carbon atoms and a cyclic alkyloxy group having 3 to 10 carbon atoms. As a straight or branched hydrocarbon chain, those having 2 to 10 carbon atoms are preferred and those having 2 to 6 carbons are more preferred. Other preferred examples are straight chain alkoxy groups having 1 to 6 carbon atoms, especially those having 1 to 4 carbon atoms. Examples of alkoxy group include methoxy, ethoxy, propoxy, isopropoxy, butoxy, isobutoxy, tert-butoxy, pentoxy, isopentoxy, neopentoxy, tert-pentoxy, hexoxy and isohexoxy groups, and the like.

The term "alkylene group" or "alkylene" means a saturated hydrocarbon chain wherein a hydrogen atom is removed from each of the terminal carbons of a straight hydrocarbon chain. Preferred examples include an alkylene group having 1 to 4 carbon atoms, specifically, methylene, ethylene, trimethylene and tetramethylene groups, and the like. When an alkylene group herein used contains 1 to 3 heteroatoms selected independently from nitrogen, sulfur and oxygen atoms, the term "alkylene" includes a group of the formula: —O—$(CH_2)_m$—O—, —S—$(CH_2)_m$—S—, —NH—$(CH_2)_m$—NH—, or —O—$(CH_2)_m$—NH— (wherein m is an integer of 1 to 4), or the like.

The term "alkanoyl group" or "alkanoyl" means a straight or branched alkylcarbonyl group having 1 to 10 carbon atoms, preferably an alkylcarbonyl group having 1 to 6 carbon atoms, more preferably an alkylcarbonyl group having 1 to 4 carbon atoms. Examples of alkanoyl group include acetyl, propionyl, butyryl, valeryl and pivaloyl groups, and the like.

The term "alkenyl group" or "alkenyl" means a straight or branched hydrocarbon chain having 2 to 10 carbon atoms and containing at least one double bond, preferably an alkenyl group having 2 to 6 carbon atoms, more preferably an alkenyl group having 2 to 4 carbon atoms Examples of alkenyl group include vinyl, 1-propenyl, allyl, isopropenyl, butenyl, butadienyl and pentenyl groups, and the like.

As herein used throughout the claims and specification, when the term "mono- or di-alkyl" refers to di-alkyl, the alkyl moieties may be independent from each other. In addition, a compound of the formula below means that it takes the configuration (2R*,4S*), wherein (2R*,4S*) refers to a mixture of (2R,4S) and (2S,4R).

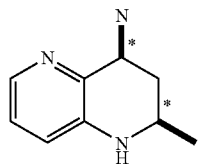

The compounds of the present invention have CETP inhibitory activity and are effective for increasing HDL cholesterol and lowering LDL cholesterol. Accordingly, the said compounds are useful in prevention and/or treatment of diseases such as arteriosclerosis, hyperlipidemia, and the like.

BEST MODE FOR CARRYING OUT THE INVENTION

Preferred compounds of the present invention are those wherein $R^5$ is a saturated or unsaturated monocyclic or bicyclic heterocyclic group containing 1 to 4 heteroatoms selected independently from oxygen, sulfur and nitrogen atoms, wherein the heterocyclic group is optionally substituted by 1 to 5 substituents selected from the following group:
halogen atom, oxo group, hydroxy group, cyano group, nitro group, carboxyl group, sulfo group, optionally substituted alkyl group, optionally substituted cycloalkyl group, optionally substituted alkenyl group, optionally substituted alkoxy group, optionally substituted cycloalkoxy group, optionally substituted alkoxycarbonyl group, carbamoyl group, optionally substituted mono- or di-alkylcarbamoyl group, optionally substituted carbamimidoyl group, optionally substituted alkylthio group, optionally substituted alkylsulfinyl group, optionally substituted alkylsulfonyl group, amino group, optionally substituted mono- or di-alkylamino group, optionally substituted alkanoylamino group, optionally substituted alkoxycarbonylamino group, optionally substituted alkylsulfonylamino group, optionally substituted mono- or di-alkylcarbamoylamino group, a saturated or unsaturated monocyclic or bicyclic heterocyclic carbonylamino group containing 1 to 4 heteroatoms selected independently from oxygen, sulfur and nitrogen atoms (the heterocyclic carbonylamino group is optionally substituted), sulfamoyl group, optionally substituted mono- or di-alkyl sulfamoyl group, optionally substituted alkanoyl group, a saturated or unsaturated monocyclic or bicyclic heterocyclic group containing 1 to 4 heteroatoms selected independently from oxygen, sulfur and nitrogen atoms (the heterocyclic group is optionally substituted), a saturated or unsaturated monocyclic or bicyclic heterocyclic oxy group containing 1 to 4 heteroatoms selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatoms selected independently from oxygen, sulfur and nitrogen atoms (the heterocyclic carbonyl group is optionally substituted); and $R^{10}$ is an aromatic ring optionally containing 1 to 3 heteroatoms selected independently from oxygen, sulfur and nitrogen atoms, which aromatic ring is optionally substituted by 1 to 4 substituents selected from the following groups: halogen atom, carboxyl group, optionally substituted alkoxycarbonyl group, carbamoyl group, optionally substituted mono- or di-alkylcarbamoyl group, optionally substituted alkyl group, optionally substituted alkoxy group, hydroxy group, nitro group, cyano group, amino group, optionally substituted mono- or di-alkylamino group, optionally substituted alkanoyl group, optionally substituted alkylthio group, and a saturated or unsaturated monocyclic or bicyclic heterocyclic group containing 1 to 4 heteroatoms selected independently from oxygen, sulfur and nitrogen atoms (the heterocyclic group is optionally substituted).

The substituent(s) for optionally substituted alkyl group, optionally substituted cycloalkyl group, optionally substituted alkenyl group, optionally substituted alkoxy group, optionally substituted cycloalkoxy group, optionally substituted alkoxycarbonyl group, optionally substituted mono- or di-alkylcarbamoyl group, optionally substituted alkylthio group, optionally substituted alkylsulfinyl group, optionally substituted alkylsulfonyl group, optionally substituted mono- or di-alkylamino group, optionally substituted alkanoylamino group, optionally substituted alkoxycarbonylamino group, optionally substituted alkylsulfonylamino group, optionally substituted mono- or di-alkylcarbamoylamino group, optionally substituted mono- or di-alkylsulfamoyl group, optionally substituted alkanoyl group, optionally substituted alkylene group, a saturated or unsaturated monocyclic or bicyclic heterocyclic carbonylamino group containing 1 to 4 heteroatoms selected independently from oxygen, sulfur and nitrogen atoms (the heterocyclic carbonylamino group is optionally substituted), a saturated or unsaturated monocyclic or bicyclic heterocyclic group containing 1 to 4 heteroatoms selected independently from oxygen, sulfur and nitrogen atoms (the heterocyclic group is optionally substituted), a saturated or unsaturated monocyclic or bicyclic heterocyclic oxy group containing 1 to 4 heteroatoms selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatoms selected independently from oxygen, sulfur and nitrogen atoms (the heterocyclic carbonyl group is optionally substituted) may be 1-5 groups selected from the following groups:

halogen atom; cyano group; hydroxy group; nitro group; carboxyl group; oxo group; thioxo group; sulfo group; cycloalkyl group optionally substituted by hydroxy group, halogen atom, carboxyl group, alkoxycarbonyl group, mono- or di-alkylamino group, phenyl group or morpholinyl group; alkoxycarbonyl group optionally substituted by hydroxy group, halogen atom, carboxyl group, alkoxycarbonyl group, mono- or di-alkylamino group, phenyl group or morpholinyl group; carbamoyl group; mono- or di-alkylcarbamoyl group optionally substituted by hydroxy group, halogen atom, carboxyl group, alkoxycarbonyl group, mono- or di-alkylamino group, phenyl group or morpholinyl group; alkyl group optionally substituted by hydroxy group, halogen atom, carboxyl group, alkoxycarbonyl group, mono- or di-alkylamino group, phenyl group or morpholinyl group; alkanoyl group optionally substituted by hydroxy group, halogen atom, carboxyl group, alkoxycarbonyl group, mono- or di-alkylamino group, phenyl group or morpholinyl group; alkoxy group optionally substituted by hydroxy group, halogen atom, carboxyl group, alkoxycarbonyl group, mono- or di-alkylamino group, phenyl group or morpholinyl group; alkanoyloxy group optionally substituted by halogen atom, hydroxy group, carboxyl group, alkoxycarbonyl group, mono- or di-alkylamino group, phenyl group or morpholinyl group; alkylthio group optionally substituted by halogen atom, hydroxy group, carboxyl group, alkoxycarbonyl group, mono- or di-alkylamino group, phenyl group or morpholinyl group; alkylsulfonyl group optionally substituted by hydroxy group, halogen atom, carboxyl group, alkoxycarbonyl group, mono- or di-alkylamino group, phenyl group or morpholinyl group; alkylsulfinyl group optionally substituted by hydroxy group, halogen atom, carboxyl group, alkoxycarbonyl group, mono- or di-alkylamino group, phenyl group or morpholinyl group; mono- or di-alkylsulfamoyl group optionally substituted by hydroxy group, halogen atom, carboxyl group, alkoxycarbonyl group, mono- or di-alkylamino group, phenyl group or morpholinyl group; amino group; mono- or di-alkylamino group optionally substituted by hydroxy group, halogen atom, carboxyl group, alkoxycarbonyl group, mono- or di-alkylamino group, phenyl group or morpholinyl group; mono- or di-alkylsulfamoylamino group optionally substituted by hydroxy group, halogen atom, carboxyl group, alkoxycarbonyl group, mono- or di-alkylamino group, phenyl group or morpholinyl group; mono- or di-alkylureido group optionally substituted by hydroxy group, halogen atom, carboxyl group, alkoxycarbonyl group, mono- or di-alkylamino group, phenyl group or morpholinyl group; and a group of the formula:

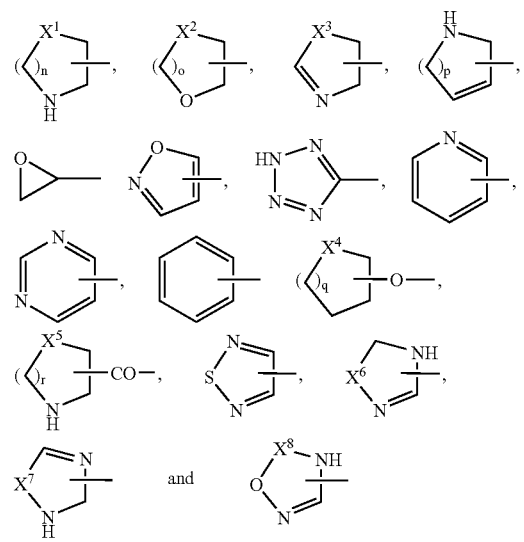

wherein $X^1$ and $X^3$ are independently $CH_2$, NH, O, S, SO or $SO_2$; $X^2$ and $X^5$ are independently $CH_2$, O, S, SO or $SO_2$; $X^4$ is NH, O, S, SO or $SO_2$; $X^6$ and $X^7$ are independently O or S; $X^8$ is S, CO or SO; and n, o, p, q and r are independently an integer of 1 to 4, wherein each group of the above formula is optionally substituted by 1 to 3 substituents selected from the following groups:

halogen atom, carboxyl group, hydroxy group, cyano group, oxo group, thioxo group, alkyl group, hydroxyalkyl group, alkoxycarbonylalkyl group, carboxyalkyl group, alkyl group substituted by halogen, morpholinylalkyl group, phenylalkyl group, alkanoyl group, hydroxyalkanoyl group, alkoxyalkanoyl group, alkoxy group, phenylalkoxy group, alkoxycarbonyl group, benzyloxycarbonyl group, mono- or di-alkylamino group, mono- or di-alkylcarbamoyl group, mono- or di-alkylsulfamoyl group, alkylsulfonyl group and tetrazolyl group.

Furthermore, the "aromatic ring optionally containing 1 to 3 heteroatoms selected independently from oxygen, sulfur and nitrogen atoms" is preferably a phenyl, naphthyl, pyridyl, quinolyl, isoquinolyl, furyl, pyrimidinyl, triazolyl or thienyl group;

The "saturated or unsaturated monocyclic or bicyclic heterocyclic group containing 1 to 4 heteroatoms selected independently from oxygen, sulfur and nitrogen atoms" is preferably a morpholinyl, thiomorpholinyl, piperazinyl, pyrrolidinyl, piperidinyl, hexahydroazepinyl, pyrrolinyl, imidazolidinyl, oxazolidinyl, tetrahydropyranyl, tetrahydrofuranyl, dioxolanyl, oxiranyl, pyrimidinyl, pyridyl, triazolyl, tetrazolyl, oxadiazolyl, dihydropyrimidinyl, pyrazinyl, thiazolyl, oxazolinyl, oxazolyl, pyridazinyl, imidazolinyl, imidazolyl, pyrazinyl, thienyl, pyrrolyl, furyl or dihydrooxazinyl group.

The "saturated or unsaturated monocyclic or bicyclic heterocyclic oxy group containing 1 to 4 heteroatoms selected independently from oxygen, sulfur and nitrogen atoms" is preferably a morpholinyloxy, thiomorpholinyloxy piperazinyloxy, pyrrolidinyloxy, piperidinyloxy, hexahydroazepinyloxy, pyrrolinyloxy, imidazolidinyloxy, oxazolidinyloxy, tetrahydropyranyloxy, tetrahydrofuranyloxy, dioxolanyloxy, oxiranyloxy, pyrimidinyloxy, pyridyloxy, triazolyloxy, tetrazolyloxy, oxadiazolyloxy, dihydropyrimidinyloxy, pyrazinyloxy, thiazolyloxy, oxazolinyloxy, oxazolyloxy, pyridazinyloxy, imidazolinyloxy, imidazolyloxy, pyrazinyloxy, thienyloxy, pyrrolyloxy, furyloxy or dihydrooxazinyloxy group.

The "saturated or unsaturated monocyclic or bicyclic heterocyclic carbonyl group containing 1 to 4 heteroatoms selected independently from oxygen, sulfur and nitrogen atoms" is preferably a morpholinylcarbonyl, thiomorpholinylcarbonyl piperazinylcarbonyl, pyrrolidinylcarbonyl, piperidinylcarbonyl, hexahydroazepinylcarbonyl, pyrrolinylcarbonyl, imidazolidinylcarbonyl, oxazolidinylcarbonyl, tetrahydropyranylcarbonyl, tetrahydrofuranylcarbonyl, dioxolanylcarbonyl, oxiranylcarbonyl pyrimidinylcarbonyl, pyridylcarbonyl, triazolylcarbonyl, tetrazolylcarbonyl, oxadiazolylcarbonyl, dihydropyrimidinylcarbonyl, pyrazinylcarbonyl, thiazolylcarbonyl, oxazolinylcarbonyl, oxazolylcarbonyl, pyridazinylcarbonyl, imidazolinylcarbonyl, imidazolylcarbonyl, pyrazinylcarbonyl, thienylcarbonyl, pyrrolylcarbonyl, furylcarbonyl or dihydrooxazinylcarbonyl group.

The "saturated or unsaturated monocyclic or bicyclic heterocyclic carbonylamino group containing 1 to 4 heteroatoms selected independently from oxygen, sulfur and nitrogen atoms" is preferably a morpholinylcarbonylamino, thiomorpholinylcarbonylamino piperazinylcarbonylamino, pyrrolidinylcarbonylamino, piperidinylcarbonylamino, hexahydroazepinylcarbonylamino, pyrrolinylcarbonylamino, imidazolidinylcarbonylamino, oxazolidinylcarbonylamino, tetrahydropyranylcarbonylamino, tetrahydrofuranylcarbonylamino, dioxolanylcarbonylamino, oxiranylcarbonylamino, pyrimidinylcarbonylamino, pyridylcarbonylamino, triazolylcarbonylamino, tetrazolylcarbonylamino, oxadiazolylcarbonylamino, dihydropyrimidinylcarbonylamino, pyrazinylcarbonylamino, thiazolylcarbonylamino, oxazolinylcarbonylamino, oxazolylcarbonylamino, pyridazinylcarbonylamino, imidazolinylcarbonylamino, imidazolylcarbonylamino, pyrazinylcarbonylamino, thienylcarbonylamino, pyrrolylcarbonylamino, furylcarbonylamino or dihydrooxazinylcarbonylamino group.

In a preferred embodiment of the present invention, $R^1$ is a hydrogen atom; an alkoxycarbonyl group optionally substituted by 1 to 5 substituents selected independently from cyano group, hydroxy group, carboxyl group, alkoxycarbonyl group, alkoxy group (said alkoxy group is optionally substituted by 1 to 3 substituents selected independently from hydroxy group, amino group, mono- or di-alkylamino group, halogen atom, carboxyl group, alkoxycarbonyl group, carboxyalkoxy group and alkoxycarbonylalkoxy group), alkylthio group, alkylsulfonyl group, alkenyl group, amino group, mono- or di-alkylamino group, tetrazolyl group, carbamoyl group, mono- or di-alkylcarbamoyl group (said mono- or di-alkylcarbamoyl group is optionally substituted by 1 to 3 substituents selected independently from carboxyl group and alkoxycarbonyl group), alkanoylamino group (said alkanoylamino group is optionally substituted by 1 to 3 substituents selected independently from carboxyl group, alkoxycarbonyl group, hydroxy group and halogen atom), halogen atom, cycloalkyl group (said cycloalkyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), phenyl group (said phenyl group is optionally substituted by 1 to 3 substituents selected independently from hydroxy group, amino group, mono- or di-alkylamino group, halogen atom, carboxyl group, alkoxycarbonyl group, carboxyalkyl group, alkoxycarbonylalkyl group, carboxyalkoxy group and alkoxycarbonylalkoxy group), morpholinyl group optionally substituted by oxo group, piperidinyl group (said piperidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), pyrrolidinyl group (said pyrrolidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), and pyrimidinyl group (said pyrimidinyl group is optionally substituted by 1 to 3 substituents selected independently from carboxyalkyl group, alkoxycarbonylalkyl group, carboxyalkoxy group and alkoxycarbonylalkoxy group); a carbamoyl group optionally substituted by alkoxy group; a dihydrooxazolyl group optionally substituted by 1 to 2 substituents selected independently from carboxyl group, alkoxycarbonyl group, alkyl group, carboxyalkyl group, alkoxycarbonylalkyl group and hydroxyalkyl group; a dihydroimidazolyl group optionally substituted by 1 to 3 substituents selected independently from carboxyl group, alkoxycarbonyl group, alkyl group, carboxyalkyl group, alkoxycarbonylalkyl group and hydroxyalkyl group; a dihydrooxazinyl group optionally substituted by 1 to 3 substituents selected independently from carboxyl group, alkoxycarbonyl group, alkyl group, carboxyalkyl group, alkoxycarbonylalkyl group and hydroxyalkyl group; mono- or di-alkylcarbamoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group); an alkyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group); an alkanoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group); a morpholinylcarbonyl group; a piperazinylcarbonyl group optionally substituted by alkyl group, carboxyalkyl group or alkoxycarbonylalkyl group;

a pyrrolidinylcarbonyl group optionally substituted by 1 to 3 substituents selected independently from carboxyl group, alkoxycarbonyl group, carboxyalkyl group and alkoxycarbonylalkyl group; or a piperidinylcarbonyl group optionally substituted by 1 to 3 substituents selected independently from carboxyl group, alkoxycarbonyl group, carboxyalkyl group and alkoxycarbonylalkyl group;

$R^5$ is a saturated or unsaturated 5- to 8-membered heterocyclic group containing 1 to 4 heteroatoms selected independently from oxygen, sulfur and nitrogen atoms; wherein said heterocyclic group is optionally substituted by 1 to 4 substituents selected from the following groups:

halogen atom
oxo group;
hydroxy group;
cyano group;
nitro group;
carboxyl group;
sulfo group;
alkyl group optionally substituted by a group selected from halogen atom, cyano group, hydroxy group, carboxyl group, alkoxycarbonyl group, carbamoyl, cycloalkyl group optionally substituted by carboxyl or alkoxycarbonyl group, phenyl group (said phenyl group is optionally substituted by alkoxy, carboxyl or alkoxycarbonyl group), sulfo group, sulfamoyl group, mono- or di-alkylcarbamoyl group, alkoxy group (said alkoxy group is optionally substituted by carboxyl, alkoxycarbonyl, hydroxy, alkoxy or phenyl group), alkanoyl group, alkanoyloxy group, alkylthio group, alkylsulfonyl group, alkylsulfinyl group, amino group, mono- or di-alkylamino group optionally substituted by alkoxy group, mono- or di-alkylsulfamoylamino group, mono- or di-alkylureido group optionally substituted by morpholinyl group, oxiranyl group, dioxolanyl group optionally substituted by alkyl group, pyrrolidinyl group (said pyrrolidinyl group is optionally substituted by oxo, alkoxycarbonyl or carboxyl group), piperidinyl group optionally substituted by carboxyl or alkoxycarbonyl group, piperazinyl group optionally substituted by alkyl group, hexahydroazepinyl group optionally substituted by carboxyl or alkoxycarbonyl group, morpholinyl group, and piperidinyloxy group optionally substituted by alkyl group;
alkenyl group optionally substituted by a group selected from cyano group, hydroxy group, carboxyl group, alkoxycarbonyl group, benzyloxycarbonyl group and tetrazolyl group;
alkoxy group optionally substituted by a group selected from halogen atom, cyano group, hydroxy group, carboxyl group, alkoxycarbonyl group, carbamoyl group, cycloalkyl group optionally substituted by carboxyl or alkoxycarbonyl group, phenyl group (said phenyl group is optionally substituted by alkoxy, carboxyl or alkoxycarbonyl group), sulfo group, sulfamoyl group, alkoxy group (said alkoxy group is optionally substituted by carboxyl, alkoxycarbonyl, hydroxy, alkoxy or phenyl group), alkanoyl group, alkanoyloxy group, alkylthio group, alkylsulfonyl group, alkylsulfinyl group, amino group, mono- or di-alkylamino group substituted by alkoxy group, mono- or di-alkylsulfamoylamino group, mono- or di-alkylureido group optionally substituted by morpholinyl group, oxiranyl group, dioxolanyl group optionally substituted by alkyl group, pyrrolidinyl group (said pyrrolidinyl group is optionally substituted by oxo, alkoxycarbonyl or carboxyl group), piperidinyl group optionally substituted by carboxyl or alkoxycarbonyl group, piperazinyl group optionally substituted by alkyl group, hexahydroazepinyl group optionally substituted by carboxyl or alkoxycarbonyl group, morpholinyl group, piperidinyloxy group optionally substituted by alkyl group, mono- or di-alkylcarbamoyl group optionally substituted by hydroxy group, pyrimidinyl group, pyridyl group and morpholinylcarbonyl group;
alkoxycarbonyl group optionally substituted by hydroxy group, carboxyl group, alkoxycarbonyl group or phenyl group; carbamoyl group;
mono- or di-alkylcarbamoyl group optionally substituted by a group selected from carboxyl group, morpholinyl group, hydroxy group and alkoxy group;
hydroxycarbamimidoyl group;
alkylthio group optionally substituted by a group selected from hydroxy group, carboxyl group and mono- or di-alkylcarbamoyl group;
alkylsulfinyl group;
alkylsulfonyl group optionally substituted by a group selected from hydroxy group, carboxyl group, alkoxycarbonyl group and mono- or di-alkylcarbamoyl group;
amino group;
mono- or di-alkylamino group optionally substituted by a group selected from hydroxy group, carboxyl group, alkoxycarbonyl group, alkoxy group, mono- or di-alkylamino group and morpholinyl group; mono- or di-alkanoylamino group optionally substituted by a group selected from hydroxy group, alkoxy group, carboxyl group, alkoxycarbonyl group and amino group;
mono- or di-alkylcarbamoylamino group optionally substituted by alkoxy group;
morpholinylcarbonylamino group;
sulfamoyl group;
mono- or di-alkylsulfamoyl group;
alkanoyl group optionally substituted by a group selected from hydroxy group, carboxyl group, alkoxycarbonyl group, alkoxy group, mono- or di-alkylamino group and morpholinyl group;
alkoxycarbonylamino group optionally substituted by carboxyl group, hydroxy group, or alkoxycarbonyl group; or
a group selected from the following groups:

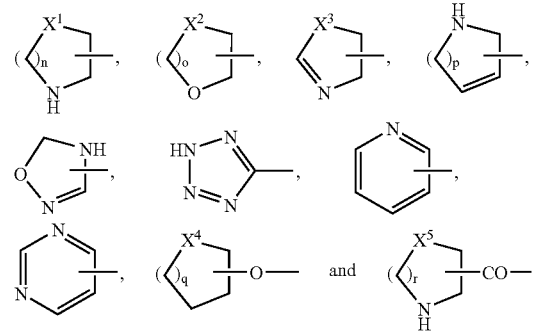

wherein $X^1$ and $X^3$ are independently $CH_2$, NH, O, S, SO or $SO_2$; $X^2$ and $X^5$ are independently $CH_2$, O, S, SO or $SO_2$; $X^4$ is NH, O, S, SO or $SO_2$;

and n, o, p, q and r are independently an integer of 1 to 4, wherein each group of the above formula is optionally substituted by a substituent(s) selected from the following groups:

carboxyl group, halogen atom, hydroxy group, cyano group, oxo group, alkyl group, hydroxyalkyl group, alkoxycarbonylalkyl group, carboxyalkyl group, morpholinylalkyl group, phenylalkyl group, alkanoyl group, hydroxyalkanoyl group, alkoxyalkanoyl group, alkoxy group, phenylalkoxy group, alkoxycarbonyl group, benzyloxycarbonyl group, mono- or di-alkylamino group, mono- or di-alkylcarbamoyl group, mono- or di-alkylsulfamoyl group, alkylsulfonyl group, dihydrooxadiazolyl group optionally substituted by oxo group, and tetrazolyl group;

$R^6$, $R^7$ and $R^8$ are independently a hydrogen atom, a halogen atom, a hydroxy group, a nitro group, a cyano group, an alkyl group, an alkoxy group, an alkoxycarbonyl group, a benzyloxycarbonyl group, a mono- or d-alkylcarbamoyl group or a mono- or di-alkylamino group, wherein said alkyl, alkoxy, alkoxycarbonyl, benzyloxycarbonyl, mono- or d-alkylcarbamoyl and mono- or di-alkylamino groups are optionally substituted by 1 to 6 substituents selected independently from halogen atom, hydroxy group, alkoxy group, alkylthio group, amino group, nitro group, cyano group, oxo group, carboxyl group, alkoxycarbonyl group and mono- or di-alkylamino group; or $R^6$ and $R^7$, or $R^7$ and $R^8$ may combine at the ends to form an alkylene group which alkylene group optionally contains 1 to 3 heteroatoms selected independently from nitrogen, sulfur and oxygen atoms;

$R^{10}$ is an aromatic monocyclic ring optionally containing 1 to 3 heteroatoms selected independently from oxygen, sulfur and nitrogen atoms;

wherein the monocyclic aromatic ring is optionally substituted by 1 to 4 substituents selected independently from halogen atom, carboxyl group, alkoxycarbonyl group, carbamoyl group, mono- or di-alkylcarbamoyl group, alkyl group, alkoxy group, hydroxy group, nitro group, cyano group, amino group, mono- or di-alkylamino group, alkanoyl group, alkylthio group, tetrazolyl group and dihydrooxazolyl group, wherein the alkyl, alkoxy, mono- or di-alkylamino, mono- or di-alkylcarbamoyl, alkanoyl and alkylthio groups are optionally substituted by a substituent(s) selected independently from halogen atom, and hydroxy, alkoxy, morpholinyl, piperidinyl, pyrrolidinyl, piperazinyl, alkylpiperazinyl and alkanoylpiperazinyl groups.

Furthermore, in the preferred compounds, the "aromatic monocyclic ring optionally containing 1 to 3 heteroatoms selected independently from oxygen, sulfur and nitrogen atoms" is a phenyl group, a pyridyl group, a pyrimidinyl group, a furyl group or a thienly group; and the "saturated or unsaturated 5- to 8-membered heterocyclic group containing 1 to 4 heteroatoms selected independently from oxygen, sulfur and nitrogen atoms" is a pyrimidinyl group, a pyridyl group, a triazolyl group, a tetrazolyl group, a oxadiazolyl group, a dihydropyrimidinyl group, a pyrazinyl group, a thiazolyl group, an oxazolyl group, an imidazolyl group, a dihydrooxazinyl group, a dihydropyrazinyl group or a pyrazolyl group.

In more preferred compounds, $R^1$ is a hydrogen atom; an alkoxycarbonyl group optionally substituted by 1 to 5 substituents selected independently from cyano group, hydroxy group, carboxyl group, alkoxycarbonyl group, alkoxy group (said alkoxy group is optionally substituted by 1 to 3 substituents selected independently from hydroxy group, amino group, mono- or di-alkylamino group, halogen atom, carboxyl group, alkoxycarbonyl group, carboxyalkoxy group and alkoxycarbonylalkoxy group), alkylthio group, alkylsulfonyl group, alkenyl group, amino group, mono- or di-alkylamino group, tetrazolyl group, carbamoyl group, mono- or di-alkylcarbamoyl group (said mono- or di-alkylcarbamoyl group is optionally substituted by 1 to 3 substituents selected independently from carboxyl group and alkoxycarbonyl group), alkanoylamino group (said alkanoylamino group is optionally substituted by 1 to 3 substituents selected independently from carboxyl group, alkoxycarbonyl group, hydroxy group and halogen atom), halogen atom, cycloalkyl group (said cycloalkyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), phenyl group (said phenyl group is optionally substituted by 1 to 3 substituents selected independently from hydroxy group, amino group, mono- or di-alkylamino group, halogen atom, carboxyl group, alkoxycarbonyl group, carboxyalkyl group, alkoxycarbonylalkyl group, carboxyalkoxy group and alkoxycarbonylalkoxy group), morpholinyl group optionally substituted by oxo group, piperidinyl group (said piperidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group and carboxyalkoxy group, alkoxycarbonylalkoxy group), pyrrolidinyl group (said pyrrolidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), and pyrimidinyl group (said pyrimidinyl group is optionally substituted by 1 to 3 substituents independently from carboxyalkyl group, alkoxycarbonylalkyl group and carboxyalkoxy group, alkoxycarbonylalkoxy group); dihydrooxazolyl group optionally substituted by 1 to 2 substituents selected independently from carboxyl group, alkoxycarbonyl group, alkyl group, carboxyalkyl group, alkoxycarbonylalkyl group and hydroxyalkyl group; or a mono- or di-alkylcarbamoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group);

$R^2$ is an alkyl group;
$R^3$ is a hydrogen atom;
$R^4$ is an alkylene group;
$R^5$ is a heterocyclic group selected from pyrimidinyl group, pyridyl group, triazolyl group, tetrazolyl group, oxadiazolyl group, dihydropyrimidinyl group, pyrazinyl group, thiazolyl group, oxazolyl group, imidazolyl group, dihydrooxazinyl group, pyrazolyl group and dihydropyrazinyl group, wherein said heterocyclic group is substituted by 1 to 4 substituents selected from the following groups:
halogen atom,
hydroxy group;
oxo group;
cyano group;
carboxyl group;

sulfo group;
alkyl group optionally substituted by a group selected from halogen atom, cyano group, hydroxy group, carboxyl group, alkoxy group optionally substituted by hydroxy or alkoxy group, alkoxycarbonyl group, mono- or di-alkylcarbamoyl group, mono- or di-alkylamino group optionally substituted by alkoxy or carboxyl group, pyrrolidinyl group optionally substituted by carboxyl or alkoxycarbonyl group, piperidinyl group optionally substituted by carboxyl or alkoxycarbonyl group, piperazinyl group optionally substituted by alkyl group, morpholinyl group, alkanoyloxy group and alkylsulfonyl group;
alkenyl group optionally substituted by a group selected from cyano group, hydroxy group, carboxyl group, alkoxycarbonyl group, benzyloxycarbonyl group, and tetrazolyl group;
alkoxy group optionally substituted by a group selected from halogen atom, cyano group, hydroxy group, carboxyl group, alkoxycarbonyl group, carbamoyl group, mono- or di-alkylcarbamoyl group optionally substituted by hydroxy group, alkoxy group (said alkoxy group is optionally substituted by hydroxy, carboxyl or alkoxy group), alkylthio group, alkylsulfonyl group, alkylsulfinyl group, mono- or di-alkylamino group optionally substituted by carboxyl or alkoxy group, morpholinyl group, pyrrolidinyl group (said pyrrolidinyl group is optionally substituted by carboxyl, alkoxy or oxo group), pyrimidinyl group optionally substituted by carboxyl or alkoxy group, optionally oxidized pyridyl group, dioxolanyl group optionally substituted by alkyl group, and morpholinylcarbonyl group;
cycloalkyl group optionally substituted by carboxyl group or alkoxycarbonyl group;
alkoxycarbonyl group optionally substituted by phenyl group;
carbamoyl group;
mono- or di-alkylcarbamoyl group optionally substituted by a group selected from morpholinyl group, carboxyl group, hydroxy group and alkoxy group;
hydroxycarbamimidoyl group;
alkylthio group optionally substituted by a group selected from hydroxy group, carboxyl group and mono- or di-alkylcarbamoyl group;
alkylsulfonyl group optionally substituted by a group selected from hydroxy group, alkoxycarbonyl group and mono- or di-alkylcarbamoyl group;
amino group;
mono- or di-alkylamino group optionally substituted by a group selected from hydroxy group, carboxyl group, alkoxycarbonyl group, alkoxy group, mono- or di-alkylamino group and morpholinyl group;
alkanoylamino group optionally substituted by a group selected from hydroxy group, alkoxy group, carboxyl group and amino group;
mono- or di-alkylureido group optionally substituted by alkoxy group; morpholinylcarbonylamino group;
morpholinyl group optionally substituted by a group selected from oxo group and carboxyl group;
piperazinyl group optionally substituted by a group selected from cyano group, alkyl group, hydroxyalkyl group, alkoxycarbonylalkyl group, carboxyalkyl group, alkanoyl group, alkoxyalkanoyl group, benzyloxycarbonyl group, mono- or di-alkylcarbamoyl group, mono- or di-alkylsulfamoyl group, alkylsulfonyl group, tetrazolyl group, and dihydrooxadiazolyl group optionally substituted by oxo group;
piperidinyl group optionally substituted by a group selected from carboxyl group, hydroxy group, alkyl group optionally substituted by hydroxy or carboxyl group, alkoxy group optionally substituted by phenyl group, alkoxycarbonyl group, oxo group and alkanoyl group;
pyrrolidinyl group optionally substituted by a group selected from carboxyl group, alkoxycarbonyl group, oxo group, and mono- or di- alkylamino group;
pyrrolinyl group optionally substituted by oxo group;
hexahydrodiazepinyl group optionally substituted by alkanoyl group;
imidazolidinyl group optionally substituted by oxo group;
pyridyl group optionally substituted by carboxyl group, hydroxy group, alkanoyl group, alkyl group or hydroxyalkyl group (said pyridyl group is optionally further oxidized);
tetrazolyl group optionally substituted by alkyl group or hydroxyalkyl group;
dihydrooxadiazolyl group optionally substituted by oxo group;
dihydroimidazolyl group;
dihydrooxazolyl group;
oxazolidinyl group optionally substituted by oxo group;
tetrahydropyridyl group optionally substituted by benzyl group;
pyrimidinyl group;
piperidinyloxy group optionally substituted by alkyl group or carboxyl group;
pyrrolidinyloxy group optionally substituted by a group selected from alkyl group, carboxyl group, alkoxycarbonyl group and alkanoyl group;
tetrahydropyranyloxy group;
tetrahydrofuranyloxy group;
optionally oxidized thianyloxy group;
morpholinylcarbonyl group;
piperazinylcarbonyl group optionally substituted by a group selected from alkanoyl group and alkyl group;
pyrrolidinylcarbonyl group optionally substituted by carboxyl group or alkoxycarbonyl group; and
piperidinylcarbonyl group optionally substituted by carboxyl group or alkoxycarbonyl group;
$R^6$ and $R^7$ are independently a hydrogen atom, an alkyl group optionally substituted by halogen atom, an alkoxy group optionally substituted by halogen atom, a hydroxy group, a cyano group, or a mono- or d-alkylamino group; or
$R^6$ and $R^7$ may combine at the ends to form an alkylenedioxy group;
$R^8$ is a hydrogen atom;
$R^{10}$ is s a phenyl or pyridyl group, which phenyl or pyridyl group is optionally substituted by 1 to 4 substituents selected from halogen atom, alkoxycarbonyl group, alkyl group optionally substituted by halogen atom, alkoxy group optionally substitute by halogen atom, hydroxy group, cyano group, amino group, mono- or di-alkylamino group and alkylthio group.

In further preferred compounds, $R^1$ is an alkoxycarbonyl group optionally substituted by 1 to 5 substituents selected independently from hydroxy group, carboxyl group, alkoxycarbonyl group, alkoxy group (said alkoxy group is optionally substituted by 1 to 3 substituents selected independently from hydroxy group, halogen atom, carboxyl group and alkoxycarbonyl group), alkenyl group, halogen atom, cycloalkyl group (said cycloalkyl group is optionally substituted by 1 to 3 substituents selected independently from hydroxy group, halogen atom, carboxyl group, alkoxycarbonyl group, carboxyalkyl group and alkoxycarbonylalkyl group), phenyl group (said phenyl group is optionally substituted by 1 to 3 substituents selected independently from hydroxy group, halogen atom, carboxyl group, alkoxycarbonyl group, carboxyalkyl group and alkoxycarbonylalkyl group), piperidinyl group (said piperidinyl group is optionally substituted by 1 to 3 substituents selected independently from hydroxy group, halogen atom, carboxyl group, alkoxycarbonyl group, carboxyalkyl group and alkoxycarbonylalkyl group), and pyrrolidinyl group (said pyrrolidinyl group is optionally substituted by 1 to 3 substituents selected independently from hydroxy group, halogen atom, carboxyl group, alkoxycarbonyl group, carboxyalkyl group and alkoxycarbonylalkyl group);

or a dihydrooxazolyl group optionally substituted by 1 or 2 substituents selected independently from carboxyl group, alkoxycarbonyl group, carboxyalkyl group, alkoxycarbonylalkyl group and hydroxyalkyl group;

$R^5$ is a pyrimidinyl group, a pyridyl group, a triazolyl group, a tetrazolyl group, an oxadiazolyl group, a dihydropyrimidinyl group, a pyrazinyl group, a thiazolyl group, an oxazolyl group, a dihydrooxazinyl group, a pyrazolyl group or a dihydropyrazinyl group, which group is substituted by 1 to 4 substituents selected from the following groups:

halogen atom;
hydroxy group;
cyano group;
carboxyl group;
alkyl group optionally substituted by a group selected from halogen atom, cyano group, hydroxy group, carboxyl group, alkoxy group optionally substituted by hydroxy or alkoxy group, alkoxycarbonyl group, mono- or di-alkylcarbamoyl group, mono- or di-alkylamino group optionally substituted by alkoxy or carboxyl group, pyrrolidinyl group optionally substituted by carboxyl or alkoxycarbonyl group, piperidinyl group optionally substituted by carboxyl or alkoxycarbonyl group, piperazinyl group optionally substituted by alkyl group, morpholinyl group, alkanoyloxy group and alkylsulfonyl group;
alkenyl group optionally substituted by a group selected from cyano group, hydroxy group and carboxyl group;
alkoxy group optionally substituted by a group selected from halogen atom, cyano group, hydroxy group, carboxyl group, alkoxycarbonyl group, carbamoyl group, mono- or di-alkylcarbamoyl group optionally substituted by hydroxy group, alkoxy group (said alkoxy group is optionally substituted by hydroxy, carboxyl or alkoxy group), alkylthio group, alkylsulfonyl group, alkylsulfinyl group, mono- or di-alkylamino group optionally substituted by carboxyl or alkoxy group, morpholinyl group, pyrrolidinyl group (said pyrrolidinyl group is optionally substituted by carboxyl, alkoxy or oxo group), pyrimidinyl group optionally substituted by carboxyl or alkoxy group, optionally oxidized pyridyl group, dioxolanyl group optionally substituted by alkyl group, and morpholinylcarbonyl group;
cycloalkyl group optionally substituted by carboxyl group or alkoxycarbonyl group;
mono- or di-alkylcarbamoyl group optionally substituted by a group
selected from morpholinyl group, carboxyl group, hydroxy group and alkoxy group;
hydroxycarbamimidoyl group;
alkylthio group optionally substituted by a group selected from hydroxy group, carboxyl group and mono- or di-alkylcarbamoyl group; amino group;
mono- or di-alkylamino group optionally substituted by a group selected from hydroxy group, carboxyl group, alkoxycarbonyl group, alkoxy group, and morpholinyl group;
alkanoylamino group optionally substituted by a group selected from hydroxy group, alkoxy group, carboxyl group and amino group; mono- or di-alkylureido group optionally substituted by alkoxy group; morpholinylcarbonylamino group;
morpholinyl group optionally substituted by oxo group;
piperazinyl group optionally substituted by a group selected from cyano group, alkyl group, hydroxyalkyl group, alkoxycarbonylalkyl group, carboxyalkyl group, alkanoyl group, alkoxyalkanoyl group, mono- or di-alkylcarbamoyl group, mono- or di-alkylsulfamoyl group and alkylsulfonyl group;
piperidinyl group optionally substituted by a group selected from carboxyl group, hydroxy group, alkyl group optionally substituted by hydroxy or carboxyl group, alkoxy group, alkoxycarbonyl group, oxo group and alkanoyl group;
pyrrolidinyl group optionally substituted by a group selected from oxo group, carboxyl group, alkoxycarbonyl group and mono- or di-alkylamino group;
hexahydrodiazepinyl group optionally substituted by alkanoyl group;
pyridyl group optionally substituted by hydroxy group, carboxyl group, alkyl group or hydroxyalkyl group (said pyridyl group is optionally further oxidized);
tetrazolyl group optionally substituted by alkyl group or hydroxyalkyl group;
dihydrooxadiazolyl group optionally substituted by oxo group;
oxazolidinyl group optionally substituted by oxo group;
tetrahydropyridyl group optionally substituted by benzyl group;
pyrimidinyl group;
piperidinyloxy group optionally substituted by alkyl group or carboxyl group;
pyrrolidinyloxy group optionally substituted by a group selected from alkyl group and alkanoyl group;
tetrahydropyranyloxy group;
tetrahydrofuranyloxy group; and
optionally oxidized thianyloxy group;

$R^{10}$ is s a phenyl or pyridyl group, which phenyl or pyridyl group is optionally substituted by 1 to 4 substituents selected from halogen atom, alkyl group optionally substituted by halogen atom, alkoxy group, hydroxy group, cyano group, amino group and mono- or di-alkylamino group.

In another embodiment of the present invention include compounds of the formula (I) wherein $R^5$ is a group of the formula:

$$R^{11}-\boxed{A}-$$

wherein Ring A is a saturated or unsaturated 5- to 8-membered heterocyclic group containing 1 to 4 heteroatoms selected independently from oxygen, sulfur and nitrogen atoms, and $R^{11}$ is a group selected from the following groups:
halogen atom;
hydroxy group;
oxo group;

cyano group;
carboxyl group;
sulfo group;
alkyl group optionally substituted by a group selected from halogen atom, cyano group, hydroxy group, carboxyl group, alkoxy group optionally substituted by hydroxy or alkoxy group, alkoxycarbonyl group, mono- or di-alkylcarbamoyl group, mono- or di-alkylamino group optionally substituted by alkoxy or carboxyl group, pyrrolidinyl group optionally substituted by carboxyl or alkoxycarbonyl group, piperidinyl group optionally substituted by carboxyl or alkoxycarbonyl group, piperazinyl group optionally substituted by alkyl group, morpholinyl group, alkanoyloxy group and alkylsulfonyl group;
alkenyl group optionally substituted by a group selected from cyano group, hydroxy group, carboxyl group, alkoxycarbonyl group, benzyloxycarbonyl group and tetrazolyl group;
alkoxy group optionally substituted by a group selected from halogen atom, cyano group, hydroxy group, carboxyl group, alkoxycarbonyl group, carbamoyl group, mono- or di-alkylcarbamoyl group optionally substituted by hydroxy group, alkoxy group (said alkoxy group is optionally substituted by hydroxy, carboxyl or alkoxy group), alkylthio group, alkylsulfonyl group, alkylsulfinyl group, mono- or di-alkylamino group optionally substituted by carboxyl or alkoxy group, morpholinyl group, pyrrolidinyl group (said pyrrolidinyl group is optionally substituted by carboxyl, alkoxy or oxo group), pyrimidinyl group optionally substituted by carboxyl or alkoxy group, optionally oxidized pyridyl group, dioxolanyl group optionally substituted by alkyl group and morpholinylcarbonyl group;
cycloalkyl group optionally substituted by carboxyl group or alkoxycarbonyl group;
alkoxycarbonyl group optionally substituted by phenyl group;
carbamoyl group;
mono- or di-alkylcarbamoyl group optionally substituted by a group selected from morpholinyl group, carboxyl group, hydroxy group and alkoxy group;
hydroxycarbamimidoyl group;
alkylthio group optionally substituted by a group selected from hydroxy group, carboxyl group and mono- or di-alkylcarbamoyl group;
alkylsulfonyl group optionally substituted by a group selected from hydroxy group, alkoxycarbonyl group and mono- or di-alkylcarbamoyl group;
amino group;
mono- or di-alkylamino group optionally substituted by a group selected from hydroxy group, carboxyl group, alkoxycarbonyl group, alkoxy group, mono- or di-alkylamino group and morpholinyl group;
alkanoylamino group optionally substituted by a group selected from hydroxy group, alkoxy group, carboxyl group and amino group;
mono- or di-alkylureido group optionally substituted by alkoxy group;
morpholinylcarbonylamino group;
morpholinyl group optionally substituted by a group selected from oxo group and carboxyl group;
piperazinyl group optionally substituted by a group selected from cyano group, alkyl group, hydroxyalkyl group, alkoxycarbonylalkyl group, carboxyalkyl group, alkanoyl group, alkoxyalkanoyl group, benzyloxycarbonyl group, mono- or di-alkylcarbamoyl group, mono- or di-alkylsulfamoyl group, alkylsulfonyl group, tetrazolyl group, and dihydrooxadiazolyl group optionally substituted by oxo group;
piperidinyl group optionally substituted by a group selected from carboxyl group, hydroxy group, alkyl group optionally substituted by hydroxy or carboxyl group, alkoxy group optionally substituted by phenyl group, alkoxycarbonyl group, oxo group, and alkanoyl group;
pyrrolidinyl group optionally substituted by a group selected from carboxyl group, alkoxycarbonyl group, oxo group, and mono- or di-alkylamino group;
pyrrolinyl group optionally substituted by oxo group;
hexahydrodiazepinyl group optionally substituted by alkanoyl group;
imidazolidinyl group optionally substituted by oxo group;
pyridyl group optionally substituted by carboxyl group, hydroxy group, alkanoyl group, alkyl group or hydroxyalkyl group (said pyridyl group is optionally further oxidized);
tetrazolyl group optionally substituted by a group selected from alkyl group and hydroxyalkyl group;
dihydrooxadiazolyl group optionally substituted by oxo group;
dihydroimidazolyl group;
dihydrooxazolyl group;
oxazolidinyl group optionally substituted by oxo group;
tetrahydropyridyl group optionally substituted by benzyl group;
pyrimidinyl group;
piperidinyloxy group optionally substituted by alkyl group or carboxyl group;
pyrrolidinyloxy group optionally substituted by a group selected from alkyl group, carboxyl group, alkoxycarbonyl group and alkanoyl group;
tetrahydropyranyloxy group;
tetrahydrofuranyloxy group;
optionally oxidized thianyloxy group;
morpholinylcarbonyl group;
piperazinylcarbonyl group optionally substituted by a group selected from alkanoyl group and alkyl group;
pyrrolidinylcarbonyl group optionally substituted by carboxyl group or alkoxycarbonyl group; and
piperidinylcarbonyl group optionally substituted by carboxyl group or alkoxycarbonyl group;

which compound is shown by the formula (I-A):

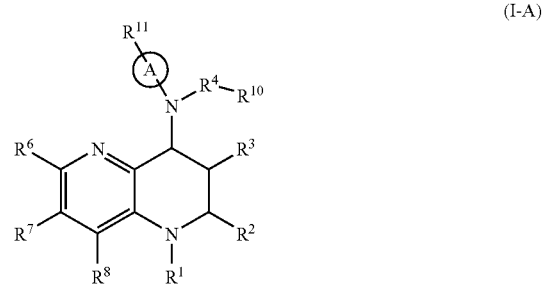

(I-A)

wherein each symbol has the same meaning as defined above.

More preferred embodiment includes compounds of the formula (I) wherein $R^1$ is a hydrogen atom; an alkoxycarbonyl group optionally substituted by 1 to 5 substituents selected independently from cyano group, hydroxy group, carboxyl group, alkoxycarbonyl group, alkoxy group (said alkoxy group is optionally substituted by 1 to 3 substituents selected independently from hydroxy group, amino group, mono- or di-alkylamino group, halogen atom, carboxyl group, alkoxycarbonyl group, carboxyalkoxy group and alkoxycarbonylalkoxy group), alkylthio group, alkylsulfonyl group, alkenyl group, amino group, mono- or di-alkylamino group, tetrazolyl group, carbamoyl group, mono- or di-alkylcarbamoyl group (said mono- or di-alkylcarbamoyl group is optionally substituted by 1 to 3 substituents selected independently from carboxyl group and alkoxycarbonyl group), alkanoylamino group (said alkanoylamino group is optionally substituted by 1 to 3 substituents selected independently from carboxyl group, alkoxycarbonyl group, hydroxy group and halogen atom), halogen atom, cycloalkyl group (said cycloalkyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), phenyl group (said phenyl group is optionally substituted by 1 to 3 substituents selected independently from hydroxy group, amino group, mono- or di-alkylamino group, halogen atom, carboxyl group, alkoxycarbonyl group, carboxyalkyl group, alkoxycarbonylalkyl group, carboxyalkoxy group and alkoxycarbonylalkoxy group), morpholinyl group optionally substituted by oxo group, piperidinyl group (said piperidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group and carboxyalkoxy group, alkoxycarbonylalkoxy group), pyrrolidinyl group (said pyrrolidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), and pyrimidinyl group (said pyrimidinyl group is optionally substituted by 1 to 3 substituents selected independently from carboxyalkyl group, alkoxycarbonylalkyl group and carboxyalkoxy group, alkoxycarbonylalkoxy group); dihydrooxazolyl group optionally substituted by 1 to 2 substituents selected independently from carboxyl group, alkoxycarbonyl group, alkyl group, carboxyalkyl group, alkoxycarbonylalkyl group and hydroxyalkyl group; or a mono- or di-alkylcarbamoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group);

$R^2$ is an alkyl group;
$R^3$ is a hydrogen atom;
$R^4$ is an alkylene group;
Ring A and $R^{11}$ are the same groups as defined above;
$R^6$ and $R^7$ are independently a hydrogen atom, an alkyl group optionally substituted by halogen atom, an alkoxy group optionally substituted by halogen atom, a hydroxy group, a cyano group, or a mono- or d-alkylamino group; or $R^6$ and $R^7$ may combine at the ends to form an alkylenedioxy group;
$R^8$ is a hydrogen atom;
$R^{10}$ is s a phenyl or pyridyl group, which phenyl or pyridyl group is optionally substituted by 1 to 4 substituents selected from halogen atom, alkoxycarbonyl group, alkyl group optionally substituted by halogen atom, alkoxy group optionally substitute by halogen atom, hydroxy group, cyano group, amino group, mono- or di-alkylamino group and alkylthio group.

Another preferred embodiment includes compounds of the formula (I) wherein Ring A is a saturated or unsaturated 5- to 8-membered heterocyclic group containing 1 to 4 heteroatoms selected independently from oxygen, sulfur and nitrogen atoms, and $R^{11}$ is a group selected from the following groups:

halogen atom,
hydroxy group;
oxo group;
cyano group;
carboxyl group;
sulfo group;
alkyl group optionally substituted by a group selected from cyano group, hydroxy group, carboxyl group, alkoxy group optionally substituted by hydroxy group, alkoxycarbonyl group, mono- or di-alkylcarbamoyl group, mono- or di-alkylamino group optionally substituted by alkoxy group, pyrrolidinyl group, piperidinyl group, piperazinyl group optionally substituted by alkyl group, morpholinyl group, alkanoyloxy group and alkylsulfonyl group;
alkenyl group optionally substituted by a group selected from cyano group, hydroxy group, carboxyl group, benzyloxycarbonyl group, and tetrazolyl group;
alkoxy group optionally substituted by a group selected from hydroxy group, carboxyl group, alkoxycarbonyl group, carbamoyl group, mono- or di-alkylcarbamoyl group optionally substituted by hydroxy group, alkoxy group optionally substituted by hydroxy group, alkylthio group, alkylsulfonyl group, alkylsulfinyl group, mono- or di-alkylamino group, morpholinyl group, pyrrolidinyl group optionally substituted by oxo group, pyrimidinyl group, optionally oxidized pyridyl group, dioxolanyl group optionally substituted by alkyl group, and morpholinylcarbonyl group;
alkoxycarbonyl group optionally substituted by phenyl group;
carbamoyl group;
mono- or di-alkylcarbamoyl group optionally substituted by a group selected from morpholinyl group and alkoxy group;
hydroxycarbamimidoyl group;
alkylthio group optionally substituted by a group selected from hydroxy group, carboxyl group and mono- or di-alkylcarbamoyl group;
alkylsulfonyl group optionally substituted by a group selected from hydroxy group, alkoxycarbonyl group and mono- or di-alkylcarbamoyl group;
amino group;
mono- or di-alkylamino group optionally substituted by a group selected from hydroxy group, carboxyl group, alkoxycarbonyl group, alkoxy group, mono- or di-alkylamino group and morpholinyl group;
alkanoylamino group optionally substituted by a group selected from hydroxy group, alkoxy group and amino group;
mono- or di-alkylureido group optionally substituted by alkoxy group;

morpholinylcarbonylamino group;

morpholinyl group optionally substituted by a group selected from oxo group and carboxyl group;

piperazinyl group optionally substituted by a group selected from cyano group, alkyl group, hydroxyalkyl group, alkoxycarbonylalkyl group, carboxyalkyl group, alkanoyl group, alkoxyalkanoyl group, benzyloxycarbonyl group, mono- or di-alkylcarbamoyl group, mono- or di-alkylsulfamoyl group, alkylsulfonyl group, tetrazolyl group, and dihydrooxadiazolyl group optionally substituted by oxo group;

piperidinyl group optionally substituted by a group selected from carboxyl group, hydroxy group, alkyl group optionally substituted by hydroxy or carboxyl group, alkoxy group optionally substituted by phenyl group, alkoxycarbonyl group, oxo group, and alkanoyl group;

pyrrolidinyl group optionally substituted by a group selected from oxo group and mono- or di-alkylamino group;

pyrrolinyl group optionally substituted by oxo group;

hexahydrodiazepinyl group optionally substituted by alkanoyl group;

imidazolidinyl group optionally substituted by oxo group;

pyridyl group optionally substituted by carboxyl group, hydroxy group, alkyl group or hydroxyalkyl group (said pyridyl group is optionally further oxidized);

tetrazolyl group optionally substituted by alkyl group or hydroxyalkyl group;

dihydrooxadiazolyl group optionally substituted by oxo group;

dihydroimidazolyl group;

dihydrooxazolyl group;

oxazolidinyl group optionally substituted by oxo group;

tetrahydropyridyl group optionally substituted by benzyl group;

pyrimidinyl group;

piperidinyloxy group optionally substituted by alkyl group;

pyrrolidinyloxy group optionally substituted by a group selected from alkyl group and alkanoyl group;

tetrahydropyranyloxy group;

tetrahydrofuranyloxy group;

optionally oxidized thianyloxy group;

morpholinylcarbonyl group;

piperazinylcarbonyl group optionally substituted by a group selected from alkanoyl group and alkyl group; and pyrrolidinylcarbonyl group.

More preferred embodiment herein includes compounds of the formula (I) wherein $R^1$ is an alkoxycarbonyl group optionally substituted by a group selected from hydroxy group and alkoxy group;

$R^2$ is an alkyl group;

$R^3$ is a hydrogen atom;

$R^4$ is an alkylene group;

Ring A and $R^1$ are the same groups as defined above;

$R^6$ and $R^7$ are independently a hydrogen atom, an alkyl group optionally substituted by halogen atom, an alkoxy group optionally substituted by halogen atom, a cyano group, or a mono- or d-alkylamino group; or $R^6$ and $R^7$ may combine at the ends to form an alkylenedioxy group;

$R^8$ is a hydrogen atom;

$R^{10}$ is s a phenyl or pyridyl group, which phenyl or pyridyl group is optionally substituted by 1 to 4 substituents selected from halogen atom, alkoxycarbonyl group, alkyl group optionally substituted by halogen atom, alkoxy group optionally substitute by halogen atom, hydroxy group, cyano group, amino group, mono- or di-alkylamino group and alkylthio group.

Examples of Ring A include a pyrimidinyl group, a pyridyl group, a triazolyl group, a tetrazolyl group, an oxadiazolyl group, a dihydropyrimidinyl group, a pyrazinyl group, a thiazolyl group, an oxazolyl group, a dihydrooxazinyl group, a pyrazolyl group, a dihydropyrazinyl group, and the like.

More preferred compounds include those wherein Ring A is a pyrimidinyl group, a tetrazolyl group or a pyridyl group; and $R^{11}$ is a group selected from the groups:

alkyl group optionally substituted by a group selected from carboxyl group, hydroxyalkoxy group, mono- or di-alkylamino group optionally substituted by alkoxy group, amino group, mono- or di-alkylcarbamoyl group and morpholinyl group:

alkenyl group optionally substituted by hydroxy group, carboxyl group or cyano group;

alkoxy group optionally substituted by a group selected from hydroxy group, carboxyl group, carbamoyl group, alkoxycarbonyl group, mono- or di-alkylcarbamoyl group optionally substituted by hydroxy group, hydroxyalkoxy group, carboxyalkoxy group, alkylsulfonyl group, alkylsulfinyl group, mono- or di-alkylamino group, morpholinyl group, oxopyrrolidinyl group, optionally oxidized pyridyl group and morpholinylcarbonyl group;

carbamoyl group;

alkylthio group optionally substituted by hydroxy group or mono- or di-alkylcarbamoyl group;

mono- or di-alkylamino group optionally substituted by hydroxy group, carboxyl group or alkoxy group;

alkanoylamino group optionally substituted by hydroxy group or alkoxy group;

mono- or di-alkylureido group optionally substituted by alkoxy group;

morpholinyl group;

piperazinyl group optionally substituted by a group selected from alkyl group, hydroxyalkyl group, alkoxycarbonylalkyl group, carboxyalkyl group, alkanoyl group and mono- or di-alkylcarbamoyl group;

piperidinyl group optionally substituted by a group selected from carboxyl group, alkoxycarbonyl group, hydroxy group, hydroxyalkyl group, carboxyalkyl group and oxo group;

pyrrolidinyl group optionally substituted by a group selected from carboxyl group and mono- or di-alkylamino group;

pyridyl group that is substituted by hydroxyalkyl group or oxidized;

tetrazolyl group optionally substituted by alkyl group or hydroxyalkyl group;

oxodihydrooxadiazolyl group;

pyrimidinyl group;

pyrrolidinyloxy group optionally substituted by alkanoyl group; and optionally oxidized thianyloxy group;

$R^6$ is a hydrogen atom, an alkyl group optionally substituted by halogen atom, an alkoxy group, a cyano group, or a mono- or d-alkylamino group; $R^{10}$ is s a phenyl group which is substituted by 1 to 3 substituents selected from halogen atom, alkyl group optionally substituted by halogen atom, alkoxy group and cyano group.

Still more preferred compounds include those wherein $R^1$ is an alkoxycarbonyl group optionally substituted by 1 to 5 substituents selected independently from hydroxy group, carboxyl group, alkoxycarbonyl group, alkoxy group (said alkoxy group is optionally substituted by 1 to 3 substituents selected independently from hydroxy group, halogen atom, carboxyl group and alkoxycarbonyl group), alkenyl group, halogen atom, cycloalkyl group (said cycloalkyl group is optionally substituted by 1 to 3 substituents selected independently from hydroxy group, halogen atom, carboxyl group, alkoxycarbonyl group, carboxyalkyl group and alkoxycarbonylalkyl group), phenyl group (said phenyl group is optionally substituted by 1 to 3 substituents selected independently from hydroxy group, halogen atom, carboxyl group, alkoxycarbonyl group, carboxyalkyl group and alkoxycarbonylalkyl group), piperidinyl group (said piperidinyl group is optionally substituted by 1 to 3 substituents selected independently from hydroxy group, halogen atom, carboxyl group, alkoxycarbonyl group, carboxyalkyl group and alkoxycarbonylalkyl group), and pyrrolidinyl group (said pyrrolidinyl group is optionally substituted by 1 to 3 substituents selected independently from hydroxy group, halogen atom, carboxyl group, alkoxycarbonyl group, carboxyalkyl group and alkoxycarbonylalkyl group); or a dihydrooxazolyl group optionally substituted by 1 or 2 substituents selected independently from carboxyl group, alkoxycarbonyl group, carboxyalkyl group, alkoxycarbonylalkyl group and hydroxyalkyl group;

$R^{11}$ is a group selected from the groups:

alkyl group optionally substituted by carboxyl group, alkoxycarbonyl group or hydroxy group, carboxyalkenyl group;

alkoxy group optionally substituted by a group selected from cyano group, hydroxy group, carboxyl group, alkoxycarbonyl group, carbamoyl group, mono- or di-alkylcarbamoyl group, mono- or di-alkylcarbamoyl group substituted by hydroxy group, hydroxyalkoxy group, alkylsulfonyl group, alkylsulfinyl group, mono- or di-alkylamino group and oxopyrrolidinyl group;

mono- or di-alkylamino group optionally substituted by carboxyl group;

alkanoylamino group optionally substituted by hydroxy group or alkoxy group;

morpholinyl group;

piperazinyl group optionally substituted by a group selected from alkyl group, alkanoyl group and mono- or di-alkylcarbamoyl group;

piperidinyl group optionally substituted by carboxyl group, alkoxycarbonyl group, hydroxy group, carboxyalkyl group or hydroxyalkyl group;

pyrrolidinyl group optionally substituted by mono- or di-alkylamino group;

pyridyl group that is substituted by hydroxyalkyl group or oxidized;

tetrazolyl group optionally substituted by hydroxyalkyl group;

pyrimidinyl group;

pyrrolidinyloxy group optionally substituted by alkyl group or alkanoyl group; and optionally oxidized thianyloxy group; and $R^{10}$ is s a phenyl group which is substituted by 1 to 3 substituents selected from alkyl group optionally substituted by halogen atom, alkoxy group and cyano group.

Still furthermore preferred compounds include those wherein $R^1$ is an alkoxycarbonyl group optionally substituted by 1 or 5 substituents selected independently from carboxyl group, alkoxycarbonyl group, halogen atom, hydroxy group and cycloalkyl group; $R^{11}$ is an alkyl group optionally substituted by carboxyl group; a carboxyalkenyl group; an alkoxy group optionally substituted by a group selected from cyano group, hydroxy group, carboxyl group, alkylthio group and alkylsulfonyl group; an mono- or di-alkylamino group optionally substituted by carboxyl group; a hydroxyalkanoylamino group; a morpholinyl group; a piperazinyl group optionally substituted by alkyl group or alkanoyl group; or a piperidinyl group optionally substituted by carboxyl group or hydroxy group;

$R^6$ is an alkyl group optionally substituted by halogen atom, an alkoxy group or a mono- or d-alkylamino group; and $R^7$ is s a hydrogen atom.

Especially preferred compounds include those wherein $R^1$ is an ethoxycarbonyl group, a hydroxyethoxycarbonyl group, a 2-fluoroethoxycarbonyl group, a 2,2-difluoroethoxycarbonyl group or a 2,2,2-trifluoroethoxycarbonyl group; $R^2$ is an ethyl group; $R^{10}$ is a phenyl group substituted by 1 to 2 substituents selected from cyano group and trifluoromethyl group; $R^6$ is a methoxy group or a trifluoromethyl group. In this regard, other examples of especially preferred compounds include those wherein $R^1$ is a carboxy($C_{2-10}$alkoxy)carbonyl group or an alkoxycarbonyl($C_{2-10}$alkoxy)carbonyl group, and $R^2$, $R^{10}$ and $R^6$ are the same as above.

Especially more preferred compounds include those wherein $R^1$ is an ethoxycarbonyl group or a hydroxyethoxycarbonyl group; $R^2$ is an ethyl group; $R^{10}$ is a phenyl group substituted by 1 to 2 substituents selected from cyano group and trifluoromethyl group; and $R^6$ is a methoxy group.

Most preferred compounds include those listed below.

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid ethyl ester;

(2R*,4S*)-4-{[3,5-Bis(trifluoromethyl)benzyl]-[5-(4-hydroxymethylpyperidine-1-yl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-methylpiperadin-1-yl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-acetylpiperadin-1-yl)pyrimidin-2-yl]}amino-2-ethyl-6-methoxy-3,4-dihydro-2H-[1,5]naphthyridine-1-carboxylic acid ethyl ester;

(2R*,4S*)-4-{[3,5-Bis(trifluoromethyl)benzyl]-[5-(hydroxyacetylamino)-pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2-methylsulfonylethoxy)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2,3-dihydroxypropoxy)-pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2-carboxyvinyl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2-carboxyethyl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid ethyl ester;

(2R,4S)-4-[[3,5-Bis(trifluoromethyl)benzyl]-(5-{[methyl-(2-carboxyethyl)]amino}pyrimidin-2-yl)]amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-carboxypyperidin-1-yl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-carboxypyperidin-1-yl)pyridin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2-carboxyethoxy)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(3-carboxypropoxy)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-carboxybutoxy)pyrimidin-2-yl]}amino-2-ethyl-6-methoxy-3,4-dihydro-2H-[1,5]naphthyridine-1-carboxylic acid ethyl ester;

(2R,4S)-4-{[5-(2-Carboxyethyl)pyrimidin-2-yl]-(3-cyano-5-trifluoromethylbenzyl)}amino-2-ethyl-6-methoxy-3,4-dihydro-2H-[1,5]naphthyridine-1-carboxylic acid ethyl ester;

(2R,4S)-4-[(3-Cyano-5-trifluoromethylbenzyl)-(5-{[methyl-(2-carboxyethyl)]-amino}pyrimidin-2-yl)]amino-2-ethyl-6-methoxy-3,4-dihydro-2H-[1,5]naphthyridine-1-carboxylic acid ethyl ester;

(2R,4S)-4-{[5-(4-Acetylpiperadin-1-yl)pyrimidin-2-yl]-[3,5-bis(trifluoromethyl)benzyl]}amino-6-dimethylamino-2-ethyl-3,4-dihydro-2H-[1,5]naphthyridine-1-carboxylic acid ethyl ester;

(2R,4S)-4-{[5-(4-Acetylpiperadin-1-yl)pyrimidin-2-yl]-[3,5-bis(trifluoromethyl)benzyl]}amino-2-ethyl-6-methyl-3,4-dihydro-2H-[1,5]naphthyridine-1-carboxylic acid ethyl ester;

(2R,4S)-4-{[3,5-Bis(trifluoromethyl)benzyl]-[5-(3-carboxypropoxy)pyrimidin-2-yl]}amino-2-ethyl-6-trifluoromethyl-3,4-dihydro-2H-[1,5]naphthyridine-1-carboxylic acid ethyl ester;

(2R,4S)-4-{[3,5-Bis(trifluoromethyl)benzyl]-[5-(2-carboxyethyl)pyrimidin-2-yl]}amino-2-ethyl-6-methoxy-3,4-dihydro-2H-[1,5]naphthyridine-1-carboxylic acid 2,2,2-trifluoroethyl ester;

(2R,4S)-4-{[3,5-Bis(trifluoromethyl)benzyl]-[5-(4-carboxypyperidin-1-yl)pyrimidin-2-yl]}amino-2-ethyl-6-methoxy-3,4-dihydro-2H-[1,5]naphthyridine-1-carboxylic acid tert-butyl ester;

(2R,4S)-4-{[3,5-Bis(trifluoromethyl)benzyl]-[5-(4-carboxypyperidin-1-yl)pyrimidin-2-yl]}amino-2-ethyl-6-methoxy-3,4-dihydro-2H-[1,5]naphthyridine-1-carboxylic acid 2-fluoroethyl ester;

(2R,4S)-4-{[3,5-Bis(trifluoromethyl)benzyl]-[5-(4-carboxypyperidin-1-yl)pyrimidin-2-yl]}amino-2-ethyl-6-methoxy-3,4-dihydro-2H-[1,5]naphthyridine-1-carboxylic acid 1-methylethyl ester;

(2R,4S)-4-{[3,5-Bis(trifluoromethyl)benzyl]-[5-(morpholin-4-yl)pyridin-2-yl]}amino-1-((R)-4-hydroxymethyl-4,5-dihydrooxazol-2-yl)-2-ethyl-6-methoxy-3,4-dihydro-2H-[1,5]naphthyridine;

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 2-carboxy-2-methylpropyl ester; or (2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 5-carboxypentyl ester; or a pharmaceutically acceptable salt thereof.

Further examples of most preferred compounds include
(2R,4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 2-carboxyethyl ester;

(2R,4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 3-carboxypropyl ester;

(2R,4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 4-carboxybutyl ester;

(2R,4S)-4-{[3,5-bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid 2-carboxyethyl ester;

(2R,4S)-4-{[3,5-bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid 3-carboxypropyl ester;

(2R,4S)-4-{[3,5-bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid 4-carboxybutyl ester;

(2R,4S)-4-{[3,5-bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid 5-carboxypentyl ester;

(2R,4S)-4-{[3,5-bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 2-carboxyethyl ester;

(2R,4S)-4-{[3,5-bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 3-carboxypropyl ester;

(2R,4S)-4-{[3,5-bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 4-carboxybutyl ester;

(2R,4S)-4-{[3,5-bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 5-carboxypentyl ester;

(2R,4S)-4-{[3,5-bis(trifluoromethyl)benzyl]-[5-(3-cyano-propoxy)pyrimidin-2-yl]}amino-2-ethyl-6-methoxy-3,4-dihydro-2H-[1,5]naphthyridine-1-carboxylic acid 2-carboxyethyl ester;

(2R,4S)-4-{[3,5-bis(trifluoromethyl)benzyl]-[5-(3-cyano-propoxy)pyrimidin-2-yl]}amino-2-ethyl-6-methoxy-3,4-dihydro-2H-[1,5]naphthyridine-1-carboxylic acid 3-carboxypropyl ester;

(2R,4S)-4-{[3,5-bis(trifluoromethyl)benzyl]-[5-(3-cyano-propoxy)pyrimidin-2-yl]}amino-2-ethyl-6-methoxy-3,4-dihydro-2H-[1,5]naphthyridine-1-carboxylic acid 4-carboxybutyl ester;

(2R,4S)-4-{[3,5-bis(trifluoromethyl)benzyl]-[5-(3-cyano-propoxy)pyrimidin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(3-cyano-propoxy)pyrimidin-2-yl]}amino-2-ethyl-6-methoxy-3,4-dihydro-2H-[1,5]naphthyridine-1-carboxylic acid 5-carboxypentyl ester;

(2R,4S)-4-{[3,5-bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 2-carboxyethyl ester;

(2R,4S)-4-{[3,5-bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 3-carboxypropyl ester;

(2R,4S)-4-{[3,5-bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 4-carboxybutyl ester;

(2R,4S)-4-{[3,5-bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 2-carboxy-2-methylpropyl ester;

(2R,4S)-4-{[3,5-bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 5-carboxypentyl ester;

(2R,4S)-4-{(3-cyano-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid 2-carboxyethyl ester;

(2R,4S)-4-{(3-cyano-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid 3-carboxypropyl ester;

(2R,4S)-4-{(3-cyano-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid 4-carboxybutyl ester;

(2R,4S)-4-{(3-cyano-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid 2-carboxy-2-methylpropyl ester;

(2R,4S)-4-{(3-cyano-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid 5-carboxypentyl ester;

(2R,4S)-4-{[3,5-bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid 2-carboxyethyl ester;

(2R,4S)-4-{[3,5-bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid 3-carboxypropyl ester;

(2R,4S)-4-{[3,5-bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid 4-carboxybutyl ester;

(2R,4S)-4-{[3,5-bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid 5-carboxypentyl ester;

(2R,4S)-4-{[3,5-bis(trifluoromethyl)benzyl]-[5-(2-methoxyethoxy)pyridin-2-yl]}amino-2-ethyl-6-methoxy-3,4-dihydro-2H-[1,5]naphthyridine-1-carboxylic acid 3-carboxypropyl ester;

(2R,4S)-4-{[3,5-bis(trifluoromethyl)benzyl]-[5-(2-methoxyethoxy)pyridin-2-yl]}amino-2-ethyl-6-methoxy-3,4-dihydro-2H-[1,5]naphthyridine-1-carboxylic acid 4-carboxybutyl ester;

(2R,4S)-4-{[3,5-bis(trifluoromethyl)benzyl]-[5-(2-methoxyethoxy)pyridin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(2-methoxyethoxy)pyridin-2-yl]}amino-2-ethyl-6-methoxy-3,4-dihydro-2H-[1,5]naphthyridine-1-carboxylic acid 5-carboxypentyl ester;

(2R,4S)-4-{(3-cyano-5-trifluoromethylbenzyl)-[5-(morpholin-4-yl)pyridin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-[1,5]naphthyridine-1-carboxylic acid 3-carboxypropyl ester;

(2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-[1,5]naphthyridine-1-carboxylic acid 4-carboxybutyl ester;

(2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-[1,5]naphthyridine-1-carboxylic acid 5-carboxypentyl ester;

(2R,4S)-4-{[3,5-bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{[3,5-bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 3-carboxypropyl ester;

(2R,4S)-4-{[3,5-bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 4-carboxybutyl ester;

(2R,4S)-4-{[3,5-bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 5-carboxypentyl ester;

(2R,4S)-4-{[3,5-bis(trifluoromethyl)benzyl]-[5-(2-methoxyethoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{[3,5-bis(trifluoromethyl)benzyl]-[5-(2-methoxyethoxy)pyrimidin-2-yl]}amino-2-ethyl-6-trifluoromethyl-3,4-dihydro-2H-[1,5]naphthyridine-1-carboxylic acid 3-carboxypropyl ester;

(2R,4S)-4-{[3,5-bis(trifluoromethyl)benzyl]-[5-(2-methoxyethoxy)pyrimidin-2-yl]}amino-2-ethyl-6-trifluoromethyl-3,4-dihydro-2H-[1,5]naphthyridine-1-carboxylic acid 4-carboxybutyl ester;

(2R,4S)-4-{[3,5-bis(trifluoromethyl)benzyl]-[5-(2-methoxyethoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(2-methoxyethoxy)pyrimidin-2-yl]}amino-2-ethyl-6-trifluoromethyl-3,4-dihydro-2H-[1,5]naphthyridine-1-carboxylic acid 5-carboxypentyl ester;

(2R,4S)-4-{[3,5-bis(trifluoromethyl)benzyl]-[5-(3-cyanopropoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{[3,5-bis(trifluoromethyl)benzyl]-[5-(3-cyanopropoxy)pyrimidin-2-yl]}amino-2-ethyl-6-trifluoromethyl-3,4-dihydro-2H-[1,5]naphthyridine-1-carboxylic acid 3-carboxypropyl ester;

(2R,4S)-4-{[3,5-bis(trifluoromethyl)benzyl]-[5-(3-cyanopropoxy)pyrimidin-2-yl]}amino-2-ethyl-6-trifluoromethyl-3,4-dihydro-2H-[1,5]naphthyridine-1-carboxylic acid 4-carboxybutyl ester;

(2R,4S)-4-{[3,5-bis(trifluoromethyl)benzyl]-[5-(3-cyanopropoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(3-cyanopropoxy)pyrimidin-2-yl]}amino-2-ethyl-6-trifluoromethyl-3,4-dihydro-2H-[1,5]naphthyridine-1-carboxylic acid 5-carboxypentyl ester;

(2R,4S)-4-{[3,5-bis(trifluoromethyl)benzyl]-(5-dimethylaminopyrimidin-2-yl)}amino-2-ethyl-6-trifluoromethyl-3,4-dihydro-2H-[1,5]naphthyridine-1-carboxylic acid 2-carboxyethyl ester;

(2R,4S)-4-{[3,5-bis(trifluoromethyl)benzyl]-(5-dimethylaminopyrimidin-2-yl)}amino-2-ethyl-6-trifluoromethyl-3,4-dihydro-2H-[1,5]naphthyridine-1-carboxylic acid 3-carboxypropyl ester;

(2R,4S)-4-{[3,5-bis(trifluoromethyl)benzyl]-(5-dimethylaminopyrimidin-2-yl)}amino-2-ethyl-6-trifluoromethyl-3,4-dihydro-2H-[1,5]naphthyridine-1-carboxylic acid 4-carboxybutyl ester;

(2R,4S)-4-{[3,5-bis(trifluoromethyl)benzyl]-(5-dimethylaminopyrimidin-2-yl)}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-bis(trifluoromethyl)benzyl]-(5-dimethylaminopyrimidin-2-yl)}amino-2-ethyl-6-trifluoromethyl-3,4-dihydro-2H-[1,5]naphthyridine-1-carboxylic acid 5-carboxypentyl ester;

(2R,4S)-4-{(3-cyano-5-trifluoromethylbenzyl)-[5-(morpholin-4-yl)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{(3-cyano-5-trifluoromethylbenzyl)-[5-(morpholin-4-yl)pyrimidin-2-yl]}amino-2-ethyl-6-trifluoromethyl-3,4-dihydro-2H-[1,5]naphthyridine-1-carboxylic acid 3-carboxypropyl ester;

(2R,4S)-4-{(3-cyano-5-trifluoromethylbenzyl)-[5-(morpholin-4-yl)pyrimidin-2-yl]}amino-2-ethyl-6-trifluoromethyl-3,4-dihydro-2H-[1,5]naphthyridine-1-carboxylic acid 4-carboxybutyl ester;

(2R,4S)-4-{(3-cyano-5-trifluoromethylbenzyl)-[5-(morpholin-4-yl)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{(3-cyano-5-trifluoromethylbenzyl)-[5-(morpholin-4-yl)pyrimidin-2-yl]}amino-2-ethyl-6-trifluoromethyl-3,4-dihydro-2H-[1,5]naphthyridine-1-carboxylic acid 5-carboxypentyl ester;

(2R,4S)-4-{[3,5-bis(trifluoromethyl)benzyl]-[5-(morpholin-4-yl)pyridin-2-yl]}amino-2-ethyl-6-trifluoromethyl-3,4-dihydro-2H-[1,5]naphthyridine-1-carboxylic acid 2-carboxyethyl ester;

(2R,4S)-4-{[3,5-bis(trifluoromethyl)benzyl]-[5-(morpholin-4-yl)pyridin-2-yl]}amino-2-ethyl-6-trifluoromethyl-3,4-dihydro-2H-[1,5]naphthyridine-1-carboxylic acid 3-carboxypropyl ester;

(2R,4S)-4-{[3,5-bis(trifluoromethyl)benzyl]-[5-(morpholin-4-yl)pyridin-2-yl]}amino-2-ethyl-6-trifluoromethyl-3,4-dihydro-2H-[1,5]naphthyridine-1-carboxylic acid 4-carboxybutyl ester;

(2R,4S)-4-{[3,5-bis(trifluoromethyl)benzyl]-[5-(morpholin-4-yl)pyridin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-bis(trifluoromethyl)benzyl]-[5-(morpholin-4-yl)pyridin-2-yl]}amino-2-ethyl-6-trifluoromethyl-3,4-dihydro-2H-[1,5]naphthyridine-1-carboxylic acid 5-carboxypentyl ester;

(2R,4S)-4-{(3-cyano-5-trifluoromethylbenzyl)-[5-(morpholin-4-yl)pyridin-2-yl]}amino-2-ethyl-6-trifluoromethyl-3,4-dihydro-2H-[1,5]naphthyridine-1-carboxylic acid 4-carboxybutyl ester; or (2R,4S)-4-{(3-cyano-5-trifluoromethylbenzyl)-[5-(morpholin-4-yl)pyridin-2-yl]}amino-2-ethyl-6-trifluoromethyl-3,4-dihydro-2H-[1,5]naphthyridine-1-carboxylic acid 2-carboxy-2-methylpropyl ester; or a pharmaceutically acceptable salt thereof.

Additionally, the present invention encompasses the following compounds shown in (1) to (8).

(1) A compound of the formula (I), wherein $R^1$ is a hydrogen atom; an alkoxycarbonyl group optionally substituted by 1 to 5 substituents selected independently from cyano group, hydroxy group, carboxyl group, alkoxycarbonyl group, alkoxy group (said alkoxy group is optionally substituted by 1 to 3 substituents selected independently from hydroxy group, amino group, mono- or di-alkylamino group, halogen atom, carboxyl group, alkoxycarbonyl group, carboxyalkoxy group and alkoxycarbonylalkoxy group), alkylthio group, alkylsulfonyl group, alkenyl group, amino group, mono- or di-alkylamino group, tetrazolyl group, carbamoyl group, mono- or di-alkylcarbamoyl group (said mono- or di-alkylcarbamoyl group is optionally substituted by 1 to 3 substituents selected independently from carboxyl group and alkoxycarbonyl group), alkanoylamino group (said alkanoylamino group is optionally substituted by 1 to 3 substituents selected independently from carboxyl group, alkoxycarbonyl group, hydroxy group and halogen atom), halogen atom, cycloalkyl group (said cycloalkyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), phenyl group (said phenyl group is optionally substituted by 1 to 3 substituents selected independently from hydroxy group, amino group, mono- or di-alkylamino group, halogen atom, carboxyl group, alkoxycarbonyl group, carboxyalkyl group, alkoxycarbonylalkyl group, carboxyalkoxy group and alkoxycarbonylalkoxy group), morpholinyl group optionally substituted by oxo group, piperidinyl group (said piperidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group and carboxyalkoxy group, alkoxycarbonylalkoxy group), pyrrolidinyl group (said pyrrolidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), and pyrimidinyl group (said pyrimidinyl group is optionally substituted by 1 to 3 substituents selected independently from carboxyalkyl group, alkoxycarbonylalkyl group and carboxyalkoxy group, alkoxycarbonylalkoxy group); dihydrooxazolyl group optionally substituted by 1 to 2 substituents selected independently from carboxyl group, alkoxycarbonyl group, alkyl group, carboxyalkyl group, alkoxycarbonylalkyl group and hydroxyalkyl group; or a mono- or di-alkylcarbamoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group);

$R^2$ is an alkyl group;
$R^3$ is a hydrogen atom;
$R^4$ is an alkylene group;
wherein $R^5$ is a group of the formula:

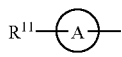

wherein Ring A is a saturated or unsaturated 5- to 8-membered heterocyclic group containing 1 to 4 heteroatoms selected independently from oxygen, sulfur and nitrogen atoms, and $R^{11}$ is a group selected from the following groups:
halogen atom,
hydroxy group;
oxo group;
cyano group;
carboxyl group;
sulfo group;
alkyl group optionally substituted by 1 to 3 substituents selected independently from halogen atom, cyano group, hydroxy group, carboxyl group, alkoxy group optionally substituted by hydroxy or alkoxy group, alkoxycarbonyl group, mono- or di-alkylcarbamoyl group, mono- or di-alkylamino group optionally substituted by alkoxy or carboxyl group, pyrrolidinyl group optionally substituted by carboxyl or alkoxycarbonyl group, piperidinyl group optionally substituted by carboxyl or alkoxycarbonyl group, piperazinyl group optionally substituted by alkyl group, morpholinyl group, alkanoyloxy group and alkylsulfonyl group;
alkenyl group optionally substituted by a group selected from cyano group, hydroxy group, carboxyl group, alkoxycarbonyl group, benzyloxycarbonyl group and tetrazolyl group;
alkoxy group optionally substituted by 1 to 3 substituents selected independently from halogen atom, cyano group, hydroxy group, carboxyl group, alkoxycarbonyl group, carbamoyl group, mono- or di-alkylcarbamoyl group optionally substituted by hydroxy group, alkoxy group (said alkoxy group is optionally substituted by hydroxy, carboxyl or alkoxy group), alkylthio group, alkylsulfonyl group, alkylsulfinyl group, mono- or di-alkylamino group optionally substituted by carboxyl or alkoxy group, morpholinyl group, pyrrolidinyl group (said pyrrolidinyl group is optionally substituted by carboxyl, alkoxy or oxo group), pyrimidinyl group optionally substituted by carboxyl or alkoxy group, optionally oxidized pyridyl group, dioxolanyl group optionally substituted by alkyl group and morpholinylcarbonyl group;
cycloalkyl group optionally substituted by carboxyl group or alkoxycarbonyl group;
alkoxycarbonyl group optionally substituted by phenyl group;
carbamoyl group;
mono- or di-alkylcarbamoyl group optionally substituted by a group selected from morpholinyl group, carboxyl group, hydroxy group and alkoxy group;
hydroxycarbamimidoyl group;
alkylthio group optionally substituted by a group selected from hydroxy group, carboxyl group and mono- or di-alkylcarbamoyl group;
alkylsulfonyl group optionally substituted by a group selected from hydroxy group, alkoxycarbonyl group and mono- or di-alkylcarbamoyl group;
amino group;
mono- or di-alkylamino group optionally substituted by a group selected from hydroxy group, carboxyl group, alkoxycarbonyl group, alkoxy group, mono- or di-alkylamino group and morpholinyl group;
alkanoylamino group optionally substituted by a group selected from hydroxy group, alkoxy group, carboxyl group and amino group;
mono- or di-alkylureido group optionally substituted by alkoxy group;
morpholinylcarbonylamino group;
morpholinyl group optionally substituted by a group selected from oxo group and carboxyl group;

piperazinyl group optionally substituted by a group selected from cyano group, alkyl group, hydroxyalkyl group, alkoxycarbonylalkyl group, carboxyalkyl group, alkanoyl group, alkoxyalkanoyl group, benzyloxycarbonyl group, mono- or di-alkylcarbamoyl group, mono- or di-alkylsulfamoyl group, alkylsulfonyl group, tetrazolyl group, and dihydrooxadiazolyl group optionally substituted by oxo group;

piperidinyl group optionally substituted by a group selected from carboxyl group, hydroxy group, alkyl group optionally substituted by hydroxy or carboxyl group, alkoxy group optionally substituted by phenyl group, alkoxycarbonyl group, oxo group, and alkanoyl group;

pyrrolidinyl group optionally substituted by a group selected from carboxyl group, alkoxycarbonyl group, oxo group, and mono- or di-alkylamino group;

pyrrolinyl group optionally substituted by oxo group;

hexahydrodiazepinyl group optionally substituted by alkanoyl group;

imidazolidinyl group optionally substituted by oxo group;

pyridyl group optionally substituted by carboxyl group, hydroxy group, alkanoyl group, alkyl group or hydroxyalkyl group (said pyridyl group is optionally further oxidized);

tetrazolyl group optionally substituted by a group selected from alkyl group and hydroxyalkyl group;

dihydrooxadiazolyl group optionally substituted by oxo group;

dihydroimidazolyl group;

dihydrooxazolyl group;

oxazolidinyl group optionally substituted by oxo group;

tetrahydropyridyl group optionally substituted by benzyl group;

pyrimidinyl group;

piperidinyloxy group optionally substituted by alkyl group or carboxyl group;

pyrrolidinyloxy group optionally substituted by a group selected from alkyl group, carboxyl group, alkoxycarbonyl group and alkanoyl group;

tetrahydropyranyloxy group;

tetrahydrofuranyloxy group;

optionally oxidized thianyloxy group;

morpholinylcarbonyl group;

piperazinylcarbonyl group optionally substituted by a group selected from alkanoyl group and alkyl group;

pyrrolidinylcarbonyl group optionally substituted by carboxyl group or alkoxycarbonyl group; and piperidinylcarbonyl group optionally substituted by carboxyl group or alkoxycarbonyl group;

$R^6$ and $R^7$ are independently a hydrogen atom, an alkyl group optionally substituted by halogen atom, an alkoxy group optionally substituted by halogen atom, a hydroxy group, a cyano group, or a mono- or d-alkylamino group; or $R^6$ and $R^7$ may combine at the ends to form an alkylenedioxy group;

$R^8$ is a hydrogen atom; and $R^{10}$ is s a phenyl or pyridyl group, which phenyl or pyridyl group is optionally substituted by 1 to 4 substituents selected from halogen atom, alkoxycarbonyl group, alkyl group optionally substituted by halogen atom, alkoxy group optionally substitute by halogen atom, hydroxy group, cyano group, amino group, mono- or di-alkylamino group and alkylthio group.

(2) The compound set forth in (1) above wherein Ring A is a pyrimidinyl group, a pyridyl group, a triazolyl group, a tetrazolyl group, an oxadiazolyl group, a dihydropyrimidinyl group, a pyrazinyl group, a thiazolyl group, an oxazolyl group, a dihydrooxazinyl group, a pyrazolyl group or a dihydropyrazinyl group.

(3) The compound set forth in (2) above, wherein Ring A is a pyrimidinyl group, a tetrazolyl group or a pyridyl group; and $R^{11}$ is a group selected from the groups:

alkyl group optionally substituted by 1 to 3 substituents selected independently from carboxyl group, hydroxyalkoxy group, mono- or di-alkylamino group optionally substituted by alkoxy group, amino group, mono- or di-alkylcarbamoyl group and morpholinyl group:

alkenyl group optionally substituted by hydroxy group, carboxyl group or cyano group;

alkoxy group optionally substituted by 1 to 3 substituents selected independently from hydroxy group, carboxyl group, carbamoyl group, alkoxycarbonyl group, mono- or di-alkylcarbamoyl group optionally substituted by hydroxy group, alkoxy group, hydroxyalkoxy group, carboxyalkoxy group, alkylsulfonyl group, alkylsulfinyl group, mono- or di-alkylamino group, morpholinyl group, oxopyrrolidinyl group, optionally oxidized pyridyl group and morpholinylcarbonyl group;

carbamoyl group;

alkylthio group optionally substituted by hydroxy group or mono- or di-alkylcarbamoyl group;

mono- or di-alkylamino group optionally substituted by hydroxy group, carboxyl group or alkoxy group;

alkanoylamino group optionally substituted by hydroxy group or alkoxy group;

mono- or di-alkylureido group optionally substituted by alkoxy group;

morpholinyl group;

piperazinyl group optionally substituted by a group selected from alkyl group, hydroxyalkyl group, alkoxycarbonylalkyl group, carboxyalkyl group, alkanoyl group and mono- or di-alkylcarbamoyl group;

piperidinyl group optionally substituted by a group selected from carboxyl group, alkoxycarbonyl group, hydroxy group, hydroxyalkyl group, carboxyalkyl group and oxo group;

pyrrolidinyl group optionally substituted by a group selected from carboxyl group and mono- or di-alkylamino group;

pyridyl group that is substituted by hydroxyalkyl group or oxidized;

tetrazolyl group optionally substituted by alkyl or hydroxyalkyl group;

oxodihydrooxadiazolyl group;

pyrimidinyl group;

pyrrolidinyloxy group optionally substituted by alkanoyl group; and optionally oxidized thianyloxy group;

$R^6$ is a hydrogen atom, an alkyl group optionally substituted by halogen atom, an alkoxy group, a cyano group, or a mono- or d-alkylamino group;

$R^{10}$ is s a phenyl group which is substituted by 1 to 3 substituents selected from halogen atom, alkyl group optionally substituted by halogen atom, alkoxy group and cyano group.

(4) The compound set forth in (3) above, wherein $R^1$ is an alkoxycarbonyl group optionally substituted by 1 to 5 substituents selected independently from hydroxy group, carboxyl group, alkoxycarbonyl group, alkoxy group (said alkoxy group is optionally substituted by 1 to 3 substituents selected independently from hydroxy group, halogen atom, carboxyl group and alkoxycarbonyl group), alkenyl group, halogen atom, cycloalkyl group (said cycloalkyl group is optionally substituted by 1 to 3 substituents selected independently from hydroxy group, halogen atom, carboxyl group, alkoxycarbonyl group, carboxyalkyl group and alkoxycarbonylalkyl group), phenyl group (said phenyl group is optionally substituted by 1 to 3 substituents selected independently from hydroxy group, halogen atom, carboxyl group, alkoxycarbonyl group, carboxyalkyl group and alkoxycarbonylalkyl group), piperidinyl group (said piperidinyl group is optionally substituted by 1 to 3 substituents selected independently from hydroxy group, halogen atom, carboxyl group, alkoxycarbonyl group, carboxyalkyl group and alkoxycarbonylalkyl group), and pyrrolidinyl group (said pyrrolidinyl group is optionally substituted by 1 to 3 substituents selected independently from hydroxy group, halogen atom, carboxyl group, alkoxycarbonyl group, carboxyalkyl group and alkoxycarbonylalkyl group); or a dihydroxazolyl group optionally substituted by 1 or 2 substituents selected independently from carboxyl group, alkoxycarbonyl group, carboxyalkyl group, alkoxycarbonylalkyl group and hydroxyalkyl group;
$R^{11}$ is a group selected from the groups:
  alkyl group optionally substituted by 1 to 3 substituents selected independently from carboxyl group, alkoxycarbonyl group and hydroxy group,
  carboxyalkenyl group;
  alkoxy group optionally substituted by 1 to 3 substituents selected independently from cyano group, hydroxy group, carboxyl group, alkoxycarbonyl group, carbamoyl group, mono- or di-alkylcarbamoyl group, mono- or di-alkylcarbamoyl group substituted by hydroxy group, alkoxy group, hydroxyalkoxy group, alkylsulfonyl group, alkylsulfinyl group, mono- or di-alkylamino group and oxopyrrolidinyl group;
  mono- or di-alkylamino group optionally substituted by carboxyl group;
  alkanoylamino group optionally substituted by hydroxy group or alkoxy group;
  morpholinyl group;
  piperazinyl group optionally substituted by a group selected from alkyl group, alkanoyl group and mono- or di-alkylcarbamoyl group;
  piperidinyl group optionally substituted by carboxyl group, alkoxycarbonyl group, hydroxy group, carboxyalkyl group or hydroxyalkyl group;
  pyrrolidinyl group optionally substituted by mono- or di-alkylamino group;
  pyridyl group that is substituted by hydroxyalkyl group or oxidized;
  tetrazolyl group optionally substituted by hydroxyalkyl group;
  pyrimidinyl group;
  pyrrolidinyloxy group optionally substituted by alkyl group or alkanoyl group; and
  optionally oxidized thianyloxy group; and
$R^{10}$ is s a phenyl group which is substituted by 1 to 3 substituents selected from alkyl group optionally substituted by halogen atom, alkoxy group and cyano group.

(5) The compound set forth in (4) above, wherein $R^1$ is an alkoxycarbonyl group optionally substituted by 1 or 5 substituents selected independently from carboxyl group, alkoxycarbonyl group, halogen atom, hydroxy group and cycloalkyl group;
$R^{11}$ is an alkyl group optionally substituted by carboxyl group; a carboxyalkenyl group; an alkoxy group optionally substituted by 1 to 3 substituents selected independently from cyano group, hydroxy group, carboxyl group, alkoxy group, alkylthio group and alkylsulfonyl group; an mono- or di-alkylamino group optionally substituted by carboxyl group; a hydroxyalkanoylamino group; a morpholinyl group; a piperazinyl group optionally substituted by alkyl group or alkanoyl group; or a piperidinyl group optionally substituted by carboxyl group or hydroxy group;
$R^6$ is an alkyl group optionally substituted by halogen atom, an alkoxy group or a mono- or d-alkylamino group; and
$R^7$ is s a hydrogen atom.

(6) The compound set forth in (5) above, wherein $R^1$ is an ethoxycarbonyl group, a hydroxyethoxycarbonyl group, a 2-fluoroethoxycarbonyl group, a 2,2-difluoroethoxycarbonyl group or a 2,2,2-trifluoroethoxycarbonyl group; $R^2$ is an ethyl group; $R^{10}$ is a phenyl group substituted by 1 to 2 substituents selected from cyano group and trifluoromethyl group; and $R^6$ is a methoxy group or a trifluoromethyl group.

(7) The compound of claim set forth in (5) above, wherein $R^1$ is a carboxy($C_{2-10}$alkoxy)carbonyl group or an alkoxycarbonyl($C_{2-10}$alkoxy)carbonyl group; $R^2$ is an ethyl group; $R^{10}$ is a phenyl group substituted by 1 to 2 substituents selected from cyano group and trifluoromethyl group; and $R^6$ is a methoxy group or a trifluoromethyl group.

(8) A compound selected from the following compounds or a pharmaceutically acceptable salt thereof.
(2R,4S)-4-{[3,5-Bis(trifluoromethyl)benzyl]-[5-(3-hydroxypropoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;
(2R,4S)-4-([3,5-Bis(trifluoromethyl)benzyl]-{5-[2-(2-hydroxyethoxy)ethoxy]pyrimidin-2-yl})amino-2-ethyl-6-trifluoromethyl-3,4-dihydro-2H-[1,5]naphthyridine-1-carboxylic acid 2-carboxy-2-methylpropyl ester;
(2R,4S)-4-{[3,5-Bis(trifluoromethyl)benzyl]-[5-(2,3-dihydroxypropoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;
(2R,4S)-4-{[3,5-Bis(trifluoromethyl)benzyl]-[5-(3-hydroxypropoxy)pyrimidin-2-yl]}amino-2-ethyl-6-trifluoromethyl-3,4-dihydro-2H-[1,5]naphthyridine-1-carboxylic acid 2-carboxyethyl ester;
(2R,4S)-4-([3,5-Bis(trifluoromethyl)benzyl]-{5-[2-(2-hydroxyethoxy)ethoxy]pyrimidin-2-yl})amino-2-ethyl-6-trifluoromethyl-3,4-dihydro-2H-[1,5]naphthyridine-1-carboxylic acid 2-carboxyethyl ester;
(2R,4S)-4-{[3,5-Bis(trifluoromethyl)benzyl]-[5-(2,3-dihydroxypropoxy)pyrimidin-2-yl]}amino-2-ethyl-6-trifluoromethyl-3,4-dihydro-2H-[1,5]naphthyridine-1-carboxylic acid 2-carboxyethyl ester;
(2R,4S)-4-{(3-Cyano-5-trifluoromethylbenzyl)-[5-(2-hydroxyethoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;
(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;
(2R,4S)-4-{[5-(3-Cyanopropoxy)pyrimidin-2-yl]-(3-Cyano-5-trifluoromethylbenzyl)}amino-2-ethyl-6-trifluoromethyl-3,4-dihydro-2H-[1,5]naphthyridine-1-carboxylic acid 2-carboxy-2-methylpropyl ester;
(2R,4S)-4-{(3-Cyano-5-trifluoromethylbenzyl)-[5-(2-hydroxyethoxy)pyrimidin-2-yl]}amino-2-ethyl-6-trifluoromethyl-3,4-dihydro-2H-[1,5]naphthyridine-1-carboxylic acid 2-carboxyethyl ester;
(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{[5-(3-Cyanopropoxy)pyrimidin-2-yl]-(3-Cyano-5-trifluoromethylbenzyl)}amino-2-ethyl-6-trifluoromethyl-3,4-dihydro-2H-[1,5]naphthyridine-1-carboxylic acid 2-carboxyethyl ester;

(2R,4S)-4-[(3-Cyano-5-trifluoromethylbenzyl)-(5-dimethylaminopyrimidin-2-yl)]amino-2-ethyl-6-trifluoromethyl-3,4-dihydro-2H-[1,5]naphthyridine-1-carboxylic acid 2-carboxyethyl ester;

(2R,4S)-4-([3,5-Bis(trifluoromethyl)benzyl]-{5-[(ethyl-methyl)amino]pyrimidin-2-yl})amino-2-ethyl-6-trifluoromethyl-3,4-dihydro-2H-[1,5]naphthyridine-1-carboxylic acid 2-carboxyethyl ester;

(2R,4S)-4-{[3,5-Bis(trifluoromethyl)benzyl]-(5-diethylaminopyrimidin-2-yl)}amino-2-ethyl-6-trifluoromethyl-3,4-dihydro-2H-[1,5]naphthyridine-1-carboxylic acid 2-carboxyethyl ester;

(2R,4S)-4-([3,5-Bis(trifluoromethyl)benzyl]-{5-[(ethyl-methyl)amino]pyrimidin-2-yl})amino-2-ethyl-6-trifluoromethyl-3,4-dihydro-2H-[1,5]naphthyridine-1-carboxylic acid 2-carboxy-2-methylpropyl ester; and (2R,4S)-4-{[3,5-Bis(trifluoromethyl)benzyl]-(5-diethylaminopyrimidin-2-yl)}amino-2-ethyl-6-trifluoromethyl-3,4-dihydro-2H-[1,5]naphthyridine-1-carboxylic acid 2-carboxy-2-methylpropyl ester.

The present compound (I) or a pharmaceutically acceptable salt thereof can be administered either orally or parenterally, and can be formulated into pharmaceutical preparations with a conventional pharmaceutically acceptable carriers used therefor.

The pharmaceutically acceptable salts of the compound (I) may include, for example, alkali metal salts such as lithium, sodium or potassium salt; alkali earth metal salts such as calcium or magnesium salt; salts with zinc or aluminum; salts with organic bases such as ammonium, choline, diethanolamine, lysine, ethylenediamine, t-butylamine, t-octylamine, tris(hydroxymethyl)aminomethane, N-methylglucosamie, triethanolamine or dehydroabiethylamine; salts with inorganic acids such as hydrochloric acid, hydrobromic acid, hydroiodic acid, sulfuric acid, nitric acid or phosphoric acid; salts with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid or toluenesulfonic acid; or salts derived form acidic amino acids such as aspartic acid or glutamic acid.

Additionally, the pharmaceutically acceptable salts of the compound (I) may include, for example, quaternary salts formed between a compound of the formula (I) and an alkyl halide or phenylalkyl halide.

Preferred pharmaceutical preparations for oral administration of the present compound (I) or a pharmaceutically acceptable salt thereof include solid formulations such as tablets, granules, capsules or powders; and liquid formulations such as solutions, suspensions or emulsions. Preferred pharmaceutical preparations for parenteral administration include injections or infusions formulated with injectable distilled-water, physiological saline or aqueous glucose solution; suppository; or inhalation preparation.

These pharmaceutical preparations comprise a compound (I) of the present invention or a pharmaceutically acceptable salt thereof and a pharmaceutically acceptable carrier which is usually used for oral or parenteral administration. The pharmaceutically acceptable carriers for oral administration include, for example, a binder (syrup, gum acacia, gelatin, sorbit, tragacanth, polyvinylpyrrolidone, and the like), an excipient (lactose, sugar, cornstarch, potassium phosphate, sorbit, glycine, and the like), a lubricant (magnesium stearate, talc, polyethylene glycol, silica, and the like), a disintegrant (potato starch, and the like), and a wetting agent (anhydrous sodium lauryl sulfate, and the like). The pharmaceutically acceptable carriers for parenteral administration include, for example, injectable distilled-water, physiological saline and aqueous glucose solution.

The dose of a compound (I) of the present invention or a pharmaceutically acceptable salt thereof varies depending on the administration route, age, body weight, disease, and condition/severity, of the patient. It however can usually be in the range of about 0.001-1,000 mg/kg/day, preferably in the range of about 0.01-100 mg/kg/day.

The compounds of the present invention have an inhibitory activity against CETP and show effects of increasing HDL cholesterol and lowering LDL cholesterol. Accordingly, they are useful in the prophylaxis or treatment of a subject (particularly, mammal including human) suffering from arteriosclerosis such as atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular diseases, angina, ischemia, cardiac ischemia, stroke, myocardial infarction, reperfusion injury, restenosis after angioplasty, hypertension, cerebral infarction, cerebral stroke, diabetes, vascular complication of diabetes, thrombotic diseases, obesity, endotoxemia, metabolic syndrome, cerebrovascular disease, coronary artery disease, ventricular dysfunction, cardiac arrhythmia, pulmonary vascular disease, reno-vascular disease, renal disease, splanchnic vascular disease, vascular hemostatic disease, fatty liver disease, steatohepatitis, inflammatory disease, autoimmune disorders and other systemic disease indications, immune function modulation, pulmonary disease, anti-oxidant disease, sexual dysfunction, cognitive dysfunction, schistosomiasis, cancer, regression of xanthoma, Alzheimer's disease, or the like.

In addition, the compounds of the present invention may be used in combination with other drugs useful for treatment of these diseases. For example, a compound of the present invention may be used in combination with an inhibitor of cholesterol synthesis such as HMG-CoA reductase inhibitor; an inhibitor of cholesterol absorption such as anion exchange resin; a triglyceride lowering agent such as fibrate, niacin and fish oil; an antihypertensive such as ACE inhibitor, angiotensin receptor blocker, calcium antagonist and beta blocker; an antiobesity agent such as central anorectic, lipase inhibitor and CB1 antagonist; an antidiabetic agent such as insulin sensitizer, D2 agonist, sulfonylurea, biguanide, α-glucosidase inhibitor, SGLT inhibitor and DPPIV inhibitor; or other cholesterol reducer such as ACAT inhibitor.

The compounds of the present invention have an improved bioavailability and useful as a CETP inhibitor. Above all, compounds having a carboxyl group at the terminal position of respective substituents $R^1$-$R^{11}$, especially those having a carboxyl group at the terminal position of $R^1$ and/or $R^5$, or $R^1$ and/or $R^{11}$ are preferred.

The compound (I) of the present invention can be prepared by the following methods.

Process 1

The compound (I) of the present invention can be prepared by condensing a compound of the formula (II):

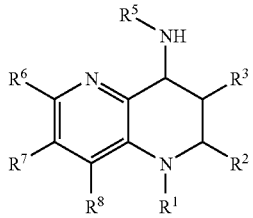

(II)

wherein the symbols have the same meaning as defined above with a compound of the formula (III):

$$R^{10}-R^{14}-Z^1 \quad (III)$$

wherein $Z^1$ is a leaving group and the other symbols have the same meaning as defined above.

The condensation can be carried out in the presence of a base in a suitable solvent.

The leaving group includes a halogen atom including chlorine atom, bromine atom, iodine atom, and a substituted sulfonyloxy group including methanesulfonyloxy group, toluenesulfonyloxy group, and trifluoro-methanesulfonyloxy group.

A conventional base can be used as the base, and for example, alkaline metal hydride including sodium hydride, potassium hydride; alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal bicarbonate including sodium bicarbonate, potassium bicarbonate; amines including triethylamine, diisopropylethylamine, methylpiperidine, dimethylaniline, 1,8-diazabicyclo[5.4.0]undecene, 1,4-diazabicyclo[2.2.2]octane, 1,5-diazabicyclo[4.3.0]nonene; pyridines including pyridine, dimethylaminopyridine, and the like can be preferably used.

Any solvent which dose not disturb the reaction can be preferably used, and such a solvent includes, for example, hydrocarbons including pentane, hexane; aromatic hydrocarbons including benzene, toluene, nitrobenzene; halogenated hydrocarbons including dichloromethane, chloroform; ethers including diethylether, tetrahydrofuran; amides including dimethylformamide, N-methylpyrrolidone, 1,3-dimethyl-imidazolidin-2-one; sulfoxides including dimethylsulfoxide; alcohols including methanol, ethanol; esters including ethyl acetate, butyl acetate; ketones including acetone, methyl ethyl ketone; nitriles including acetonitrile; water, or a mixed solvent thereof.

The reaction is carried out from under cooling to under heating, preferably from −78° C. to 200° C., more preferably from −30° C. to 100° C.

Process 2

Among the compound of the formula (I-A), a compound of the formula (I-b):

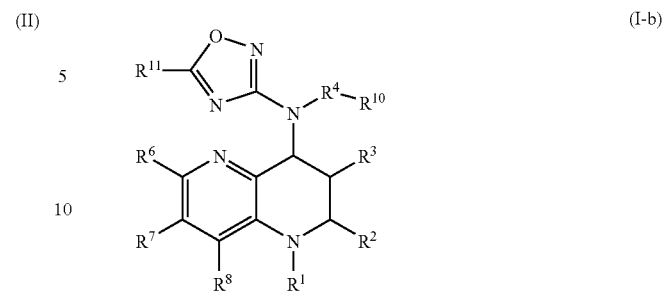

(I-b)

wherein the symbols have the same meaning as defined above can be prepared by (a) cyanating a compound of the formula (II-A):

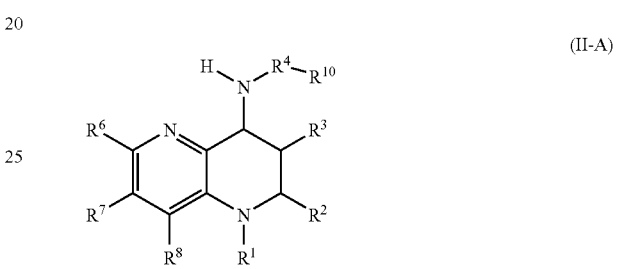

(II-A)

wherein the symbols have the same meaning as defined above to provide a compound of the formula (II-B):

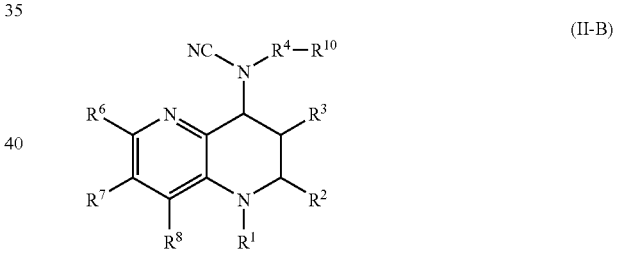

(II-B)

wherein the symbols have the same meaning as defined above, (b) reacting the compound (II-B) with hydroxylamine or a salt thereof to provide a compound of the formula (II-C):

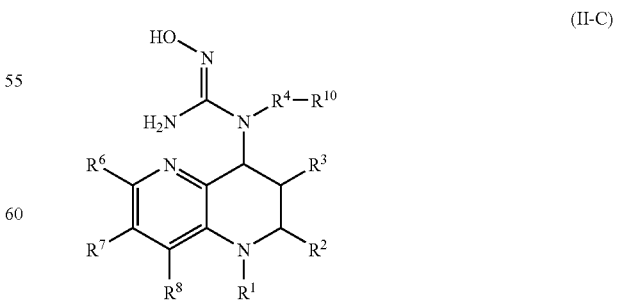

(II-C)

wherein the symbols have the same meaning as defined above, (c) alkanoylating the compound (II-C) to provide a compound of the formula (II-D):

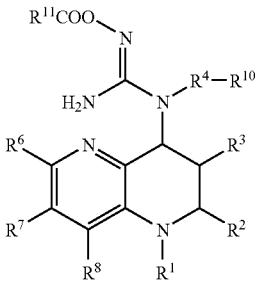

(II-D)

wherein the symbols have the same meaning as defined above, and further
(d) cyclizing the compound (II-D) with a base.

The cyanation in the process (a) can be carried out by reacting a halogenated cyanogen in the presence of a base in a suitable solvent.

Cyanogen bromide is preferable as the halogenated cyanogen.

A conventional base can be preferably used as the base, and alkaline metal carbonate including potassium carbonate, or alkaline metal bicarbonate including sodium bicarbonate can be preferably used.

Any solvent which dose not disturb the reaction can be used and the solvent referred to in the PROCESS 1 can be preferably used.

The reaction with hydroxylamine in the process (b) can be carried out in the presence of a base in a suitable solvent.

Tertiary alkylamines including triethylamine, diisopropylethylamine, and the like can be preferably used as the base.

Any solvent which dose not disturb the reaction can be used and the solvent referred to in the PROCESS 1 can be preferably used.

The alkanoylation in the process (c) can be carried out with an alkanoyl halide in the presence of a base in a suitable solvent.

A conventional base can be used as the base, and amines including triethylamine or diisopropylethylamine, or pyridines including pyridine, 4-dimethylaminopyridine can be preferably used.

Any solvent which dose not disturb the reaction can be used and the solvent referred to in the PROCESS 1 can be preferably used.

In the cyclization in the process (d), a conventional base can be used as the base, and amines including triethylamine or diisopropylethylamine; pyridines including pyridine, 4-dimethylaminopyridine; alkaline metal carbonate including potassium carbonate; or alkaline metal alkoxide including sodium methoxide can be preferably used.

Any solvent which dose not disturb the reaction can be used and the solvent referred to in the PROCESS 1 can be preferably used.

Additionally, the cyclization following the alkanoylating can also be carried out in situ.

The reaction is carried out from under cooling to under heating, preferably from −50° C. to 100° C., more preferably from 0° C. to 50° C.

Process 3

Among the compound of the formula (I-A), a compound of the formula (I-c):

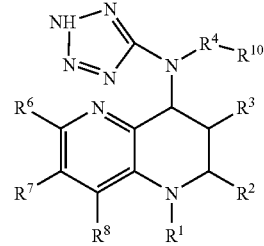

(I-c)

wherein the symbols have the same meaning as defined above can be prepared by reacting a compound of the formula (II-B):

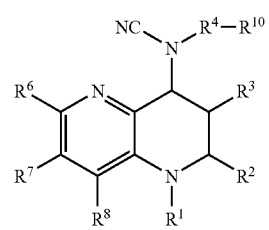

(II-B)

wherein the symbols have the same meaning as defined above with sodium azide.

The reaction can be carried out in the presence of ammonium chloride in a suitable solvent.

Any solvent which dose not disturb the reaction can be used and the solvent referred to in the PROCESS 1 can be preferably used.

The reaction is carried out from under cooling to under heating, preferably from −50° C. to 150° C., more preferably from 20° C. to 100° C.

Additionally, a substituent(s) of compound (I) of the present invention can be converted into different one(s) within the scope of the compound (I) according to the following methods as appropriate.

In the following each process, a conventional base can be used as a base, and unless otherwise specified, the base referred to in the PROCESS 1 can be preferably used.

Additionally, in the following each process, a conventional acid can be used as an acid, and unless otherwise specified, a mineral acid such as hydrochloric acid, nitric acid, sulfuric acid, or an organic acid represented by sulfonic acids (e.g., methanesulfonic acid, p-toluenesulfonic acid, trifluoromethanesulfonic acid) or carboxylic acids (e.g., acetic acid, trifluoroacetic acid) can be preferably used.

Further additionally, in the following each process, any solvent which dose not disturb the reaction can be used, and as such, the solvent referred to in the PROCESS 1 can be preferably used.

The leaving group includes a halogen atom such as chlorine atom, bromine atom, iodine atom, and a substituted sulfonyloxy group such as methanesulfonyloxy group, trifluoromethanesulfonyloxy group, and toluenesulfonyloxy group.

In addition, in the following each process, "a saturated or unsaturated monocyclic or bicyclic heterocyclic group having one to four heteroatoms independently selected from oxygen atom, sulfur atom and nitrogen atom" in $R^5$ is simply referred to as "a heterocyclic group".

(1) Among the compound (I-A), the compound wherein Ring A is a tetrazolyl group and $R^{11}$ is an optionally substituted alkyl group can be prepared by alkylating a compound wherein Ring A is a tetrazolyl group and $R^{11}$ is a hydrogen atom.

The alkylation of the compound can be carried out by reacting it with a compound of the formula:

$$R^{114}-Z^2$$

wherein $R^{114}$ is an optionally substituted alkyl group and $Z^2$ is a leaving group in a suitable solvent in the presence or absence of a base, or by reacting with a compound of the formula:

$$R^{114}-OH$$

wherein the symbols have the same meaning as defined above in a suitable solvent in the presence of a phosphine and an azodicarboxylic ester.

The reaction proceeds more preferably when a catalytic amount of an alkaline metal iodide (for example, potassium iodide, and the like) is added.

Both phosphines and azodicarboxylic esters which usually employed in Mitsunobu reaction can be preferably used. Phosphines include, for example, triphenylphosphine, tributylphosphine, and the like, and azodicarboxylic esters include diethyl azodicarboxylate, diisopropyl azodiformate, and the like.

(2) Among the compound (I-A), the compound wherein Ring A is 2-oxodihydropyrimidinyl group and $R^{11}$ is an optionally substituted alkyl group can be prepared by alkylating a compound wherein Ring A is 2-hydroxypyrimidinyl group and $R^{11}$ is a hydrogen atom with a compound of the formula:

$$R^{114}-Z^2$$

wherein the symbols have the same meaning as defined above.

The reaction can be carried out in the same manner as (1).

(3) The compound wherein $R^5$ is a heterocyclic group substituted by an optionally substituted amino group or a group of the formula:

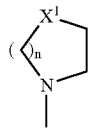

wherein the symbols have the same meaning as defined above can be prepared by coupling a compound wherein $R^5$ is a heterocyclic group substituted by a halogen atom or an optionally substituted alkylsulfonyloxy group with a corresponding amine or a compound of the formula:

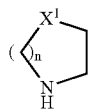

wherein the symbols have the same meaning as defined above.

The coupling reaction can be carried out in the presence of a palladium catalyst, and in the presence or absence of a base in a suitable solvent.

As the palladium catalyst, a conventional palladium catalyst including palladium acetate, tetrakis(triphenylphosphine)palladium, tris-(dibenzylideneacetone)dipalladium, dichlorobis(triphenylphosphine)-palladium, dichlorobis(tri-o-tolylphosphine)palladium or bis-(triphenylphosphine)palladium acetate, and the like can be used.

As the base, alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal bicarbonate including sodium bicarbonate, potassium bicarbonate; alkaline metal phosphate including potassium phosphate; amines including triethylamine, diisopropylethylamine, methylpiperidine, dicyclohexylmethylamine; pyridines including pyridine, 4-dimethylaminopyridine, and the like can be preferably used.

Additionally, phosphines may be added in the present reaction. As the phosphines, triphenylphosphine, tributylphosphine, tri-tert-butylphosphonium tetrafluoroborate, 1,3-bis(diphenylphosphino)propane, 2,2'-bis(diphenylphosphino)-1,1'-binaphthyl, 1,1'-bis(diphenylphosphino)-ferrocene, 2-(di-tert-butylphosphino)biphenyl, 2-dicyclohexylphosphino-2'-(N,N-dimethylamino)biphenyl, 2-(dicyclohexylphosphino)biphenyl, and the like can be preferably used.

(4) The compound wherein $R^5$ is a heterocyclic group substituted by an optionally substituted amino group or a group of the formula:

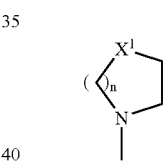

wherein the symbols have the same meaning as defined above can also be prepared by reacting a compound wherein $R^5$ is a heterocyclic group substituted by a halogen atom or an optionally substituted alkylsulfonyl group with a corresponding amine or a compound of the formula:

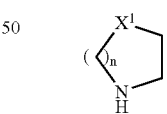

wherein the symbols have the same meaning as defined above.

The reaction can be carried out by optionally adding a copper catalyst in the presence or absence of a base in a suitable solvent.

Copper iodide, copper bromide, copper chloride, copper acetate, copper trifluoromethanesulfonate, and the like can be preferably used as the copper catalyst.

The same base as referred to in (3) can be preferably used.

Additionally, the reaction proceeds more preferably when N,N'-dimethylethylenediamine, 1,10-phenanthroline, ethylene glycol, phenylphenol, or the like is added.

(5) The compound wherein $R^5$ is a heterocyclic group substituted by an optionally substituted amino group can be prepared by coupling a compound wherein $R^5$ is a heterocyclic group substituted by a halogen atom or an optionally substituted alkylsulfonyloxy group with a compound of the formula:

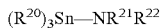

$(R^{20})_3Sn—NR^{21}R^{22}$ wherein $R^{20}$ is an alkyl group and $NR^{21}R^{22}$ is an optionally substituted amino group.

The coupling reaction can be carried out in the presence of a palladium catalyst in the presence or absence of a base in a suitable solvent.

The same palladium catalyst, base, and phosphines as referred to in (3) can be preferably used.

(6) The compound wherein $R^5$ is a heterocyclic group substituted by a cyano group can be prepared by cyanating a compound wherein $R^5$ is a heterocyclic group substituted by a halogen atom or an optionally substituted alkylsulfonyloxy group.

The cyanation can be carried out by reacting a starting compound with a metal cyanide including sodium cyanide, potassium cyanide, or zinc cyanide in the presence of a palladium catalyst in a suitable solvent.

The same palladium catalyst as that described in (3) can be preferably used.

(7) The compound wherein $R^5$ is a heterocyclic group substituted by an optionally substituted alkoxycarbonyl group can be prepared by reacting a compound wherein $R^5$ is a heterocyclic group substituted by a halogen atom or an optionally substituted alkylsulfonyloxy group with a corresponding alkylalcohol under carbon monoxide using a palladium catalyst in the presence of a base in a suitable solvent.

The same palladium catalyst and base as those described in (3) can be preferably used.

Additionally, the reaction can be more preferably carried out by adding a ligand, and phosphines referred to in (3) can be preferably used as the ligand.

(8) The compound wherein $R^5$ is a heterocyclic group substituted by an optionally substituted alkenyl group can be prepared by coupling a compound wherein $R^5$ is a heterocyclic group substituted by a halogen atom or an optionally substituted alkylsulfonyloxy group with a corresponding alkene.

The coupling reaction can be carried out in the presence of a palladium catalyst in the presence or absence of a base in a suitable solvent.

The same palladium catalyst as that described in (3) can be preferably used.

The same base as referred to in (3) can be preferably used and silver carbonate can also be used.

Additionally, the reaction can be more preferably carried out by adding a ligand, and phosphines referred to in (3) can be preferably used as the ligand.

(9) The compound wherein $R^5$ is a heterocyclic group substituted by an optionally substituted alkoxy group can be prepared by alkoxylating a compound wherein $R^5$ is a heterocyclic group substituted by a halogen atom or an optionally substituted alkylsulfonyloxy group.

The alkoxylation can be carried out by optionally adding a copper catalyst to react a starting compound with a corresponding alcohol in a suitable solvent or neat in the presence of a base.

The same base as previously described in (3), in particular, cesium carbonate can be preferably used.

The copper catalyst as described in (4) can be preferably used.

Additionally, the reaction proceeds more preferably when 1,10-phenanthroline, 2-aminopyridine, or the like is added.

(10) The compound wherein $R^5$ is a heterocyclic group substituted by an optionally substituted alkoxy group can be prepared by reacting a compound wherein $R^5$ is a heterocyclic group substituted by an alkylsulfonyl group with a corresponding alkaline metal alkoxide in a suitable solvent. The corresponding alkaline metal alkoxide can be obtained by treating a corresponding alkylalcohol with alkaline metal hydride or alkaline metal.

(11) The compound wherein $R^5$ is a heterocyclic group substituted by an optionally substituted alkylthio group can be prepared by reacting a compound wherein $R^5$ is a heterocyclic group substituted by a halogen atom or an optionally substituted alkylsulfonyloxy group with a corresponding alkylthiol.

The reaction can be carried out in the same manner as previously described in (9) and facilitated by adding 1,10-phenanthroline or ethylene glycol.

(12) The compound wherein $R^5$ is a heterocyclic group substituted by an optionally substituted heterocyclic group can be prepared by coupling a compound wherein $R^5$ is a heterocyclic group substituted by a halogen atom or an optionally substituted alkylsulfonyloxy group with a corresponding heterocyclic boronic acid or a corresponding heterocyclic boronic ester.

The coupling can be carried out in the presence of a palladium catalyst, and in the presence or absence of a base in a suitable solvent.

The reaction can be carried out in the same manner as (3).

(13) The compound wherein $R^5$ is a heterocyclic group substituted by an optionally substituted heterocyclic group can be prepared by coupling a compound wherein $R^5$ is a heterocyclic group substituted by a halogen atom or an optionally substituted alkylsulfonyloxy group with a corresponding heterocyclic alkyl tin compound.

The reaction can be carried out in the same manner as (5).

(14) The compound wherein $R^5$ is a heterocyclic group substituted by an alkoxycarbonylalkylsulfonyl group can be prepared by reacting a compound wherein Rs is a heterocyclic group substituted by a halogen atom or an optionally substituted alkylsulfonyloxy group with an alkoxycarbonylalkylsulfinic acid alkaline metal salt.

The alkoxycarbonylalkylsulfinic acid alkaline metal salt can be prepared according to the method described, for example, in Baskin et al., Tetrahedron Lett., 43, 8479 (2002).

Additionally, the present reaction can be carried out in the presence of a copper catalyst in a suitable solvent according to the method described in the said literature.

The same copper catalyst as described in (4) can be used, and in particular, copper iodide can be preferably used.

(15) The compound having a group of the formula:

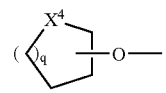

wherein the symbols have the same meaning as defined above as a substituent on $R^5$ can be prepared by condensing a compound having a hydroxy group as a substituent on $R^5$ with a compound of the formula:

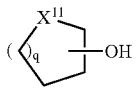

wherein $X^{11}$ is O, SO, $SO_2$ or $NR^P$ ($R^P$ is a protecting group) and q is an integer from 1 to 4, and if needed, removing a protecting group for amino group.

As a protecting group, a conventional protecting group including benzyloxycarbonyl group, tert-butoxycarbonyl group, and the like can be used.

The reaction can be carried out in a suitable solvent in the presence of phosphines and azodicarboxylic esters. The reaction can be carried out in the same manner as (1).

The removal of a protecting group can be carried out in a conventional manner including catalytic reduction, acid-treatment, and the like, depending on the type of a protecting group.

(16) The compound having an aminoalkyl group as a substituent on $R^5$ can be prepared by catalytically reducing a compound having a cyano group or a cyanoalkyl group as a substituent on $R^5$.

The catalytic reduction can be carried out by using a catalyst under hydrogen in a suitable solvent according to a conventional manner. The catalyst includes a palladium catalyst such as palladium-carbon, a nickel catalyst such as Raney nickel, a platinum catalyst such as platinum-carbon, and the like.

(17) The compound having an optionally substituted mono- or di-alkylsulfamoylaminoalkyl group as a substituent on $R^5$ can be prepared by reacting a compound having an aminoalkyl group as a substituent on $R^5$ with a corresponding halogenated mono- or di-alkylsulfamoyl.

The reaction can be carried out in a suitable solvent in the presence of a base.

(18) The compound having an optionally substituted mono-alkylcarbamoylaminoalkyl group as a substituent on $R^5$ can be prepared by reacting a compound having an aminoalkyl group as a substituent on $R^5$ with a corresponding alkyl isocyanate in a suitable solvent.

(19) The compound having a group of the formula:

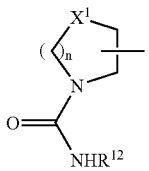

wherein $R^{12}$ is an alkyl group and the other symbols have the same meaning as defined above as a substituent on $R^5$ can be prepared by reacting a compound having a group of the formula:

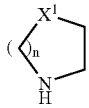

wherein the symbols have the same meaning as defined above as a substituent on $R^5$ with a corresponding alkyl isocyanate ($R^{12}NCO$). The reaction can be carried out in the same manner as (18).

(20) The compound having an optionally substituted mono- or di-alkylcarbamoylamino group as a substituent on $R^5$ can be prepared by condensing a compound having an amino group as a substituent on $R^5$ with an optionally substituted mono- or di-alkylamine using a carbonylating agent in a suitable solvent in the presence or absence of a base.

A conventional carbonylating agent such as carbonyldiimidazole, phosgene, triphosgene, and the like can be used.

(21) The compound having a morpholinylcarbonylamino group as a substituent on $R^5$ can be prepared by condensing a compound having an amino group as a substituent on $R^5$ with morpholine using a carbonylating agent in a suitable solvent. The reaction can be carried out in the same manner as (20).

(22) The compound having a group of the formula:

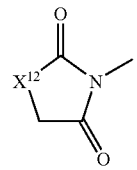

wherein $X^{12}$ is O or NH as a substituent on $R^5$ can be prepared by treating a compound having a group of the formula:

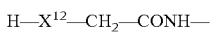

$$H-X^{12}-CH_2-CONH-$$

wherein the symbols have the same meaning as defined above as a substituent on $R^5$ with a carbonylating agent in a suitable solvent.

The reaction can be carried out in the same manner as (20).

(23) The compound having an optionally substituted carbamoyl group as a substituent on $R^5$ can be prepared by condensing a compound having a carboxyl group as a substituent on $R^5$ with a desirable amine.

The condensation can be carried out using a condensing agent in a suitable solvent. A conventional condensing agent such as dicyclohexylcarbodiimide, 1-ethyl-3-(3-dimethylaminopropyl)carbodiimide, carbonyldiimidazole, and the like can be preferably used.

Additionally, the condensation can be more preferably carried out by adding an activating agent including 1-hydroxybenzotriazole, 1-hydroxysuccinimide, and the like.

(24) The compound having a group of the formula:

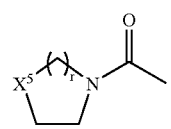

wherein the symbols have the same meaning as defined above as a substituent on $R^5$ can be prepared by condensing a compound having a carboxyl group as a substituent on $R^5$ with a compound of the formula:

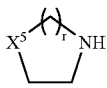

wherein the symbols have the same meaning as defined above.

The reaction can be carried out in the same manner as (23).

(25) The compound containing a tetrazolyl group as a substituent on $R^5$ can be prepared by reacting the compound containing a cyano group as a substituent on $R^5$ with an alkaline metal azide in the presence of an acid in a suitable solvent.

The alkaline metal azide includes sodium azide, lithium azide, and the like.

An ammonium salt of a halogenated hydrogen including ammonium chloride is preferable as the acid.

(26) The compound having an optionally substituted alkyl tetrazolyl group as a substituent on $R^5$ can be prepared by alkylating a compound having a tetrazolyl group as a substituent on $R^5$.

The alkylation can be carried out in the same manner as (1).

(27) The compound having an optionally substituted amino group or a group of the formula:

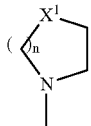

wherein the symbols have the same meaning as defined above as a substituent on $R^5$ can be prepared by reacting a compound having a halogen atom or an optionally substituted alkylsulfonyloxy group as a substituent on $R^5$ with a corresponding amine or a compound of the formula:

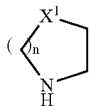

wherein the symbols have the same meaning as defined above.

The reaction can be preferably carried out in the presence or absence of a base in a suitable solvent.

(28) The compound having an optionally substituted alkylamino group or a group of the formula:

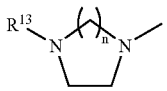

wherein $R^{13}$ is an alkyl group optionally substituted by a hydroxy group, an alkoxycarbonyl group, a morpholinyl group or a phenyl group, and n has the same meaning as defined above as a substituent on $R^5$ can be prepared by reacting a compound having an amino group or a group of the formula:

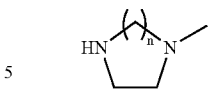

wherein the symbols have the same meaning as defined above as a substituent on $R^5$ with a corresponding alkyl halide or a corresponding sulfonic alkyl ester.

The sulfonic alkyl ester including methanesulfonic ester, toluenesulfonic ester, trifluoromethanesulfonic ester, and the like can be preferably used.

The reaction can be preferably carried out in the presence or absence of a base in a suitable solvent.

(29) The compound having a group of the formula:

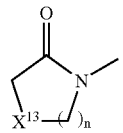

wherein $X^{13}$ is O or NH, and the other symbols have the same meaning as defined above as a substituent on $R^5$ can be prepared by ring-closure of a compound having a group of the formula:

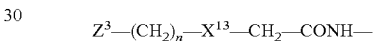

$$Z^3-(CH_2)_n-X^{13}-CH_2-CONH-$$

wherein $Z^3$ is a leaving group and the other symbols have the same meaning as defined above as a substituent on $R^5$.

The reaction can be preferably carried out in the presence or absence of a base in a suitable solvent.

(30) The compound containing a carboxyl group as a substituent on $R^5$ can be prepared by hydrolyzing a compound having an alkoxycarbonyl group as a substituent on $R^5$.

The hydrolysis can be carried out by treating a starting compound with a base or an acid in a suitable solvent according to a conventional manner. An alkaline metal hydroxide can be preferably used as the base.

(31) The compound containing a carboxyl group as a substituent on $R^5$ can be prepared by hydrolyzing a compound containing a cyano group as a substituent on $R^5$.

The hydrolysis can be carried out by treating a starting compound with an acid in a suitable solvent.

(32) The compound containing a carbamoyl group as a substituent on $R^5$ can be prepared by hydrolyzing a compound containing a cyano group as a substituent on $R^5$.

The hydrolysis can be carried out by treating a starting compound with an acid in a suitable solvent.

(33) The compound having a carboxyalkyl group as a substituent on $R^5$ can also be prepared by catalytically reducing a compound having a carboxyalkenyl group, a benzyloxycarbonylalkenyl group or a benzyloxycarbonylalkyl group as a substituent on $R^5$.

The catalytic reduction can be carried out in the same manner as (16).

(34) The compound having a hydroxy group as a substituent on $R^5$ can be prepared by hydrolyzing a compound having an alkanoyloxy group as a substituent on $R^5$.

The hydrolysis can be carried out in the same manner as (30).

(35) The compound containing sulfin (SO) or sulfoxide ($SO_2$) in a substituent on $R^5$ can be prepared by oxidizing a compound having S in a substituent on $R^5$ (for example, a compound having a thiomorpholinyl group or an alkylthio group as a substituent on $R^5$).

The oxidation can be carried out by treating a starting compound with an oxidizing agent in a suitable solvent.

Peroxides such as hydrogen peroxide, m-chloroperbenzoic acid, acetyl hydroperoxide, and the like can be preferably used as the oxidizing agent.

(36) The compound containing N-oxide in a substituent on $R^5$ can be prepared by oxidizing a compound having N in a substituent on $R^5$ (for example, a compound having a pyridyl group as a substituent on $R^5$).

The oxidation can be carried out in the same manner as (35).

(37) The compound having 1,2-dihydroxyalkyl group as a substituent on $R^5$ can be prepared by treating a compound having an alkyl group substituted by mono- or di-alkyldioxolanyl group as a substituent on $R^5$ with an acid in a suitable solvent.

A strongly acidic resin can also be preferably used as the acid, in addition to those previously described.

(38) The compound having an alkyl group substituted by a hydroxy group and an optionally substituted alkoxy group as substituents on $R^5$ can be prepared by reacting a compound having an oxiranylalkyl group as a substituent on $R^5$ with an alkaline metal salt of corresponding alcohol in a suitable solvent.

The alkaline metal salt of alcohol includes a lithium salt, a sodium salt, a potassium salt, and the like.

(39) The compound having an alkyl group substituted by a hydroxy group and an amino group, or an alkyl group substituted by a hydroxy group and an optionally substituted mono- or di-alkylamino group as substituents on $R^5$ can be prepared by reacting a compound having an oxiranylalkyl group as a substituent on $R^5$ with ammonia or a corresponding mono- or di-alkylamine in a suitable solvent.

(40) The compound having a hydroxycarbamimidoyl group as a substituent on $R^5$ can be prepared by reacting a compound having a cyano group as a substituent on $R^5$ with hydroxylamine or a salt thereof in a suitable solvent.

The reaction can be carried out in the presence of a base in a suitable solvent.

(41) The compound having an oxodihydrooxadiazolyl group as a substituent on $R^5$ can be prepared by reacting a compound having a hydroxycarbamimidoyl group as a substituent on $R^5$ with a carbonylating agent in a suitable solvent in the presence or absence of a base.

The same carbonylating agent as that described in (20) can be used.

(42) The compound having a sulfo group as a substituent on $R^5$ can be prepared by hydrolyzing a compound having an alkoxy-carbonylalkylsulfonyl group as a substituent on $R^5$.

The hydrolysis can be carried out in the same manner as (30).

(43) The compound having a sulfamoyl group as a substituent on $R^5$ can be prepared by condensing a compound having a sulfo group as a substituent on $R^5$ with a desirable amine.

The condensation can be carried out by treating a compound having a sulfo group as a substituent on $R^5$ with a halogenating agent in a suitable solvent, followed by reacting the resulting compound with a desirable amine in the presence or absence of a base.

A conventional halogenating agent including thionyl halide, phosphorus oxyhalide, or the like can be used.

(44) The compound having a hydroxyalkyl group as a substituent on $R^5$ can be prepared by reducing a compound having a carboxyalkyl group as a substituent on $R^5$, or by converting the carboxyl group into an acid anhydride or an ester and reducing the resulting compound.

A process for conversion into an acid anhydride can be carried out by reacting a starting compound with a halogenated alkyl formate in a suitable solvent in the presence of a base.

A process for conversion into an ester can be carried out by reacting a starting compound with an alcohol in the presence of a condensing agent in a suitable solvent. This process can be carried out in the same manner as (23) except that a desirable alcohol is used in place of amine.

The reduction can be carried out by treating the resulting compound with a reducing agent in a suitable solvent.

Boron hydrides (sodium borohydride, diborane, borane-dimethylsulfide complex, and the like), aluminum hydrides (lithium aluminum hydride, diisobutylaluminum hydride, and the like) can be preferably used as the reducing agent.

(45) The compound having a hydroxyalkyl group as a substituent on $R^5$ can be prepared by reducing a compound having an alkoxycarbonylalkyl group as a substituent on $R^5$.

The reduction can be carried out in the same manner as (44).

(46) The compound wherein $R^{10}$ is an aromatic group substituted by a cyano group, optionally having one to three heteroatoms independently selected from oxygen atom, sulfur atom and nitrogen atom (hereinafter referred to as "an aromatic group"), can be prepared by cyanating a compound wherein $R^{10}$ is an aromatic group substituted by a halogen atom.

The cyanation can be carried out in the same manner as (6).

(47) The compound wherein $R^1$ is a hydrogen atom can be prepared by acid-treatment or reduction of a compound wherein $R^1$ is a tertbutoxycarbonyl group or a benzyloxycarbonyl group.

The acid-treatment can be carried out in the same manner as (37) and the reduction can be carried out in the same manner as (33).

(48) The compound wherein $R^1$ is an optionally substituted alkoxycarbonyl group, or an optionally substituted carbamoyl group can be prepared by reacting a compound wherein $R^1$ is a hydrogen atom with a carbonylating agent along with a desirable alcohol or a desirable amine in a suitable solvent.

The reaction can be carried out in the same manner as (20).

(49) The compound having an iodine atom as a substituent on $R^5$ can be prepared by iodizing the compound having a bromine atom as a substituent on $R^5$.

The iodization can be carried out by reacting with a corresponding alkaline metal iodide in a suitable solvent while adding a copper catalyst, if desired.

The same copper catalyst as that described in (4) can be used.

Additionally, the reaction proceeds more preferably when N,N'-dimethylethylenediamine, 1,10-phenanthroline, ethylene glycol, or the like is added.

(50) The compound having an amino group as a substituent on $R^5$ can be prepared by reacting a compound having a carboxyl group as a substituent on $R^5$ under Curtius rearrangement reaction condition.

Curtius rearrangement reaction can be carried out using a conventional azidating agent (e.g., diphenylphosphorylazide) in a suitable solvent in the presence or absence of a base.

The reaction may also be carried out by adding an alcohol to provide a compound having an optionally substituted alkoxycarbonylamino group as a substituent on $R^5$, followed by removing the alkoxycarbonyl group.

The removal of the alkoxycarbonyl group can be carried out in a conventional manner such as acid-treatment or reduction depending on the type of alkoxycarbonyl group to be removed. The acid-treatment can be carried out in the same manner as (37) and the reduction can be carried out in the same manner as (33).

(51) The compound having a hydroxy group as a substituent on $R^5$ can be prepared by catalytically reducing a compound having a benzyloxy group as a substituent on $R^5$. The reduction can be carried out in the same manner as (33).

(52) The compound having an oxo group as a substituent on $R^5$ can be prepared by oxidizing a compound having a hydroxy group as a substituent on $R^5$.

The oxidation can be carried out by using an oxidizing agent in a suitable solvent.

A conventional oxidizing agent can be used as the oxidizing agent, such as chromate-pyridine complex, pyridinium chlorochromate, pyridinium dichromate, Dess-Martin reagent (1,1,1-tris(acetoxy)-1,1-dihydro-1,2-benziodoxol-3-(1H)-one), dimethylsulfoxide, and the like.

(53) The compound containing an optionally substituted alkoxy group as a substituent on $R^5$ can be prepared by alkylating a compound containing a hydroxy group as a substituent on $R^5$.

The alkylation can be carried out by using a corresponding compound in the same manner as (1).

(54) The compound having an optionally substituted alkanoylamino group as a substituent on $R^5$ can be obtained by condensing the compound having an amino group as a substituent on $R^5$ with a corresponding carboxylic acid or a reactive derivative thereof.

The condensation with the corresponding carboxylic acid can be preferably carried out in a suitable solvent in the presence of a condensing agent. The reaction can be carried out in the same manner as (23).

Additionally, the condensation with the reactive derivative of the corresponding carboxylic acid can be carried out in a suitable solvent or neat in the presence or absence of a base.

The reactive derivative includes an acid halide, an acid anhydride, an activated ester, an activated amide, and the like.

(55) The compound having a group of the formula:

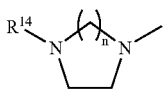

wherein $R^{14}$ is an alkanoyl group optionally substituted by a hydroxy group or an alkoxy group, and n has the same meaning as defined above as a substituent on $R^5$ can be prepared by condensing a compound of a group of the formula:

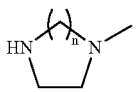

wherein the symbols have the same meaning as defined above as a substituent on $R^5$ with a corresponding carboxylic acid or a reactive derivative thereof.

The reaction can be carried out in the same manner as (54).

(56) The compound having a maleimide group as a substituent on $R^5$ can be prepared by reacting a compound having an amino group as a substituent on $R^5$ with a maleic anhydride. The reaction can be carried out in a suitable solvent.

(57) The compound having an alkyl group substituted by a pyridyl group and a hydroxy group as substituents on $R^5$ can be prepared by reacting a compound having, as a substituent on $R^5$, an alkyl group substituted by a pyridyl group of which nitrogen atom is oxidized with a trifluoroacetic anhydride. The reaction can be carried out in a suitable solvent.

(58) The compound having a halogen atom as a substituent on $R^5$ can be prepared by treating a compound having a hydroxy group as a substituent on $R^5$ with a halogenating agent.

As the halogenating agent, a conventional halogenating agent including thionyl chloride, phosphorus oxychloride, as well as carbon tetrahalide (e.g., carbon tetrachloride, carbon tetrabromide, and the like) and phosphines (e.g., triphenylphosphine, tritolylphosphine, triethylphosphine, and the like) can be preferably used.

(59) The compound having a cyanoalkyl group as a substituent on $R^5$ can be prepared by reducing a compound having a cyanoalkenyl group as a substituent on $R^5$.

The reduction can be carried out by treating a starting compound with a reducing agent or by catalytically reducing the same in a suitable solvent.

Any reducing agent can be used subject that it reduces only a double bond without affecting a cyano group. For example, sodium bis(2-methoxyethoxy)aluminum hydride in the presence of a copper bromide can be preferably used.

The catalytic reduction can be carried out in the same manner as (33).

(60) The compound having a hydroxyalkyl group as a substituent on $R^5$ can be prepared by reducing a compound having a formyl group as a substituent on $R^5$.

The reduction can be carried out by treating a starting compound with a reducing agent in a suitable solvent.

The reaction can be carried out in the same manner as the process for reducing in (45).

(61) The compound wherein $R^6$ is a hydroxy group can be prepared by demethylating a compound wherein $R^6$ is a methoxy group.

The demethylation can be carried out by treating a starting compound with a demethylating agent in a suitable solvent.

As the demethylating agent, a conventional agent including trimethylsilyl iodide, hydrogen bromide/acetic acid, boron tribromide, concentrated sulfuric acid, and the like can be used.

(62) The compound wherein $R^6$ is an optionally substituted alkoxy group can be prepared by alkylating a compound wherein $R^6$ is a hydroxy group.

The alkylation can be carried out in the same manner as (1).

(63) The compound wherein $R^6$ is an optionally substituted alkylsulfonyloxy group can be prepared by alkylsulfonylating a compound wherein $R^6$ is a hydroxy group.

The alkylsulfonylation can be carried out by reacting a corresponding alkylsulfonyl halide or a corresponding alkylsulfonic anhydride in a suitable solvent in the presence or absence of a base.

(64) The compound wherein $R^6$ is a cyano group can be prepared by cyanating a compound wherein $R^6$ is an optionally substituted alkylsulfonyloxy group.

(65) The compound wherein $R^6$ is an aminoalkyl group can be prepared by reducing a compound wherein $R^6$ is a cyano group.

The reduction can be carried out in the same manner as (16). (66) The compound wherein $R^6$ is an alkyl group can be prepared by alkylating a compound wherein $R^6$ is an optionally substituted alkylsulfonyloxy group.

The alkylation can be carried out by reacting alkyl aluminums in the presence of a palladium catalyst, a silver catalyst and a copper catalyst in a suitable solvent.

Tetrakis(triphenylphosphine)palladium as the palladium catalyst, silver carbonate as the silver catalyst, copper (I) chloride as the copper catalyst can be preferably used.

(67) The compound having an imidazolinyl group or an oxazolinyl group as a substituent on $R^5$ can be prepared by (i) reacting a compound containing a cyano group as a substituent on $R^5$ with a desirable alcohol in the presence of an acid in a suitable solvent or neat to provide a compound containing an alkoxycarbonimidoyl group as a substituent on $R^5$, and (ii) reacting the compound containing an alkoxycarbonimidoyl group as a substituent on $R^5$ with 2-aminoethanol or ethylene diamine in a suitable solvent or neat.

(68) The compound having a carboxyl group as a substituent on $R^1$ can be prepared by (i) oxidizing a compound containing a hydroxyalkyl group as a substituent on $R^1$ in the same manner as (52) to provide a compound containing an oxo group as a substituent on $R^1$, and (ii) oxidizing the compound containing an oxo group as a substituent on $R^1$.

The oxidization for the second step can be carried out by using an oxidizing agent in a suitable solvent. Sodium chlorite, Silver(I) oxide, Sodium periodate and the like can be preferably used as the oxidizing agent.

(69) The compound having a carboxyl group as a substituent on $R^1$ can be directly prepared by oxidizing a compound containing a hydroxyalkyl group as a substituent on $R^1$.

The oxidization can be carried out by using Jones reagent, potassium permanganate, and the like as the oxidizing agent.

(70) The compound wherein $R^1$ is hydrogen atom can be prepared by treating a compound wherein $R^1$ is ethoxycarbonyl group with a silyl halides or a base. Trimethylsilyl iodide can be preferably used as the silyl halides. Sodium hydroxide can be preferably used as the base.

(71) Among the compound (I-A), the compound wherein $R^{11}$ is a hydroxyl group can be prepared by (i) reacting a compound wherein $R^{11}$ is a halogen atom with diboron or borane to provide a compound wherein $R^{11}$ is a boronic esters, and (ii) reacting the compound wherein $R^{11}$ is a boronic esters with peroxides.

Hydrogen peroxide solution, m-chloroperbenzoic acid or OXONE™ (Manufactured by DuPont) can be preferably used as the peroxides.

In each process for preparing a compound of the formula (I) described above, when protection of a functional group contained in any compound is needed, the protection can be carried out in a conventional manner as appropriate. General statement related to protecting groups and their use is provided by Greene, Protective Groups in Organic Synthesis, John Wiley and Sons, New York, 1991.

When an amino group is protected by a benzyloxycarbonyl group, the protecting group can be removed by catalytic reduction under hydrogen in a suitable solvent.

When a hydroxy group is protected by a benzyl group, the protecting group can also be removed by catalytic reduction in a similar manner as above.

When an amino group is protected by a t-butoxycarbonyl group, the protecting group can be removed by treatment with an acid (e.g., hydrochloric acid, trifluoroacetic acid, toluenesulfonic acid, and the like) in a suitable solvent.

When a hydroxy group is protected by a tetrahydropyranyl group, the protecting group can also be removed by treatment with an acid in a similar manner as above.

The reactions (1) to (71) for conversion of $R^1$, $R^5$, $R^6$ or $R^{11}$ can also be applied for conversion in the same manner of an other substituent of the present compound (I) as appropriate.

The starting compound (II) is a novel compound, and can be prepared by condensing a compound of the formula (V):

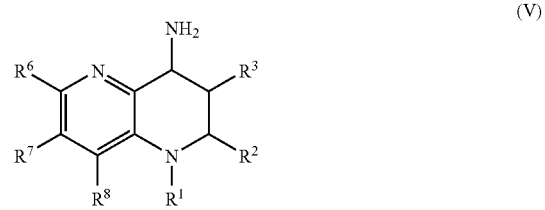

(V)

wherein the symbols have the same meaning as defined above with a compound of the formula (IV):

$R^5\text{—}Z^4$ (IV)

wherein $Z^4$ is a leaving group and $R^5$ has the same meaning as defined above.

The leaving group includes a halogen atom including chlorine atom, bromine atom, iodine atom, and a substituted sulfonyloxy group including methanesulfonyloxy group, trifluoromethanesulfonyloxy group, and toluenesulfonyloxy group.

The reaction can be carried out in a suitable solvent (for example, 1,4-dioxane, dimethylformamide, 1,3-dimethylimidazolidinone, and the like) in the presence or absence of a base (for example, diisopropylethylamine, and the like) from room temperature to under heating.

The reaction can also be carried out by adding a palladium catalyst (for example, tris(dibenzylidenacetone)dipalladium) and a phosphine [for example, triphenylphosphine, tributylphosphine, or 2-(di-tert-butylphosphino)biphenyl] at room temperature in the presence of a base (for example, sodium tert-butoxide), if desired.

The compound (V) is a novel compound and can be prepared according to the following scheme

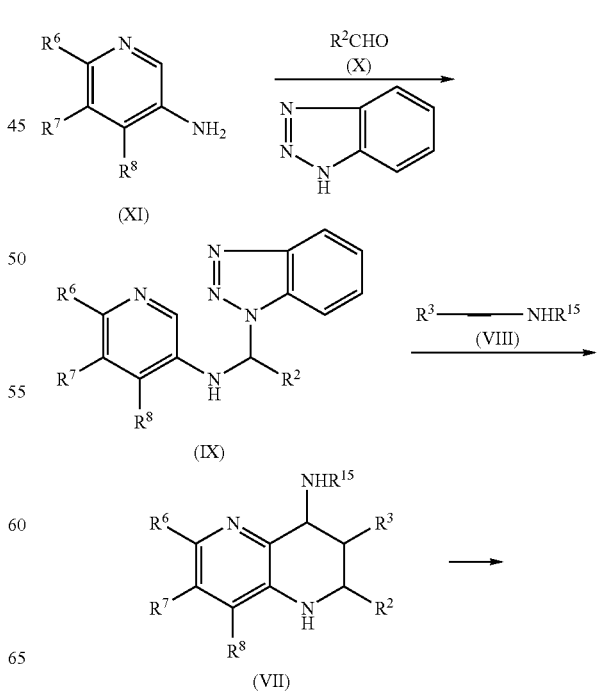

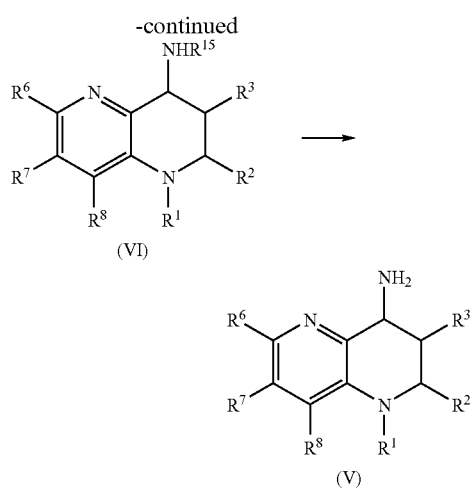

(VI)

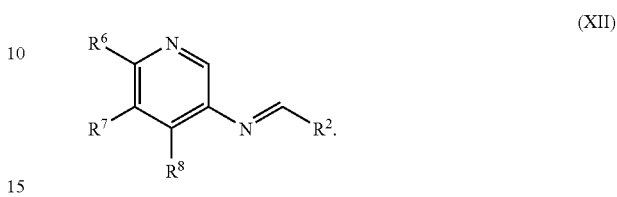

(V)

wherein R[15] is a protecting group for amino group or an asymmetric group and the other symbols have the same meaning as defined as above.

A conventional protecting group including a benzyloxycarbonyl group can be used as the protecting group for amino group. Additionally, an optically-active compound (V) can be prepared by substituting an asymmetric group (for example, an optically-active α-substituted benzyloxycarbonyl group having a chiral center at the benzyl position, such as α-methylbenzyloxycarbonyl group) for a protecting group for amino group, resolving diastereomers in the process for preparation of compound (VI) or compound (VII), and removing the asymmetric group.

A compound of the formula (IX) can be prepared by reacting benzotriazole, a compound of the formula (XI) and an aldehyde of the formula (X) in a suitable solvent (for example, toluene) at room temperature.

A compound of the formula (VII) can be prepared by reacting a compound of the formula (IX) with a compound of the formula (VIII) in the presence of an acidic catalyst (for example, an organic acid including p-toluenesulfonic acid, acetic acid, methanesulfonic acid, or Lewis acid including boron trifluoride-diethylether complex, titanium tetrachloride, aluminum chloride) in a suitable solvent (for example, toluene, methylene chloride, tetrahydrofuran, and the like) under heating or at room temperature (for example, 0° C. to 150° C., preferably 25° C. to 120° C.).

A compound of the formula (VI) can be prepared by alkanoylation, alkoxycarbonylation, alkylation, and the like of a compound of the formula (VII) as appropriate.

A compound of the formula (V) can be prepared by removing a protecting group for amino group or an asymmetric group of a compound of the formula (VI). The removal can be carried out in a conventional manner including acid-treatment, base-treatment, reduction, and the like, depending on the type of the group. When a benzyloxycarbonyl group or an α-substituted benzyloxycarbonyl group is used, they can be removed by catalytic reduction in a suitable solvent (for example, ethanol, methanol, tetrahydrofuran, acetic acid, and the like) under hydrogen. The removal of a protecting group for amino group or an asymmetric group of a compound of the formula (VII) can be carried out in the same manner as the removal of the groups of a compound of the formula (VI).

When an asymmetric group such as α-substituted benzyloxycarbonyl group is substituted for a protecting group for amino group, resolution of a diastereomer can be carried out in a conventional manner such as recrystallization or column chromatography.

A compound of the formula (VII) can also be prepared by reacting a compound of the formula (VIII) with a compound of the formula (XII):

(XII)

This reaction can be carried out in the same manner as the reaction of a compound of the formula (VIII) with a compound of the formula (IX).

Additionally, respective substituents R[1], R[5], R[6], R[7] and R[8] can be converted into a desirable substituent in accordance with any one of processes from (1) to (71).

The compound of the formula (II-A) can be prepared by condensing a compound of the formula (V) with a compound of the formula (III):

$$R^{10}-R^4-Z^1 \quad (III)$$

wherein the symbols have the same meaning as defined above.

The condensation can be carried out in the same manner as that described in WO00/17165 or PROCESS 1 above.

Many of starting materials and reagents for preparation of the aforementioned compounds are either commercially available or disclosed in literatures, or can be readily prepared by a method that is disclosed in literatures or used generally in the organic synthesis.

As used herein, "3,4-dihydro-2H-naphthyridine" represents the same structure as "1,2,3,4-tetrahydronaphthyridine".

Experiment

The inhibitory activity of the compounds of the present invention against CETP was tested in this experiment.

Preparation of Acceptor Microemulsion

A solution of 1-Palmitoyl-2-oleoyl-sn-glycero-3-phosphocholine (3.5 mg), cholesteryl oleate (3 mg) and triolein (0.7 mg) in chloroform was mixed and lipid was air-dried under nitrogen gas to remove solvent. Dioxane (0.25 ml) was then added and the mixture was stirred for dissolution. The resultant lipid solution (0.2 ml) was slowly injected under the surface of Tris-saline-EDTA(TSE) buffer solution [10 mM Tris/HCl (pH 7.4), 0.15 M NaCl, 2 mM EDTA] (10 ml) with Hamilton syringe, while sonicating in ice-bath. After 1-hour-sonication in ice-bath, the solution was stored at 4° C.

Preparation of Donor Microemulsion

A solution of egg PC (phosphatidylcholine) (0.33 mg) and BODIPY-CE (0.62 mg) in chloroform was mixed. After removing solvent by air-drying lipid under nitrogen gas, TSE buffer solution (3 ml) was added and the solution was sonicated in ice-bath. This solution was filtered to sterilize through 0.22 μm filter and stored at 4° C.

Inhibitory Activity against CETP in vitro

A test solution was prepared using dimethyl sulfoxide as a solvent. Plasma from a healthy volunteer was diluted to 0.64% with TSE buffer, and to the resultant plasma solution (187 μl) was added a test solution (3 μl) or the solvent alone followed by incubation at 37° C. for 24 hours. After addition of TSE buffer solution (10 µl) containing 5% donor microemulsion and 5% acceptor microemulsion, the mixture was incubated at 37° C. for 3 hours. Before and after the incubation, the fluorescence intensity was measured at Ex.550 nm/Em.600 nm. CETP activity was defined as the difference between the measurements obtained before incubation and after incubation. The decreasing rate of the difference in the sample was defined as the inhibition rate of CETP activity. $IC_{50}$ for each sample was calculated from the inhibition rate of CETP activity.

Results

| Example No. | $IC_{50}$ (nM) |
|---|---|
| 22 | 0.39 |
| 116 | 0.11 |
| 269 | 1.9 |
| 337 | 0.4 |
| 356 | 0.98 |
| 383 | 4.6 |
| 409 | 0.83 |

EXAMPLES

The present invention is illustrated in more detail by Examples, but the present invention should not be construed to be limited thereto.

In Examples, the compounds having a structure of the formula:

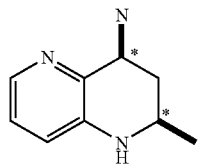

indicate that the Configuration thereof is (2R*,4S*). Besides, Me means a methyl group.

Example 1

(1) A solution of 5-amino-2-methoxypyridine (10 g) in toluene (20 ml) is added dropwise to a suspension of benzotriazole (9.6 g) in toluene (150 ml). Then, a solution of propionaldehyde (6.35 ml) in toluene (20 ml) is added thereto dropwise at 30° C. or below, and the mixture is stirred at room temperature overnight. The suspension is filtered and the resulting crystals are washed with ether to give (1-benzotriazol-1-yl-propyl)-(6-methoxypyridin-3-yl)amine (19.7 g). mp.:109.3-110.3° C.

(2) (1-Benzotriazol-1-yl-propyl)-(6-methoxypyridin-3-yl) amine (15 g) and N-vinyl-carbamic acid benzyl ester (9.4 g) are dissolved in toluene (200 ml), then thereto is added p-toluenesulfonic acid monohydrate(100 mg), and the mixture is stirred at 80° C. for 4 hours under nitrogen flow. After allowing to cooled to room temperature, the reaction solution is added to a mixture of a saturated aqueous sodium hydrogen carbonate solution and ethyl acetate. The organic layer is washed with a saturated brine, dried over sodium sulfate, and concentrated under reduced pressure. The resulting residue is purified by column chromatography (silica gel; hexane:ethyl acetate=8:1→4:1) to give (2R*, 4S*)-(2-ethyl-6-methoxy-1,2,3,4-tetrahydro-[1,5] naphthyridin-4-yl) carbamic acid benzyl ester (14.31 g). MS (m/z): 342 [M+H]$^+$ (3) (2R*,4S*)-(2-Ethyl-6-methoxy-1,2,3,4-tetrahydro-[1,5] naphthyridin-4-yl) carbamic acid benzyl ester (5.1 g) and pyridine (18 ml) are dissolved in methylene chloride (150 ml), then thereto is added ethyl chloroformate (14.3 ml) dropwise under ice-cooling, and the mixture is stirred at the same temperature for 30 minutes. An aqueous citric acid solution is added to the reaction solution. The organic layer is washed with a saturated brine, dried over sodium sulfate, and concentrated under reduced pressure. The resulting residue is purified by column chromatography (silica gel; hexane:ethyl acetate=4:1→2:1) to give (2R*,4S*)-4-benzyloxycarbonylamino-2-ethyl-6-methoxy-3,4-dihydro-2H-[1,5]naphthyridine-1-carboxylic acid ethyl ester (5.58 g). MS (m/z): 414 [M+H]$^+$ (4) (2R*,4S*)-4-Benzyloxycarbonylamino-2-ethyl-6-methoxy-3,4-dihydro-2H-[1,5]naphthyridine-1-carboxylic acid ethyl ester (5.5 g) and ammonium formate (2.09 g) are dissolved in methanol (50 ml), thereto is added 10% palladium/carbon (550 mg) under nitrogen flow, and the mixture is stirred at 40° C. for 30 minutes. The catalyst is removed by filtration and then the filtrate is concentrated under reduce pressure. A saturated aqueous sodium hydrogen carbonate solution and methylene chloride are added to the residue. The organic layer is washed with a saturated brine, dried over sodium sulfate, and concentrated under reduced pressure. The resulting residue is purified by column chromatography (silica gel; chloroform:methanol=90:1→20:1) to give (2R*,4S*)-4-amino-2-ethyl-6-methoxy-3,4-dihydro-2H-[1,5]naphthyridine-1-caboxylic acid ethyl ester (3.88 g). MS (m/z): 280 [M+H]$^+$ (5) (2R*,4S*)-4-Amino-2-ethyl-6-methoxy-3,4-dihydro-2H-[1,5]naphthyridine-1-carboxylic acid ethyl ester (2 g) and 5-bromo-2-chloropyrimidine (3.46 g) are dissolved in N,N-dimethylformamide (20 ml), and the mixture is heated to 150° C. and stirred for 5 hours. After cooling to room temperature, a saturated aqueous sodium hydrogen carbonate solution and ethyl acetate are added to the reaction solution. The organic layer is washed with a saturated brine, dried over magnesium sulfate, and concentrated under reduced pressure. The resulting residue is purified by column chromatography (silica gel; hexane:ethyl acetate=19:1→7:3) to give (2R*,4S*)-4-(5-bromopyrimidin-2-yl)amino-2-ethyl-6-methoxy-3,4-dihydro-2H-[1,5] naphthyridine-1-carboxylic acid ethyl ester (1.08 g). MS (m/z): 436/438 [M+H]$^+$ (6) (2R*,4S*)-4-(5-Bromopyrimidin-2-yl)amino-2-ethyl-6-methoxy-3,4-dihydro-2H-[1,5]naphthyridine-1-carboxylic acid ethyl ester (150 mg) is dissolved in N,N-dimethylformamide (2 ml), then thereto is added sodium hydride (17 mg, 62.7%) at room temperature, and the mixture is stirred for 10 minutes. After adding 3,5-bis(trifluoromethyl)benzyl bromide (158 mg), the mixture is stirred at room temperature for 10 minutes. Water and ethyl acetate are added to the reaction mixture. The organic layer is washed with a saturated brine, dried over magnesium sulfate, and concentrated under reduce pressure. The resulting residue is purified by column chromatography (silica gel; hexane:ethyl acetate=49:1→3:1) to give (2R*,4S*)-4-{[3, 5-bis(trifluoromethyl)benzyl]-(5-bromopyrimidin-2-yl)

}amino-2-ethyl-6-methoxy-3,4-dihydro-2H-[1,5]naphthyridine-1-carboxylic acid ethyl ester (190 mg). MS (m/z): 662/664 [M+H]$^+$

Example 2

(1) (S)-1-Phenylethylalchol (16.1 g) and pyridine (10.7 ml) are dissolved in chloroform (100 ml), and thereto is added a solution (100 ml) of p-nitrophenyl chloroformate (26.6 g) in chloroform. The reaction solution is stirred at room temperature for 1 hour. The reaction solution is concentrated under reduced pressure, and the resulting residue is purified by column chromatography (silica gel; hexane:ethyl acetate=85:15→70:30) to give p-nitrophenyl (S)-1-phenylethyl carbonate (35.6 g).

(2) (2 R*,4S*)-4-Amino-2-ethyl-6-methoxy-3,4-dihydro-2H-[1,5]naphthyridine-1-carboxylic acid ethyl ester (34.3 g), p-nitrophenyl (S)-1-phenylethyl carbonate (35.3 g) and triethylamine (17.1 ml) are dissolved in acetonitrile (250 ml) and the mixture is heated under reflux for 3 hours. The reaction solution is partitioned by adding ethyl acetate and a saturated aqueous sodium hydrogen carbonate solution. The organic layer is washed with a saturated brine, dried over magnesium sulfate, and concentrated under reduced pressure. The resulting residue is purified by column chromatography (silica gel; chloroform:hexane:ethyl acetate=10:10:1) to give (2R*,4S*)-2-ethyl-6-methoxy-4-[(S)-1-phenylethoxycarbonylamino]-3,4-dihydro-2H-[1,5]naphthyridine-1-carboxylic acid ethyl ester (44.0 g). MS (m/z): 428 [M+H]$^+$ (3) (2R*,4S*)-2-Ethyl-6-methoxy-4-[(S)-1-phenylethoxycarbonylamino]-3,4-dihydro-2H-[1,5]naphthyridine-1-carboxylic acid ethyl ester (44.0 g) is recrystallized from hexane (100 ml) to give (2R,4S)-2-ethyl-6-methoxy-4-[(S)-1-phenylethoxycarbonylamino]-3,4-dihydro-2H-[1,5]naphthyridine-1-carboxylic acid ethyl ester (13.83 g). MS (m/z): 428 [M+H]$^+$ (4) Ten % palladium/carbon (2.0 g) is added to a solution (85 ml) of (2R,4S)-2-ethyl-6-methoxy-4-[(S)-1-phenylethoxycarbonylamino]-3,4-dihydro-2H-[1,5]naphthyridine-1-carboxylic acid ethyl ester (8.49 g) in ethanol and stirred under hydrogen for 4 hours. Palladium/carbon is removed by filtration, and the filtrate is concentrated under reduced pressure to give (2R,4S)-4-amino-2-ethyl-6-methoxy-3,4-dihydro-2H-[1,5]naphthyridine-1-carboxylic acid ethyl ester (5.56 g). MS (m/z): 280 [M+H]$^+$ (5) (2R,4S)-4-Amino-2-ethyl-6-methoxy-3,4-dihydro-2H-[1,5]naphthyridine-1-carboxylic acid ethyl ester (5.49 g) and 5-bromo-2-chloropyrimidin (9.5 g) are dissolved in 1,4-dioxane (100 ml), then thereto is added N,N-diisopropylethylamine (8.55 ml), and the mixture is heated under reflux for 5 hours. The reaction solution is concentrated under reduced pressure, and the residue is purified by column chromatography (silica gel; hexane:ethyl acetate=95:5→80:20) to give (2R,4S)-2-ethyl-6-methoxy-4-(5-bromopyrimidin-2-yl)amino-3,4-dihydro-2H-[1,5]naphthyridine-1-carboxylic acid ethyl ester (8.29 g). MS (m/z): 436/438 [M+H]$^+$ (6) (2R,4S)-2-Ethyl-6-methoxy-4-(5-bromopyrimidin-2-yl)amino-3,4-dihydro-2H-[1,5]naphthyridine-1-carboxylic acid ethyl ester (8.20 g) is dissolved in N,N-dimethylformamide (75 ml), then thereto is added sodium hydride (62.7%, 942 mg) under ice-cooling, and the mixture is stirred for 30 minutes. After adding 3,5-bis(trifluoromethyl)benzyl bromide (8.7 g), the mixture is stirred for 30 minutes. Water and ethyl acetate are added to the reaction solution. The organic layer is washed with a saturated brine, dried over magnesium sulfate, and concentrated under reduced pressure. The resulting residue is purified by column chromatography (silica gel; hexane:ethyl acetate=95:5→80:20) to give (2R,4S)-4-{[3,5-bis(trifluoromethyl)benzyl]-(5-bromopyrimidin-2-yl)}amino-2-ethyl-6-methoxy-3,4-dihydro-2H-[1,5]naphthyridine-1-carboxylic acid ethyl ester (8.01 g). MS (m/z): 662/664 [M+H]$^+$

Example 3

(1) (2S,4R)-(2-Ethyl-6-methoxy-1,2,3,4-tetrahydro-[1,5]naphthyridin-4-yl)carbamic acid (S)-1-phenylethyl ester (840 mg) and pyridine (0.956 ml) are dissolved in methylene chloride (5 ml). After adding dropwise a solution (5 ml) of ethyl chloroformate (1.13 ml) in methylene chloride under ice-cooling, the mixture is stirred at room temperature for one hour. The reaction solution is washed with 1N aqueous sodium hydroxide solution, 1N hydrochloric acid and a saturated brine, dried over magnesium sulfate, and concentrated under reduced pressure. The resulting residue is purified by column chromatography (silica gel; hexane: ethyl acetate=90:10→60:40) to give (2S,4R)-2-ethyl-6-methoxy-4-[(S)-1-phenylethoxycarbonylamino]-3,4-dihydro-2H-[1,5]naphthyridine-1-carboxylic acid ethyl ester (1.00 g). MS (m/z): 428 [M+H]$^+$ (2) Ten % palladium/carbon (100 mg) is added to a solution (10 ml) of (2S,4R)-2-ethyl-6-methoxy-4-[(S)-1-phenylethoxycarbonylamino]-3,4-dihydro-2H-[1,5]naphthyridine-1-carboxylic acid ethyl ester (1.00 g) in ethanol, and the mixture is stirred for 3 hours under hydrogen. Palladium/carbon is removed by filtration, and the filtrate is concentrated under reduced pressure to give (2S,4R)-4-amino-2-ethyl-6-methoxy-3,4-dihydro-2H-[1,5]naphthyridine-1-carboxylic acid ethyl ester (619 mg). MS (m/z): 280 [M+H]$^+$ (3) (2S,4R)-4-Amino-2-ethyl-6-methoxy-3,4-dihydro-2H-[1,5]naphthyridine-1-carboxylic acid ethyl ester (610 mg) and 5-bromo-2-chloropyrimidine (1.06 g) are dissolved in 1,4-dioxane (5 ml), then thereto is added N,N-diisopropylethylamine (0.951 ml), and the mixture is heated under reflux overnight. The reaction solution is concentrated under reduced pressure, and the residue is purified by column chromatography (silica gel; hexane:ethyl acetate=95:5→80:20) to give (2S,4R)-2-ethyl-6-methoxy-4-(5-bromopyrimidin-2-yl)amino-3,4-dihydro-2H-[1,5]naphthyridine-1-carboxylic acid ethyl ester (853 mg). MS (m/z): 436/438 [M+H]$^+$.

(4) (2S,4R)-2-Ethyl-6-methoxy-4-(5-bromopyrimidin-2-yl)amino-3,4-dihydro-2H-[1,5]naphthyridine-1-carboxylic acid ethyl ester (735 mg) is dissolved in N,N-dimethylformamide (5 ml), sodium hydride (62.7%, 84 mg) is added thereto under ice-cooling, and the mixture is stirred for 30 minutes. After adding 3,5-bis(trifluoromethyl)benzyl bromide (0.463 ml), the mixture is stirred at room temperature for 30 minutes. Water and ethyl acetate are added to the reaction solution. The organic layer is washed with a saturated brine, dried over magnesium sulfate, and concentrated under reduced pressure. The resulting residue is purified by column chromatography (silica gel; hexane: ethyl acetate=95:5→75:25) to give (2 S,4R)-4-{[3,5-bis(trifluoromethyl)benzyl]-(5-bromopyrimidin-2-yl)}- amino-2-ethyl-6-methoxy-3,4-dihydro-2H-[1,5]naphthyridine-1-carboxylic acid ethyl ester (950 mg). MS (m/z): 662/664 [M+H]+

Example 4

(2R*,4S*)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid ethyl ester (8.38 g) is dissolved in 1,4-dioxane (36 ml), then thereto are added sodium iodide (11.4 g), copper iodide (360 mg) and N,N'-dimethylethylenediamine (420 μl), and the mixture is stirred at 105° C. for 24 hours under nitrogen flow. After allowing to cool to room temperature, water is added to the reaction mixture, followed by extraction with ethyl acetate twice. The organic layer is washed with a saturated brine, dried over magnesium sulfate, then thereto is added a small amount of NH-silica gel, and filtered. The filtrate is concentrated under reduced pressure. Isopropyl ether and ethyl acetate are added to the resulting residue and the precipitated solid is collected by filtration to give (2R*,4S*)-4-{[3,5-bis(trifluoromethyl)benzyl]-(5-iodopyrimidin-2-yl)}amino-2-ethyl-6-methoxy-3,4-dihydro-2H-[1,5]naphthyridine-1-carboxylic acid ethyl ester (7.23 g). MS (m/z): 710 [M+H]+

Example 5

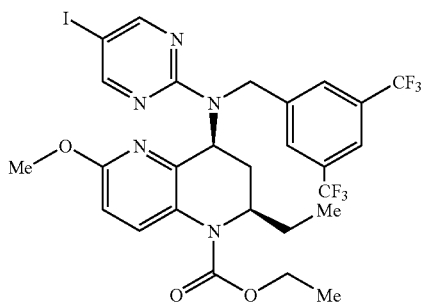

The corresponding starting compounds are treated in a similar manner to Example 4 to give the above compound. MS (m/z): 710 [M+H]+.

Example 6

(2R*,4S*)-4-{[3,5-Bis(trifluoromethyl)benzyl]-(5-bromopyrimidin-2-yl)}amino-2-ethyl-6-methoxy-3,4-dihydro-2H-[1,5]naphthyridine-1-carboxylic acid ethyl ester (6 g) is dissolved in N,N-dimethylformamide (20 ml), and thereto are added palladium acetate (200 mg), 1,1'-bis(diphenyl-phosphino)ferrocene (1 g), benzyl alcohol (18.6 ml) and triethylamine (12.6 ml). The mixture is bubbled with carbon monoxide at room temperature for 5 minutes, heated to 90° C. and stirred under carbon monoxide overnight. The reaction solution is cooled to room temperature, then thereto is added a saturated aqueous sodium hydrogen carbonate solution, and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=8:1, followed by NH-silica gel; hexane:ethyl acetate=10:1) to give (2R*,4S*)-4-{(5-benzyloxy-carbonylpyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (5.64 g). MS (m/z): 718 [M+H]+

Example 7

(2R*,4S*)-4-{(5-Benzyloxycarbonylpyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (752 mg) is dissolved in a mixed solution of tetrahydrofuran (18 ml) and methanol (6 ml), then thereto is added 10% palladium/carbon (300 mg), and the mixture is stirred at room temperature for 4 hours and 30 minutes under hydrogen. The reaction solution is filtered, and concentrated under reduced pressure to give (2R*,4S*)-4-{[3,5-bis(trifluoromethyl)benzyl]-(5-carboxypyrimidin-2-yl)}amino-2-ethyl-6-methoxy-3,4-dihydro-2H-[1,5]naphthyridine-1-carboxylic acid ethyl ester (564 mg). MS (m/z): 628 [M+H]+

Example 8

(2R*,4S*)-4-{[3,5-Bis(trifluoromethyl)benzyl]-(5-carboxypyrimidin-2-yl)}amino-2-ethyl-6-methoxy-3,4-dihydro-2H-[1,5]naphthyridine-1-carboxylic acid ethyl ester (150 mg) is dissolved in N,N-dimethylformamide (4 ml) and thereto are added morpholine (0.03 ml) and 1-hydroxybenzotriazole (50 mg) at room temperature. 1-(3-Dimethylaminopropyl)-3-ethylcarbodiimide monohydrochloride (70 mg) is added to the mixture under ice-cooling, triethylamine (0.04 ml) is added thereto dropwise, and the mixture is stirred at room temperature overnight. A saturated aqueous sodium hydrogen carbonate solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=4:1→1:1) to give (2R*,4S*)-4-{[3,5-bis(trifluoromethyl)benzyl]-[5-(morpholin-4-carbonyl) pyrimidin-2-yl]}amino-2-ethyl-6-methoxy-3,4-dihydro-2H-[1,5]naphthyridine-1-carboxylic acid ethyl ester (142 mg). MS (m/z): 697 [M+H]+

Examples 9-13

The corresponding starting compounds are treated in a similar manner to Example 8 to give the compounds as listed in Table 1.

TABLE 1

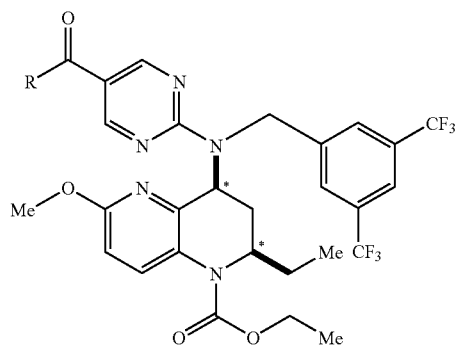

| Example No. | R | Physical properties, etc. |
|---|---|---|
| 9 | pyrrolidin-1-yl | MS (m/z): 681 [M + H]+ |

TABLE 1-continued

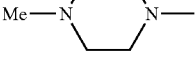

| Example No. | R | Physical properties, etc. |
|---|---|---|
| 10 | ![Me-N piperazine-N-] | MS (m/z): 710 [M + H]$^+$ |
| 11 | ![Me-C(=O)-N piperazine-N-] | MS (m/z): 738 [M + H]$^+$ |
| 12 | ![Me-O-CH2CH2-N(Me)H-] | MS (m/z): 685 [M + H]$^+$ |
| 13 | ![morpholine-N-CH2CH2-N(Me)H-] | MS (m/z): 740 [M + H]$^+$ |

Example 14

(1) (2R*,4S*)-4-{[3,5-Bis(trifluoromethyl)benzyl]-(5-carboxypyrimidin -2-yl)}amino-2-ethyl-6-methoxy-3,4-dihydro-2H-[1,5]naphthyridine-1-carboxylic acid ethyl ester (3 g) is dissolved in toluene (100 ml), then thereto added triethylamine (2 ml), diphenylphosphoryl azide (1.5 ml) and benzyl alcohol (0.5 ml) at room temperature, and the mixture is heated to 90° C. and stirred for 4 hours. The reaction solution is cooled to room temperature, then thereto is added a saturated aqueous sodium hydrogen carbonate solution and the mixture is extracted with ethyl acetate. The organic layer is washed with a saturated brine, dried over magnesium sulfate, and concentrated under reduced pressure. The resulting residue is purified by column chromatography (NH-silica gel; hexane:ethyl acetate=17:3→7:3) to give (2R*,4S*)-4-{(5-benzyloxycarbonylaminopyrimidin-2-yl)-[3,5-bis(trifluoromethyl) benzyl]}amino-2-ethyl-6-methoxy-3,4-dihydro-2H-[1,5] naphthyridine-1-carboxylic acid ethyl ester (2.27 g). MS (m/z): 733 [M+H]$^+$ (2) (2R*,4S*)-4-{(5-Benzyloxycarbonylaminopyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (2.27 g) is dissolved in a mixed solution of tetrahydrofuran (60 ml). After adding methanol (40 ml), 10% palladium/carbon (400 mg), the mixture is stirred at room temperature under hydrogen for 3 hours. The reaction solution is filtered, and concentrated under reduced pressure. The resulting residue is purified by column chromatography (silica gel; hexane:ethyl acetate=4:1→3:2) to give (2R*,4S*)-4-{(5-aminopyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (1.46 g). MS (m/z): 599 [M+H]$^+$ Example 15

(2R*,4S*)-4-{[3,5-Bis(trifluoromethyl)benzyl]-(5-bromopyrimidin-2-yl)}amino-2-ethyl-6-methoxy-3,4-dihydro-2H-[1,5]naphthyridine-1-carboxylic acid ethyl ester (250 mg) is dissolved in toluene (2 ml), and thereto are added tris(dibenzylideneacetone)dipalladium (6.9 mg), sodium tert-butoxide (54.8 mg), 2-(di-tert-butylphosphino)biphenyl (9.0 mg) and pyrrolidine (47 μl). The mixture is stirred at room temperature for 45 minutes under nitrogen flow, then heated to 80° C, and stirred for 18 hours. After cooling to room temperature, ether is added to the reaction solution. The mixture is filtered, and the filtrate is concentrated under reduced pressure. The resulting residue is purified by column chromatography (silica gel; hexane:ethyl acetate=9:1→7:3) to give (2R*,4S*)-4-{[3,5-bis(trifluoromethyl)benzyl]-[5-(pyrrolidin-1-yl)pyrimidin-2-yl]}amino-2-ethyl-6-methoxy-3,4-dihydro-2H-[1,5]naphthyridine-1-carboxylic acid ethyl ester (158.5 mg). MS (m/z): 653 [M+H]$^+$.

Examples 16-30

The corresponding starting compounds are treated in a similar manner to Example 15 to give the compounds as listed in Table 2.

TABLE 2

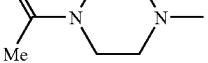

| Example No. | Configuration | R'RN— | Physical properties, etc. |
|---|---|---|---|
| 16 | (2R*,4S*) | ![pyrrolidine-N-Me with N-Me] | MS (m/z): 696 [M + H]$^+$ |
| 17 | (2R,4S) | ![pyrrolidine-N-Me with N-Me] | MS (m/z): 696 [M + H]$^+$ |
| 18 | (2R*,4S*) | ![Me-O-CH2CH2-N(Me)H-] | MS (m/z): 657 [M + H]$^+$ |

TABLE 2-continued

[Structure: R'RN-substituted pyrimidine linked to N-[3,5-bis(trifluoromethyl)benzyl], attached to 6-methoxy-3,4-dihydro-2H-[1,5]naphthyridine with 2-ethyl group and 1-carboxylic acid ethyl ester; positions labeled 2 and 4]

| Example No. | Configuration | R'RN— | Physical properties, etc. |
|---|---|---|---|
| 19 | (2R*,4S*) | Me-O-CH2CH2-N(Me)- | MS (m/z): 671 [M + H]+ |
| 20 | (2R*,4S*) | (Me-O-CH2CH2)2N- | MS (m/z): 715 [M + H]+ |
| 21 | (2R*,4S*) | morpholin-4-yl | MS (m/z): 669 [M + H]+ |
| 22 | (2R,4S) | morpholin-4-yl | MS (m/z): 669 [M + H]+ |
| 23 | (2R,4S) | 4-(2-methylaminoethyl)morpholine | MS (m/z): 712 [M + H]+ |
| 24 | (2R,4S) | Me2N- | MS (m/z): 627 [M + H]+ |
| 25 | (2S,4R) | morpholin-4-yl | MS (m/z): 669 [M + H]+ |
| 26 | (2R*,4S*) | 1-methyl-4-(ethoxycarbonyl)piperidin-4-yl | MS (m/z): 739 [M + H]+ |
| 27 | (2R*,4S*) | 1-methyl-3-(ethoxycarbonyl)piperidin-3-yl | MS (m/z): 739 [M + H]+ |
| 28 | (2R*,4S*) | 4-(benzyloxy)-1-methylpiperidin-4-yl | MS (m/z): 773 [M + H]+ |
| 29 | (2R,4S) | 4-(benzyloxy)-1-methylpiperidin-4-yl | MS (m/z): 773 [M + H]+ |
| 30 | (2R*,4S*) | 1-methylpiperidin-1-yl | MS (m/z): 667 [M + H]+ |

Example 31

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid ethyl ester (120 mg) is dissolved in ethyl acetate (1 ml) and thereto is added 4N—HCl/ethyl acetate (0.09 m). The solvent is concentrated under reduced pressure, ether and hexane are added thereto and the precipitated powder is filtered to give (2R,4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid ethyl ester hydrochloride (112 mg). MS (m/z): 669 [M+H]+.

Example 32

(2R*,4S*)-4-{[3,5-Bis(trifluoromethyl)benzyl]-(5-iodopyrimidin-2-yl)}amino-2-ethyl-6-methoxy-3,4-dihydro-2H-[1,5]naphthyridine-1-carboxylic acid ethyl ester (200 mg) is dissolved in isopropanol (1 ml), then thereto are added copper iodide (2.7 mg), ethylene glycol (31 µl), potassium phosphate (119 mg) and 2-methylaminoethanol (20 µl), and the mixture is heated to 80° C. under nitrogen flow, and stirred for 20 hours. After adding distilled water, the mixture is extracted with ether. The organic layer is washed with a saturated brine, dried over magnesium sulfate, and concentrated under reduced pressure. The resulting residue is purified by column chromatography (silica gel; hexane:ethyl acetate=9:1→3:7) to give (2R*,4S*)-4-([3,5-bis(trifluoromethyl)benzyl]-{5-[methyl-(2-hydroxyethyl)]-aminopyrimidin-2-yl})amino-2-ethyl-6-methoxy-3,4-dihydro-2H-[1,5]naphthyridine-1-carboxylic acid ethyl ester (58.2 mg). MS (m/z): 657 [M+H]⁺.

Examples 33 and 34

The corresponding starting compounds are treated in a similar manner to Example 32 to give the compounds as listed in Table 3.

TABLE 3

| Example No. | R'RN— | Physical properties, etc. |
|---|---|---|
| 33 | HO-CH₂CH₂-N(H)(Me)- | MS (m/z): 643 [M + H]⁺ |
| 34 | (HOCH₂CH₂)₂N-Me | MS (m/z): 687 [M + H]⁺ |

Example 35

(2R*,4S*)-4-{[3,5-Bis(trifluoromethyl)benzyl]-(5-bromo-pyrimidin-2-yl)}amino-2-ethyl-6-methoxy-3,4-dihydro-2H-[1,5]naphthyridine-1-carboxylic acid ethyl ester (500 mg) is dissolved in toluene (2 ml), and thereto are added copper iodide (7.2 mg), 2-phenylphenol (25.5 mg), potassium phosphate (318.4 mg) and (±)-piperidin-3-yl-methanol (172.8 mg). The mixture is heated to 80° C. under nitrogen flow and stirred for 5 days. After addition of distilled water, the mixture is extracted with ether. The organic layer is washed with a saturated brine, dried over magnesium sulfate, and concentrated under reduced pressure. The resulting residue is purified by column chromatography (NH-silica gel; hexane:ethyl acetate=9:1→4:1) to give (2R*,4S*)-4-{([3,5-bis(trifluoromethyl)benzyl]-[5-(3-hydroxymethylpiperidin-1-yl) pyrimidin-2-yl]}amino-2-ethyl-6-methoxy-3,4-dihydro-2H-[1,5]naphthyridine-1-carboxylic acid ethyl ester (22.8 mg). MS (m/z): 697 [M+H]⁺.

Example 36

To a solution of (2R*,4S*)-4-{[3,5-bis(trifluoromethyl)benzyl]-[5-(4-ethoxycarbonylpiperidin-1-yl)pyrimidin-2-yl]}amino-2-ethyl-6-methoxy-3,4-dihydro-2H-[1,5]naphthyridine-1-carboxylic acid ethyl ester (245 mg) in ethanol (2 ml) is added aqueous 2N-potassium hydroxide solution (0.332 ml) and the mixture is heated under reflux at 50° C. for 1 hour. The reaction solution is diluted with ethyl acetate and acidified with 1N-hydrochloric acid. The organic layer is washed with a saturated brine, dried over magnesium sulfate, and concentrated under reduced pressure. The resulting residue is purified by column chromatography (silica gel; chloroform to chloroform:methanol=90:10) to give (2R*,4S*)-4-{[3,5-bis(trifluoromethyl)benzyl]-[5-(4-carboxypiperidin-1-yl) pyrimidin-2-yl]}amino-2-ethyl-6-methoxy-3,4-dihydro-2H-[1,5]naphthyridine-1-carboxylic acid ethyl ester (210 mg). MS (m/z): 711 [M+H]⁺.

Example 37

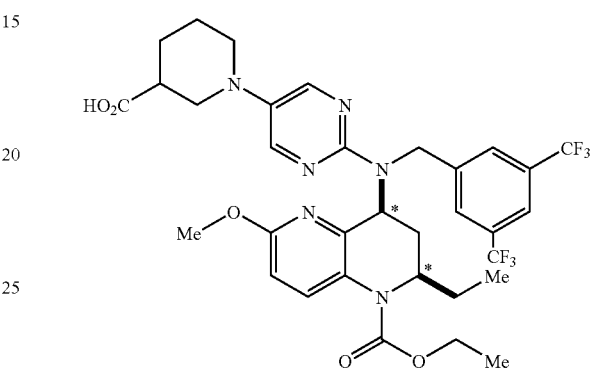

The corresponding starting compounds are treated in a similar manner to Example 36 to give the above compound. MS (m/z): 711 [M+H]⁺.

Example 38

To a solution (1.5 ml) of (2R*,4S*)-4-{[3,5-bis(trifluoromethyl)benzyl]-[5-(4-ethoxycarbonylpiperidin-1-yl)pyrimidin-2-yl]}amino-2-ethyl-6-methoxy-3,4-dihydro-2H-[1,5]naphthyridine-1-carboxylic acid ethyl ester (120 mg) in tetrahydrofuran is added diisobutylaluminum hydride (1M solution in toluene, 0.486 ml) under ice-cooling, and the mixture is stirred for 1 hour. A saturated aqueous ammonium chloride solution is added to the reaction solution and the mixture is extracted with ethyl acetate. The organic layer is washed with a saturated brine, dried over magnesium sulfate, and concentrated under reduced pressure. The resulting residue is purified by column chromatography (NH-silica gel; hexane:ethyl acetate=80:20→70:30) to give (2R*,4S*)-4-{[3,5-bis(trifluoromethyl)benzyl]-[5-(4-hydroxymethylpiperidin-1-yl)pyrimidin-2-yl]}amino-2-ethyl-6-methoxy-3,4-dihydro-2H-[1,5]naphthyridine-1-carboxylic acid ethyl ester (110. mg). MS (m/z): 697 [M+H]⁺.

Example 39

To a solution of (2R*,4S*)-4-{[5-(4-benzyloxypiperidin-1-yl) pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (700 mg) in ethanol (10 ml) is added 10% palladium/carbon (100 mg), and the mixture is stirred under hydrogen overnight. Palladium/carbon is removed by filtration, and the filtrate is concentrated under reduced pressure. The resulting residue is purified by column chromatography (NH-silica gel; hexane:ethyl acetate=80: 20→50:50) to give (2R*,4S*)-4-{[3,5-bis(trifluoromethyl) benzyl]-[5-(4-hydroxypiperidin-1-yl) pyrimidin- 2-yl]}amino-2-ethyl-6-methoxy-3,4-dihydro-2H-[1,5]naphthyridine-1-carboxylic acid ethyl ester (313 mg). MS (m/z): 683 [M+H]+.

Example 40

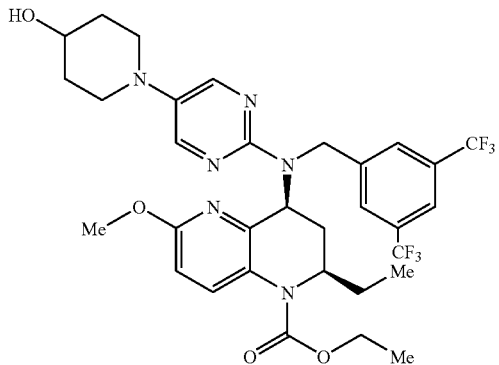

The corresponding starting compounds are treated in a similar manner to Example 39 to give the above compound. MS (m/z): 683(M+H)+

Example 41

To a solution (1 ml) of (2R*,4S*)-4-{[3,5-bis(trifluoromethyl)benzyl]-[5-(4-hydroxypiperidin-1-yl)pyrimidin-2-yl]}amino-2-ethyl-6-methoxy-3,4-dihydro-2H-[1,5]naphthyridine-1-carboxylic acid ethyl ester (100 mg) is added 1,1,1-tris(acetoxy)-1,1-dihydro-1,2-benziodooxol-3-(1H)-one (74 mg), and the mixture is stirred at room temperature for 3 hours. The reaction solution is concentrated under reduced pressure, and the resulting residue is purified by column chromatography (silica gel; hexane:ethyl acetate=90:10→60:40) to give (2R*,4S*)-4-{[3,5-bis(trifluoromethyl)benzyl]-[5-(4-oxopiperidin-1-yl)pyrimidin-2-yl]}amino-2-ethyl-6-methoxy-3,4-dihydro-2H-[1,5]naphthyridine-1-carboxylic acid ethyl ester (51 mg). MS (m/z): 681 [M+H]+

Example 42

To a solution (2 ml) of (2R*,4S*)-4-{1[3,5-bis(trifluoromethyl)benzyl]-[5-(4-hydroxypiperidin-1-yl) pyrimidin-2-yl]}amino-2-ethyl-6-methoxy-3,4-dihydro-2H-[1,5]naphthyridine-1-carboxylic acid ethyl ester (140 mg) in N,N-dimethylformamide is added sodium hydride (62.7%, 9.4 mg), and the mixture is stirred at room temperature for 10 minutes. Methyl iodide (0.019 ml) is added thereto, and the mixture is stirred at room temperature for 2 hours. Water and ethyl acetate are added thereto, the organic layer is 5 washed with a saturated brine, dried over magnesium sulfate, and concentrated under reduced pressure. The resulting residue is purified by column chromatography (silica gel; hexane:ethyl acetate=90:10→60:40) to give (2R*,4S*)-4-{[3,5-bis(trifluoromethyl)benzyl]-[5-(4-methoxypiperidin-1-yl)pyrimidin-2-yl]}amino-2-ethyl-6-methoxy-3,4-dihydro-2H-[1,5]naphthyridine-1-carboxylic acid ethyl ester (71 mg). MS (m/z): 697 [M+H]+

Examples 43-47

The corresponding starting compounds are treated in a similar manner to Example 15 to give the compounds as listed in Table 4.

TABLE 4

| Example No. | Configuration | R— | Physical properties, etc. |
|---|---|---|---|
| 43 | (2R*,4S*) | [benzyl-O-C(=O)-CH2-] | MS (m/z): 802 [M + H]+ |
| 44 | (2R,4S) | [benzyl-O-C(=O)-CH2-] | MS (m/z): 802 [M + H]+ |
| 45 | (2R,4S) | Me-CH2-O-C(=O)-CH2- | MS (m/z): 740 [M + H]+ |
| 46 | (2R*,4S*) | Me— | MS (m/z): 682 [M + H]+ |
| 47 | (2R,4S) | Me— | MS (m/z): 682 [M + H]+ |

Example 48

(2R*,4S*)-4-{[5-(4-Benzyloxycarbonylpiperazin-1-yl) pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (938 mg) is dissolved in a mixture solvent of tetrahydrofuran:methanol (1:1) (6 mL), then thereto is added 10% palladium/carbon (300 mg), and the mixture is stirred at room temperature under hydrogen flow for 13 hours. The catalyst is removed by filtration, and the filtrate is concentrated. The resulting residue is purified by column chromatography (silica gel; chloroform:methanol=10:0→9:1) to give (2R*,4S*)-4-{[3,5-bis(trifluoromethyl)benzyl]-[5-(piperazin-1-yl)pyrimidin-2-yl]}amino-2- ethyl-6-methoxy-3,4-dihydro-2H-[1,5]naphthyridine-1-carboxylic acid ethyl ester (786 mg). MS (m/z): 668 [M+H]⁺

Example 49

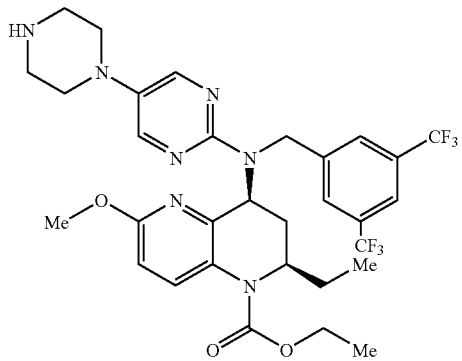

The corresponding starting compounds are treated in a similar manner to Example 48 to give the above compound. MS (m/z): 668 [M+H]⁺

Example 50

(2R*,4S*)-4-{[3,5-Bis(trifluoromethyl)benzyl]-[5-(piperazin-1-yl)-pyrimidin-2-yl]}amino-2-ethyl-6-methoxy-3,4-dihydro-2H-[1,5]naphthyridine-1-carboxylic acid ethyl ester (110 mg) is dissolved in methylene chloride (1 ml), then thereto are added triethylamine (0.1 ml) and acetyl chloride (19 μl), and the mixture is stirred at room temperature under nitrogen flow for 2 hours. After adding distilled water, the mixture is extracted with ethyl acetate. The organic layer is washed with a saturated brine, dried over magnesium sulfate, and concentrated under reduced pressure. The resulting residue is purified by column chromatography (silica gel; chloroform:methanol=9:1) to give (2R*,4S*)-4-{[5-(4-acetylpiperazin-1-yl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (103.6 mg). MS (m/z): 710 [M+H]⁺

Examples 51-55

The corresponding starting compounds are treated in a similar manner to Example 50 to give the compounds as listed in Table 5.

TABLE 5

| Example No. | Configuration | R— | Physical properties, etc. |
|---|---|---|---|
| 51 | (2R,4S) | Me-C(=O)- | MS (m/z): 710 [M + H]⁺ |
| 52 | (2R*,4S*) | MeO-CH₂-C(=O)- | MS (m/z): 740 [M + H]⁺ |
| 53 | (2R,4S) | MeO-CH₂-C(=O)- | MS (m/z): 740 [M + H]⁺ |
| 54 | (2R*,4S*) | Me-S(=O)₂- | MS (m/z): 746 [M + H]⁺ |
| 55 | (2R*,4S*) | Me₂N-S(=O)₂- | MS (m/z): 775 [M + H]⁺ |

Example 56

(2R*,4S*)-4-{[3,5-Bis(trifluoromethyl)benzyl]-[5-(piperazin-1-yl)pyrimidin-2-yl]}amino-2-ethyl-6-methoxy-3,4-dihydro-2H-[1,5]naphthyridine-1-carboxylic acid ethyl ester (150 mg) is dissolved in N,N-dimethylformamide (1 ml), then thereto are added 2-iodoethanol (26 μl) and excess potassium carbonate, and the mixture is heated to 50° C. under nitrogen flow and stirred for 5 hours. After adding distilled water, the mixture is extracted with ethyl acetate. The organic layer is washed with a saturated brine, dried over magnesium sulfate, and concentrated under reduced pressure. The resulting residue is purified by column chromatography (silica gel; chloroform:methanol=19:1→9:1) to give (2R*,4-{[3,5-bis(trifluoromethyl)benzyl]-[5-[4-(2-hydroxyethyl)piperazin-1-yl]pyrimidin-2-yl]}amino-2-ethyl-6-methoxy-3,4-dihydro-2H-[1,5]naphthyridine-1-carboxylic acid ethyl ester (128 mg). MS (m/z): 712 [M+H]⁺

Examples 57 and 58

The corresponding starting compounds are treated in a similar manner to Example 56 to give the compounds as listed in Table 6.

TABLE 6

[Structure: R-N-piperazine connected to pyrimidine, connected to N with 3,5-bis(trifluoromethyl)benzyl group and naphthyridine core with OMe, Me substituents, N-C(O)-O-Et carbamate]

| Example No. | R— | Physical properties, etc. |
|---|---|---|
| 57 | Me-CH₂-O-C(=O)-CH₂- | MS (m/z): 754 [M + H]⁺ |
| 58 | Me-CH₂-O-C(=O)-CH₂-CH₂- | MS (m/z): 768 [M + H]⁺ |

Examples 59 and 60

The corresponding starting compounds are treated in a similar manner to Example 36 to give the compounds as listed in Table 7.

TABLE 7

[Similar structure as Table 6]

| Example No. | R— | Physical properties, etc. |
|---|---|---|
| 59 | HO-C(=O)-CH₂- | MS (m/z): 726 [M + H]⁺ |
| 60 | HO-C(=O)-CH₂-CH₂- | MS (m/z): 740 [M + H]⁺ |

Example 61

(2R*,4S*)-4-{[3,5-Bis(trifluoromethyl)benzyl]-[5-(piperazin-1-yl)pyrimidin-2-yl]}amino-2-ethyl-6-methoxy-3,4-dihydro-2H-[1,5]naphthyridine-1-carboxylic acid ethyl ester (110 mg) is dissolved in methylene chloride (1 ml), triethylamine (0.1 ml) and ethyl isocyanate (20 μl) are added thereto and stirred at room temperature under nitrogen flow for 2 hours. A distilled water is added to the mixture and extracted with ethyl acetate. The organic layer is washed with a saturated brine, dried over magnesium sulfate, and concentrated under reduced pressure. The resulting residue is purified by column chromatography (silica gel; hexane: ethyl acetate=4:1→1:1) to give (2R*,4S*)-4-{1[3,5-bis(trifluoromethyl)benzyl]-[5-(4-ethylcarbamoylpiperazin-1-yl)pyrimidin-2-yl]}amino-2-ethyl-6-methoxy-3,4-dihydro-2H-[1,5]naphthyridine-1-carboxylic acid ethyl ester (104.4 mg). MS (m/z): 739 [M+H]⁺

Example 62

(2R*,4S*)-4-{(5-Aminopyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (150 mg) is dissolved in N,N-dimethylformamide (4 ml), then thereto are added acetyl chloride (0.03 ml) and triethylamine (0.1 ml), and the mixture is stirred at room temperature for 1 hour. A saturated aqueous sodium hydrogen carbonate solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane: ethyl acetate=4:1→1:1) to give (2R*,4S*)-4-{(5-acetylaminopyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (132 mg). MS (m/z): 641 [M+H]⁺

Examples 63-65

The corresponding starting compounds are treated in a similar manner to Example 62 to give the compounds as listed in Table 8.

TABLE 8

[Structure: R-C(=O)-NH-pyrimidine, connected to N with 3,5-bis(trifluoromethyl)benzyl and naphthyridine core with OMe, Me substituents, N-C(O)-O-Et carbamate]

| Example No. | R— | MS (m/z) |
|---|---|---|
| 63 | Me-O-CH₂- | MS (m/z): 671 [M + H]⁺ |
| 64 | Cl-CH₂-CH₂-CH₂- | MS (m/z): 703/705 [M + H]⁺ |
| 65 | Cl-CH₂-CH₂-O-CH₂- | MS (m/z): 705/707 [M + H]⁺ |

Example 66

(2R*,4S*)-4-{(5-Aminopyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (500 mg) is dissolved in N,N-dimethylformamide (4 ml), carbobenzyloxyglycine (210 mg) and 1-hydroxybenzotriazole (170 mg) are added thereto at room temperature, 1-ethyl-3-(3-dimethylaminopropyl)carbodiimide hydrochloride (240 mg) is added under ice-cooling, triethylamine (0.15 ml) is added dropwise and then stirred at room temperature overnight. A saturated aqueous sodium hydrogen carbonate solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=4:1→1:1) to give (2R*,4S*)-4-({5-[(2-benzyloxycarbonylamino)acetylamino]pyrimidin-2-yl}-[3,5-bis(trifluoromethyl)benzyl])amino-2-ethyl-6-methoxy-3,4-dihydro-2H-[1,5]naphthyridine-1-carboxylic acid ethyl ester (631 mg). MS (m/z): 790 [M+H]$^+$

Examples 67 and 68

The corresponding starting compounds are treated in a similar manner to Example 66 to give the compounds as listed in Table 9.

TABLE 9

| Example No. | R— | Physical properties, etc. |
|---|---|---|
| 67 |  | MS (m/z): 657 [M + H]$^+$ |
| 68 |  | MS (m/z): 791 [M + H]$^+$ |

Example 69

(2R*,4S*)-4-({5-[2-(Benzyloxycarbonylamino)acetylamino]pyrimidin-2-yl}-[3,5-bis(trifluoromethyl)benzyl]}amino-2-ethyl-6-methoxy-3,4-dihydro-2H-[1,5]naphthyridine-1-carboxylic acid ethyl ester (631 mg) is dissolved in methanol (10 ml), 10% palladium/carbon (100 mg) is added thereto and then the mixture is stirred at room temperature under hydrogen for 30 minutes. The reaction solution is filtered, and concentrated under reduced pressure. The resulting residue is purified by column chromatography (silica gel; chloroform:methanol=1:0→9:1) to give (2R*,4S*)-4-{[5-(2-aminoacetylamino)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (463 mg). MS (m/z): 626 [M+H]$^+$

Example 70

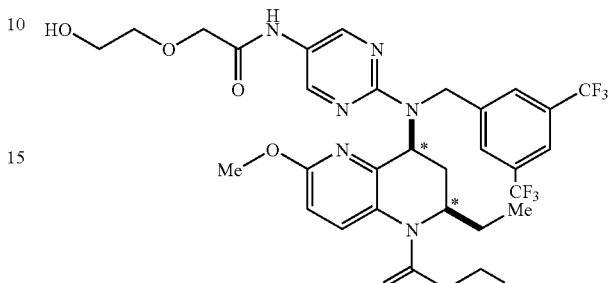

The corresponding starting compounds are treated in a similar manner to Example 39 to give the above compound. MS (m/z): 701 [M+H]$^+$

Example 71

(2R*,4S*)-4-{(5-Aminopyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (150 mg) is dissolved in methylene chloride (4 ml), then thereto are added carbodiimidazole (60 mg) and triethylamine (0.1 ml), and the mixture is stirred at room temperature for 1 hour. Morpholine (0.05 ml) is added to the reaction solution, and the mixture is stirred at room temperature for 2 hours and 30 minutes. A saturated aqueous sodium hydrogen carbonate solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=7:3→1:1→0:1) to give (2R*,4S*)-4-[[3,5-bis(trifluoromethyl)benzyl]-(5-{[(morpholin-4-yl)carbonyl]amino}pyrimidin-2-yl)]amino-2-ethyl-6-methoxy-3,4-dihydro-2H-[1,5]naphthyridine-1-carboxylic acid ethyl ester (154 mg). MS (m/z): 712 [M+H]$^+$

Example 72

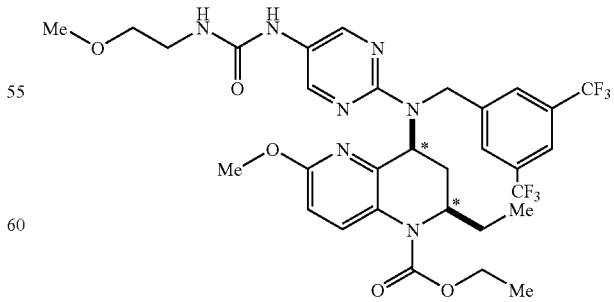

The corresponding starting compounds are treated in a similar manner to Example 71 to give the above compound. MS (m/z): 700 [M+H]$^+$

Example 73

(2R*,4S*)-4-{[5-(2-Aminoacetylamino)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (150 mg) is dissolved in N,N-dimethylformamide (4 ml), then thereto are added carbodiimidazole (40 mg) and triethylamine (0.08 ml), and the mixture is stirred at room temperature for 3 hours and 30 minutes. A saturated aqueous sodium hydrogen carbonate solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=3:2→3:7) to give (2R*,4S*)-4-{[3,5-bis(trifluoromethyl)benzyl]-[5-(2,5-dioxoimidazolidin-1-yl)pyrimidin-2-yl]}amino-2-ethyl-6-methoxy-3,4-dihydro-2H-[1,5]naphthyridine-1-carboxylic acid ethyl ester (126 mg). MS (m/z): 682 [M+H]+

Example 74

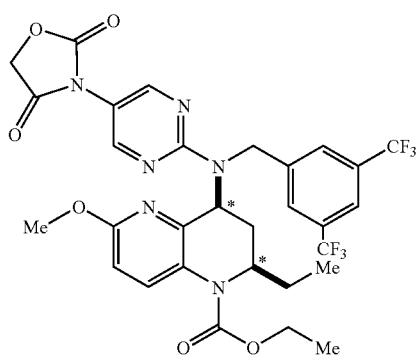

The corresponding starting compounds are treated in a similar manner to Example 73 to give the above compound. MS (m/z): 683 [M+H]+

Example 75

(2R*,4S*)-4-{[3,5-Bis(trifluoromethyl)benzyl]-[5-(4-chlorobutyrylamino)pyrimidin-2-yl]}amino-2-ethyl-6-methoxy-3,4-dihydro-2H-[1,5]naphthyridine-1-carboxylic acid ethyl ester (283 mg) is dissolved in N,N-dimethylformamide (4 ml), then thereto is added sodium hydride (18 mg) under ice-cooling, and the mixture is stirred at room temperature overnight. Water is added to the reaction solution and the mixture is extracted with ether. The organic layer is washed with a saturated brine, dried over magnesium sulfate, and concentrated under reduced pressure. The resulting residue is purified by column chromatography (silica gel; hexane:ethyl acetate=7:3→1:1) to give (2R*,4S*)-4-{[3,5-bis(trifluoromethyl)benzyl]-[5-(2-oxopyrrolidin-1-yl)pyrimidin-2-yl]}amino-2-ethyl-6-methoxy-3,4-dihydro-2H-[1,5]naphthyridine-1-carboxylic acid ethyl ester (132 mg). MS (m/z): 667 [M+H]+

Example 76

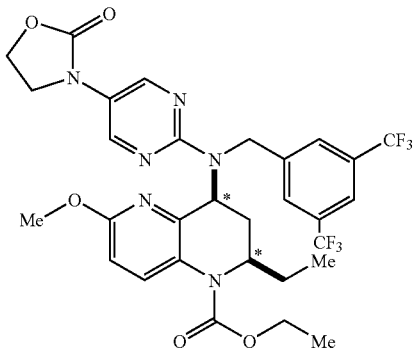

The corresponding starting compounds are treated in a similar manner to Example 75 to give the above compound. MS (m/z): 669 [M+H]+

Example 77

(1) (2R*,4S*)-4-([3,5-Bis(trifluoromethyl)benzyl]-{15-[2-(2-hydroxyethoxy)acetylamino]pyrimidin-2-yl})amino-2-ethyl-6-methoxy-3,4-dihydro-2H-[1,5]naphthyridine-1-carboxylic acid ethyl ester (90 mg) is dissolved in chloroform (4 ml), then thereto are added mesyl chloride (0.1 ml) and triethylamine (0.2 ml) under ice-cooling, and the mixture is stirred at room temperature for 2 hours. Water is added to the reaction solution and the mixture is extracted with chloroform. The organic layer is washed with a saturated brine, dried over magnesium sulfate, and concentrated under reduced pressure to give (2R*,4S*)-4-([3,5-bis(trifluoromethyl)benzyl]-{5-[2-(2-methanesulfonyloxyethoxy)acetylamino]pyrimidin-2-yl})amino-2-ethyl-6-methoxy-3,4-dihydro-2H-[1,5]naphthyridine-1-carboxylic acid ethyl ester (143 mg).

(2) (2R*,4S*)-4-([3,5-Bis(trifluoromethyl)benzyl]-{5-[2-(2-methanesulfonyloxyethoxy)acetylamino]pyrimidin-2-yl})amino-2-ethyl-6-methoxy-3,4-dihydro-2H-[1,5]naphthyridine-1-carboxylic acid ethyl ester (143 mg) is dissolved in tetrahydrofuran (4 ml), sodium tert-butoxide (48 mg) is added thereto and then the mixture is stirred at room temperature for 4 hours and 30 minutes. A saturated aqueous ammonium chloride solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane: ethyl acetate=4:1→1:1) to give (2R*,4S*)-4-{[3,5-bis(trifluoromethyl)benzyl]-[5-(3-oxomorpholin-4-yl)pyrimidin-2-yl]}amino-2-ethyl-6-methoxy-3,4-dihydro-2H-[1,5]naphthyridine-1-carboxylic acid ethyl ester (51 mg). MS (m/z): 683 [M+H]+

Example 78

(2R*,4S*)-4-{(5-Aminopyrimidin-2-yl)-[3,5-bis(trifluoromethyl)benzyl]}-amino-2-ethyl-6-methoxy-3,4-dihydro-2H-[1,5]naphthyridine-1-carboxylic acid ethyl ester (300 mg) is dissolved in toluene (10 ml), then thereto is added maleic anhydride (150 mg), and the mixture is heated under reflux for 1 hour and 30 minutes. After cooling to room temperature, a saturated aqueous ammonium chloride solution is added to the reaction solution, followed by extraction with ethyl acetate. The organic layer is washed with a saturated brine, dried over magnesium sulfate, and concentrated under reduced pressure. The resulting residue is purified by column chromatography (silica gel; hexane:ethyl acetate=4:1→3:2) to give (2R*,4S*)-4-{[3,5-bis(trifluoromethyl)benzyl]-[5-(2,5-dioxo-2,5-dihydropyrrol-1-yl)pyrimidin-2-yl]}amino-2-ethyl-6-methoxy-3,4-dihydro-2H-[1,5]naphthyridine-1-carboxylic acid ethyl ester (77 mg). MS (m/z): 679 [M+H]$^+$

Example 79

(2R*,4S*)-4-{1[3,5-Bis(trifluoromethyl)benzyl]-(5-iodopyrimidin-2-yl)}-amino-2-ethyl-6-methoxy-3,4-dihydro-2H-[1,5]naphthyridine-1-carboxylic acid ethyl ester (3.50 g) is dissolved in toluene (10 ml), then thereto are added benzyl alcohol (1.02 ml), copper iodide (94 mg), 1,10-phenanthroline (178 mg) and cesium carbonate (1.61 g), and the mixture is stirred at 100° C. under nitrogen flow for 6 hours. The mixture is allowed to cool to room temperature, then thereto are added benzyl alcohol (0.51 ml), copper iodide (94 mg), 1,10-phenanthroline (178 mg), cesium carbonate (0.80 g) and toluene (2 ml), and the mixture is stirred at 100° C. under nitrogen flow overnight. The reaction mixture is allowed to cool to room temperature, then thereto are added benzyl alcohol (0.51 ml), copper iodide (94 mg), 1,10-phenanthroline (178 mg) and cesium carbonate (0.80 g), and the mixture is stirred at 100° C. under nitrogen flow for 5 hours. After allowing to cool to room temperature, water and ethyl acetate are added to the reaction solution, and the insoluble materials are removed by filtration on Celite™. The organic layer of filtrate is washed with a saturated brine, dried over magnesium sulfate, and concentrated under reduced pressure. Copper iodide (94 mg), 1,10-phenanthroline (178 mg), cesium carbonate (1.61 g) and toluene (5 ml) are added to the resultant residue and stirred at 100° C. under nitrogen flow overnight. After allowing to cool to room temperature, water and ethyl acetate are added to the reaction solution, and the insoluble materials are removed by filtration on Celite™. The organic layer of filtrate is washed with a saturated brine, dried over magnesium sulfate, and concentrated under reduced pressure. The resulting residue is purified by column chromatography (silica gel; hexane: ethyl acetate=10:1) to give (2R*,4S*)-4-{1[3,5-bis(trifluoromethyl)benzyl]-(5-benzyloxypyrimidin-2-yl)}amino-2-ethyl-6-methoxy-3,4-dihydro-2H-[1,5]naphthyridine-1-carboxylic acid ethyl ester (2.25 g). MS (m/z): 690 [M+H]$^+$

Examples 80 and 81

The corresponding starting compounds are treated in a similar manner to Example 79 to give the compounds as listed in Table 10.

TABLE 10

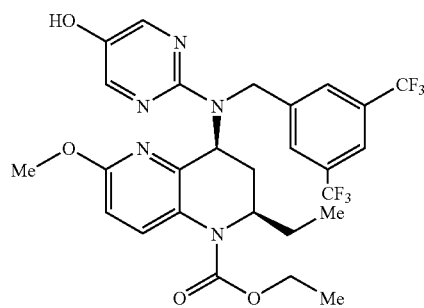

| Example No. | Configuration | R— | Physical properties, etc. |
|---|---|---|---|
| 80 | (2R,4S) | (benzyl) | MS (m/z): 690 [M + H]$^+$ |
| 81 | (2R*,4S*) | (morpholinopropyl) | MS (m/z): 713 [M + H]$^+$ |

Example 82

(2R*,4S*)-4-{[3,5-Bis(trifluoromethyl)benzyl]-(5-benzyloxypyrimidin-2-yl)}amino-2-ethyl-6-methoxy-3,4-dihydro-2H-[1,5]naphthyridine-1-carboxylic acid ethyl ester (1.52 g) is dissolved in methanol (270 ml), then thereto is added 10% palladium/carbon, and the mixture is stirred at room temperature under hydrogen for 30 minutes. The reaction mixture is filtered, and the filtrate is concentrated under reduced pressure to give (2R*,4S*)-4-{[3,5-bis(trifluoromethyl)benzyl]-(5-hydroxypyrimidin-2-yl)}-amino-2-ethyl-6-methoxy-3,4-dihydro-2H-[1,5]naphthyridine-1-carboxylic acid ethyl ester (1.33 g). MS (m/z): 600 [M+H]$^+$

Example 83

The corresponding starting compounds are treated in a similar manner to Example 82 to give the above compound. MS (m/z): 600 [M+H]$^+$

Example 84

(2R*,4S*)-4-{[3,5-Bis(trifluoromethyl)benzyl]-(5-hydroxypyrimidin-2-yl)}amino-2-ethyl-6-methoxy-3,4-dihydro-2H-[1,5]naphthyridine-1-carboxylic acid ethyl ester (150 mg) is dissolved in N,N-dimethylformamide (1 ml), then thereto is added sodium hydride (63%,11 mg) under ice-cooling, and the mixture is stirred at 0° C. for 30 minutes. Methyl iodide (23 µl) is added thereto, and the mixture is stirred for 2 hours under ice-cooling. To the reaction mixture is added 10% aqueous citric acid solution, and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=4:1) to give (2R*,4S*)-4-{[3,5-bis(trifluoromethyl)benzyl]-(5-methoxypyrimidin-2-yl)}amino-2-ethyl-6-methoxy-3,4-dihydro-2H-[1,5]naphthyridine-1-carboxylic acid ethyl ester (120 mg). MS (m/z): 614 [M+H]$^+$ Examples 85-88

The corresponding starting compounds are treated in a similar manner to Example 84 to give the compounds as listed in Table 11.

TABLE 11

| Example No. | R— | Physical properties, etc. |
|---|---|---|
| 85 | Me—O—C(=O)—CH₂— (ethoxycarbonylmethyl) | MS (m/z): 686 [M + H]$^+$ |
| 86 | H₂N—C(=O)— | MS (m/z): 657 [M + H]$^+$ |
| 87 | Me—O—C(=O)— | MS (m/z): 672 [M + H]$^+$ |
| 88 | Me—O—CH₂CH₂— | MS (m/z): 658 [M + H]$^+$ |

Example 89

(2R*,4S*)-4-{[3,5-Bis(trifluoromethyl)benzyl]-(5-hydroxypyrimidin-2-yl)}amino-2-ethyl-6-methoxy-3,4-dihydro-2H-[1,5]naphthyridine-1-carboxylic acid ethyl ester (150 mg) is dissolved in N,N-dimethylformamide (1 ml), then thereto are added potassium carbonate (200 mg) and 2-bromoethanol (162 µl), and the mixture is stirred at 60° C. overnight. To the reaction mixture is added 10% aqueous citric acid solution, and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=2:1) to give (2R*,4S*)-4-{[3,5-bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid ethyl ester (95 mg). MS (m/z): 644 [M+H]$^+$ Examples 90-92

The corresponding starting compounds are treated in a similar manner to Example 89 to give the compounds as listed in Table 12.

TABLE 12

| Example No. | Configuration | R— | Physical properties, etc. |
|---|---|---|---|
| 90 | (2R,4S) | HO—CH₂CH₂CH₂— | MS (m/z): 644 [M + H]$^+$ |
| 91 | (2R*,4S*) | HO—CH₂CH₂CH₂CH₂— | MS (m/z): 658 [M + H]$^+$ |
| 92 | (2R*,4S*) | HO—CH₂CH₂—O—CH₂CH₂— | MS (m/z): 688 [M + H]$^+$ |

Example 93

(2R*,4S*)-4-{[3,5-Bis(trifluoromethyl)benzyl]-(5-hydroxypyrimidin-2-yl)}amino-2-ethyl-6-methoxy-3,4-dihydro-2H-[1,5]naphthyridine-1-carboxylic acid ethyl ester (150 mg) is dissolved in tetrahydrofuran (1 ml), then thereto are added pyrimidin-2-ylmethanol (41 mg) and triphenylphosphine (98 mg). After adding dropwise 40% diethyl azodicarboxylate-toluene solution (163 µl) under ice-cooling, the mixture is stirred at room temperature for 1 hour and 30 minutes. Water is added to the reaction mixture and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=2:1) to give (2R*,4S*)-4-{[3,5-bis(trifluoromethyl)benzyl]-[5-(pyrimidin-2-ylmethoxy)pyrimidin-2-yl]}amino-2-ethyl-6-methoxy-3,4-dihydro-2H-[1,5]naphthyridine-1-carboxylic acid ethyl ester (118 mg). MS (m/z): 692 [M+H]$^+$ Examples 94-107

The corresponding starting compounds are treated in a similar manner to Example 93 to give the compounds as listed in Table 13.

TABLE 13

| Example No. | Configuration | R— | Physical properties, etc. |
|---|---|---|---|
| 94 | (2R*,4S*) | (2-pyridyl)propyl | MS (m/z): 705 [M + H]+ |
| 95 | (2R,4S) | (2-pyridyl)propyl | MS (m/z): 705 [M + H]+ |
| 96 | (2R*,4S*) | (tetrahydro-2H-pyran-4-yl)methyl | MS (m/z): 684 [M + H]+ |
| 97 | (2R,4S) | (tetrahydrofuran-3-yl)methyl | MS (m/z): 670 [M + H]+ |
| 98 | (2R*,4S*) | (1-methylpiperidin-4-yl)methyl | MS (m/z): 697 [M + H]+ |
| 99 | (2R*,4S*) | (1-methylpiperidin-3-yl)methyl | MS (m/z): 697 [M + H]+ |
| 100 | (2R,4S) | (1-methylpyrrolidin-3-yl)methyl | MS (m/z): 683 [M + H]+ |
| 101 | (2R*,4S*) | ((S)-1-benzylpyrrolidin-3-yl)methyl | MS (m/z): 759 [M + H]+ |
| 102 | (2R*,4S*) | (2-oxopyrrolidin-1-yl)propyl | MS (m/z): 711 [M + H]+ |

TABLE 13-continued

| Example No. | Configuration | R— | Physical properties, etc. |
|---|---|---|---|
| 103 | (2R,4S) | (2,2-dimethyl-1,3-dioxolan-4-yl)ethyl | MS (m/z): 714 [M + H]+ |
| 104 | (2R*,4S*) | (dimethylamino)propyl | MS (m/z): 671 [M + H]+ |
| 105 | (2R,4S) | (dimethylamino)propyl | MS (m/z): 671 [M + H]+ |
| 106 | (2R*,4S*) | (methylthio)propyl | MS (m/z): 674 [M + H]+ |
| 107 | (2R*,4S*) | ethyl 2,2-dimethyl-2-...oxyacetate | MS (m/z): 714 [M + H]+ |

Example 108

(2R*,4S*)-4-{[3,5-bis(trifluoromethyl)benzyl]-(5-ethoxycarbonyl-methoxypyrimidin-2-yl)}amino-2-ethyl-6-methoxy-3,4-dihydro-2H-[1,5]naphthyridine-1-carboxylic acid ethyl ester (128 mg) is dissolved in methanol (3 ml), then thereto is added 1M aqueous sodium hydroxide solution (2 ml), and the mixture is stirred at room temperature for 2 hours. To the reaction mixture is added 10% aqueous citric acid solution, and the mixture is extracted with ethyl acetate. The organic layer is washed with a saturated brine, dried over magnesium sulfate, and concentrated under reduced pressure. The resulting residue is purified by column chromatography (silica gel; chloroform:methanol=19:1) to give (2R*,4S*)-4-{[3,5-bis(trifluoromethyl)benzyl]-(5-carboxymethoxypyrimidin-2-yl)}amino-2-ethyl-6-methoxy-3,4-dihydro-2H-[1,5]naphthyridine-1-carboxylic acid ethyl ester (100 mg). MS (m/z): 658 [M+H]+

Example 109

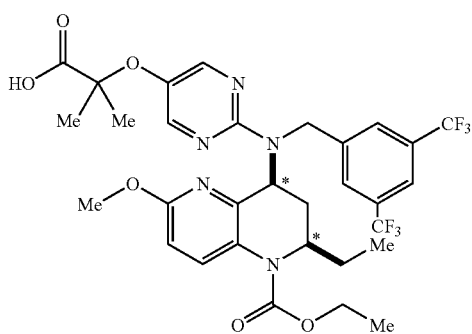

The corresponding starting compounds are treated in a similar manner to Example 108 to give the above compound. MS (m/z): 686 [M+H]+

Example 110

(2R*,4S*)-4-{[3,5-Bis(trifluoromethyl)benzyl]-(5-carboxymethoxypyrimidin-2-yl)}amino-2-ethyl-6-methoxy-3,4-dihydro-2H-[1,5]naphthyridine-1-carboxylic acid ethyl ester (150 mg) is dissolved in N,N-dimethylformamide (1 ml), then thereto is added morpholine (30 µl). After addition of 1-(3-dimethylaminopropyl)-3-ethylcarbodiimide monohydrochloride (66 mg) and 1-hydroxybenzotriazole hydrate (46 mg) under ice-cooling, the mixture is stirred at room temperature for 4 hours. Water is added to the reaction mixture and the mixture is extracted with ethyl acetate. The organic layer is washed with a saturated brine, dried over magnesium sulfate, and concentrated under reduced pressure. The resulting residue is purified by column chromatography (silica gel; chloroform:methanol=19:1) to give (2R*,4S*)-4-([3,5-bis(trifluoromethyl)benzyl]-{5-[2-(morpholin-4-yl)-2-oxoethoxy]pyrimidin-2-yl})amino-2-ethyl-6-methoxy-3,4-dihydro-2H-[1,5]naphthyridine-1-carboxylic acid ethyl ester (138 mg). MS (m/z): 727 [M+H]+

Examples 111-113

The corresponding starting compounds are treated in a similar manner to Example 110 to give the compounds as listed in Table 14.

TABLE 14

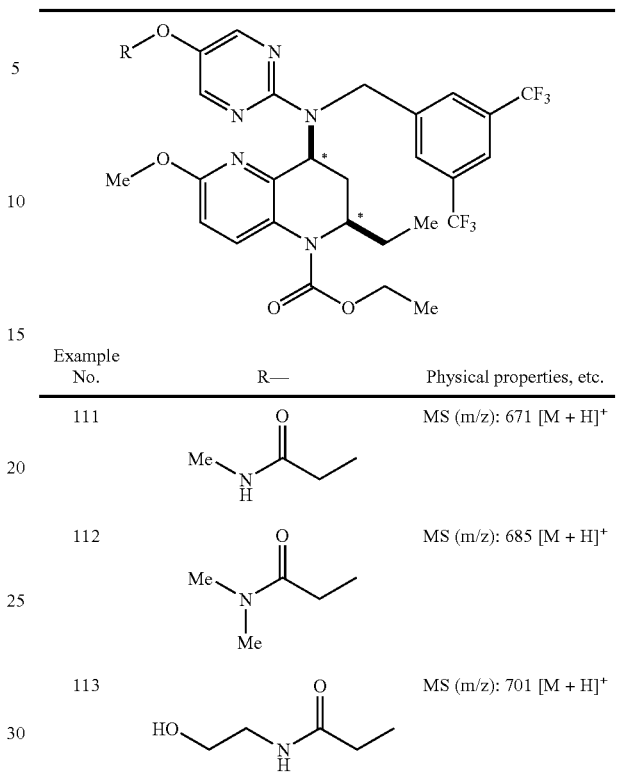

| Example No. | R— | Physical properties, etc. |
|---|---|---|
| 111 | Me–NH–C(=O)–CH2CH3– | MS (m/z): 671 [M + H]+ |
| 112 | Me–N(Me)–C(=O)–CH2CH3– | MS (m/z): 685 [M + H]+ |
| 113 | HO–CH2CH2–NH–C(=O)–CH2CH3– | MS (m/z): 701 [M + H]+ |

Example 114

(2R*,4S*)-4-{[3,5-Bis(trifluoromethyl)benzyl]-[5-(2-methylsulfanyl-ethoxy)pyrimidin-2-yl]}amino-2-ethyl-6-methoxy-3,4-dihydro-2H-[1,5]naphthyridine-1-carboxylic acid ethyl ester (150 mg) is dissolved in chloroform (1 ml), then thereto is added m-chloroperbenzoic acid (60 mg) is added thereto, and the mixture is stirred at room temperature for 2 hours. After addition of a saturated aqueous sodium hydrogen carbonate solution, the reaction mixture is extracted with ethyl acetate. The organic layer is washed with a saturated brine, dried over magnesium sulfate, and concentrated under reduced pressure. The resulting residue is purified by column chromatography (silica gel; chloroform:methanol=19:1) to give (2R*,4S*)-4-{[3,5-bis(trifluoromethyl)benzyl]-[5-(2-methylsulfinylethoxy)pyrimidin-2-yl]}amino-2-ethyl-6-methoxy-3,4-dihydro-2H-[1,5]naphthyridine-1-carboxylic acid ethyl ester (125 mg). MS (m/z): 690 [M+H]+

Example 115

(2R*,4S*)-4-{[3,5-Bis(trifluoromethyl)benzyl]-[5-(2-methylsulfanyl-ethoxy)pyrimidin-2-yl]}amino-2-ethyl-6-methoxy-3,4-dihydro-2H-[1,5]naphthyridine-1-carboxylic acid ethyl ester (226 mg) is dissolved in chloroform (1.5 ml), then thereto is added m-chloroperbenzoic acid (248 mg), and the mixture is stirred at room temperature for 40 minutes. A saturated aqueous sodium hydrogen carbonate solution is added thereto, and the mixture is extracted with ethyl acetate. The organic layer is washed with a saturated aqueous sodium hydrogen carbonate solution followed by a saturated brine, dried over magnesium sulfate, and concentrated under reduced pressure. The resulting residue is purified by column chromatography (silica gel; chloroform:methanol=19:1) to give (2R*,4S*)-4-{[3,5-bis(trifluoromethyl)benzyl]-[5-(2-methanesulfonylethoxy)-pyrimidin-2-yl]}amino-2-ethyl-6-methoxy-3,4-dihydro-2H-[1,5]naphthyridine-1-carboxylic acid ethyl ester (182 mg). MS (m/z): 706 [M+H]⁺

Example 116

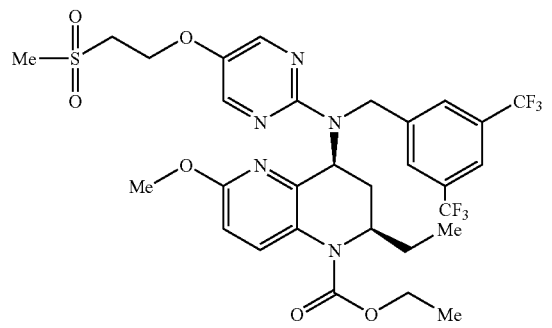

The corresponding starting compounds are treated in a similar manner to Example 115 to give the above compound. MS (m/z): 706 [M+H]⁺

Example 117

To a solution (10 ml) of (2R,4S)-4-{[3,5-bis(trifluoromethyl)benzyl]-[5-[2-(pyridin-2-yl)ethoxy]pyrimidin-2-yl]}amino-2-ethyl-6-methoxy-3,4-dihydro-2H-[1,5]naphthyridine-1-carboxylic acid ethyl ester (200 mg) in chloroform is added m-chloroperbenzoic acid (79 mg), and the mixture is stirred at room temperature for 2 hours. The reaction solution is concentrated under reduced pressure, and the resulting residue is purified by column chromatography (NH-silica gel; hexane:ethyl acetate=75:25→0:100) to give (2R,4S)-4-{[3,5-bis(trifluoromethyl)benzyl]-[5-[2-(1-oxypyridin-2-yl)ethoxy]pyrimidin-2-yl]}amino-2-ethyl-6-methoxy-3,4-dihydro-2H-[1,5]naphthyridine-1-carboxylic acid ethyl ester (173 mg). MS (m/z): 721 [M+H]⁺

Example 118

A mixture of (2R,4S)-4-([3,5-bis(trifluoromethyl)benzyl]-{5-[2-(1-oxypyridin-2-yl)ethoxy]pyrimidin-2-yl})amino-2-ethyl-6-methoxy-3,4-dihydro-2H-[1,5]naphthyridine-1-carboxylic acid ethyl ester (115 mg), trifluoroacetic anhydride (0.226 ml) and N,N-dimethylformamide (5 ml) is stirred at room temperature overnight. The reaction solution is partitioned by adding ethyl acetate and an aqueous saturated sodium bicarbonate solution. The organic layer is washed with a saturated brine, dried over magnesium sulfate, and concentrated under reduced pressure. The resulting residue is purified by tin layer silica gel chromatography (hexane:ethyl acetate=1:1) to give (2R,4S)-4-([3,5-bis(trifluoromethyl)benzyl]-{5-[2-hydroxy-2-(pyridin-2-yl)ethoxy]pyrimidin-2-yl})amino-2-ethyl-6-methoxy-3,4-dihydro-2H-[1,5]naphthyridine-1-carboxylic acid ethyl ester (24 mg). MS (m/z): 721 [M+H]⁺

Example 119

(2R*,4S*)-4-({5-[((S)-1-Benzylpyrrolidin-3-yl)oxy]pyrimidin-2-yl}-[3,5-bis(trifluoromethyl)benzyl])amino-2-ethyl-6-methoxy-3,4-dihydro-2H-[1,5]naphthyridine-1-carboxylic acid ethyl ester (280 mg) is dissolved in methanol (5 ml), then thereto is added 10% palladium/carbon (50 mg), and the mixture is stirred at room temperature under hydrogen overnight. The reaction solution is filtered, and the filtrate is concentrated under reduced pressure. The resulting residue is purified by column chromatography (NH-silica gel; hexane: ethyl acetate=4:1→3:2→0:1) to give (2R*,4S*)-4-([3,5-bis(trifluoromethyl)benzyl]-{5-[((S)-pyrrolidin-3-yl)oxy]pyrimidin-2-yl})amino-2-ethyl-6-methoxy-3,4-dihydro-2H-[1, 5]naphthyridine-1-carboxylic acid ethyl ester (168 mg). MS (m/z): 669 [M+H]⁺

Example 120

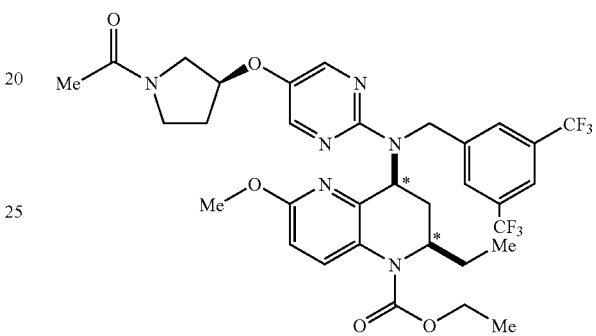

The corresponding starting compounds are treated in a similar manner to Example 50 to give the above compound. MS (m/z): 711 [M+H]⁺

Example 121

(2R,4S)-4-([3,5-bis(trifluoromethyl)benzyl]-{5-[(2,2-dimethyl-1,3-dioxolan-4-yl)methoxy]pyrimidin-2-yl}) amino-2-ethyl-6-methoxy-3,4-dihydro-2H-[1,5]naphthyridine-1-carboxylic acid ethyl ester (147 mg) is dissolved in tetrahydrofuran (2 ml), then thereto is added 1N-hydrochloric acid (2 ml), and the mixture is stirred overnight. A saturated aqueous sodium hydrogen carbonate solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=3:2→3:7) to give (2R,4S)-4-{[3,5-bis(trifluoromethyl)benzyl]-[5-(2,3-dihydroxypropoxy)-pyrimidin-2-yl]}amino-2-ethyl-6-methoxy-3,4-dihydro-2H-[1,5]naphthyridine-1-carboxylic acid ethyl ester (72 mg). MS (m/z): 674 [M+H]⁺

Example 122

(2R*,4S*)-4-{[3,5-Bis(trifluoromethyl)benzyl]-(5-iodopyrimidin-2-yl)}-amino-2-ethyl-6-methoxy-3,4-dihydro-2H-[1,5]naphthyridine-1-carboxylic acid ethyl ester (200 mg) is dissolved in 2-methoxyethanol (1.0 ml), then thereto are added copper iodide (21 mg), 1,10-phenanthroline (41 mg) and cesium carbonate (368 mg), and the mixture is stirred at 110° C. under nitrogen flow over 15 hours. After cooling to room temperature, water is added to the reaction mixture, followed by extraction with ethyl acetate. The organic layer is washed with a saturated brine twice, dried over magnesium sulfate, a small amount of NH-silica gel is added thereto, the mixture is filtered, and the filtrate is concentrated under reduced pressure. The resulting residue is purified by column chromatography (silica gel; hexane:ethyl acetate=3:1) to give ethyl (2R*,4S*)-4-{[3,5-bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 2-methoxyethyl ester (38 mg). MS (m/z): 688 [M+H]+

Example 123

(2R,4S)-4-{[3,5-Bis(trifluoromethyl)benzyl]-(5-iodopyrimidin-2-yl)}-amino-2-ethyl-6-methoxy-3,4-dihydro-2H-[1,5]naphthyridine-1-carboxylic acid ethyl ester (400 mg) is dissolved in isopropyl alcohol (2 ml), then thereto are added 2-mercaptoethanol (96 μl), copper iodide (20 mg), ethylene glycol (62 μl) and potassium carbonate (156 mg), and the mixture is stirred at 80° C. under nitrogen flow overnight. After cooling to room temperature, water is added to the reaction mixture, followed by extraction with ethyl acetate. The organic layer is washed with a saturated brine twice, dried over magnesium sulfate, and concentrated under reduced pressure. The resulting residue is purified by column chromatography (silica gel; hexane:ethyl acetate=2:1→1:1) to give (2R,4S)-4-{[3,5-bis(trifluoromethyl)benzyl]-[5-(2-hydroxyethylsulfanyl)pyrimidin-2-yl]}-amino-2-ethyl-6-methoxy-3,4-dihydro-2H-[1,5]naphthyridine-1-carboxylic acid ethyl ester (110 mg). MS (m/z): 660 [M+H]+

Example 124

(2R,4S)-4-{[3,5-Bis(trifluoromethyl)benzyl]-(5-iodopyrimidin-2-yl)}amino-2-ethyl-6-methoxy-3,4-dihydro-2H-[1,5]naphthyridine-1-carboxylic acid ethyl ester (400 mg) is dissolved in isopropyl alcohol (2 ml), then thereto are added thioglycolic acid methyl ester (120 μl), copper iodide (20 mg), ethylene glycol (62 μl) and potassium carbonate (156 mg), and the mixture is stirred at 80° C. under nitrogen flow overnight. After allowing to cool to room temperature, water is added to the reaction mixture, followed by extraction with ethyl acetate. The organic layer is washed with a saturated brine twice, dried over magnesium sulfate, and concentrated under reduced pressure. The resulting residue is dissolved in methanol (6 ml), then thereto are added 1M-aqueous sodium hydroxide solution (3 ml) and tetrahydrofuran (6 ml), and the mixture is stirred at room temperature for 10 minutes. Ten % aqueous citric acid solution is added to the reaction mixture and the mixture is extracted with ethyl acetate. The organic layer is washed with a saturated brine twice, dried over magnesium sulfate, and concentrated under reduced pressure. The resulting residue is purified by column chromatography (silica gel; hexane:ethyl acetate=2:1→1:1) to give (2R,4S)-4-{[3,5-bis(trifluoromethyl)benzyl]-(5-carboxymethylsulfanyl-pyrimidin-2-yl)}amino-2-ethyl-6-methoxy-3,4-dihydro-2H-[1,5]naphthyridine-1-carboxylic acid ethyl ester (153 mg).MS (m/z): 674 [M+H]+

Example 125

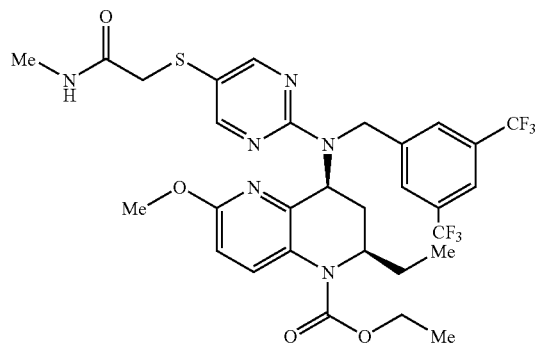

The corresponding starting compounds are treated in a similar manner to Example 110 to give the above compound. MS (m/z): 687 [M+H]+

Examples 126 and 127

The corresponding starting compounds are treated in a similar manner to Example 115 to give the compounds as listed in Table 15.

TABLE 15

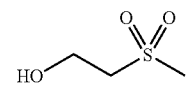

| Example No. | R | Physical properties, etc. |
|---|---|---|
| 126 | ![HO-CH2CH2-SO2-] | MS (m/z): 692 [M + H]+ |
| 127 | ![Me-NH-CO-CH2-SO2-] | MS (m/z): 719 [M + H]+ |

Example 128

(2R*,4S*)-4-{[3,5-Bis(trifluoromethyl)benzyl]-(5-carboxypyrimidin-2-yl)}amino-2-ethyl-6-methoxy-3,4-dihydro-2H-[1,5]naphthyridine-1-carboxylic acid ethyl ester (100 mg) is dissolved in tetrahydrofuran (2 ml), then thereto are added ethyl chloroformate (0.02 ml) and triethylamine (0.04 ml) under ice-cooling, and the mixture is stirred for 30 minutes. The reaction solution is filtered, sodium borohydride (18 mg) is added to the filtrate, and the mixture is stirred for 1 hour and 40 minutes. To the reaction solution is added 1N-hydrochloric acid and the mixture is extracted with ethyl acetate. The organic layer is washed successively with water, a saturated aqueous sodium hydrogen carbonate solution and a saturated brine, dried over magnesium sulfate, and concentrated under reduced pressure. The resulting residue is purified by column chromatography (silica gel; hexane: ethyl acetate=4:1→3:2) to give (2R*,4S*)-4-{[3,5-bis(trifluoromethyl)benzyl]-[5-(hydroxymethyl)pyrimidin-2-yl]}amino-2-ethyl-6-methoxy-3,4-dihydro-2H-[1,5]naphthyridine-1-carboxylic acid ethyl ester (80 mg). MS (m/z): 614 [M+H]$^+$ Example 129

(2R*,4S*)-4-{[3,5-Bis(trifluoromethyl)benzyl]-(5-hydroxymethylpyrimidin-2-yl)}amino-2-ethyl-6-methoxy-3,4-dihydro-2H-[1,5]naphthyridine-1-carboxylic acid ethyl ester (150 mg) is dissolved in tetrahydrofuran (4 ml), then thereto are added sodium hydride (12 mg) and methyl iodide (0.02 ml) under ice-cooling, and the mixture is stirred at room temperature for 3 hours and 30 minutes. A saturated aqueous sodium hydrogen carbonate solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane: ethyl acetate=4:1→3:2) to give (2R*,4S*)-4-{[3,5-bis(trifluoromethyl)benzyl]-(5-methoxymethylpyrimidin-2-yl)}amino-2-ethyl-6-methoxy-3,4-dihydro-2H-[1,5]naphthyridine-1-carboxylic acid ethyl ester (92 mg). MS (m/z): 628 [M+H]$^+$ Example 130

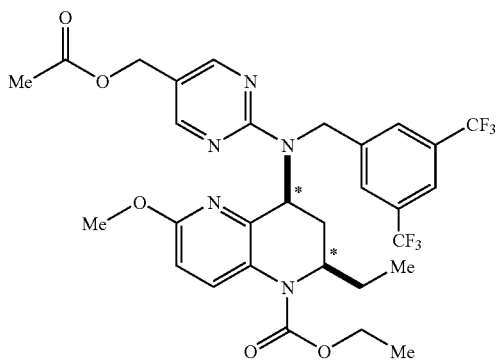

The corresponding starting compounds are treated in a similar manner to Example 129 to give the above compound. MS (m/z): 656 [M+H]$^+$ Example 131

(1) (2R*,4S*)-4-{[3,5-bis(trifluoromethyl)benzyl]-[5-(hydroxymethyl)pyrimidin-2-yl]}amino-2-ethyl-6-methoxy-3,4-dihydro-2H-[1,5]naphthyridine-1-carboxylic acid ethyl ester (300 mg) is dissolved in N,N-dimethylformamide (4 ml), then thereto is added sodium hydride (28 mg) under ice-cooling, and the mixture is stirred for 30 minutes. 2-(2-Bromoethoxy)tetrahydropyran (0.15 ml) is added to the reaction solution, and the mixture is stirred at room temperature for 2 hours and 30 minutes. After addition of sodium hydride (28 mg) and 2-(2-bromoethoxy)-tetrahydropyran (0.15 ml), the mixture is stirred at 50° C. for 2 hours and 30 minutes. After cooling to room temperature, a saturated aqueous sodium hydrogen carbonate solution is added to the reaction solution, followed by extraction with ethyl acetate. The organic layer is washed with a saturated brine, dried over magnesium sulfate, and concentrated under reduced pressure. The resulting residue is purified by column chromatography (silica gel; hexane: ethyl acetate=4:1→3:2) to give (2R*,4S*)-4-[[3,5-bis(trifluoromethyl)benzyl]-(5-{2-[(tetrahydropyran-2-yl)oxy]ethoxymethyl}pyrimidin-2-yl)]amino-2-ethyl-6-methoxy-3,4-dihydro-2H-[1,5]naphthyridine-1-carboxylic acid ethyl ester (201 mg). MS (m/z): 742 [M+H]$^+$ (2) (2R*,4S*)-4-[[3,5-Bis(trifluoromethyl)benzyl]-(5-{2-[(tetrahydropyran-2-yl)oxy]ethoxymethyl}pyrimidin-2-yl)]amino-2-ethyl-6-methoxy-3,4-dihydro-2H-[1,5]naphthyridine-1-carboxylic acid ethyl ester (200 mg) is dissolved in methanol (5 ml), then thereto is added 1N-hydrochloric acid (1 ml), and the mixture is stirred for 1 hour and 30 minutes. After adding a saturated aqueous sodium hydrogen carbonate solution, the mixture is extracted with ethyl acetate. The organic layer is washed with a saturated brine, dried over magnesium sulfate, and concentrated under reduced pressure. The resulting residue is purified by column chromatography (silica gel; hexane: ethyl acetate=4:1→1:1) to give (2R*,4S*)-4-([3,5-bis(trifluoromethyl)benzyl]-{5-[(2-hydroxy)ethoxymethyl]-pyrimidin-2-yl})amino-2-ethyl-6-methoxy-3,4-dihydro-2H-[1,5]naphthyridine-1-carboxylic acid ethyl ester (124 mg). MS (m/z): 658 [M+H]$^+$ Example 132

(1) (2R*,4S*)-4-{[3,5-Bis(trifluoromethyl)benzyl]-[5-(hydroxymethyl)-pyrimidin-2-yl]}amino-2-ethyl-6-methoxy-3,4-dihydro-2H-[1,5]naphthyridine-1-carboxylic acid ethyl ester (1 g) is dissolved in methylene chloride (20 ml), then thereto are added triphenylphosphine (855 mg) and carbon tetrabromide (1.35 g), and the mixture is stirred for 3 hours. A saturated aqueous sodium hydrogen carbonate solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane: ethyl acetate=9:1→4:1) to give (2R*,4S*)-4-{[3,5-bis(trifluoromethyl)benzyl]-[5-(bromomethyl)pyrimidin-2-yl]}amino-2-ethyl-6-methoxy-3,4-dihydro-2H-[1,5]naphthyridine-1-carboxylic acid ethyl ester (690 mg). MS (m/z): 676/678 [M+H]$^+$ (2) Morpholine (0.02 ml) is dissolved in N,N-dimethylformamide (2 ml), then thereto is added sodium hydride (9 mg) under ice-cooling, and the mixture is stirred for 30 minutes. (2R*,4S*)-4-{[3,5-Bis(trifluoromethyl)benzyl]-[5-(bromomethyl)pyrimidin-2-yl]}amino-2-ethyl-6-methoxy-3,4-dihydro-2H-[1,5]naphthyridine-1-carboxylic acid ethyl ester (112 mg) is added to the reaction solution under ice-cooling, and the mixture is stirred at room temperature for 1 hour and 30 minutes. A saturated aqueous sodium hydrogen carbonate solution is added to the reaction solution and the mixture is extracted with ethyl acetate. The organic layer is washed with a saturated brine, dried over magnesium sulfate, and concentrated under reduced pressure. The resulting residue is purified by column chromatography (silica gel; hexane: ethyl acetate=3:1→1:1) to give (2R*,4S*)-4-([3,5-bis(trifluoromethyl)benzyl]-{5-[(morpholin-4-yl)methyl]pyrimidin-2-yl})

amino-2-ethyl-6-methoxy-3,4-dihydro-2H-[1,5]naphthyridine-1-carboxylic acid ethyl ester (33 mg). MS (m/z): 683 [M+H]⁺

Examples 133-136

The corresponding starting compounds are treated in a similar manner to Example 132 to give the compounds as listed in Table 16.

TABLE 16

| Example No. | R | Physical properties, etc. |
|---|---|---|
| 133 | pyrrolidin-1-yl-methyl | MS (m/z): 667 [M + H]⁺ |
| 134 | 4-methylpiperazin-1-yl-methyl | MS (m/z): 696 [M + H]⁺ |
| 135 | (2-methoxyethyl)(methyl)aminomethyl | MS (m/z): 671 [M + H]⁺ |
| 136 | piperidin-1-yl-methyl | MS (m/z): 681 [M + H]⁺ |

Example 137

(2R*,4S*)-4-{[3,5-Bis(trifluoromethyl)benzyl]-(5-bromopyrimidin-2-yl)}amino-2-ethyl-6-methoxy-3,4-dihydro-2H-[1,5]naphthyridine-1-carboxylic acid ethyl ester (367 mg), acrylic acid benzyl ester (180 mg), tris (dibenzylideneacetone)dipalladium (61 mg), dicyclohexylmethylamine (162 mg) and tri-t-butyl phosphonium tetrafluoroborate (39 mg) are dissolved in 1,4-dioxane (4 ml), and the mixture is stirred at room temperature under nitrogen flow for 3 days. An aqueous citric acid solution and ethyl acetate are added to the reaction solution and the organic layer is washed with a saturated brine, dried over magnesium sulfate, and concentrated under reduced pressure. The resulting residue is purified by column chromatography (silica gel; hexane: ethyl acetate=23:2→3:2) to give (2R*,4S*)-4-{[5-(2-benzyloxycarbonylvinyl)pyrimidin-2-yl]-[3,5-bis(trifluoromethyl)benzyl]}amino-2-ethyl-6-methoxy-3,4-dihydro-2H-[1,5] naphthyridine-1-carboxylic acid ethyl ester (372 mg). MS (m/z): 744 [M+H]⁺

Examples 138-139

The corresponding starting compounds are treated in a similar manner to Example 137 to give the compounds as listed in Table 17.

TABLE 17

| Example | Configuration | R— | Physical properties, etc. |
|---|---|---|---|
| 138 | (2R,4S) | benzyl (E)-but-2-enoate ester group | MS (m/z): 744 [M + H]⁺ |
| 139 | (2R*,4S*) | NC-CH=CH-CH₃ | MS (m/z): 635 [M + H]⁺ |

Example 140

(2R,4S)-4-{[5-(2-Benzyloxycarbonylvinyl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (2.02 g) is dissolved in a mixture of tetrahydrofuran (50 ml) and methanol (9 ml). After addition of 10% palladium/carbon (600 mg), the mixture is stirred at room temperature under hydrogen for 2 hours and 30 minutes. The reaction solution is filtered, and concentrated under reduced pressure. The resulting residue is purified by column chromatography (silica gel; hexane: ethyl acetate=3:2→0:1) to give (2R,4S)-4-{[3,5-bis(trifluoromethyl)benzyl]-[5-(2-carboxyvinyl)pyrimidin-2-yl]}amino-2-ethyl-6-methoxy-3,4-dihydro-2H-[1,5]naphthyridine-1-carboxylic acid ethyl ester (1.7 g). MS (m/z): 654 [M+H]⁺

Example 141

(2R,4S)-4-{[3,5-Bis(trifluoromethyl)benzyl]-[5-(2-carboxyvinyl)pyrimidin-2-yl]}amino-2-ethyl-6-methoxy-3,4-dihydro-2H-[1,5]naphthyridine-1-carboxylic acid ethyl ester (500 mg) is dissolved in a mixed solution of tetrahydrofuran (15 ml) and methanol (5 ml), then thereto is added 10% palladium/carbon (160 mg), and the mixture is stirred at room temperature under hydrogen for 3 hours and 30 minutes. The reaction solution is filtered, and concentrated under reduced pressure to give (2R,4S)-4-{[3,5-bis(trifluoromethyl)benzyl]-[5-(2-carboxyethyl)-pyrimidin-2-yl]}amino-2-ethyl-6- methoxy-3,4-dihydro-2H-[1,5]naphthyridine-1-carboxylic acid ethyl ester (498 mg). MS (m/z): 656 [M+H]+

Example 142

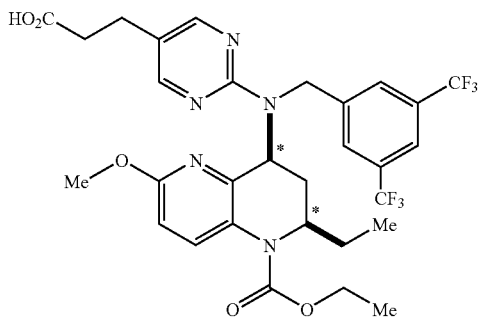

The corresponding starting compounds are treated in a similar manner to Example 141 to give the above compound. MS (m/z): 656 [M+H]+

Example 143

(2R,4S)-4-{[3,5-Bis(trifluoromethyl)benzyl]-[5-(2-carboxyvinyl)pyrimidin-2-yl]}amino-2-ethyl-6-methoxy-3,4-dihydro-2H-[1,5]naphthyridine-1-carboxylic acid ethyl ester (200 mg) is dissolved in tetrahydrofuran (4 ml), then thereto are added ethyl chloroformate (0.04 ml) and triethylamine (0.06 ml) under ice-cooling, and the mixture is stirred for 30 minutes. The reaction solution is filtered, then thereto is added sodium borohydride (58 mg), and the mixture is stirred for 1 hour and 30 minutes under ice-cooling. 1N-Hydrochloric acid is added to the reaction solution and the mixture is extracted with ethyl acetate. The organic layer is washed with water, a saturated aqueous sodium hydrogen carbonate solution and a saturated brine successively, dried over magnesium sulfate, and concentrated under reduced pressure. The resulting residue is purified by column chromatography (silica gel; hexane: ethyl acetate=4:1→3:2) to give (2R,4S)-4-{[3,5-bis(trifluoromethyl)benzyl]-[5-(3-hydroxypropenyl)pyrimidin-2-yl]}amino-2-ethyl-6-methoxy-3,4-dihydro-2H-[1,5]naphthyridine-1-carboxylic acid ethyl ester (155 mg). MS (m/z): 640 [M+H]+

Example 144

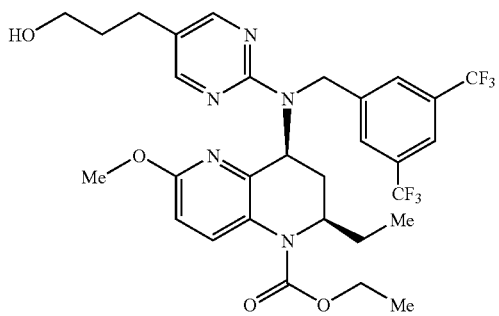

The corresponding starting compounds are treated in a similar manner to Example 143 to give the above compound. MS (m/z): 642 [M+H]+

Example 145

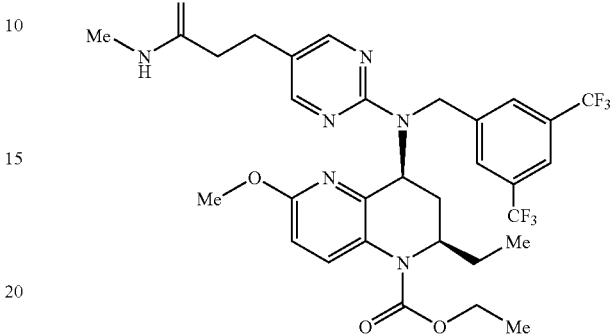

The corresponding starting compounds are treated in a similar manner to Example 110 to give the above compound. MS (m/z): 669 [M+H]+

Example 146

To a suspension (1 ml) of copper bromide (227 mg) in tetrahydrofuran is added dropwise 65% solution (982 mg) of bis(2-methoxyethoxy)aluminum sodium hydride in toluene under ice-cooling, and the mixture is stirred at the same temperature for 30 minutes. The reaction solution is cooled to −78°C., and thereto is added 2-butanol (0.29 ml). Subsequently, a solution (0.5 ml) of (2R*,4S*)-4-{[3,5-bis(trifluoromethyl)benzyl]-[5-(2-cyanovinyl)pyrimidin-2-yl]}amino-2-ethyl-6-methoxy-3,4-dihydro-2H-[1,5]naphthyridine-1-carboxylic acid ethyl ester (100 mg) in tetrahydrofuran is added thereto dropwise, and the mixture is stirred at the same temperature for 2 hours. After allowing to warm to room temperature, the mixture is stirred for additional 2 hours. To the reaction solution is added a saturated aqueous ammonium chloride solution, and the mixture is partitioned by adding ethyl acetate. The organic layer is washed with a saturated brine, dried over magnesium sulfate, and concentrated under reduced pressure. The resulting residue is purified by tin layer silica gel chromatography (hexane: ethyl acetate=2:1) to give (2R*,4S*)-4-{[3,5-bis(trifluoromethyl)benzyl]-[5-(2-cyanoethyl)pyrimidin-2-yl]}amino-2-ethyl-6-methoxy-3,4-dihydro-2H-[1,5]naphthyridine-1-carboxylic acid ethyl ester (74 mg). MS (m/z): 637 [M+H]+

Example 147

A mixture of (2R*,4S*)-4-{[3,5-bis(trifluoromethyl)benzyl]-[5-(2-cyanovinyl)pyrimidin-2-yl]}amino-2-ethyl-6-methoxy-3,4-dihydro-2H-[1,5]naphthyridine-1-carboxylic acid ethyl ester (385 mg), sodium azide (99 mg), ammonium chloride (81 mg) and N,N-dimethylformamide (5 ml) is stirred at 100°C. overnight. The mixture is partitioned by adding ethyl acetate and a saturated brine. The organic layer is washed with a saturated brine, dried over magnesium sulfate, and concentrated under reduced pressure. The resulting residue is purified by column chromatography (silica gel; chloroform to chloroform:methanol=5:1) to give (2R*,4S*)-4-{[3,5-bis(trifluoromethyl)benzyl]-{5-[2-(tetrazole-5-yl)

vinyl]pyrimidin-2-yl)}amino-2-ethyl-6-methoxy-3,4-dihydro-2H-[1,5]naphthyridine-1-carboxylic acid ethyl ester (155 mg). MS (m/z): 678 [M+H]⁺

Example 148

(2R*,4S*)-4-{[3,5-Bis(trifluoromethyl)benzyl]-(5-iodopyrimidin-2-yl)}amino-2-ethyl-6-methoxy-3,4-dihydro-2H-[1,5]naphthyridine-1-carboxylic acid ethyl ester (250 mg) is dissolved in N,N-dimethylformamide (2 ml), then thereto are added pyridine-4-boronic acid (87 mg), tetrakis(triphenylphosphine)palladium (81 mg) and potassium carbonate (117 mg), and the mixture is stirred at 100° C. under nitrogen flow for 2 hours. After allowing to cool to room temperature, water is added to the reaction mixture, followed by extraction with ethyl acetate. The organic layer is washed with a saturated brine, dried over magnesium sulfate, and concentrated under reduced pressure. The resulting residue is purified by column chromatography (NH-silica gel; hexane: ethyl acetate=4:1) to give (2R*,4S*)-4-{[3,5-bis(trifluoromethyl)benzyl]-[5-(pyridin-4-yl)pyrimidin-2-yl]}amino-2-ethyl-6-methoxy-3,4-dihydro-2H-[1,5]naphthyridine-1-carboxylic acid ethyl ester (131 mg). MS (m/z): 661 [M+H]⁺

Examples 149 and 150

The corresponding starting compounds are treated in a similar manner to Example 148 to give the compounds as listed in Table 18.

TABLE 18

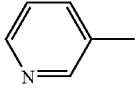

| Example No. | Configuration | R— | Physical properties, etc. |
|---|---|---|---|
| 149 | (2R*,4S) | 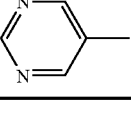 | MS (m/z): 661 [M + H]⁺ |
| 150 | (2R,4S) | 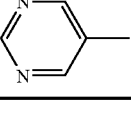 | MS (m/z): 662 [M + H]⁺ |

Example 151

(2R,4S)-4-{[3,5-Bis(trifluoromethyl)benzyl]-(5-iodopyrimidin-2-yl)}amino-2-ethyl-6-methoxy-3,4-dihydro-2H-[1,5]naphthyridine-1-carboxylic acid ethyl ester (200 mg) is dissolved in toluene (2 ml), then thereto are added 2-tributylstannylpyridine (105 μl) and tetrakis(triphenylphosphine)palladium (16 mg), and the mixture is stirred at 100° C. under nitrogen flow overnight. After allowing to cool to room temperature, 10% aqueous potassium fluoride solution is added to the reaction mixture, followed by extraction with ethyl acetate. The organic layer is washed with a 10% aqueous potassium fluoride solution and a saturated brine successively, dried over magnesium sulfate, and concentrated under reduced pressure. The resulting residue is purified by column chromatography (silica gel; hexane: ethyl acetate=4:1) to give (2R,4S)-4-{[3,5-bis(trifluoromethyl)benzyl]-[5-(pyridin-2-yl)pyrimidin-2-yl]}amino-2-ethyl-6-methoxy-3,4-dihydro-2H-[1,5]naphthyridine-1-carboxylic acid ethyl ester (138 mg). MS (m/z): 661 [M+H]⁺

Example 152

(2R,4S)-4-{[3,5-Bis(trifluoromethyl)benzyl]-(5-iodopyrimidin-2-yl)}amino-2-ethyl-6-methoxy-3,4-dihydro-2H-[1,5]naphthyridine-1-carboxylic acid ethyl ester (250 mg) is dissolved in N,N-dimethylformamide (2 ml), then thereto are added 5-formylpyridin-3-boronic acid pinacol ester (164 mg), tetrakis(triphenylphosphine)palladium (81 mg) and sodium carbonate (90 mg), and the mixture is stirred at 100° C. overnight under nitrogen flow. After allowing to cool to room temperature, a saturated aqueous sodium hydrogen carbonate solution is added to the reaction mixture and the mixture is extracted with ethyl acetate. The organic layer is washed with a saturated brine, dried over magnesium sulfate, and concentrated under reduced pressure. The resulting residue is purified by column chromatography (NH-silica gel; hexane: ethyl acetate=2:1) to give (2R,4S)-4-{[3,5-bis(trifluoromethyl)benzyl]-[5-(5-formylpyridin-3-yl)pyrimidin-2-yl]}amino-2-ethyl-6-methoxy-3,4-dihydro-2H-[1,5]naphthyridine-1-carboxylic acid ethyl ester (119 mg). MS (m/z): 689 [M+H]⁺

Example 153

(2R,4S)-4-{[3,5-bis(trifluoromethyl)benzyl]-[5-(5-formylpyridin-3-yl)pyrimidin-2-yl]}amino-2-ethyl-6-methoxy-3,4-dihydro-2H-[1,5]naphthyridine-1-carboxylic acid ethyl ester (118 mg) is dissolved in tetrahydrofuran (1.5 ml), then thereto is added 1M-diisobutylaluminum hydride-tetrahydrofuran solution (0.33 ml) dropwise under ice-cooling and the mixture is stirred for 1 hours under nitrogen flow under ice-cooling. A aqueous saturated ammonium chloride solution is added to the reaction mixture and the mixture is extracted with ethyl acetate. The organic layer is washed with a saturated brine, dried over magnesium sulfate, and concentrated under reduced pressure. The resulting residue is purified by column chromatography (silica gel; hexane: ethyl acetate=1:1) to give (2R,4S)-4-{[3,5-bis(trifluoromethyl)benzyl]-[5-(5-hydroxymethylpyridin-3-yl)pyrimidin-2-yl]}amino-2-ethyl-6-methoxy-3,4-dihydro-2H-[1,5]naphthyridine-1-carboxylic acid ethyl ester (84 mg). MS (m/z): 691 [M+H]⁺

Example 154

(2R*,4S*)-4-{[3,5-Bis(trifluoromethyl)benzyl]-(5-iodopyrimidin-2-yl)}amino-2-ethyl-6-methoxy-3,4-dihydro-2H-[1,5]naphthyridine-1-carboxylic acid ethyl ester (350 mg) is dissolved in 1,4-dioxane (1 ml), then thereto are added pyrrolidin-2-one (100 mg), tris(dibenzylideneacetone)-dipalladium (23 mg), 9,9-dimethyl-4,5-bis(diphenylphosphino)xanthene (21 mg) and cesium carbonate (241 mg) and the mixture is stirred at 100° C. under nitrogen flow overnight. After allowing to cool to room temperature, water is added to the reaction mixture, followed by extraction with ethyl acetate. The organic layer is washed with a saturated brine, dried over magnesium sulfate, then thereto is added a small amount of NH-silica gel, the mixture is filtered, and the filtrate is concentrated under reduced pressure. The resulting residue is purified by column chromatography (silica gel; hexane: ethyl acetate=4:1) to give (2R*,4S*)-4-{[3,5-bis(trifluoromethyl)benzyl]-(pyrimidin-2-yl)}amino-2-ethyl-6-methoxy-3,4-dihydro-2H-[1,5]naphthyridine-1-carboxylic acid ethyl ester (105 mg). MS (m/z): 584 [M+H]$^+$ Example 155

(1) A mixture of (2R*,4S*)-4-amino-2-ethyl-6-methoxy-3,4-dihydro-2H-[1,5]naphthyridine-1-carboxylic acid ethyl ester (300 mg), 2-chloro-4,6-dimethoxypyrimidin (468 mg), N,N-diisopropylethylamine (0.467 ml) and 1,4-dioxane (5 ml) is heated under reflux for 2 days. The reaction solution is concentrated under reduced pressure, and the resulting residue is purified by column chromatography (silica gel; hexane: ethyl acetate=80:20→60:40) to give (2R*,4S*)-4-(4,6-dimethoxypyrimidin-2-yl)amino-2-ethyl-6-methoxy-3,4-dihydro-2H-[1,5]naphthyridine-1-carboxylic acid ethyl ester (280 g). MS (m/z): 418 [M+H]$^+$
(2) (2R*,4S*)-4-(4,6-Dimethoxypyrimidin-2-yl)amino-2-ethyl-6-methoxy-3,4-dihydro-2H-[1,5]naphthyridine-1-carboxylic acid ethyl ester (260 mg) is dissolved in N,N-dimethylformamide (1 ml), then thereto is added sodium hydride (62.7%, 31 mg) under ice-cooling, and the mixture is stirred for 15 minutes. Then, 3,5-bis(trifluoromethyl)benzyl bromide (0.171 ml) is added thereto, and the mixture is stirred at room temperature for 2 hours. Water and ethyl acetate are added to the reaction solution, the organic layer is washed with a saturated brine, dried over magnesium sulfate, and concentrated under reduced pressure. The resulting residue is purified by column chromatography (silica gel; hexane: ethyl acetate=90:10→60:40) to give (2R*,4S*)-4-{[3,5-bis(trifluoromethyl)benzyl]-(4,6-dimethoxypyrimidin-2-yl)}amino-2-ethyl-6-methoxy-3,4-dihydro-2H-[1,5]naphthyridine-1-carboxylic acid ethyl ester (285 mg). MS (m/z): 644 [M+H]$^+$ Example 156

(1) (2R*,4S*)-4-(5-Bromopyridin-2-yl)amino-2-ethyl-6-methoxy-3,4-dihydro-2H-[1,5]naphthyridine-1-carboxylic acid ethyl ester (250 mg) is dissolved in N,N-dimethylformamide (3 ml), then thereto is added sodium hydride (28 mg) under ice-cooling, and the mixture is stirred for 30 minutes. 1-Bromomethyl-3,5-dimethylbenzene (171 mg) is added to the reaction solution and the mixture is stirred at room temperature for one day. Water is added to the reaction solution and the mixture is extracted with ether. The organic layer is washed with a saturated brine, dried over magnesium sulfate, and concentrated under reduced pressure. The resulting residue is purified by column chromatography (silica gel; hexane:ethyl acetate=9:1 4:1) to give (2R*,4S*)-4-[(5-bromopyrimidin-2-yl)-(3,5-dimethylbenzyl)]amino-2-ethyl-6-methoxy-3,4-dihydro-2H-[1,5]naphthyridine-1-carboxylic acid ethyl ester (268 mg). MS (m/z): 554/556 [M+H]$^+$
(2) (2R*,4S*)-4-[(5-Bromopyrimidin-2-yl)-(3,5-dimethylbenzyl)]amino-2-ethyl-6-methoxy-3,4-dihydro-2H-[1,5]naphthyridine-1-carboxylic acid ethyl ester (268 mg) is dissolved in toluene (10 ml), then thereto are added tris(dibenzylideneacetone)dipalladium (44 mg), sodium tert-butoxide (70 mg), 2-(di-tert-butylphosphino)biphenyl (57 mg) and morpholine (0.06 ml), and the mixture is stirred at room temperature under nitrogen for 1 hour. The reaction solution is heated to 50° C. and stirred for 1 hour. NH-Silica gel is added to the reaction solution and the mixture is filtered. A saturated aqueous sodium hydrogen carbonate solution is added to the filtrate and the mixture is extracted with ether. The organic layer is washed with a saturated brine, dried over magnesium sulfate, and concentrated under reduced pressure. The residue is purified by column chromatography (silica gel; hexane: ethyl acetate=3:1→1:1) to give (2R*,4S*)-4-{(3,5-dimethylbenzyl)-[5-(mor-pholin-4-yl)pyrimidin-2-yl]}amino-2-ethyl-6-methoxy-3,4-dihydro-2H-[1,5]naphthyridine-1-carboxylic acid ethyl ester (168 mg). MS (m/z): 561 [M+H]$^+$ Example 157

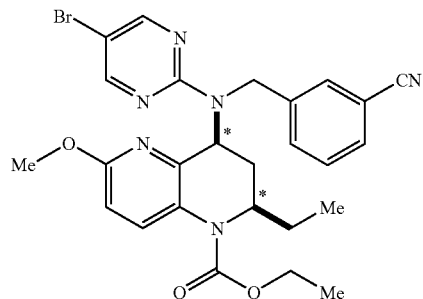

The corresponding starting compounds are treated in a similar manner to Example 156-(1) to give the above compound. MS (m/z): 551/553 [M+H]$^+$ Example 158

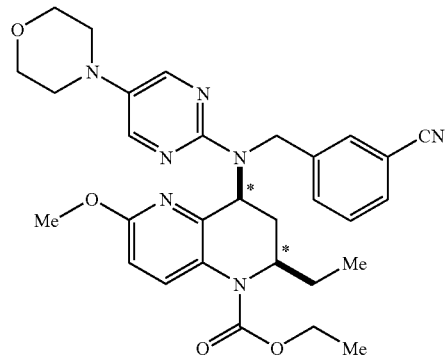

The corresponding starting compounds are treated in a similar manner to Example 156-(2) to give the above compound. MS (m/z): 558 [M+H]$^+$ Example 159

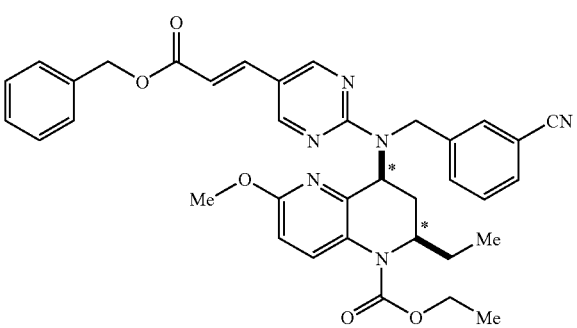

The corresponding starting compounds are treated in a similar manner to Example 137 to give the above compound. MS (m/z): 633 [M+H]+

Example 160

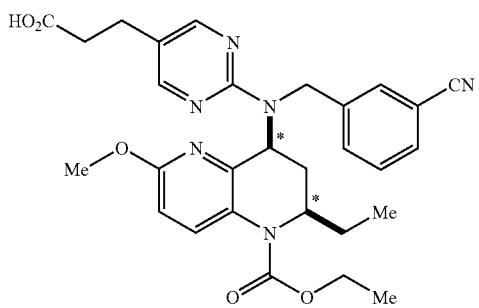

The corresponding starting compounds are treated in a similar manner to Example 141 to give the above compound. MS (m/z): 545 [M+H].

Example 161-176

The corresponding starting compounds are treated in a similar manner to Example 156 to give the compounds as listed in Table 19.

TABLE 19

| Example No. | R | Physical properties, etc. |
|---|---|---|
| 161 | 3,5-di(OMe)-phenyl with ethyl | MS (m/z): 593 [M + H]+ |
| 162 | 3-OMe-phenyl with ethyl | MS (m/z): 563 [M + H]+ |
| 163 | Cl-phenyl with ethyl | MS (m/z): 567/569 [M + H]+ |

TABLE 19-continued

| Example No. | R | Physical properties, etc. |
|---|---|---|
| 164 | CF3-phenyl with ethyl | MS (m/z): 601 [M + H]+ |
| 165 | F-phenyl with ethyl | MS (m/z): 551 [M + H]+ |
| 166 | OCHF2-phenyl with ethyl | MS (m/z): 599 [M + H]+ |
| 167 | OCF3-phenyl with ethyl | MS (m/z): 617 [M + H]+ |
| 168 | CO2Me-phenyl with ethyl | MS (m/z): 591 [M + H]+ |
| 169 | Me-phenyl with ethyl | MS (m/z): 547 [M + H]+ |
| 170 | 3,5-di-F-phenyl with ethyl | MS (m/z): 569 [M + H]+ |

TABLE 19-continued

[Structure: morpholine-pyrimidine-N(R)-methoxy-naphthyridine with ethyl carbamate and methyl substituent]

| Example No. | R | Physical properties, etc. |
|---|---|---|
| 171 | 3-chloro-4-fluorobenzyl | MS (m/z): 585/587 [M + H]+ |
| 172 | 2-trifluoromethyl-4-fluorobenzyl | MS (m/z): 619 [M + H]+ |
| 173 | 2,3,4-trifluorobenzyl | MS (m/z): 587 [M + H]+ |
| 174 | 3,5-dichlorobenzyl | MS (m/z): 601/603 [M + H]+ |
| 175 | 3-methyl-5-trifluoromethylbenzyl | MS (m/z): 615 [M + H]+ |
| 176 | 3-cyano-5-trifluoromethylbenzyl | MS (m/z): 656 [M + H]+ |

Example 177

(1) (2R*,4S*)-4-(5-Bromopyrimidin-2-yl)amino-2-ethyl-6-methoxy-3,4-dihydro-2H-[1,5]naphthyridine-1-carboxylic acid ethyl ester (1 g), tris(dibenzylideneacetone)dipalladium (210 mg), sodium tert-butoxide (661 mg), 2-(di-tert-butylphosphino)biphenyl (137 mg) and morpholine (400 μl) are dissolved in toluene (10 ml), and the mixture is stirred at 40° C. under nitrogen flow for 19 hours. After cooling to room temperature, a saturated brine and ethyl acetate are added to the reaction solution. The organic layer is dried over magnesium sulfate, and concentrated under reduced pressure. The resulting residue is purified by column chromatography (NH-silica gel; hexane: ethyl acetate=9:12:1) to give (2R*,4S*)-2-ethyl-6-methoxy-4-[5-(morpholin-4-yl)pyrimidin-2-yl]amino-3,4-dihydro-2H-[1,5]naphthyridine-1-carboxylic acid ethyl ester (560 mg). MS (m/z): 443 [M+H]+

(2) (2R*,4S*)-2-Ethyl-6-methoxy-4-[5-(morpholin-4-yl)pyrimidin-2-yl]amino-3,4-dihydro-2H-[1,5]naphthyridine-1-carboxylic acid ethyl ester (118 mg) is dissolved in N,N-dimethylformamide (2 ml), then thereto is added sodium hydride (62.7%, 13 mg) under nitrogen flow under ice-cooling, and the mixture is stirred at room temperature for 30 minutes. After addition of 4-fluorobenzyl bromide (86 μl) under ice-cooling, the mixture is stirred at room temperature overnight. Water and ethyl acetate are added to the mixture, the mixture is washed with a saturated brine, the organic layer is dried over magnesium sulfate, and concentrated under reduced pressure. The resulting residue is purified by column chromatography (silica gel; hexane: ethyl acetate=2:1→1:1) to give (2R*,4S*)-2-ethyl-4-{(4-fluorobenzyl)-[5-(morpholin-4-yl)pyrimidin-2-yl]}amino-6-methoxy-3,4-dihydro-2H-[1,5]naphthyridine-1-carboxylic acid ethyl ester (93 mg). MS (m/z): 551 [M+H]+

Examples 178-183

The corresponding starting compounds are treated in a similar manner to Example 177-(2) to give the compounds as listed in Table 20.

TABLE 20

[Structure: morpholine-pyrimidine-N(R)-methoxy-naphthyridine with ethyl carbamate and methyl substituent]

| Example No. | R | Physical properties, etc. |
|---|---|---|
| 178 | 2,4-difluorobenzyl | MS (m/z): 569 [M + H]+ |
| 179 | 3-trifluoromethyl-5-fluorobenzyl | MS (m/z): 619 [M + H]+ |

TABLE 20-continued

| Example No. | R | Physical properties, etc. |
|---|---|---|
| 180 | 3-bromo-benzyl (Br on benzyl with ethyl) | MS (m/z): 611/613 [M + H]$^+$ |
| 181 | 2,4-dichloro-benzyl with ethyl | MS (m/z): 601/603 [M + H]$^+$ |
| 182 | benzyl with Me and F and ethyl | MS (m/z): 565 [M + H]$^+$ |
| 183 | benzyl-S—CF$_3$ with ethyl | MS (m/z): 633 [M + H]$^+$ |

Example 184

Trimethylsilyl chloride (4.6 ml) is added dropwise to a suspension of (2R,4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid ethyl ester (2.4 g), sodium iodide (5.4 g) and acetonitrile (50 ml) at 80° C. After addition, the reaction solution is cooled to room temperature, and a saturated aqueous sodium thiosulfate solution and ethyl acetate are added thereto. The organic layer is washed with a saturated brine, dried over magnesium sulfate, and concentrated under reduced pressure. The resulting residue is purified by column chromatography (silica gel; hexane: ethyl acetate=2:1→0:1) to give (2R,4S)-4-{[3,5-bis(trifluoromethyl)benzyl]-[5-(morpholin-4-yl)pyrimidin-2-yl]}amino-2-ethyl-6-hydroxy-3,4-dihydro-2H-[1,5]naphthyridine-1-carboxylic acid ethyl ester (988 mg). MS (m/z): 655 [M+H]$^+$

Example 185

(2R,4S)-4-{[3,5-Bis(trifluoromethyl)benzyl]-[5-(morpholin-4-yl)pyrimidin-2-yl]}amino-2-ethyl-6-hydroxy-3,4-dihydro-2H-[1,5]naphthyridine-1-carboxylic acid ethyl ester (207 mg) is dissolved in N,N-dimethylformamide (3 ml), then thereto is added sodium hydride (62.7%, 15 mg) under ice-cooling, and the mixture is stirred at room temperature for 30 minutes. After addition of ethyl iodide (50 µl) under ice-cooling, the mixture is stirred at room temperature for 2 hours. Water and ethyl acetate are added to the mixture, the organic layer is washed with a saturated brine, dried over magnesium sulfate, and concentrated under reduced pressure. The resulting residue is purified by column chromatography (silica gel; hexane: ethyl acetate=9:1→7:3) to give (2R,4S)-4-{[3,5-bis(trifluoromethyl)benzyl]-[5-(morpholin-4-yl)pyrimidin-2-yl]}amino-6-ethoxy-2-ethyl-3,4-dihydro-2H-[1,5]naphthyridine-1-carboxylic acid ethyl ester (141 mg). MS (m/z): 683 [M+H]$^+$

Example 186

(2R,4S)-4-{[3,5-Bis(trifluoromethyl)benzyl]-[5-(morpholin-4-yl)pyrimidin-2-yl]}amino-2-ethyl-6-hydroxy-3,4-dihydro-2H-[1,5]naphthyridine-1-carboxylic acid ethyl ester (100 mg), cesium carbonate (55 mg) and 2-chloro-2,2-difluoroacetic acid methyl ester (44 mg) are dissolved in N,N-dimethylformamide (1 ml) and stirred at 75° C. for 17 hours. The reaction solution is cooled to room temperature, and thereto are added an aqueous citric acid solution and ethyl acetate. The organic layer is washed with a saturated brine, dried over magnesium sulfate, and concentrated under reduced pressure. The resulting residue is purified by column chromatography (silica gel; hexane: ethyl acetate=9:1→4:1) to give (2R,4S)-4-{[3,5-bis(trifluoromethyl)benzyl]-[5-(morpholin-4-yl)pyrimidin-2-yl]}amino-6-difluoromethoxy-2-ethyl-3,4-dihydro-2H-[1,5]naphthyridine-1-carboxylic acid ethyl ester (101 mg). MS (m/z): 705 [M+H]$^+$

Example 187

(2R,4S)-4-{[3,5-Bis(trrifluoromethyl)benzyl]-[5-(morpholin-4-yl)pyrimidin-2-yl]}amino-2-ethyl-6-hydroxy-3,4-dihydro-2H-[1,5]naphthyridine-1-carboxylic acid ethyl ester (775 mg) and pyridine (287 µl) are dissolved in methylene chloride (5 ml), then thereto is added trifluoromethanesulfonic anhydride (240 µl) dropwise under ice-cooling and the mixture is stirred at the same temperature for 4 hours. An aqueous citric acid solution is added to the reaction solution, the organic layer is washed with a saturated aqueous sodium hydrogen carbonate solution, followed by a saturated brine, dried over magnesium sulfate, and concentrated under reduced pressure. The resulting residue is purified by column chromatography (silica gel; hexane: ethyl acetate=6:1→2:1) to give (2R,4S)-4-{[3,5-bis(trifluoromethyl)benzyl]-[5-(morpholin-4-yl)pyrimidin-2-yl]}amino-2-ethyl-6-trifluoromethanesulfonyloxy-3,4-dihydro-2H-[1,5]naphthyridine-1-carboxylic acid ethyl ester (567 mg). MS (m/z): 787 [M+H]$^+$

Example 188

A mixture of (2R,4S)-4-{[3,5-Bis(trifluoromethyl)benzyl]-[5-(morpholin-4-yl)pyrimidin-2-yl]}amino-2-ethyl-6-trifluoromethanesulfonyloxy-3,4-dihydro-2H-[1,5]naphthyridine-1-carboxylic acid ethyl ester (732 mg), tetrakis(triphenylphosphine)palladium (catalytic amount), zinc cyanide (142 mg) and N,N-dimethylformamide (10 ml) is stirred at 95° C. under nitrogen flow for 8 hours. After cooling to room temperature, water and ethyl acetate are added to the reaction solution. The organic layer is washed with a saturated brine, dried over magnesium sulfate, and concentrated under reduced pressure. The resulting residue is purified by column chromatography (silica gel; hexane: ethyl acetate=4:1→2:1) to give (2R,4S)-4-{[3,5-bis(trifluoromethyl)benzyl]-[5-(morpholin-4-yl)pyrimidin-2-yl]}amino-6-cyano-2-ethyl-3,4-dihydro-2H-[1,5]naphthyridine-1-carboxylic acid ethyl ester (572 mg). MS (m/z): 664 [M+H]$^+$ Example 189

(2R,4S)-4-{[3,5-Bis(trifluoromethyl)benzyl]-[5-(morpholin-4-yl)pyrimidin-2-yl]}amino-6-cyano-2-ethyl-3,4-dihydro-2H-[1,5]naphthyridine-1-carboxylic acid ethyl ester (458 mg) is dissolved in ethanol (5 ml), then thereto is added a catalytic amount of Raney nickel, and the mixture is stirred at room temperature under hydrogen for 5 hours. The catalyst is removed by filtration, and the filtrate is concentrated under reduced pressure. The resulting residue is purified by column chromatography (NH-silica gel; hexane: ethyl acetate=1:2→0:1) to give (2R,4S)-6-aminomethyl-4-{[3,5-bis(trifluoromethyl)benzyl]-[5-(morpholin-4-yl)pyrimidin-2-yl]}amino-2-ethyl-3,4-dihydro-2H-[1,5]naphthyridine-1-carboxylic acid ethyl ester (211 mg). MS (m/z): 668 [M+H]$^+$ Example 190

(2R,4S)-4-{[3,5-Bis(trifluoromethyl)benzyl]-[5-(morpholin-4-yl)pyrimidin-2-yl]}amino-2-ethyl-6-trifluoromethanesulfonyloxy-3,4-dihydro-2H-[1,5]naphthyridine-1-carboxylic acid ethyl ester (250 mg) is dissolved in 1,4-dioxane (3 ml), and thereto are added a catalytic amount of tetrakis(triphenylphosphine)palladium, a catalytic amount of silver carbonate and a catalytic amount of copper (I) chloride under nitrogen flow. After adding dropwise trimethylaluminum-hexane solution (1M, 480 µl), the mixture is stirred at 60° C. for 30 minutes. After cooling to room temperature, a saturated aqueous sodium hydrogen carbonate solution and ethyl acetate are added to the reaction solution. The organic layer is washed with a saturated brine, dried over magnesium sulfate, and concentrated under reduced pressure. The resulting residue is purified by column chromatography (NH-silica gel; hexane: ethyl acetate=9:1→4:1) to give (2R,4S)-4-{[3,5-bis(trifluoromethyl)benzyl]-[5-(morpholin-4-yl)pyrimidin-2-yl]}amino-2-ethyl-6-methyl-3,4-dihydro-2H-[1,5]naphthyridine-1-carboxylic acid ethyl ester (153 mg). MS (m/z): 653 [M+H]$^+$ Example 191

(1) 5-Amino-2-methoxypyridine (5.0 g) is dissolved in methylene chloride (100 ml) and thereto is added sodium sulfate (3.5 g). The reaction solution is cooled to −25° C., then thereto is added acetaldehyde (2.26 ml), and the mixture is stirred at the same temperature for 2 hours and 30 minutes. Sodium sulfate is removed by filtration, and the filtrate is cooled to −25° C. After adding N-vinyl-carbamic acid benzyl ester (7.12 g) and boron trifluoride-diethylether complex (0.51 ml), the mixture is stirred at the same temperature for 1 hour, and then at room temperature overnight. The reaction solution is concentrated under reduced pressure, and the resulting residue is purified by column chromatography (silica gel; hexane: ethyl acetate=9:1→3:1) to give (2R*,4S*)-(6-methoxy-2-methyl-1,2,3,4-tetrahydro-[1,5]naphthyridin-4-yl)carbamic acid benzyl ester (8.56 g). MS (m/z): 328 [M+H]$^+$ (2) (2R*,4S*)-(6-Methoxy-2-methyl-1,2,3,4-tetrahydro-[1,5]naphthyridin-4-yl)carbamic acid benzyl ester (8.55 g) and pyridine (10.6 ml) are dissolved in methylene chloride (75 ml), then thereto is added ethyl chloroformate (12.5 ml) dropwise under ice-cooling, and the mixture is stirred at the same temperature for 2 hours. An aqueous citric acid solution is added to the reaction solution, the organic layer is washed with a saturated brine, dried over sodium sulfate, and concentrated under reduced pressure. The resulting residue is purified by column chromatography (silica gel; hexane: ethyl acetate=9:1→3:1) to give (2R*,4S*)-4-benzyloxycarbonylamino-6-methoxy-2-methyl-3,4-dihydro-2H-[1,5]naphthyridine-1-carboxylic acid ethyl ester (6.18 g). MS (m/z): 400 [M+H]$^+$ (3) (2R*,4S*)-4-Benzyloxycarbonylamino-6-methoxy-2-methyl-3,4-dihydro-2H-[1,5]naphthyridine-1-carboxylic acid ethyl ester (5.83 g) is dissolved in a mixture solvent of ethanol (60 ml) and tetrahydrofuran (60 ml), then thereto is added 10% palladium/carbon (500 mg), and the mixture is stirred at room temperature under hydrogen for 7 hours. The catalyst is removed by filtration, the filtrate is concentrated under reduced pressure to give (2R*,4S*)-4-amino-6-methoxy-2-methyl-3,4-dihydro-2H-[1,5]naphthyridine-1-carboxylic acid ethyl ester (3.85 g). MS (m/z): 266 [M+H]$^+$ (4) (2R*,4S*)-4-Amino-6-methoxy-2-methyl-3,4-dihydro-2H-[1,5]naphthyridine-1-carboxylic acid ethyl ester (3.80 g), 5-bromo-2-chloropyrimidin (6.92 g) and N,N-diisopropylethylamine (6.23 ml) are dissolved in 1,4-dioxane (50 ml) and the mixture is heated under reflux for 4 hours. After cooling to room temperature, the reaction solution is partitioned by adding a saturated aqueous sodium hydrogen carbonate solution and ethyl acetate. The organic layer is washed with a saturated brine, dried over magnesium sulfate, and concentrated under reduced pressure. The resulting residue is purified by column chromatography (silica gel; hexane: ethyl acetate=9:1→6:4) to give (2R*,4S*)-4-(5-bromopyrimidin-2-yl)amino-6-methoxy-2-methyl-3,4-dihydro-2H-[1,5]naphthyridine-1-carboxylic acid ethyl ester (5.92 g). MS (m/z): 422/424 [M+H]$^+$ (5) (2R*,4S*)-4-(5-Bromopyrimidin-2-yl)amino-6-methoxy-2-methyl-3,4-dihydro-2H-[1,5]naphthyridine-1-carboxylic acid ethyl ester (5.9 g) is dissolved in N,N-dimethylformamide (60 ml), then thereto is added sodium hydride (62.7%, 697 mg) at room temperature, and the mixture is stirred for 10 minutes. After adding 3,5-bis(trifluoromethyl) benzyl bromide (3.85 ml), the mixture is stirred at room temperature for 2 hours. Water and ethyl acetate is added to the reaction solution, the organic layer is washed with a saturated brine, dried over magnesium sulfate, and concentrated under reduced pressure. The resulting residue is crystallized from diisopropyl ether and hexane to give (2R*,4S*)-4-{[3,5-bis(trifluoromethyl)benzyl]-(5-bromopyrimidin-2-yl)}amino-6-methoxy-2-methyl-3,4-dihydro-2H-[1,5]naphthyridine-1-carboxylic acid ethyl ester (6.1 g). MS (m/z): 648/650 [M+H]$^+$ Examples 192-195

The corresponding starting compounds are treated in a similar manner to Example 15 to give the compounds as listed in Table 21.

TABLE 21

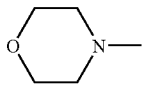

| Example No. | R | Physical properties, etc. |
|---|---|---|
| 192 |  | MS (m/z): 655 [M + H]+ |
| 193 | 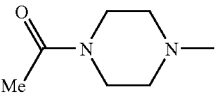 | MS (m/z): 668 [M + H]+ |
| 194 | 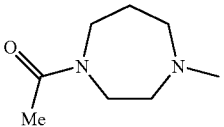 | MS (m/z): 696 [M + H]+ |
| 195 | 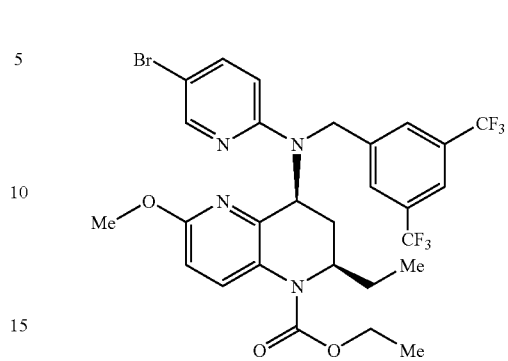 | MS (m/z): 710 [M + H]+ |

Example 196

(1) (2R*,4S*)-4-Amino-2-ethyl-6-methoxy-3,4-dihydro-2H-[1,5]naphthyridine-1-carboxylic acid ethyl ester (3 g), 2,5-dibromopyridine (5.09 g), tris(dibenzylideneacetone)dipalladium (196 mg), sodium tert-butoxide (2.1 g), 2-dicyclohexylphosphino-2'-(N,N-dimethylamino)biphenyl (169 mg) are dissolved in toluene (30 ml), and the mixture is stirred at room temperature under. nitrogen flow overnight. A saturated brine and ethyl acetate are added to the reaction solution and the organic layer is dried over magnesium sulfate, and concentrated under reduced pressure. The resulting residue is purified by column chromatography (silica gel; hexane: ethyl acetate=9:1→8:1) to give (2R*,4S*)-4-(5-bromopyridin-2-yl)amino-2-ethyl-6-methoxy-3,4-dihydro-2H-[1,5]naphthyridine-1-carboxylic acid ethyl ester (306 mg). MS (m/z): 435/437 [M+H]+

(2) The resulting product is treated in a similar manner to Example 1-(6) to give (2R*,4S*)-4-{[3,5-bis(trifluoromethyl)benzyl]-(5-bromopyridin-2-yl)}amino-2-ethyl-6-methoxy-3,4-dihydro-2H-[1,5]naphthyridine-1-carboxylic acid ethyl ester (207 mg). MS (m/z): 661/663 [M+H]+

Example 197

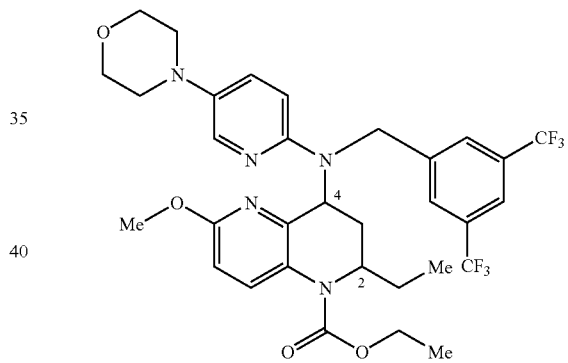

The corresponding starting compounds are treated in a similar manner to Example 196 to give the above compound. MS (m/z): 661/663 [M+H]+

Examples 198 and 199

The corresponding starting compounds are treated in a similar manner to Example 15 to give the compounds as listed in Table 22.

TABLE 22

| Example No. | Configuration | Physical properties, etc. |
|---|---|---|
| 198 | (2R*,4S*) | MS (m/z): 668 [M + H]+ |
| 199 | (2R,4S) | MS (m/z): 668 [M + H]+ |

Example 200

(1) (2R*,4S*)-4-Amino-2-ethyl-6-methoxy-3,4-dihydro-2H-[1,5]naphthyridine-1-carboxylic acid ethyl ester (3.3 g), 6-chloronicotinonitrile (4.9 g) and N,N-diisopropylethylamine (4.1 ml) are dissolved in 1,4-dioxane (25 ml), and the mixture is stirred under reflux for 24 hours. A saturated brine and ethyl acetate are added to the reaction solution, the organic layer is dried over magnesium sulfate, and concentrated under reduced pressure. The resulting residue is purified by column chromatography (silica gel; hexane: ethyl acetate=4:1) to give (2R*,4S*)-4-(5-cyanopyridin-2-yl)amino-2-ethyl-6-methoxy-3,4-dihydro-2H-[1,5]naphthyridine-1-carboxylic acid ethyl ester (4.13 g). MS (m/z): 382 [M+H]+

(2) The resulting product is treated in a similar manner to Example 1-(6) to give (2R*,4S*)-4-{[3,5-bis(trifluoromethyl)benzyl]-(5-cyanopyridin-2-yl)}amino-2-ethyl-6-methoxy-3,4-dihydro-2H-[1,5]naphthyridine-1-carboxylic acid ethyl ester (4.53 g). MS (m/z): 608 [M+H]+

Example 201

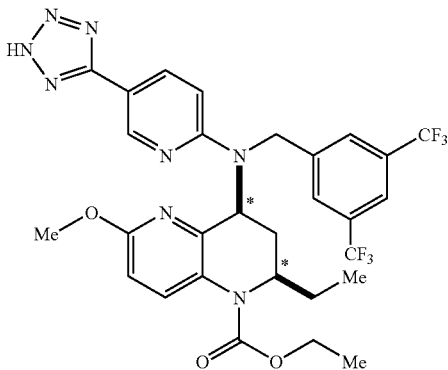

The corresponding starting compounds are treated in a similar manner to Example 147 to give the above compound. MS (m/z): 651 [M+H]+

Example 202

(2R*,4S*)-4-{[3,5-Bis(trifluoromethyl)benzyl]-[5-(tetrazol-5-yl)pyridin-2-yl]}amino-2-ethyl-6-methoxy-3,4-dihydro-2H-[1,5]naphthyridine-1-carboxylic acid ethyl ester (120 mg), potassium carbonate (51 mg) and excess of 2-bromoethanol are dissolved in N,N-dimethylformamide (3 ml), and the mixture is stirred at 50° C. for 2 hours. Water and ethyl acetate are added to the reaction solution and the organic layer is washed with a saturated brine, dried over magnesium sulfate, and concentrated under reduced pressure. The resulting residue is purified by column chromatography (silica gel; hexane: ethyl acetate=2:1→1:1) to give (2R*,4S*)-4-([3,5-bis(trifluoromethyl)benzyl]-{5-[2-(2-hydroxyethyl)-2H-tetrazole-5-yl]pyridin-2-yl})amino-2-ethyl-6-methoxy-3,4-dihydro-2H-[1,5]naphthyridine-1-carboxylic acid ethyl ester (119 mg). MS (m/z): 695 [M+H]+

Example 203

A suspension of (2R*,4S*)-4-{[3,5-Bis(trifluoromethyl)benzyl]-(5-cyanopyridin-2-yl)}amino-2-ethyl-6-methoxy-3,4-dihydro-2H-[1,5]naphthyridine-1-carboxylic acid ethyl ester (127 mg) and conc. hydrochloric acid (2 ml) is stirred under reflux for 2 hours. Water and ethyl acetate are added to the reaction solution, the organic layer is washed with a saturated brine, dried over sodium sulfate, and concentrated under reduced pressure. The resulting residue is purified by column chromatography (silica gel; chloroform:methanol=19:1→9:1) to give (2R*,4S*)-4-{[3,5-bis(trifluoromethyl)benzyl]-(5-carboxypyridin-2-yl)}amino-2-ethyl-6-methoxy-3,4-dihydro-2H-[1,5]naphthyridine-1-carboxylic acid ethyl ester (48 mg). MS (m/z): 627 [M+H]+

Example 204

(2R*,4S*)-4-{[3,5-Bis(trifluoromethyl)benzyl]-(5-cyanopyridin-2-yl)}amino-2-ethyl-6-methoxy-3,4-dihydro-2H-[1,5]naphthyridine-1-carboxylic acid ethyl ester (1.5 g) is dissolved in ethanol (30 ml) and thereto is added acetyl chloride (14 ml) at 0° C. dropwise. After addition dropwise, the mixture is stirred at room temperature overnight. A saturated aqueous sodium hydrogen carbonate solution and ethyl acetate are added to the reaction solution, the organic layer is washed with a saturated brine, dried over magnesium sulfate, and concentrated under reduced pressure. The resulting residue is purified by column chromatography (silica gel; hexane:ethyl acetate=9:1→1:1) to give (2R*,4S*)-4-{[3,5-bis(trifluoromethyl)benzyl]-(5-ethoxycarbonimidoylpyridin-2-yl)}amino-2-ethyl-6-methoxy-3,4-dihydro-2H-[1,5]naphthyridine-1-carboxylic acid ethyl ester (221 mg), [MS (m/z): 654 [M+H]+], (2R*,4S*)-4-{[3,5-bis(trifluoromethyl)benzyl]-(5-carbamoylpyridin-2-yl)}amino-2-ethyl-6-methoxy-3,4-dihydro-2H-[1,5]naphthyridine-1-carboxylic acid ethyl ester (404 mg)[MS (m/z): 626 [M+H]+]and (2R*,4S*)-4-{[3,5-bis(trifluoromethyl)benzyl]-(5-ethoxycarbonylpyridin-2-yl)}amino-2-ethyl-6-methoxy-3,4-dihydro-2H-[1,5]naphthyridine-1-carboxylic acid ethyl ester (596 mg)[MS (m/z): 655 [M+H]+].

Example 205

(2R*,4S*)-4-{[3,5-Bis(trifluoromethyl)benzyl]-(5-ethoxycarbonimidoylpyridin-2-yl)}amino-2-ethyl-6-methoxy-3,4-dihydro-2H-[1,5]naphthyridine-1-carboxylic acid ethyl ester (100 mg) and ethylenediamine (150 µl) are dissolved in ethanol (3 ml), and the mixture is stirred under reflux for 4 hours. After cooling to room temperature, a saturated brine and ethyl acetate are added to the reaction solution. The organic layer is dried over magnesium sulfate, and concentrated under reduced pressure. The resulting residue is purified by column chromatography (NH-silica gel; hexane: ethyl acetate=1:1→1:2) to give (2R*,4S*)-4-{[3,5-bis(trifluoromethyl)benzyl]-[5-(4,5-dihydro-1H-imidazol-2-yl)pyridin-2-yl]}amino-2-ethyl-6-methoxy-3,4-dihydro-2H-[1,5]naphthyridine-1-carboxylic acid ethyl ester (96 mg). MS (m/z): 651 [M+H]+

Example 206

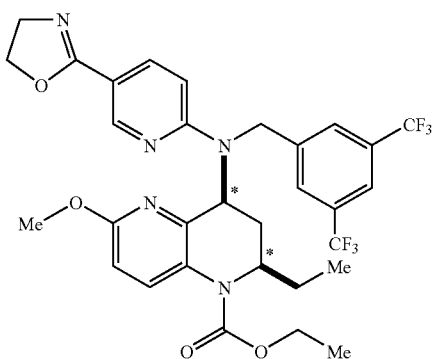

The corresponding starting compounds are treated in a similar manner to Example 205 to give the above compound. MS (m/z): 652 [M+H]+

Example 207

(1) (2R*,4S*)-4-Amino-2-ethyl-6-methoxy-3,4-dihydro-2H-[1,5]naphthyridine-1-carboxylic acid ethyl ester (2.13 g) is dissolved in 1,4-dioxane (40 ml), then thereto are added diisopropylethylamine (4 ml) and 5-chloropyrazine-2-carboxylic acid benzyl ester (1.9 g), and the mixture is heated to 110° C. under nitrogen flow and stirred for 20 hours. After adding distilled water, the mixture is extracted with ether. The organic layer is washed with a saturated brine, dried over magnesium sulfate, and concentrated under reduced pressure. The resulting residue is purified by column chromatography (silica gel; hexane: ethyl acetate=4:1→1:1) to give (2R*,4S*)-4-(5-benzyloxycarbonylpyrazin-2-yl)amino-2-ethyl-6-methoxy-3,4-dihydro-2H-[1,5]naphthyridine-1-carboxylic acid ethyl ester (2.24 g). MS (m/z): 492 [M+H]$^+$ (2) (2R*,4S*)-4-(5-Benzyloxycarbonylpyrazin-2-yl)amino-2-ethyl-6-methoxy-3,4-dihydro-2H-[1,5]naphthyridine-1-carboxylic acid ethyl ester (2.2 g) is dissolved in N,N-dimethylformamide (20 ml), then thereto is added sodium hydride (62.7%, 223 mg) under ice-cooling, and the mixture is stirred for 10 minutes. After adding 3,5-bistrifluorobenzyl bromide (1 ml), the mixture is stirred at room temperature for 20 hours. After adding distilled water, the mixture is extracted with ether. The organic layer is washed with a saturated brine, dried over magnesium sulfate, and concentrated under reduced pressure. The resulting residue is purified by column chromatography (silica gel; hexane: ethyl acetate=9:1→4:1) to give (2R*,4S*)-4-{(5-benzyloxycarbonylpyrazin-2-yl)-[3,5-bis(trifluoromethyl)benzyl]}amino-2-ethyl-6-methoxy-3,4-dihydro-2H-[1,5]naphthyridine-1-carboxylic acid ethyl ester (2.39 g). MS (m/z): 718 [M+H]$^+$ Example 208

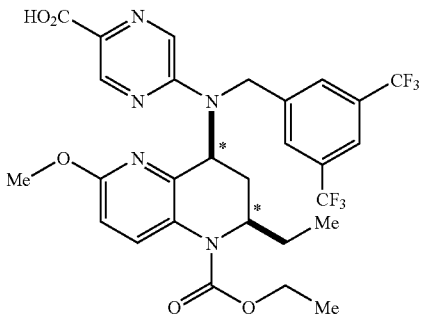

The corresponding starting compounds are treated in a similar manner to Example 7 to give the above compound. MS (m/z): 628 [M+H]$^+$ Example 209

(2R*,4S*)-4-{[3,5-Bis(trifluoromethyl)benzyl]-[5-carboxypyrazin-2-yl]}amino-2-ethyl-6-methoxy-3,4-dihydro-2H-[1,5]naphthyridine-1-carboxylic acid ethyl ester (1 g) is dissolved in toluene (8 mL), then thereto are added triethylamine (0.67 mL) and diphenylphosphoryl azide (0.52 mL), and the mixture is stirred at room temperature under nitrogen flow for 1 hour. After adding a saturated aqueous sodium hydrogen carbonate solution, the mixture is stirred at room temperature for 2 hours. The mixture is extracted with ether, the organic layer is dried over magnesium sulfate, and concentrated under reduced pressure. The resulting residue is dissolved in toluene (8 mL) and stirred at 80° C. for 5 days. After adding water, the mixture is extracted with ether. The organic layer is dried over magnesium sulfate, and concentrated under reduced pressure. The resulting residue is purified by column chromatography (NH-silica gel; hexane: ethyl acetate=4:1→1:1) to give (2R*,4S*)-4-{(5-aminopyrazin-2-yl)-[3,5-bis(trifluoromethyl)benzyl]}amino-2-ethyl-6-methoxy-3,4-dihydro-2H-[1,5]naphthyridine-1-carboxylic acid ethyl ester (540 mg). MS (m/z): 599 [M+H]$^+$ Example 210

(1) (2R*,4S*)-4-Amino-2-ethyl-6-methoxy-3,4-dihydro-2H-[1,5]naphthyridine-1-carboxylic acid ethyl ester (5 g) is dissolved in toluene (50 ml), then thereto are added tris(dibenzylideneacetone)dipalladium (293 mg), sodium tert-butoxide (3.8 g), 2-(di-tert-butylphosphino)biphenyl (376 mg) and 2,6-dichloropyrazine (4.7 g), and the mixture is stirred at room temperature under nitrogen flow for 23 hours. After adding a saturated aqueous sodium hydrogen carbonate solution, the mixture is extracted with ether. The organic layer is washed with a saturated brine, dried over magnesium sulfate, and concentrated under reduced pressure. The resulting residue is purified by column chromatography (silica gel; hexane: ethyl acetate=6:1→3:1) to give (2R*,4S*)-4-(6-chloropyrazin-2-yl)amino-2-ethyl-6-methoxy-3,4-dihydro-2H-[1,5]naphthyridine-1-carboxylic acid ethyl ester (5.3 g). MS (m/z): 392 [M+H]$^+$ (2) (2R*,4S*)-4-(6-Chloropyrazin-2-yl)amino-2-ethyl-6-methoxy-3,4-dihydro-2H-[1,5]naphthyridine-1-carboxylic acid ethyl ester (1.1 g) is dissolved in N,N-dimethylformamide (15 ml), then thereto is added sodium hydride (62.7%, 139.7 mg) under ice-cooling, and the mixture is stirred for 15 minutes. After adding 3,5-bistrifluorobenzyl bromide (0.94 ml), the mixture is stirred at room temperature for 20 hours. After adding distilled water, the mixture is extracted with ether. The organic layer is washed with a saturated brine, dried over magnesium sulfate, and concentrated under reduced pressure. The resulting residue is purified by column chromatography (silica gel; hexane: ethyl acetate=9:1→7:3) to give (2R*,4S*)-4-{[3,5-bis(trifluoromethyl)benzyl]-(6-chloropyrazin-2-yl)}amino-2-ethyl-6-methoxy-3,4-dihydro-2H-[1,5]naphthyridine-1-carboxylic acid ethyl ester (900 mg). MS (m/z): 618/620 [M+H]$^+$ Example 211

(2R*,4S*)-4-{[3,5-Bis(trifluoromethyl)benzyl]-(6-chloropyrazin-2-yl)}amino-2-ethyl-6-methoxy-3,4-dihydro-2H-[1,5]naphthyridine-1-carboxylic acid ethyl ester (300 mg) is dissolved in 1,3-dimethylimidazolidinone (2 ml), then thereto are added diisopropylethylamine (0.13 ml) and morpholine (0.6 ml), and the mixture is heated to 100° C. and stirred for 3 days. After adding distilled water, the mixture is extracted with ether. The organic layer is washed with a saturated brine, dried over magnesium sulfate, and concentrated under reduced pressure. The resulting residue is purified by column chromatography (NH-silica gel; hexane: ethyl acetate=9:1→7:3) to give (2R*,4S*)-4-{[3,5-bis(trifluoromethyl)benzyl]-[6-(morpholin-4-yl)pyrazin-2-yl]}amino-2-ethyl-6-methoxy-3,4-dihydro-2H-[1,5]naphthyridine-1-carboxylic acid ethyl ester (223.2 mg). MS (m/z): 669 [M+H]$^+$ Examples 212 and 213

The corresponding starting compounds are treated in a similar manner to Example 211 to give the compounds as listed in Table 23.

TABLE 23

| Example No. | R | Physical properties, etc. |
|---|---|---|
| 212 | Me-O-CH2CH2-NH- | MS (m/z): 657 [M + H]+ |
| 213 | Me-O-CH2CH2-N(Me)- | MS (m/z): 671 [M + H]+ |

Example 214

(1) (2R*,4S*)-4-Amino-2-ethyl-6-methoxy-3,4-dihydro-2H-[1,5]naphthyridine-1-carboxylic acid ethyl ester (300 mg) is dissolved in isopropanol (5 ml), then thereto are added copper iodide (10.3 mg), ethylene glycol (0.12 ml), potassium phosphate (454 mg) and 4-(5-iodopyrimidin-2-yl)morpholine (311.5 mg), and the mixture is heated to 80° C. and stirred under nitrogen flow for 20 hours. After adding distilled water, the mixture is extracted with ether. The organic layer is washed with a saturated brine, dried over magnesium sulfate, and concentrated under reduced pressure. The resulting residue is purified by column chromatography (NH-silica gel; hexane: ethyl acetate=17:3→3:1) to give (2R*,4S*)-2-ethyl-6-mithoxy-4-[2-(morpholin-4-yl)pyrimidin-5-yl]amino-3,4-dihydro-2H-[1,5]naphthyridine-1-carboxylic acid ethyl ester (122.2 mg). MS (m/z): 443 [M+H]+

(2) (2R*,4S*)-2-Ethyl-6-methoxy-4-[2-(morpholin-4-yl)pyrimidin-5-yl]amino-3,4-dihydro-2H-[1,5]naphthyridine-1-carboxylic acid ethyl ester (50 mg) is dissolved in acetonitrile (0.5 ml), then thereto is added sodium hydride (62.7%, 5.4 mg) at room temperature, and the mixture is stirred for 10 minutes. After adding 3,5-bis(trifluoromethyl)benzyl bromide (27 µl), the mixture is stirred for 22 hours. After adding distilled water, the mixture is extracted with ether. The organic layer is washed with a saturated brine, dried over magnesium sulfate, and concentrated under reduced pressure. The resulting residue is purified by column chromatography (silica gel; hexane: ethyl acetate=9:1→4:1) to give (2R*,4S*)-4-{[3,5-bis(trifluoromethyl)benzyl]-[2-(morpholin-4-yl)pyrimidin-5-yl]}amino-2-ethyl-6-methoxy-3,4-dihydro-2H-[1,5]naphthyridine-1-carboxylic acid ethyl ester (24.8 mg). MS (m/z): 669 [M+H]+

Example 215

(2R,4S)-4-{[3,5-Bis(trifluoromethyl)benzyl]-[5-(morpholin-4-yl)pyrimidin-2-yl]}amino-2-ethyl-6-trifluoromethanesulfonyloxy-3,4-dihydro-2H-[1,5]naphthyridine-1-carboxylic acid ethyl ester (250 mg) is dissolved in 1,4-dioxane (3 ml), and thereto are added a catalytic amount of tetrakis(triphenylphosphine)palladium, a catalytic amount of silver carbonate and a catalytic amount of copper (I) chloride under nitrogen flow. After adding dropwise a triethylaluminum-hexane solution (1M, 480 µl), the mixture is stirred at 60° C. for 30 minutes. After cooling to room temperature, a saturated aqueous sodium hydrogen carbonate solution and ethyl acetate are added to the reaction solution. The organic layer is washed with a saturated brine, dried over magnesium sulfate, and concentrated under reduced pressure. The resulting residue is purified by column chromatography (NH-silica gel; hexane: ethyl acetate=9:1→4:1) to give (2R,4S)-4-{[3,5-bis(trifluoromethyl)benzyl]-[5-(morpholin-4-yl)-pyrimidin-2-yl]}amino-2,6-diethyl-3,4-dihydro-2H-[1,5]naphthyridine-1-carboxylic acid ethyl ester (83 mg); MS (m/z): 667 [M+H]+ and (2R,4S)-4-{[3,5-bis(trifluoromethyl)benzyl]-[5-(morpholin-4-yl)pyrimidin-2-yl]}amino-2-ethyl-3,4-dihydro-2H-[1,5]naphthyridine-1-carboxylic acid ethyl ester (77mg). MS (m/z): 639 [M+H]+.

Example 216

(2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid ethyl ester (18 g) is dissolved in N,N-dimethylformamide (60 ml), and thereto are added palladium acetate (611 mg), 1,1'-bis(diphenylphosphino)-ferrocene (3.02 g), ethanol (31.7 ml) and triethylamine (37.9 ml). The mixture is purged by carbon monoxide at room temperature for 10 minutes, then is heated at 90° C. and stirred overnight under carbon monoxide. The reaction solution is cooled to room temperature, and thereto is added saturated brine and extracted with ethyl acetate. The organic layer is washed with saturated brine, dried over magnesium sulfate, and concentrated under reduced pressure. The resulting residue is purified by column chromatography (silica gel; hexane:ethyl acetate=8:1) to give (2R,4S)-4-{[3,5-bis(trifluoromethyl)benzyl]-(5-ethoxycarbonylpyrimidin-2-yl)}amino-2-ethyl-6-methoxy-3,4-dihydro-2H-[1,5]naphthyridine-1-carboxylic acid ethyl ester (12.4 g). MS (m/z): 656 [M+H]+.

Example 217

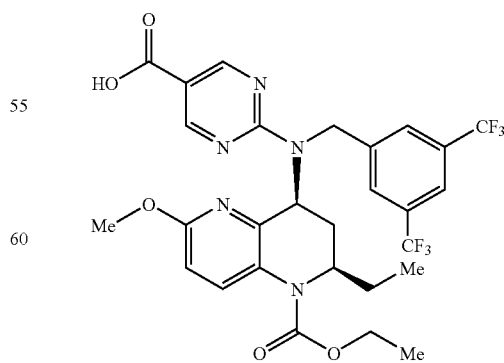

A corresponding starting compound is treated in a similar manner to Example 36 to give the compound of Example 217. MS (m/z): 628 [M+H]+

Example 218

(2R,4S)-4-{[3,5-Bis(trifluoromethyl)benzyl]-(5-carboxy-pyrimidin-2-yl)}amino-2-ethyl-6-methoxy-3,4-dihydro-2H-[1,5]naphthyridine-1-carboxylic acid ethyl ester (200 mg) is dissolved in N,N-dimethylformamide (2 ml), and thereto are added triethylamine (53 μl), 3-methylaminopropionic acid tert-butyl ester hydrochloride (101.14 mg), 1-hydroxybenzotriazole hydrate (65 mg) and 1-(3-dimethylaminopropyl)-3-ethylcarbodiimide hydrochloride (92 mg) under ice-cooling. The mixture is stirred at room temperature for 21 hours. The reaction solution is concentrated under reduced pressure, then the residue is partitioned by adding a saturated aqueous sodium bicarbonate solution and ethyl acetate, and the organic layer is concentrated under reduced pressure. The resulting residue is dissolved in a solution (2 ml) of 4N hydrochloric acid in 1,4-dioxane and stirred at room temperature for 1 hour. To the reaction solution is added excessive saturated aqueous sodium bicarbonate solution, and the mixture is neutralized with 1N HCl, then extracted with ethyl acetate and concentrated under reduced pressure. The resulting residue is purified by column chromatography (silica gel; chloroform:methanol=1:0→19:1) to give (2R,4S)-4-([3,5-bis-(trifluoromethyl)benzyl]-{5-[(2-carboxyethyl)methylcarbamoyl]pyrimidin-2-yl})amino-2-ethyl-6-methoxy-3,4-dihydro-2H-[1,5]naphthyridine-1-carboxylic acid ethyl ester (223 mg). MS (m/z): 713 [M+H]+.

Example 219

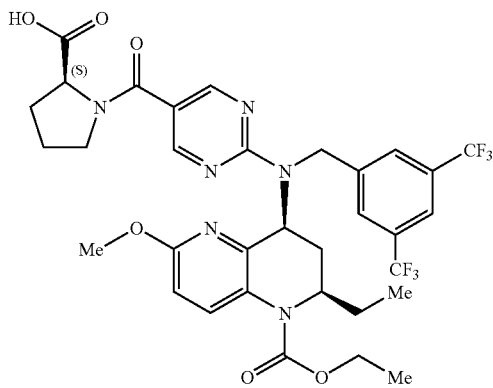

A corresponding starting compound is treated in a similar manner to Example 218 to give the compound of Example 219. MS (m/z): 725 [M+H]+

Example 220

(2R,4S)-4-{[3,5-Bis(trifluoromethyl)benzyl]-(5-carboxy-pyrimidin-2-yl)}amino-2-ethyl-6-methoxy-3,4-dihydro-2H-[1,5]naphthyridine-1-carboxylic acid ethyl ester (200 mg) is dissolved in N,N-dimethylformamide (2 ml), and thereto are added triethylamine (53 μl), 3-aminopropionic acid methyl ester hydrochloride (67 mg), 1-hydroxybenzotriazole hydrate (65 mg) and 1-(3-dimethylaminopropyl)-3-ethylcarbodiimide hydrochloride (92 mg) under ice-cooling. The mixture is stirred for 21 hours. The reaction solution is concentrated under reduced pressure, then the residue is partitioned by adding a saturated aqueous sodium bicarbonate solution and ethyl acetate, and the organic layer is concentrated under reduced pressure. The resulting residue is dissolved in methanol (2 ml), and thereto is added 5N aqueous NaOH solution (1 ml), and the mixture is stirred at room temperature for 2 hours. To the reaction solution is added 6N HCl (0.85 ml), and then the mixture is extracted with ethyl acetate and the organic layer is concentrated under reduced pressure. The resulting residue is purified by column chromatography (silica gel; chloroform:methanol=1:0→19: 1) to give (2R, 4S)-4-([3,5-bis(trifluoromethyl)benzyl]-{5-[(2-carboxyethyl)carbamoyl]pyrimidin-2-yl})amino-2-ethyl-6-methoxy-3,4-dihydro-2H-[1,5]naphthyridine-1-carboxylic acid ethyl ester (190 mg). MS (m/z): 699 [M+H]+.

Examples 221-222

Corresponding starting compounds are treated in a similar manner to Example 220 to give the compounds listed in Table 24.

TABLE 24

| Example No. | R | Physical properties, etc. |
|---|---|---|
| 221 | HO–CH2–C(O)–NH–Me | MS (m/z): 685 [M + H]+ |
| 222 | HO–CH2–C(O)–N(Me)–Me | MS (m/z): 699 [M + H]+ |

Example 223

(1) (2R,4S)-4-{[3,5-Bis(trifluoromethyl)benzyl]-(5-carboxypyrimidin-2-yl)}amino-2-ethyl-6-methoxy-3,4-dihydro-2H-[1,5]naphthyridine-1-carboxylic acid ethyl ester (200 mg) is dissolved in N,N-dimethylformamide (2 ml), and thereto are added triethylamine (67 μl), O-(tert-butyldimethylsilyl)-serine methyl ester (112.02 mg), 1-hydroxybenzotriazole hydrate (64.86 mg) and 1-(3-dimethylaminopropyl)-3-ethylcarbodiimide hydrochloride (92.02 mg). The mixture is stirred at room temperature for 2.5 hours. The reaction solution is concentrated under reduced pressure, then the residue is partitioned by adding a saturated aqueous sodium bicarbonate solution and ethyl acetate, and the organic layer is concentrated under reduced pressure. The resulting residue is dissolved in tetrahydrofuran (2 ml), and thereto is added 1M tetrabutylammonium fluoride-tetrahydrofuran solution (0.55 ml)

and the mixture is stirred at room temperature for 10 minutes. The reaction solution is concentrated under reduced pressure, and the resulting residue is purified by column chromatography (silica gel; chloroform:methanol=1: 0→19:1) to give (2R,4S)-4-{[3,5-bis(trifluoromethyl)benzyl]-[5-(2-hydroxy-1-methoxy-carbonylethylcarbamoyl) pyrimidin-2-yl]}amino-2-ethyl-6-methoxy-3,4-dihydro-2H-[1,5]naphthyridine-1-carboxylic acid ethyl ester (229.5 mg). MS (m/z): 729 [M+H]$^+$.

(2) (2R,4S)-4-{[3,5-Bis(trifluoromethyl)benzyl]-[5-(2-hydroxy-1-methoxycarbonylethylcarbamoyl)pyrimidin-2-yl]}amino-2-ethyl-6-methoxy-3,4-dihydro-2H-[1,5] naphthyridine-1-carboxylic acid ethyl ester (220 mg) is dissolved in methanol (3 ml), and thereto is added 2N aqueous NaOH solution (3 ml), and the mixture is stirred at room temperature for 23 hours. The reaction solution is partitioned by adding 6N HCl (1 ml) and chloroform, and the organic layer is dried over magnesium sulfate, then concentrated under reduced pressure. The resulting residue is purified by column chromatography (silica gel; chloroform:methanol=49:1→19:1) to give (2R,4S)-4-{[3,5-bis (trifluoromethyl)benzyl]-[5-(1-carboxy-2-hydroxy-ethyl-carbamoyl)pyrimidin-2-yl]}amino-2-ethyl-6-methoxy-3, 4-dihydro-2H-[1,5]naphthyridine-1-carboxylic acid ethyl ester (133.5 mg). MS (m/z): 713 [M−H]$^-$.

Example 224

(1) (2R,4S)-4-{[3,5-Bis(trifluoromethyl)benzyl]-(5-bromopyrimidin-2-yl)}amino-2-ethyl-6-methoxy-3,4-dihydro-2H-[1,5]naphthyridine-1-carboxylic acid ethyl ester (300 mg) is dissolved in toluene (5 ml), and thereto are added tris(dibenzylideneacetone)dipalladium (41 mg), sodium tert-butoxide (65 mg), 2-(di-tert-butylphosphino) biphenyl (54 mg) and 3-methylaminopropionic acid tert-butyl ester (108 mg). The mixture is stirred overnight under nitrogen at room temperature. The reaction solution is cooled to room temperature, then partitioned by adding ethyl acetate and saturated brine. The organic layer is washed with saturated brine and dried over magnesium sulfate, then concentrated under reduced pressure. The resulting residue is purified by column chromatography (silica gel; hexane:ethyl acetate=9:1→3:1) to give (2R, 4S)-4-[[3,5-bis-(trifluoromethyl)benzyl]-(5-{[methyl-(2-tert-butoxycarbonylethyl)]amino}-pyrimidin-2-yl)] amino-2-ethyl-6-methoxy-3,4-dihydro-2H-[1,5] naphthyridine-1-carboxylic acid ethyl ester (106 mg). MS (m/z): 741 [M+H]$^+$.

(2) (2R,4S)-4-[[3,5-Bis(trifluoromethyl)benzyl]-(5-{[methyl-(2-tert-butoxycarbonylethyl)]amino}pyrimidin-2-yl)]amino-2-ethyl-6-methoxy-3,4-dihydro-2H-[1,5]naphthyridine-1-carboxylic acid ethyl ester (100 mg) is dissolved in 4N HCl/ethyl acetate solution (1 ml), and stirred at room temperature for 30 minutes. The reaction solution is partitioned by adding a saturated aqueous sodium hydrogen carbonate solution and ethyl acetate. The organic layer is washed with saturated brine, dried over magnesium sulfate, then concentrated under reduced pressure, and the resulting residue is purified by column chromatography (silica gel; hexane:ethyl acetate=4:1→0:1) to give (2R,4S)-4-[[3,5-bis(trifluoromethyl)-benzyl]-(5-{[methyl-(2-carboxyethyl)]amino}pyrimidin-2-yl)]amino-2-ethyl-6-methoxy-3,4-dihydro-2H-[1,5]naphthyridine-1-carboxylic acid ethyl ester (55 mg). MS (m/z): 685 [M+H]$^+$.

Example 225

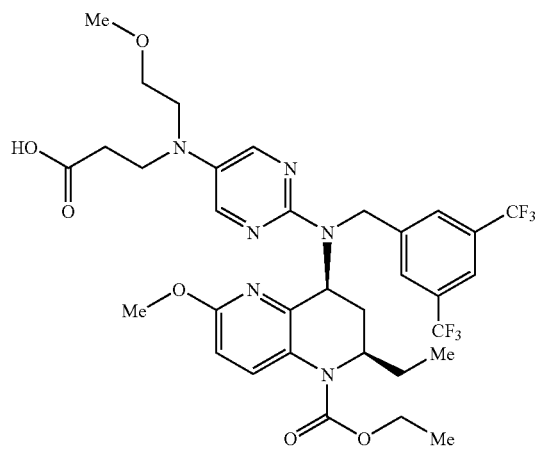

A corresponding starting compound is treated in a similar manner to Example 224 to give the compound of Example 225. MS (m/z): 729 [M+H]$^+$ Example 226

(1) (2R,4S)-4-{[3,5-Bis(trifluoromethyl)benzyl]-(5-carboxypyrimidin-2-yl)}amino-2-ethyl-6-methoxy-3,4-dihydro-2H-[1,5]naphthyridine-1-carboxylic acid ethyl ester (1 g) is dissolved in toluene (25 ml), and thereto are added triethylamine (0.66 ml), diphenylphosphoryl azide (0.52 ml) and benzyl alcohol (0.2 ml). The mixture is heated at 90° C. and stirred overnight. The reaction solution is cooled to room temperature, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; hexane: ethyl acetate=4:1→3:2) to give (2R,4S)-4-{(5-benzyloxy-carbonylaminopyrimidin-2-yl)-[3,5-bis(trifluoromethyl) benzyl]}amino-2-ethyl-6-methoxy-3,4-dihydro-2H-[1,5] naphthyridine-1-carboxylic acid ethyl ester (1.1 g). MS (m/z): 733 [M+H]$^+$.

(2) (2R,4S)-4-{(5-Benzyloxycarbonylaminopyrimidin-2-yl)-[3,5-bis-(trifluoromethyl)benzyl]}amino-2-ethyl-6-methoxy-3,4-dihydro-2H-[1,5]naphthyridine-1-carboxylic acid ethyl ester (1.1 g) is dissolved in N,N-dimethylformamide (15 ml), and thereto is added 63% sodium hydride (69 mg) under ice-cooling. The reaction mixture is stirred for 30 minutes, and thereto is added ethyl 4-bromobutyrate (0.33 ml) under ice-cooling, and the mixture is stirred at room temperature for 2.5 hours. The mixture is partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (NH-silica gel; hexane:ethyl acetate=9:1→7:3) to give (2R,4S)-4-({5-[benzyloxycarbonyl-(3-ethoxycarbonyl-propyl)]aminopyrimidin-2-yl}-[3,5-bis(trifluoromethyl)

benzyl])amino-2-ethyl-6-methoxy-3,4-dihydro-2H-[1,5]naphthyridine-1-carboxylic acid ethyl ester (898 mg). MS (m/z): 847 [M+H]⁺.

(3) (2R,4S)-4-({5-[Benzyloxycarbonyl-(3-ethoxycarbonylpropyl)]-aminopyrimidin-2-yl}-[3,5-bis(trifluoromethyl)benzyl])amino-2-ethyl-6-methoxy-3,4-dihydro-2H-[1,5]naphthyridine-1-carboxylic acid ethyl ester (300 mg) is dissolved in methanol (12 ml), and thereto is added 1N aqueous NaOH solution (2 ml). The mixture is stirred at room temperature for 1 day. To the mixture is added 1N HCl, and the reaction solution is concentrated under reduced pressure. The residue is partitioned by adding ethyl acetate. The organic layer is washed with saturated brine and dried over magnesium sulfate, then concentrated under reduced pressure. The resulting residue is purified by column chromatography (silica gel; chloroform:methanol=1:0→9:1) to give (2R,4S)-4-({5-[benzyloxycarbonyl-(3-carboxypropyl)]aminopyrimidin-2-yl}-[3,5-bis(trifluoromethyl)-benzyl])amino-2-ethyl-6-methoxy-3,4-dihydro-2H-[1,5]naphthyridine-1-carboxylic acid ethyl ester (219 mg). MS (m/z): 819 [M+H]⁺.

(4) (2R,4S)-4-({5-[Benzyloxycarbonyl-(3-carboxypropyl)]aminopyrimidin-2-yl}-[3,5-bis(trifluoromethyl)benzyl])amino-2-ethyl-6-methoxy-3,4-dihydro-2H-[1,5]naphthyridine-1-carboxylic acid ethyl ester (154 mg) is dissolved in methanol (5 ml), and thereto is added 10% palladium-carbon (25 mg). The mixture is stirred for 1.5 hours under hydrogen. The reaction solution is filtered, and then concentrated under reduced pressure. The resulting residue is purified by column chromatography (silica gel; chloroform:methanol=9:1→7:3) to give (2R,4S)-4-{[3,5-bis(trifluoromethyl)-benzyl]-[5-(3-carboxypropyl)aminopyrimidin-2-yl]}amino-2-ethyl-6-methoxy-3,4-dihydro-2H-[1,5]naphthyridine-1-carboxylic acid ethyl ester (98 mg). MS (m/z): 685 [M+H]⁺.

Example 227

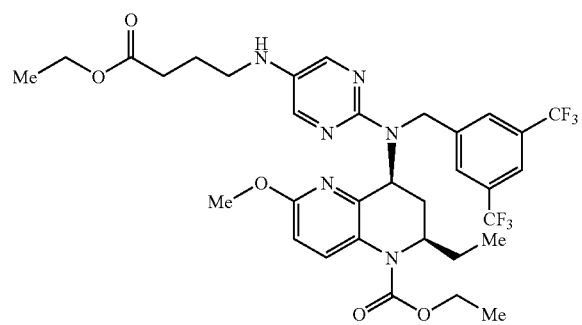

A corresponding starting compound is treated in a similar manner to Example 226 (4) to give the compound of Example 227. MS (m/z): 599 [M+H]⁺

Example 228

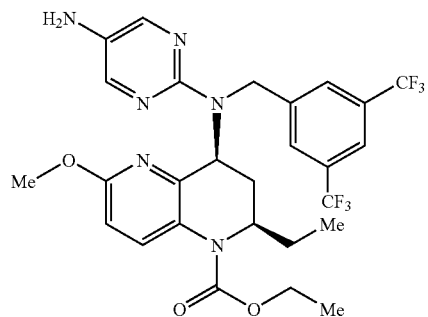

A corresponding starting compound is treated in a similar manner to Example 14 to give the compound of Example 228. MS (m/z): 657 [M+H]⁺

Example 229

(2R,4S)-4-{(5-Aminopyrimidin-2-yl)-[3,5-bis(trifluoromethyl)benzyl]}-amino-2-ethyl-6-methoxy-3,4-dihydro-2H-[1,5]naphthyridine-1-carboxylic acid ethyl ester (500 mg) is dissolved in acetonitrile (10 ml), and thereto is added oxetan-2-one (0.08 ml). The mixture is heated to reflux for 3 days. The reaction solution is cooled to room temperature, and concentrated under reduced pressure. The resulting residue is purified by column chromatography (silica gel; chloroform:methanol=1:0→4:1) to give (2R,4S)-4-{[3,5-bis(trifluoromethyl)benzyl]-[5-(2-carboxyethyl)amino-pyrimidin-2-yl]}amino-2-ethyl-6-methoxy-3,4-dihydro-2H-[1,5]naphthyridine-1-carboxylic acid ethyl ester (199 mg). MS (m/z): 671 [M+H]⁺.

Example 230

(2R,4S)-4-{[3,5-Bis(trifluoromethyl)benzyl]-[5-(2-carboxyethyl)-aminopyrimidin-2-yl]}amino-2-ethyl-6-methoxy-3,4-dihydro-2H-[1,5]naphthyridine-1-carboxylic acid ethyl ester (300 mg) is dissolved in a mixture of tetrahydrofuran (5 ml) and methanol (1 ml), and thereto is added a 2.0M solution of trimethylsilyl diazomethane in hexane (0.5 ml). The mixture is stirred at room temperature for 30 minutes. The reaction solution is concentrated under reduced pressure, and the resulting residue is purified by column chromatography (silica gel; hexane:ethyl acetate=7:3→3:2) to give (2R,4S)-4-{[3,5-bis(trifluoromethyl)benzyl]-[5-(2-methoxy-carbonylethyl)aminopyrimidin-2-yl]}amino-2-ethyl-6-methoxy-3,4-dihydro-2H-[1,5]naphthyridine-1-carboxylic acid ethyl ester (232 mg). MS (m/z): 685 [M+H]⁺.

Example 231

(1) (2R,4S)-4-{(5-Benzyloxycarbonylaminopyrimidin-2-yl)-[3,5-bis-(trifluoromethyl)benzyl]}amino-2-ethyl-6-methoxy-3,4-dihydro-2H-[1,5]naphthyridine-1-carboxylic acid ethyl ester (300 mg) is dissolved in tetrahydrofuran (5 ml), and thereto is added 63% sodium hydride (20 mg) under ice-cooling. The mixture is stirred for 30 minutes, and thereto is added methyl iodide (30 µl) under ice-cooling. The resulting mixture is stirred overnight at room temperature, and then partitioned by adding water and ethyl acetate. The organic layer is washed with saturated brine and dried over magnesium sulfate, then concentrated under reduced pressure. The resulting residue is purified by column chromatography (silica gel; hexane:ethyl acetate=9:1-4:1) to give (2R,4S)-4-[[3,5-bis(trifluoromethyl)benzyl]-(5-{[methyl-(benzyloxycarbonyl)]amino}-pyrimidin-2-yl)]amino-2-ethyl-6-methoxy-3,4-dihydro-2H-[1,5]naphthyridine-1-carboxylic acid ethyl ester (275 mg). MS (m/z): 747 [M+H]$^+$.

(2) (2R,4S)-4-[[3,5-Bis(trifluoromethyl)benzyl]-(5-{[methyl-(benzyloxycarbonyl)]amino}pyrimidin-2-yl)]amino-2-ethyl-6-methoxy-3,4-dihydro-2H-[1,5]naphthyridine-1-carboxylic acid ethyl ester (1.34 g) is dissolved in methanol (20 ml), and thereto is added 10% palladium-carbon (250 mg). The mixture is stirred for 3 hours under hydrogen. The reaction solution is filtered, and then the filtrate is concentrated under reduced pressure. The resulting residue is purified by column chromatography (NH-silica gel; hexane:ethyl acetate=17:3→7:3) to give (2R,4S)-4-{[3,5-bis-(trifluoromethyl)benzyl]-(5-methylaminopyrimidin-2-yl)}amino-2-ethyl-6-methoxy-3,4-dihydro-2H-[1,5]naphthyridine-1-carboxylic acid ethyl ester (698 mg). MS (m/z): 613 [M+H]$^+$.

Example 232

(2R,4S)-4-{[3,5-Bis(trifluoromethyl)benzyl]-(5-methylaminopyrimidin-2-yl)}amino-2-ethyl-6-methoxy-3,4-dihydro-2H-[1,5]naphthyridine-1-carboxylic acid ethyl ester (150 mg) is dissolved in N,N-dimethylformamide (5 ml), and thereto are added ethyl 4-bromobutyrate (13 µl) and potassium carbonate (50 mg). The mixture is heated at 50° C. and stirred for 2 hours. The reaction solution is cooled to room temperature, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; hexane:ethyl acetate=9:1→3:2) to give (2R,4S)-4-([3,5-bis(trifluoromethyl)benzyl]-{5-[(3-ethoxycarbonylpropyl)-methyl]aminopyrimidin-2-yl})amino-2-ethyl-6-methoxy-3,4-dihydro-2H-[1,5]naphthyridine-1-carboxylic acid ethyl ester (85 mg). MS (m/z): 727 [M+H]$^+$.

Example 233

(1) (2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid ethyl ester (300 mg) is dissolved in toluene (4 ml), and thereto are added tris(dibenzylideneacetone)dipalladium (42 mg), sodium tert-butoxide (65 mg), 2-(di-tert-butylphosphino) biphenyl (54 mg) and piperidin-4-yl-ethyl acetate (116 mg). The mixture is stirred overnight at room temperature under nitrogen flow, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (NH-silica gel; hexane:ethyl acetate=9:1→7:3) to give (2R,4S)-4-{[3,5-bis(trifluoromethyl)benzyl]-[5-(4-ethoxy-carbonylmethylpiperazin-1-yl)pyrimidin-2-yl]}amino-2-ethyl-6-methoxy-3,4-dihydro-2H-[1,5]naphthyridine-1-carboxylic acid ethyl ester (125 mg). MS (m/z): 753 [M+H]$^+$.

(2) (2R,4S)-4-{[3,5-Bis(trifluoromethyl)benzyl]-[5-(4-ethoxycarbonyl-methylpiperazin-1-yl)pyrimidin-2-yl]}amino-2-ethyl-6-methoxy-3,4-dihydro-2H-[1,5]naphthyridine-1-carboxylic acid ethyl ester (106 mg) is dissolved in methanol (8 ml), and thereto is added 1N aqueous NaOH solution (3 ml). The mixture is stirred at room temperature for 3.5 hours, and partitioned by adding 1N HCl and ethyl acetate. The organic layer is washed with saturated brine and dried over magnesium sulfate, then concentrated under reduced pressure. The resulting residue is purified by column chromatography (silica gel; chloroform:methanol=1:0→9:1) to give (2R,4S)-4-{[3,5-bis(trifluoromethyl)benzyl]-[5-(4-carboxymethylpiperazin-1-yl)pyrimidin-2-yl]}amino-2-ethyl-6-methoxy-3,4-dihydro-2H-[1,5]naphthyridine-1-carboxylic acid ethyl ester (70 mg). MS (m/z): 725 [M+H]$^+$.

(3) (2R,4S)-4-{[3,5-Bis(trifluoromethyl)benzyl]-[5-(4-carboxymethyl-piperazin-1-yl)pyrimidin-2-yl]}amino-2-ethyl-6-methoxy-3,4-dihydro-2H-[1,5]naphthyridine-1-carboxylic acid ethyl ester (62 mg) is dissolved in ethanol (3 ml), and thereto is added 1N aqueous NaOH solution (84 µl). The mixture is stirred at room temperature for 5 minutes. The reaction solution is concentrated under reduced pressure to give (2R,4S)-4-{[3,5-bis-(trifluoromethyl)benzyl]-[5-(4-carboxymethylpiperazin-1-yl)pyrimidin-2-yl]}-amino-2-ethyl-6-methoxy-3,4-dihydro-2H-[1,5]naphthyridine-1-carboxylic acid ethyl ester sodium salt (56 mg). MS (m/z): 723 [M−Na]$^−$.

Examples 234-235

Corresponding starting compounds are treated in a similar manner to Example 233 (1)-(2) to give the compounds listed in Table 25.

TABLE 25

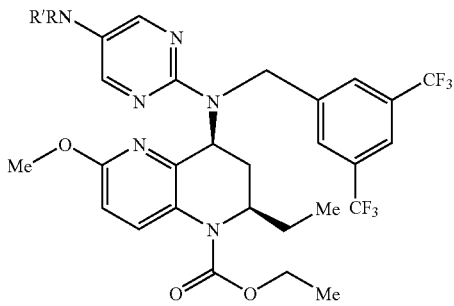

| Example No. | R'RN— | Physical properties, etc. |
|---|---|---|
| 234 | (piperidine-4-carboxylic acid) | MS (m/z): 711 [M + H]$^+$ |
| 235 | (morpholine-3-carboxylic acid) | MS (m/z): 713 [M + H]$^+$ |

Example 236

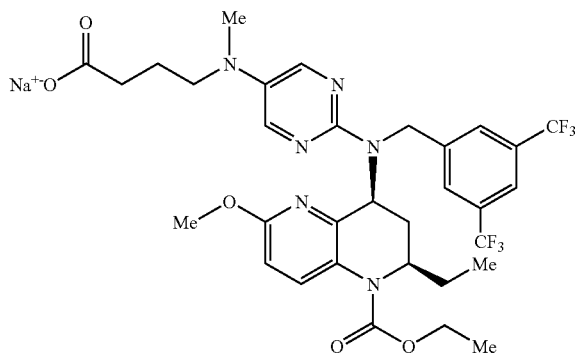

A corresponding starting compound is treated in a similar manner to Example 233 (2)-(3) to give the compound of Example 236. MS (m/z): 697 [M−Na]⁻

Examples 237-238

Corresponding starting compounds are treated in a similar manner to Example 233 (3) to give the compounds listed in Table 26.

TABLE 26

| Example No. | R'RN— | Physical properties, etc. |
|---|---|---|
| 237 | (Na⁺O-carbonyl-piperidin-1-yl) | MS (m/z): 711 [M + H]⁺ |
| 238 | (Na⁺O-propanoyl-NHMe) | MS (m/z): 669 [M − Na]⁻ |

Example 239

(2R,4S)-4-{[3,5-Bis(trifluoromethyl)benzyl]-[5-(piperazin-1-yl)pyrimidin-2-yl]}amino-2-ethyl-6-methoxy-3,4-dihydro-2H-[1,5]naphthyridine-1-carboxylic acid ethyl ester (200 mg) is dissolved in ethanol (3 ml), and thereto are added sodium bicarbonate (76.4 mg) and cyanogen bromide (35 mg). The mixture is stirred at room temperature for 13 hours, and partitioned by adding water and diethyl ether to the reaction solution. The resulting mixture is washed with saturated brine, then dried over magnesium sulfate, and concentrated under reduced pressure. The resulting residue is purified by column chromatography (silica gel; hexane:ethyl acetate=4:1→3:2) to give (2R,4S)-4-{[3,5-bis(trifluoromethyl)-benzyl]-[5-(4-cyanopiperazin-1-yl)pyrimidin-2-yl]}amino-2-ethyl-6-methoxy-3,4-dihydro-2H-[1,5]naphthyridine-1-carboxylic acid ethyl ester (183 mg). MS (m/z): 693 [M+H]⁺.

Example 240

(1) Hydroxylamine hydrochloride (45.2 mg) is dissolved in dimethylsulfoxide (1.5 ml), and thereto is added triethylamine (90.6 μl). To the reaction solution is added tetrahydrofuran, and the insoluble materials are removed by filtration and the filtrate is evaporated to remove tetrahydrofuran under reduced pressure. To the resulting solution is added (2R,4S)-4-{[3,5-bis(trifluoromethyl)benzyl]-[5-(4-cyanopiperazin-1-yl)pyrimidin-2-yl]}amino-2-ethyl-6-methoxy-3,4-dihydro-2H-[1,5]naphthyridine-1-carboxylic acid ethyl ester (80 mg), and the mixture is heated at 75° C. and stirred for 15 hours. The reaction solution is cooled to room temperature, and partitioned by adding water and ethyl acetate. The organic layer is washed with water and saturated brine, dried over magnesium sulfate, then concentrated under reduced pressure to give the crude material of (2R,4S)-4-([3,5-bis(trifluoromethyl)benzyl]-{5-[4-(N-hydroxycarbamimidoyl)piperazin-1-yl]pyrimidin-2-yl})amino-2-ethyl-6-methoxy-3,4-dihydro-2H-[1,5]naphthyridine-1-carboxylic acid ethyl ester. MS (m/z): 726 [M+H]⁺.

(2) The crude material of (2R,4S)-4-([3,5-bis(trifluoromethyl)benzyl]-{5-[4-(N-hydroxycarbamimidoyl)piperazin-1-yl]pyrimidin-2-yl})amino-2-ethyl-6-methoxy-3,4-dihydro-2H-[1,5]naphthyridine-1-carboxylic acid ethyl ester is dissolved in acetonitrile (1 ml), and thereto is added carbodiimidazole (29 mg). The mixture is heated at 60° C. and stirred for 17 hours. The reaction solution is cooled to room temperature, and partitioned by adding 1N HCl and ethyl acetate. The resulting solution is washed with water and saturated brine, then dried over magnesium sulfate, and concentrated under reduced pressure. The resulting residue is purified by column chromatography (silica gel; chloroform:methanol=1:0→9:1) to give (2R,4S)-4-([3,5-bis(trifluoromethyl)benzyl]-{5-[4-(5-oxo-4,5-dihydro-[1,2,4]oxadiazol-3-yl)piperazin-1-yl]pyrimidin-2-yl}) amino-2-ethyl-6-methoxy-3,4-dihydro-2H-[1,5] naphthyridine-1-carboxylic acid ethyl ester (42 mg). MS (m/z): 752 [M+H]⁺.

Example 241

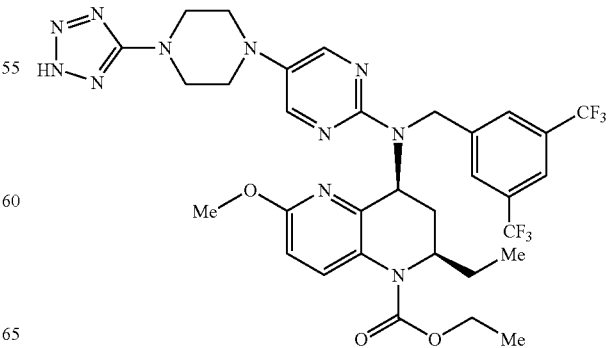

A corresponding starting compound is treated in a similar manner to Example 147 to give the compound of Example 241. MS (m/z): 736 [M+H]+

Example 242

(1) (2R,4S)-4-{(5-Aminopyrimidin-2-yl)-[3,5-bis(trifluoromethyl)benzyl]}-amino-2-ethyl-6-methoxy-3,4-dihydro-2H-[1,5]-naphthyridine-1-carboxylic acid ethyl ester (200 mg) is dissolved in N,N-dimethylformamide (4 ml), and thereto are added 4-tert-butyl (S)-2-tert-butoxycarbonylaminosuccinate (123 mg) and 1-hydroxybenzotriazole (68 mg), then added under ice-cooling 1-(3-dimethylaminopropyl)-3-ethylcarbodiimide monohydrochloride (96 mg) and triethylamine (0.06 ml). The mixture is stirred at room temperature for 2 hours, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; hexane:ethyl acetate=4:1→3:2) to give (2R,4S)-4-{[3,5-bis(trifluoromethyl)benzyl]-[5-((S)-3-tert-butoxycarbonyl-2-tert-butoxycarbonylaminopropionylamino)pyrimidin-2-yl]}amino-2-ethyl-6-methoxy-3,4-dihydro-2H-[1,5]-naphthyridine-1-carboxylic acid ethyl ester (242 mg). MS (m/z): 870 [M+H]+.

(2) (2R,4S)-4-{[3,5-Bis(trifluoromethyl)benzyl]-[5-((S)-3-tert-butoxy-carbonyl-2-tert-butoxycarbonylaminopropionylamino)pyrimidin-2-yl]}-amino-2-ethyl-6-methoxy-3,4-dihydro-2H-[1,5]-naphthyridine-1-carboxylic acid ethyl ester (235 mg) is dissolved in dichloromethane (10 ml), and thereto is added trifluoroacetic acid (1 ml). The mixture is stirred at room temperature for 2 hours, and then concentrated under reduced pressure. The resulting residue is purified by column chromatography (silica gel; chloroform:methanol=9:1→0:1) to give (2R,4S)-4-{[5-((S)-2-amino-3-carboxypropionylamino)pyrimidin-2-yl]-[3,5-bis(trifluoromethyl)benzyl]}-amino-2-ethyl-6-methoxy-3,4-dihydro-2H-[1,5]-naphthyridine-1-carboxylic acid ethyl ester (103 mg). MS (m/z): 712 [M−H]−.

Example 243

(1) (2R,4S)-4-{(5-Aminopyrimidin-2-yl)-[3,5-bis(trifluoromethyl)benzyl]}-amino-2-ethyl-6-methoxy-3,4-dihydro-2H-[1,5]naphthyridine-1-carboxylic acid ethyl ester (273 mg) is dissolved in N,N-dimethylformamide (5 ml), and thereto are added methyl 3-chlorocarbonylpropionate (67 µl) and triethylamine (0.19 ml) under ice-cooling. The mixture is stirred at room temperature for 1 hour, and partitioned by adding water and ethyl acetate. The organic layer is washed with saturated brine and dried over magnesium sulfate, then concentrated under reduced pressure. The resulting residue is purified by column chromatography (silica gel; hexane:ethyl acetate=4:1→1:1) to give (2R,4S)-4-{[3,5-bis(trifluoromethyl)-benzyl]-[5-(3-methoxycarbonylpropionylamino)pyrimidin-2-yl]}amino-2-ethyl-6-methoxy-3,4-dihydro-2H-[1,5]naphthyridine-1-carboxylic acid ethyl ester (138 mg) as a crude product. MS (m/z): 713 [M+H]+.

(2) The crude product (130 mg) of (2R,4S)-4-{[3,5-bis(trifluoromethyl)-benzyl]-[5-(3-methoxycarbonylpropionylamino)pyrimidin-2-yl]}amino-2-ethyl-6-methoxy-3,4-dihydro-2H-[1,5]naphthyridine-1-carboxylic acid ethyl ester is treated in a similar manner to Example 233 (2) to give (2R,4S)-4-{[3,5-bis(trifluoromethyl)benzyl]-[5-(3-carboxypropionylamino)pyrimidin-2-yl]}amino-2-ethyl-6-methoxy-3,4-dihydro-2H-[1,5]naphthyridine-1-carboxylic acid ethyl ester (121 mg). MS (m/z): 699 [M+H]+.

Example 244

(2R,4S)-4-{[3,5-Bis(trifluoromethyl)benzyl]-(5-carboxypyrimidin-2-yl)}amino-2-ethyl-6-methoxy-3,4-dihydro-2H-[1,5]naphthyridine-1-carboxylic acid ethyl ester (500 mg) is dissolved in toluene (10 ml), and thereto are added triethylamine (0.66 ml), diphenylphosphoryl azide (0.52 ml) and methanol (1 ml). The mixture is heated at 60° C. and stirred for 2 days. The reaction solution is cooled to room temperature, a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; hexane:ethyl acetate=4:1→3:2) to give (2R,4S)-4-{[3,5-bis(trifluoromethyl)benzyl]-(5-methoxy-carbonylaminopyrimidin-2-yl)}amino-2-ethyl-6-methoxy-3,4-dihydro-2H-[1,5]naphthyridine-1-carboxylic acid ethyl ester (25 mg). MS (m/z): 657 [M+H]+.

Example 245

(2R,4S)-4-{[3,5-Bis(trifluoromethyl)benzyl]-(5-aminopyrimidin-2-yl)}-amino-2-ethyl-6-methoxy-3,4-dihydro-2H-[1,5]naphthyridine-1-carboxylic acid ethyl ester (400 mg) is dissolved in dichloromethane (5 ml), and thereto are added N,N'-carbonyldiimidazole (162 mg) and triethylamine (0.28 ml). The mixture is stirred at room temperature for 1.5 hours, then thereto is added ethane-1,2-diol (75 µl). The mixture is stirred for 3 days, and partitioned by adding water and ethyl acetate. The organic layer is washed with saturated brine and dried over magnesium sulfate, then concentrated under reduced pressure. The resulting residue is purified by column chromatography (silica gel; chloroform:methanol=1:0→9:1) to give (2R,4S)-4-{[3,5-bis(trifluoromethyl)benzyl]-[5-(2-hydroxyethoxycarbonylamino)pyrimidin-2-yl]}amino-2-ethyl-6-methoxy-3,4-dihydro-2H-[1,5]naphthyridine-1-carboxylic acid ethyl ester (222 mg). MS (m/z): 687 [M+H]+.

Examples 246-248

Corresponding starting compounds are treated in a similar manner to Example 245 to give the compounds listed in Table 27.

TABLE 27

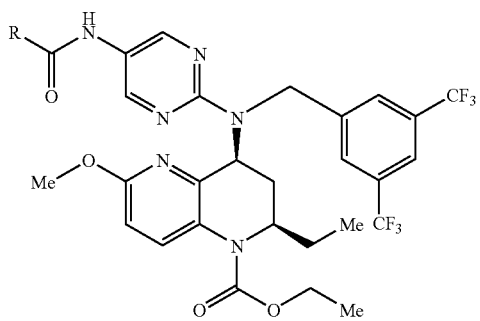

| Example No. | R— | Physical properties, etc. |
|---|---|---|
| 246 | HO~~~O~ | MS (m/z): 701 [M + H]$^+$ |
| 247 | HO~~~~O~ | MS (m/z): 715 [M + H]$^+$ |
| 248 | Me-dioxolane-CH2-O-Me | MS (m/z): 757 [M + H]$^+$ |

Example 249

(2R,4S)-4-{[3,5-Bis(trifluoromethyl)benzyl]-[5-(2-hydroxyethoxy-carbonylamino)pyrimidin-2-yl]}amino-2-ethyl-6-methoxy-3,4-dihydro-2H-[1,5]naphthyridine-1-carboxylic acid ethyl ester (192 mg) is dissolved in acetone (5 ml), and thereto is added 2.67M chromium (VI) oxide in dilute sulfuric acid solution (320 μl) under ice-cooling. The mixture is stirred for 4.5 hours, and partitioned by adding sodium bisulfite, water and ethyl acetate. The organic layer is washed with saturated brine and dried over magnesium sulfate, then concentrated under reduced pressure. The resulting residue is purified by column chromatography (silica gel; chloroform:methanol=9:1→7:3) to give (2R,4S)-4-{[3,5-bis(trifluoromethyl)-benzyl]-(5-carboxymethoxycarbonylaminopyrimidin-2-yl)}amino-2-ethyl-6-methoxy-3,4-dihydro-2H-[1,5]naphthyridine-1-carboxylic acid ethyl ester (78 mg). MS (m/z): 701 [M+H]$^+$.

Examples 250-251

Corresponding starting compounds are treated in a similar manner to Example 249 to give the compounds listed in Table 28.

TABLE 28

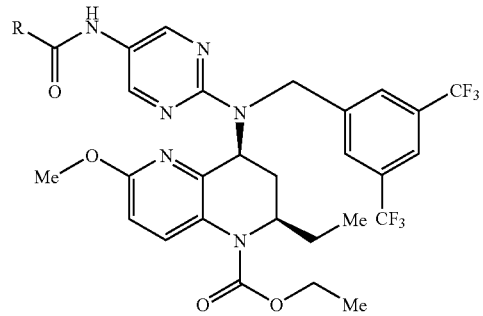

| Example No. | R— | Physical properties, etc. |
|---|---|---|
| 250 | HO-CO-CH2-O-CH2-O-Me | MS (m/z): 715 [M + H]$^+$ |
| 251 | HO-CO-CH2CH2-O-Me | MS (m/z): 729 [M + H]$^+$ |

Example 252

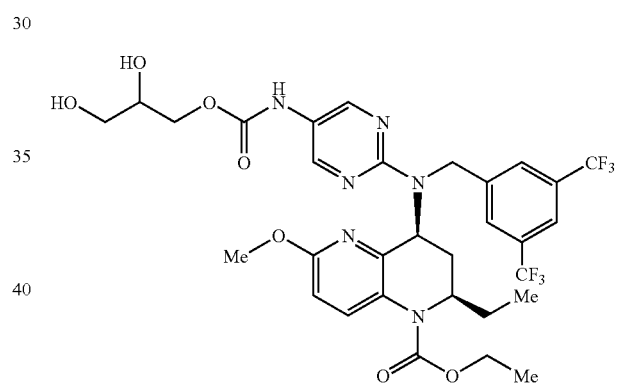

A corresponding starting compound is treated in a similar manner to Example 121 to give the compound of Example 252. MS (m/z): 717 [M+H]$^+$

Example 253

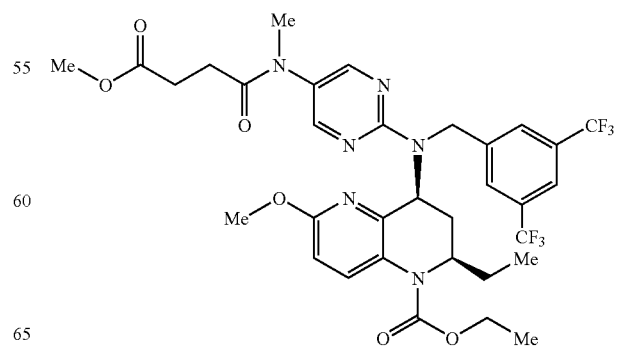

A corresponding starting compound is treated in a similar manner to Example 243 (1) to give the compound of Example 253. MS (m/z): 727 [M+H]+

Example 254

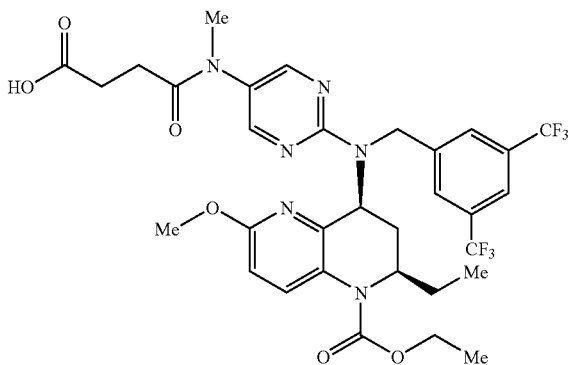

A corresponding starting compound is treated in a similar manner to Example 233 (2) to give the compound of Example 254. MS (m/z): 713 [M+H]+

Example 255

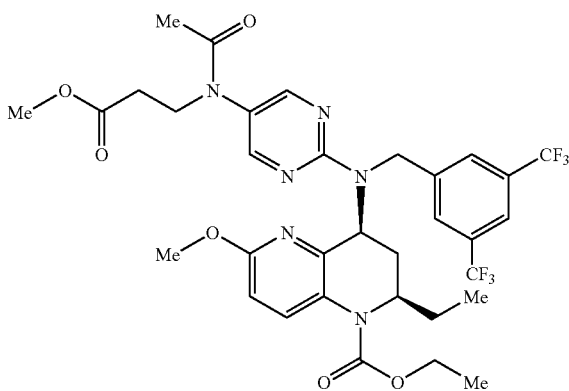

A corresponding starting compound is treated in a similar manner to Example 62 to give the compound of Example 255. MS (m/z): 727 [M+H]+

Example 256

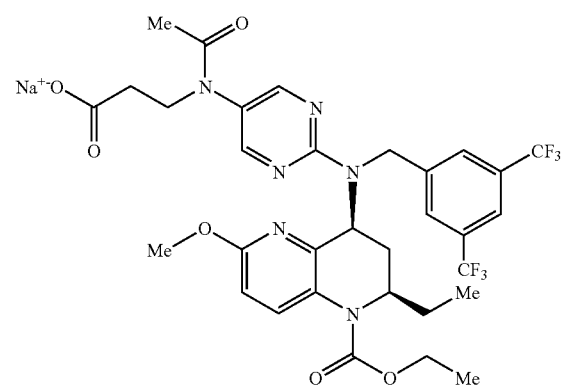

A corresponding starting compound is treated in a similar manner to Example 233 (2)-(3) to give the compound of Example 256. MS (m/z): 711 [M−Na]−

Example 257

(1) (2R,4S)-4-{(5-Aminopyrimidin-2-yl)-[3,5-bis(trifluoromethyl)benzyl]}-amino-2-ethyl-6-methoxy-3,4-dihydro-2H-[1,5]naphthyridine-1-carboxylic acid ethyl ester (300 mg) is dissolved in N,N-dimethylformamide (4 ml), and thereto are added methyl chlorocarbonate (116 μl) and triethylamine (280 μl). The mixture is stirred at room temperature for 4 hours, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; hexane:ethyl acetate=9:1→7:3) to give (2R,4S)-4-{[3,5-bis(trifluoromethyl)benzyl]-(5-methoxycarbonylaminopyrimidin-2-yl)}amino-2-ethyl-6-methoxy-3,4-dihydro-2H-[1,5]naphthyridine-1-carboxylic acid ethyl ester (247 mg). MS (m/z): 657 [M+H]+.

(2) (2R,4S)-4-{[3,5-Bis(trifluoromethyl)benzyl]-(5-methoxycarbonyl-aminopyrimidin-2-yl)}amino-2-ethyl-6-methoxy-3,4-dihydro-2H-[1,5]naphthyridine-1-carboxylic acid ethyl ester (238 mg) is treated in a similar manner to Example 226 (2) and (3) to give (2R,4S)-4-[[3,5-bis(trifluoromethyl)benzyl]-(5-{[(3-carboxypropyl)-(methoxycarbonyl)]-amino}pyrimidin-2-yl]amino-2-ethyl-6-methoxy-3,4-dihydro-2H-[1,5]naphthyridine-1-carboxylic acid ethyl ester (187 mg). MS (m/z): 743 [M+H]+.

Example 258

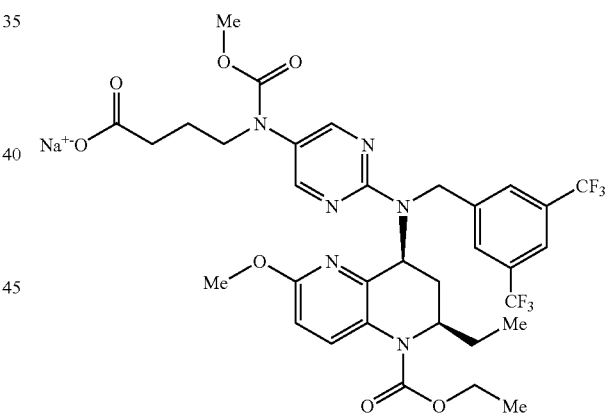

A corresponding starting compound is treated in a similar manner to Example 233 (3) to give the compound of Example 258. MS (m/z): 741 [M−Na]−

Example 259

(1) (2R*,4S*)-4-{[3,5-Bis(trifluoromethyl)benzyl]-(5-hydroxypyrimidin-2-yl)}amino-2-ethyl-6-methoxy-3,4-dihydro-2H-[1,5]naphthyridine-1-carboxylic acid ethyl ester (200 mg) is dissolved in tetrahydrofuran (2 ml), and thereto are added methyl lactate (174 mg) and triphenylphosphine (438 mg), then added dropwise a solution (0.73 ml) of 40% diethyl azodicarboxylate in toluene under water-cooling. The mixture is stirred at room temperature for 3 hours, and thereto is added water. The resulting solution is extracted with ethyl acetate, and the organic layer is washed with saturated brine and dried over magnesium sulfate, then concentrated under reduced pressure. To the resulting residue are added methylene chloride, isopropyl ether and hexane, and the precipitated insoluble materials are removed by filtration and the filtrate is concentrated under reduced pressure. The resulting residue is purified by column chromatography (silica gel; hexane:ethyl acetate=6:1) to give (2R*,4S*)-4-{[3,5-bis(trifluoromethyl)benzyl]-[5-(1-methoxycarbonylethoxy)pyrimidin-2-yl]}amino-2-ethyl-6-methoxy-3,4-dihydro-2H-[1,5]naphthyridine-1-carboxylic acid ethyl ester (157 mg). MS (m/z): 686 [M+H]$^+$.

(2) (2R*,4S*)-4-{[3,5-Bis(trifluoromethyl)benzyl]-[5-(1-methoxycarbonyl-ethoxy)pyrimidin-2-yl]}amino-2-ethyl-6-methoxy-3,4-dihydro-2H-[1,5]naphthyridine-1-carboxylic acid ethyl ester (154 mg) is dissolved in tetrahydrofuran (2 ml), and thereto is added dropwise a solution (1.12 ml) of 1M diisobutylaluminum hydride in toluene under ice-cooling and the mixture is stirred at 0° C. for 3 hours. To the reaction mixture is added a 10% aqueous citric acid solution, and the resulting mixture is extracted with ethyl acetate. The organic layer is washed with saturated brine and dried over magnesium sulfate, then concentrated under reduced pressure. The resulting residue is purified by column chromatography (silica gel; hexane: ethyl acetate=2:1) to give (2R*,4S*)-4-{[3,5-bis(trifluoromethyl)-benzyl]-[5-(2-hydroxy-1-methylethoxy)pyrimidin-2-yl]}amino-2-ethyl-6-methoxy-3,4-dihydro-2H-[1,5]naphthyridine-1-carboxylic acid ethyl ester (88 mg). MS (m/z): 658 [M+H]$^+$.

Examples 260-264

Corresponding starting compounds are treated in a similar manner to Example 259 (1) to give the compounds listed in Table 29.

TABLE 29

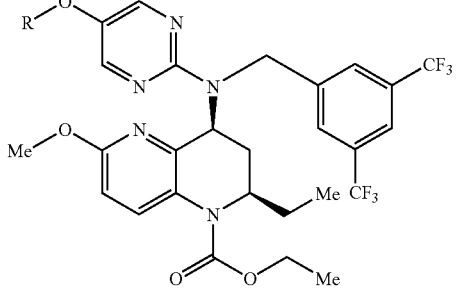

| Example No. | R— | Physical properties, etc. |
|---|---|---|
| 260 | HO∼O∼ | MS (m/z): 688 [M + H]$^+$ |
| 261 | (tetrahydrothiopyran-3-yl) | MS (m/z): 700 [M + H]$^+$ |
| 262 | (S)-2,2-dimethyl-4-ethyl-1,3-dioxolane | MS (m/z): 714 [M + H]$^+$ |
| 263 | (R)-2,2-dimethyl-4-ethyl-1,3-dioxolane | MS (m/z): 714 [M + H]$^+$ |
| 264 | 4-methylcyclohexanecarbonyloxyethyl | MS (m/z): 754 [M + H]$^+$ |

Example 265

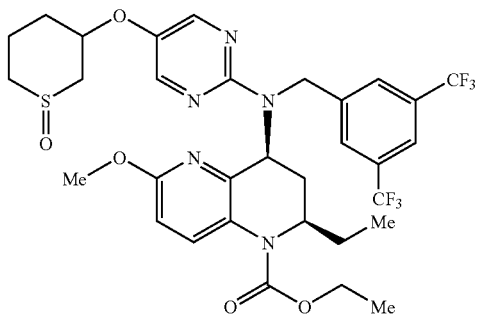

A corresponding starting compound is treated in a similar manner to Example 114 to give the compound of Example 265. MS (m/z): 716 [M+H]$^+$ Examples 266-267

Corresponding starting compounds are treated in a similar manner to Example 121 to give the compounds listed in Table 30.

TABLE 30

| Example No. | R— | Physical properties, etc. |
|---|---|---|
| 266 | HO—, HO— (R) ethyl | MS (m/z): 674 [M + H]+ |
| 267 | HO—, HO— (S) ethyl | MS (m/z): 674 [M + H]+ |

Example 268

(2R,4S)-4-{[3, 5-Bis(trifluoromethyl)benzyl]-(5-hydroxypyrimidin-2-yl)}amino-2-ethyl-6-methoxy-3,4-dihydro-2H-[1,5]naphthyridine-1-carboxylic acid ethyl ester (170 mg) is dissolved in methylene chloride (3 ml), and thereto are added 4-methoxycarbonylphenylboronic acid (51 mg), copper (II) acetate (52 mg), triethylamine (79 μl) and molecular sieves 4A (170 mg). The mixture is stirred overnight at room temperature. The insoluble materials are removed by filtration and the filtrate is partitioned by adding ethyl acetate and saturated brine. The organic layer is washed with saturated brine and dried over magnesium sulfate, then concentrated under reduced pressure. The resulting residue is purified by column chromatography (silica gel; hexane:ethyl acetate=9:1→3:1) to give (2R,4S)-4-{[3,5-bis(trifluoromethyl)benzyl]-[5-(4-methoxycarbonylphenoxy)-pyrimidin-2-yl]}amino-2-ethyl-6-methoxy-3,4-dihydro-2H-[1,5]naphthyridine-1-carboxylic acid ethyl ester (132 mg). MS (m/z): 734 [M+H]+.

Example 269

(2R,4S)-4-{[3,5-Bis(trifluoromethyl)benzyl]-(5-hydroxypyrimidin-2-yl)}amino-2-ethyl-6-methoxy-3,4-dihydro-2H-[1,5]naphthyridine-1-carboxylic acid ethyl ester (150 mg) is dissolved in tetrahydrofuran (3 ml), and thereto are added at room temperature potassium tert-butoxide (28 mg) and β-propiolactone (16 μl). The reaction solution is stirred overnight at room temperature, and then partitioned by adding ethyl acetate and 1N HCl. The organic layer is washed with saturated brine and dried over magnesium sulfate, then concentrated under reduced pressure. The resulting residue is purified by column chromatography (silica gel; chloroform:methanol=1:0→9:1) and LC/MS (CAPCEL PAK MGII (SHISEIDO), water:methanol=60:40→0:100, 40 ml/min) to give (2R,4S)-4-{[3,5-bis(trifluoromethyl)benzyl]-[5-(2-carboxyethoxy)pyrimidin-2-yl]}amino-2-ethyl-6-methoxy-3,4-dihydro-2H-[1,5]naphthyridine-1-carboxylic acid ethyl ester (12 mg). MS (m/z): 672 [M+H]+.

Example 270

(1) (2R,4S)-4-{[3,5-Bis(trifluoromethyl)benzyl]-(5-hydroxypyrimidin-2-yl)}amino-2-ethyl-6-methoxy-3,4-dihydro-2H-[1,5]naphthyridine-1-carboxylic acid ethyl ester (3.5 g) and ethyl 4-bromobutyrate (928 μl) is dissolved in N,N-dimethylformamide (20 ml), and thereto is added potassium carbonate (969 mg). The mixture is stirred overnight at 50° C. The reaction solution is cooled to room temperature, and partitioned by adding ethyl acetate and water. The organic layer is washed with saturated brine and dried over magnesium sulfate, then concentrated under reduced pressure. The resulting residue is purified by column chromatography (silica gel; hexane:ethyl acetate=9:1→3:1) to give (2R,4S)-4-{[3,5-bis(trifluoromethyl)benzyl]-[5-(3-ethoxycarbonylpropoxy)pyrimidin-2-yl]}amino-2-ethyl-6-methoxy-3,4-dihydro-2H-[1,5]naphthyridine-1-carboxylic acid ethyl ester (3.77 g). MS (m/z): 714 [M+H]+.

(2) (2R,4S)-4-{[3,5-Bis(trifluoromethyl)benzyl]-[5-(3-ethoxycarbonyl-propoxy)pyrimidin-2-yl]}amino-2-ethyl-6-methoxy-3,4-dihydro-2H-[1,5]naphthyridine-1-carboxylic acid ethyl ester (3.71 g) is dissolved in ethanol (35 ml), and thereto is added 2N aqueous NaOH solution (7.8 ml). The mixture is stirred overnight at room temperature. The reaction solution is concentrated under reduced pressure, and the residue is partitioned by adding ethyl acetate and 1N HCl. The organic layer is washed with saturated brine and dried over magnesium sulfate, then concentrated under reduced pressure. The resulting residue is purified by column chromatography (silica gel; chloroform:methanol=1:0→9:1) to give (2R,4S)-4-{[3,5-bis(trifluoromethyl)benzyl]-[5-(3-carboxypropoxy)pyrimidin-2-yl]}amino-2-ethyl-6-methoxy-3,4-dihydro-2H-[1,5]naphthyridine-1-carboxylic acid ethyl ester (3.55 g). MS (m/z): 686 [M+H]+.

Example 271

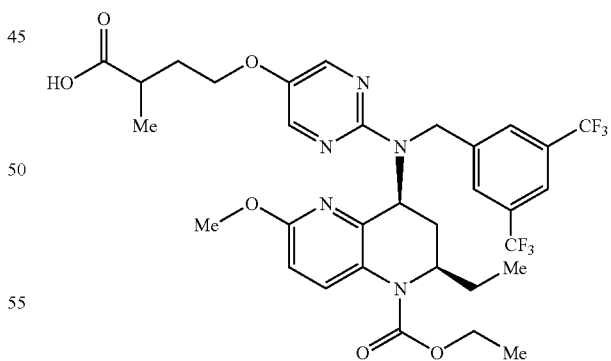

A corresponding starting compound is treated in a similar manner to Example 270 to give the compound of Example 271. MS (m/z): 700 [M+H]+

Examples 272-275

Corresponding starting compounds are treated in a similar manner to Example 270 (1) to give the compounds listed in Table 31.

TABLE 31

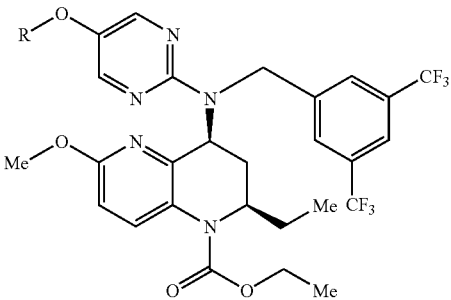

| Example No. | R— | Physical properties, etc. |
|---|---|---|
| 272 | Me~O~C(=O)-(CH2)4- | MS (m/z): 728 [M + H]+ |
| 273 | Me~O~C(=O)-(CH2)5- | MS (m/z): 742 [M + H]+ |
| 274 | Me~O~C(=O)-(CH2)6- | MS (m/z): 756 [M + H]+ |
| 275 | 3-methyl-2-oxotetrahydrofuran-3-yl | MS (m/z): 684 [M + H]+ |

Examples 276-280

Corresponding starting compounds are treated in a similar manner to Example 270 (2) to give the compounds listed in Table 32.

TABLE 32

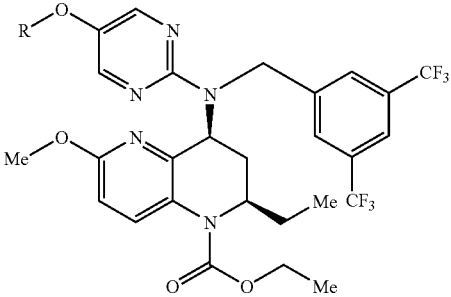

| Example No. | R— | Physical properties, etc. |
|---|---|---|
| 276 | 4-methylcyclohexanecarboxylic acid | MS (m/z): 726 [M + H]+ |
| 277 | 4-methylbenzoic acid | MS (m/z): 720 [M + H]+ |
| 278 | HO-C(=O)-(CH2)4- | MS (m/z): 700 [M + H]+ |
| 279 | HO-C(=O)-(CH2)5- | MS (m/z): 714 [M + H]+ |
| 280 | HO-C(=O)-(CH2)6- | MS (m/z): 728 [M + H]+ |

Example 281

(2R,4S)-4-{[3,5-Bis(trifluoromethyl)benzyl]-[5-(2-oxotetrahydrofuran-3-yloxy)pyrimidin-2-yl]}amino-2-ethyl-6-methoxy-3,4-dihydro-2H-[1,5]naphthyridine-1-carboxylic acid ethyl ester (150 mg) is dissolved in ethanol (1 ml), and thereto is added 2N aqueous NaOH solution (1 ml). The mixture is stirred at room temperature for 3 hours, and partitioned by adding 1N HCl (2 ml) and ethyl acetate to the reaction solution. The organic layer is concentrated under reduced pressure. The resulting residue is purified by column chromatography (silica gel; chloroform:methanol=19:1→9:1). The resulting residue is dissolved in ethanol (1 ml), and thereto is added 2N aqueous NaOH solution (81 μl), then concentrated under reduced pressure to give (2R,4S)-4-{[3,5-bis-(trifluoromethyl)benzyl]-[5-(1-carboxy-3-hydroxypropoxy)pyrimidin-2-yl]}-amino-2-ethyl-6-methoxy-3,4-dihydro-2H-[1,5]naphthyridine-1-carboxylic acid ethyl ester sodium salt (114 mg). MS (m/z): 700 [M−Na]−.

Example 282

(1) (2R,4S)-4-{[3,5-bis(trifluoromethyl)benzyl]-(5-ethoxycarbonyl-pyrimidin-2-yl)}amino-2-ethyl-6-methoxy-3,4-dihydro-2H-[1,5]naphthyridine-1-carboxylic acid ethyl ester (1.0 g) is dissolved in tetrahydrofuran (7 ml), and thereto is added 1M-diisobutylaluminum hydride-tetrahydrofuran solution (3.36 ml) under ice-cooling. The mixture is stirred at room temperature for 2 hours. To the reaction solution is added a saturated aqueous ammonium chloride solution, and the mixture is extracted with ethyl acetate.

The organic layer is washed with saturated brine and dried over magnesium sulfate, then concentrated under reduced pressure. The resulting residue is purified by column chromatography (silica gel; hexane:ethyl acetate=9:1→2:3) to give (2R,4S)-4-{[3,5-bis-(trifluoromethyl)benzyl]-(5-hydroxymethylpyrimidin-2-yl)}amino-2-ethyl-6-methoxy-3,4-dihydro-2H-[1,5]naphthyridine-1-carboxylic acid ethyl ester (760 mg). MS (m/z): 614 [M+H]+.

(2) (2R,4S)-4-{[3,5-Bis(trifluoromethyl)benzyl]-(5-hydroxymethyl-pyrimidin-2-yl)}amino-2-ethyl-6-methoxy-3,4-dihydro-2H-[1,5]naphthyridine-1-carboxylic acid ethyl ester (735 mg) is dissolved in chloroform (5 ml), and thereto is added manganese dioxide (2 g). The mixture is stirred overnight at room temperature. The manganese dioxide is removed by filtration and the filtrate is concentrated under reduced pressure. The resulting residue is purified by column chromatography (silica gel; chloroform:methanol=9:1→1:1) to give (2R,4S)-4-{[3,5-bis-(trifluoromethyl)benzyl]-(5-formylpyrimidin-2-yl)}amino-2-ethyl-6-methoxy-3,4-dihydro-2H-[1,5]naphthyridine-1-carboxylic acid ethyl ester (450 mg). MS (m/z): 612 [M+H]+.

(3) (2R,4S)-4-{[3,5-Bis(trifluoromethyl)benzyl]-(5-formylpyrimidin-2-yl)}-amino-2-ethyl-6-methoxy-3,4-dihydro-2H-[1,5]naphthyridine-1-carboxylic acid ethyl ester (185 mg), L-proline tert-butyl ester (62 mg), acetic acid (35 µl) are dissolved in 1,2-dichloroethane (3 ml), and thereto is added sodium triacetoxyborohydride (128 mg). The mixture is stirred at room temperature for 2 hours, and partitioned by adding a saturated aqueous sodium hydrogen carbonate solution and ethyl acetate to the reaction solution. The organic layer is washed with saturated brine and dried over magnesium sulfate, then concentrated under reduced pressure. The resulting residue is purified by column chromatography (silica gel; hexane:ethyl acetate=9:1→1:1) to give (2R,4S)-4-{[3,5-bis(trifluoromethyl)-benzyl]-[5-(2-(S)-tert-butoxycarbonylpyrrolidin-1-ylmethyl)pyrimidin-2-yl]}amino-2-ethyl-6-methoxy-3,4-dihydro-2H-[1,5]naphthyridine-1-carboxylic acid ethyl ester (200 mg). MS (m/z): 767 [M+H]+.

Example 283

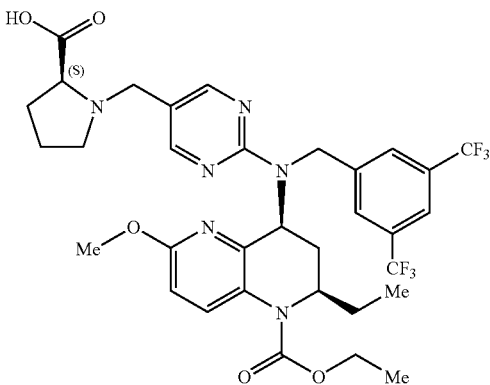

A corresponding starting compound is treated in a similar manner to Example 224 (2) to give the compound of Example 283. MS (m/z): 711 [M+H]+

Example 284

(1) (2R,4S)-4-{[3,5-Bis(trifluoromethyl)benzyl]-(5-carboxypyrimidin-2-yl)}amino-2-ethyl-6-methoxy-3,4-dihydro-2H-[1,5]naphthyridine-1-carboxylic acid ethyl ester (335 mg) is dissolved in methylene chloride (2 ml), and thereto are added oxalyl chloride (70 µl) and drops of N,N-dimethylformamide. The mixture is stirred at room temperature for 1 hour. The reaction solution is concentrated under reduced pressure, and the residue is dissolved in tetrahydrofuran (1 ml) and acetonitrile (1 ml), and thereto are added triethylamine (93 µl) and 2M trimethylsilyl diazomethane-hexane solution (587 µl). The mixture is stirred overnight at room temperature. The reaction solution is concentrated under reduced pressure, and to the residue are added 2,6-lutidine (500 µl) and benzyl alcohol (500 µl). The mixture is stirred at 150° C. for 15 minutes. The reaction solution is cooled to room temperature, and extracted by adding ethyl acetate and 1N HCl. The organic layer is washed with a saturated sodium bicarbonate water and saturated brine and dried over magnesium sulfate, then concentrated under reduced pressure. The resulting residue is purified by column chromatography (silica gel; hexane:ethyl acetate=9:1→3:1) to give (2R,4S)-4-{(5-benzyloxycarbonylmethylpyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (60 mg). MS (m/z): 732 [M+H]+.

(2) (2R,4S)-4-{(5-Benzyloxycarbonylmethylpyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester (53 mg) is dissolved in ethanol (0.5 ml), and thereto is added 10% palladium-carbon (10 mg). The mixture is stirred under hydrogen at room temperature for 3 hours. The palladium-carbon is filtered, and then the filtrate is concentrated under reduced pressure to give (2R,4S)-4-{[3,5-bis(trifluoromethyl)benzyl]-(5-carboxymethylpyrimidin-2-yl)}amino-2-ethyl-6-methoxy-3,4-dihydro-2H-[1,5]naphthyridine-1-carboxylic acid ethyl ester (44 mg). MS (m/z): 642 [M+H]+.

Example 285

(2R,4S)-4-{[3,5-Bis(trifluoromethyl)benzyl]-(5-hydroxymethyl-pyrimidin-2-yl)}amino-2-ethyl-6-methoxy-3,4-dihydro-2H-[1,5]naphthyridine-1-carboxylic acid ethyl ester (130 mg) is dissolved in acetone (2.5 ml), and thereto are added potassium carbonate (108 mg) and ethyl bromoacetate (0.129 ml). The mixture is stirred at room temperature for 6 days. The reaction solution is concentrated under reduced pressure, and thereto is added water. The mixture is stirred for 40 hours, and partitioned by adding chloroform to the reaction solution. The organic layer is dried over magnesium sulfate, then concentrated under reduced pressure to give (2R,4S)-4-{[3,5-bis(trifluoromethyl)benzyl]-(5-carboxymethoxymethylpyrimidin-2-yl)}amino-2-ethyl-6-methoxy-3,4-dihydro-2H-[1,5]naphthyridine-1-carboxylic acid ethyl ester (33.8 mg). MS (m/z): 672 [M+H]+.

Example 286

(1) (2R,4S)-4-{[3,5-Bis(trifluoromethyl)benzyl]-(5-hydroxymethyl-pyrimidin-2-yl)}amino-2-ethyl-6-methoxy- 3,4-dihydro-2H-[1,5]naphthyridine-1-carboxylic acid ethyl ester (170 mg) is dissolved in dimethylsulfoxide (45 µl), and thereto are added 5N aqueous NaOH solution (5 µl) and acrylic acid tert-butyl ester (0.14 ml). The mixture is stirred at room temperature for 1 hour, and partitioned by adding water and diethyl ether to the reaction solution. The organic layer is dried over magnesium sulfate, and then concentrated under reduced pressure. The resulting residue is purified by column chromatography (silica gel; hexane:ethyl acetate=9:1→4:1) to give (2R,4S)-4-{[3,5-bis(trifluoromethyl)-benzyl]-[5-(2-tert-butoxycarbonylethoxymethyl)pyrimidin-2-yl]}amino-2-ethyl-6-methoxy-3,4-dihydro-2H-[1,5]naphthyridine-1-carboxylic acid ethyl ester (161 mg). MS (m/z): 742 [M+H]$^+$.

(2) (2R,4S)-4-{[3,5-Bis(trifluoromethyl)benzyl]-[5-(2-tert-butoxycarbonylethoxymethyl)pyrimidin-2-yl]}amino-2-ethyl-6-methoxy-3,4-dihydro-2H-[1,5]naphthyridine-1-carboxylic acid ethyl ester (155 mg) is dissolved in a solution (3 mL) of 4N HCl in 1,4-dioxane, and the mixture is stirred at room temperature for 1 hour. The reaction solution is concentrated under reduced pressure, and the resulting residue is purified by column chromatography (silica gel; chloroform:methanol=1:0→9:1) to give (2R,4S)-4-{[3,5-bis(trifluoromethyl)benzyl]-[5-(2-carboxyethoxymethyl)-pyrimidin-2-yl]}amino-2-ethyl-6-methoxy-3,4-dihydro-2H-[1,5]naphthyridine-1-carboxylic acid ethyl ester (145 mg). MS (m/z): 686 [M+H]$^+$.

Example 287

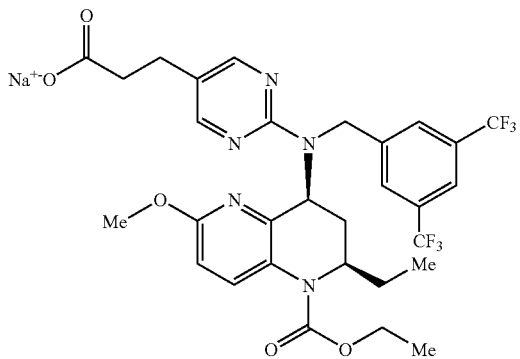

A corresponding starting compound is treated in a similar manner to Example 233 (3) to give the compound of Example 287. MS (m/z): 656 [M+H]$^+$ Example 288

(1) (2R,4S)-4-{[3,5-Bis(trifluoromethyl)benzyl]-(5-hydroxymethyl-pyrimidin-2-yl)}amino-2-ethyl-6-methoxy-3,4-dihydro-2H-[1,5]naphthyridine-1-carboxylic acid ethyl ester (526 mg) is dissolved in chloroform (3 ml), and thereto is added manganese dioxide (1.5 g). The mixture is stirred at room temperature for 19 hours. The reaction solution is filtered through Celite™, and the filtrate is concentrated under reduced pressure to give (2R,4S)-4-{[3,5-bis(trifluoromethyl)benzyl]-(5-formylpyrimidin-2-yl)}amino-2-ethyl-6-methoxy-3,4-dihydro-2H-[1,5]naphthyridine-1-carboxylic acid ethyl ester (500 mg). MS (m/z): 612 [M+H]$^+$.

(2) (2R,4S)-4-{[3,5-Bis(trifluoromethyl)benzyl]-(5-formylpyrimidin-2-yl)}-amino-2-ethyl-6-methoxy-3,4-dihydro-2H-[1,5]naphthyridine-1-carboxylic acid ethyl ester (200 mg) is dissolved in toluene (3 ml), and thereto are added benzyloxycarbonylamino(dimethoxyphosphoryl)acetic acid methyl ester (238 mg) and 1,8-diazabicyclo[5,4,0]undec-7-ene (98 µl). The mixture is stirred at room temperature for 18 hours, and partitioned by adding 1N HCl and ethyl acetate to the reaction solution. The organic layer is washed with water and saturated brine, then dried over magnesium sulfate, and concentrated under reduced pressure. The resulting residue is purified by column chromatography (silica gel; hexane:ethyl acetate=4:1→1:1) to give (2R,4S)-4-{[5-((Z)-2-benzyloxycarbonylamino-2-methoxycarbonylvinyl)-pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (209 mg). MS (m/z): 817 [M+H]$^+$.

(3) (2R,4S)-4-{[5-((Z)-2-Benzyloxycarbonylamino-2-methoxycarbonyl-vinyl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (200 mg) is dissolved in methanol (4 ml), and thereto is added 10% palladium-carbon (140 mg). The mixture is stirred under hydrogen at room temperature for 22 hours. The reaction solution is filtered and the filtrate is concentrated under reduced pressure. The resulting residue is purified by column chromatography (silica gel; chloroform:methanol=1:0→19:1) to give (2R,4S)-4-{[5-(2-amino-2-methoxycarbonylethyl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (118 mg). MS (m/z): 685 [M+H]$^+$.

Example 289

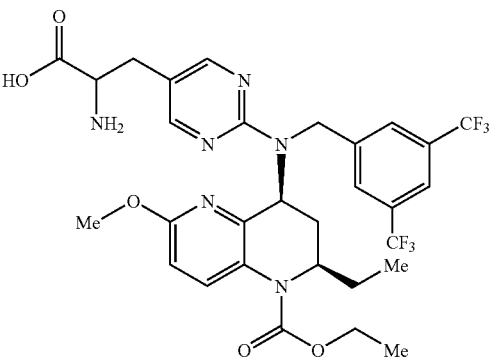

A corresponding starting compound is treated in a similar manner to Example 233 (2) to give the compound of Example 289. MS (m/z): 671 [M+H]$^+$ Example 290

(1) (2R,4S)-4-{[3,5-Bis(trifluoromethyl)benzyl]-[5-(3-hydroxypropyl)-pyrimidin-2-yl]}amino-2-ethyl-6-methoxy-3,4-dihydro-2H-[1,5]naphthyridine-1-carboxylic acid ethyl ester (940 mg) is dissolved in dichloromethane (20 ml), and thereto are added triphenylphosphine (850 mg) and carbon tetrabromide (1.0 g). The mixture is stirred at room temperature for 1 hour, and partitioned by adding water and chloroform. The organic layer is washed with saturated brine and dried over magnesium sulfate, then concentrated under reduced pressure. The resulting residue is purified by column chromatography (silica gel; hexane: ethyl acetate=9:1→4:1) to give (2R,4S)-4-{[3,5-bis(trifluoromethyl)-benzyl]-[5-(3-bromopropyl)pyrimidin-2-yl]}amino-2-ethyl-6-methoxy-3,4-dihydro-2H-[1,5]naphthyridine-1-carboxylic acid ethyl ester (576 mg) as a crude product. MS (m/z): 704/706 [M+H]$^+$.

(2) The crude product (150 mg) of (2R,4S)-4-{[3,5-bis(trifluoromethyl)-benzyl]-[5-(3-bromopropyl)pyrimidin-2-yl]}amino-2-ethyl-6-methoxy-3,4-dihydro-2H-[1,5]naphthyridine-1-carboxylic acid ethyl ester is dissolved in N,N-dimethylformamide (4 ml), and thereto is added morpholine (60 μl). The mixture is stirred at room temperature for 2 days, and partitioned by adding water and ethyl acetate. The organic layer is washed with saturated brine and dried over magnesium sulfate, then concentrated under reduced pressure. The resulting residue is purified by column chromatography (silica gel; chloroform:methanol=1: 0→19:1) to give (2R,4S)-4-([3,5-bis(trifluoromethyl)benzyl]-{5-[3-(morpholin-4-yl)propyl]-pyrimidin-2-yl}]amino-2-ethyl-6-methoxy-3,4-dihydro-2H-[1,5]naphthyridine-1-carboxylic acid ethyl ester (114 mg). MS (m/z): 711 [M+H]$^+$.

Example 291

(1) The crude product (230 mg) of (2R,4S)-4-{[3,5-bis(trifluoromethyl)-benzyl]-[5-(3-bromopropyl)pyrimidin-2-yl]}amino-2-ethyl-6-methoxy-3,4-dihydro-2H-[1,5]naphthyridine-1-carboxylic acid ethyl ester is dissolved in tetrahydrofuran (4 ml), and thereto is added 15% sodium methanethiolate solution (0.3 ml). The mixture is stirred at room temperature for 4.5 hours, and partitioned by adding water and ethyl acetate. The organic layer is washed with saturated brine and dried over magnesium sulfate, then concentrated under reduced pressure. The resulting residue is purified by column chromatography (silica gel; hexane: ethyl acetate=4:1→3:2) to give (2R,4S)-4-{[3,5-bis(trifluoromethyl)benzyl]-[5-(3-methylsulfanyl-propyl)pyrimidin-2-yl]}amino-2-ethyl-6-methoxy-3,4-dihydro-2H-[1,5]naphthyridine-1-carboxylic acid ethyl ester (216 mg) as a crude product. MS (m/z): 672 [M+H]$^+$.

(2) The crude product (210 mg) of (2R,4S)-4-{[3,5-bis(trifluoromethyl)-benzyl]-[5-(3-methylsulfanylpropyl)pyrimidin-2-yl]}amino-2-ethyl-6-methoxy-3,4-dihydro-2H-[1,5]naphthyridine-1-carboxylic acid ethyl ester is dissolved in chloroform (4 ml), and thereto is added m-chloroperbenzoic acid (160 mg). The mixture is stirred at room temperature for 2 hours, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; hexane: ethyl acetate=7:3→2:3) to give (2R,4S)-4-{[3,5-bis-(trifluoromethyl)-benzyl]-[5-(3-methanesulfonylpropyl)pyrimidin-2-yl]}amino-2-ethyl-6-methoxy-3,4-dihydro-2H-[1,5]naphthyridine-1-carboxylic acid ethyl ester (63 mg). MS (m/z): 704 [M+H]$^+$.

Example 292

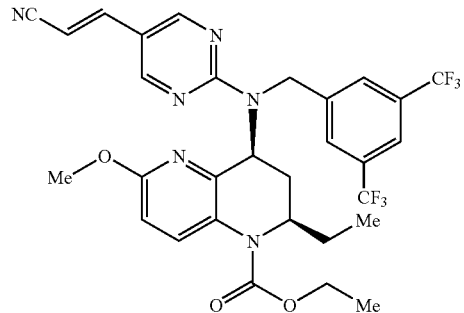

A corresponding starting compound is treated in a similar manner to Example 137 to give the compound of Example 292. MS (m/z): 635 [M+H]$^+$ Example 293

Copper (I) bromide (746 mg) is suspended in tetrahydrofuran (5 ml), and thereto is added dropwise a 65% toluene solution (3.23 g) of sodium bis(2-methoxyethoxy)aluminum hydride under ice-cooling under nitrogen and the mixture is stirred for 30 minutes. The reaction solution is cooled to −78° C., and thereto are added 2-butanol (954 μl) and (2R,4S)-4-{[3,5-bis-(trifluoromethyl)benzyl]-[5-(2-cyanovinyl)pyrimidin-2-yl]}amino-2-ethyl-6-methoxy-3,4-dihydro-2H-[1,5]naphthyridine-1-carboxylic acid ethyl ester (330 mg). The mixture is stirred at the same temperature for 2 hours, and then stirred at room temperature for 2 hours. To the reaction solution is added a saturated aqueous ammonium chloride solution, and the insoluble materials are removed by filtration through Celite™ and the resulting filtrate is partitioned by adding ethyl acetate and water. The organic layer is washed with saturated brine and dried over magnesium sulfate, then concentrated under reduced pressure. The resulting residue is purified by column chromatography (silica gel; hexane:ethyl acetate=4:1→3:2) to give (2R,4S)-4-{[3,5-bis(trifluoromethyl)benzyl]-[5-(2-cyanoethyl)pyrimidin-2-yl]}-amino-2-ethyl-6-methoxy-3,4-dihydro-2H-[1,5]naphthyridine-1-carboxylic acid ethyl ester 254 (mg). MS (m/z): 637 [M+H]$^+$.

Example 294

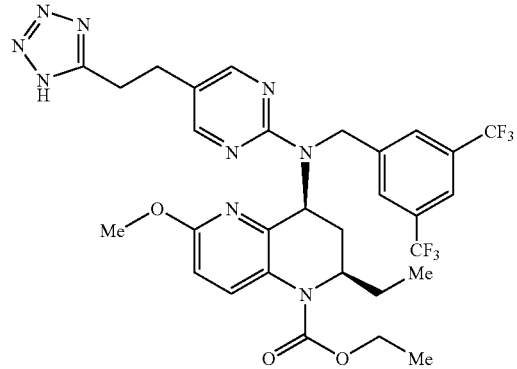

A corresponding starting compound is treated in a similar manner to Example 147 to give the compound of Example 294. MS (m/z): 680 [M+H]$^+$

Example 295

(1) (2R,4S)-4-{[3,5-Bis(trifluoromethyl)benzyl]-[5-(3-hydroxypropyl)-pyrimidin-2-yl]}amino-2-ethyl-6-methoxy-3,4-dihydro-2H-[1,5]naphthyridine-1-carboxylic acid ethyl ester (1 g) and triphenylphosphine (491 mg) are dissolved in dichloromethane (10 ml), and thereto is added carbon tetrabromide (775 mg). The mixture is stirred overnight at room temperature. The reaction solution is concentrated under reduced pressure, and the resulting residue is purified by column chromatography (silica gel; hexane:ethyl acetate=9:1→4:1) to give (2R,4S)-4-{[3,5-bis(trifluoromethyl)benzyl]-[5-(3-bromopropyl)pyrimidin-2-yl]}amino-2-ethyl-6-methoxy-3,4-dihydro-2H-[1,5]naphthyridine-1-carboxylic acid ethyl ester (955 mg). MS (m/z): 704/706 [M+H]$^+$.

(2) (2R,4S)-4-{[3,5-Bis(trifluoromethyl)benzyl]-[5-(3-bromopropyl)-pyrimidin-2-yl]}amino-2-ethyl-6-methoxy-3,4-dihydro-2H-[1,5]naphthyridine-1-carboxylic acid ethyl ester (946 mg) and sodium 3-methoxy-3-oxopropan-1-sulfinate (281 mg) are dissolved in dimethylsulfoxide (8 ml), and the mixture is stirred overnight under nitrogen flow at room temperature. To the reaction solution are added water and ethyl acetate, and the organic layer is washed with saturated brine, then dried over magnesium sulfate, and concentrated under reduced pressure. The resulting residue is purified by column chromatography (silica gel; hexane:ethyl acetate=2:1→1:1) to give (2R,4S)-4-([3,5-bis(trifluoromethyl)benzyl]-{5-[3-(2-methoxycarbonylethanesulfonyl)propyl]-pyrimidin-2-yl})amino-2-ethyl-6-methoxy-3,4-dihydro-2H-[1,5]naphthyridine-1-carboxylic acid ethyl ester (801 mg). MS (m/z): 776 [M+H]$^+$.

(3) (2R,4S)-4-([3,5-Bis(trifluoromethyl)benzyl]-{5-[3-(2-methoxy-carbonylethanesulfonyl)propyl]pyrimidin-2-yl})amino-2-ethyl-6-methoxy-3,4-dihydro-2H-[1,5]naphthyridine-1-carboxylic acid ethyl ester (200 mg) and 2N aqueous NaOH solution (516 µl) are dissolved in ethanol (3 ml), and the mixture is stirred at room temperature for 30 minutes. To the reaction solution is added 2N aqueous HCl solution (520 µl), and the mixture is stirred overnight. To the reaction mixture is added ethyl acetate, and the organic layer is washed with saturated brine and dried over magnesium sulfate, then concentrated under reduced pressure. The resulting residue is purified by column chromatography (silica gel; chloroform:methanol=9:1→4:1) to give (2R,4S)-4-{[3,5-bis(trifluoromethyl)-benzyl]-[5-(3-sulfopropyl)pyrimidin-2-yl]}amino-2-ethyl-6-methoxy-3,4-dihydro-2H-[1,5]naphthyridine-1-carboxylic acid ethyl ester (96 mg). MS (m/z): 704 [M−H]$^+$.

Example 296

(2R,4S)-4-{[3,5-Bis(trifluoromethyl)benzyl]-[5-(3-sulfopropyl)-pyrimidin-2-yl]}amino-2-ethyl-6-methoxy-3,4-dihydro-2H-[1,5]naphthyridine-1-carboxylic acid ethyl ester (125 mg) is dissolved in thionyl chloride (3 ml) and stirred at 80° C. for 2 hours. The reaction solution is cooled to room temperature, and then concentrated under reduced pressure. To the resulting residue is added chloroform (3 ml), then added a solution (2 ml) of 7N ammonia in methanol under ice-cooling. The mixture is stirred at room temperature for 3 hours. To the reaction solution are added water and ethyl acetate, and the organic layer is washed with saturated brine and dried over magnesium sulfate, then concentrated under reduced pressure. The resulting residue is purified by column chromatography (silica gel; hexane:ethyl acetate=4:1→1:1) to give (2R,4S)-4-{[3,5-bis(trifluoromethyl)benzyl]-[5-(3-methoxysulfonylpropyl)pyrimidin-2-yl]}amino-2-ethyl-6-methoxy-3,4-dihydro-2H-[1,5]naphthyridine-1-carboxylic acid ethyl ester (29 mg) MS (m/z): 720 [M+H]$^+$, and (2R,4S)-4-{[3,5-bis(trifluoromethyl)benzyl]-[5-(3-sulfamoylpropyl)pyrimidin-2-yl]}-amino-2-ethyl-6-methoxy-3,4-dihydro-2H-[1,5]naphthyridine-1-carboxylic acid ethyl ester (10 mg) MS (m/z): 705 [M+H]$^+$.

Example 297

(2R,4S)-4-{[3,5-Bis(trifluoromethyl)benzyl]-[5-(2-cyanoethyl)-pyrimidin-2-yl]}amino-2-ethyl-6-methoxy-3,4-dihydro-2H-[1,5]naphthyridine-1-carboxylic acid ethyl ester (500 mg) is dissolved in ethanol (5 ml), and thereto are added sodium carbonate (292 mg) and hydroxylamine hydrochloride (192 mg). The mixture is heated at 80° C. and stirred for 31.5 hours. The reaction solution is cooled to room temperature, and partitioned by adding water and ethyl acetate. The organic layer is washed with saturated brine, then dried over magnesium sulfate, and concentrated under reduced pressure. The resulting residue is purified by column chromatography (silica gel; chloroform:methanol=1:0→19:1) to give (2R,4S)-4-([3,5-bis(trifluoromethyl)benzyl]-{5-[2-(N-hydroxycarbamimidoyl)ethyl]pyrimidin-2-yl})amino-2-ethyl-6-methoxy-3,4-dihydro-2H-[1,5]naphthyridine-1-carboxylic acid ethyl ester (297 mg) MS (m/z): 670 [M+H]$^+$, and (2R,4S)-4-{[3,5-bis(trifluoromethyl)benzyl]-[5-(2-carbamoylethyl)pyrimidin-2-yl]}amino-2-ethyl-6-methoxy-3,4-dihydro-2H-[1,5]naphthyridine-1-carboxylic acid ethyl ester (140 mg) MS (m/z): 655 [M+H]$^+$.

Example 298

(2R,4S)-4-([3,5-Bis(trifluoromethyl)benzyl]-{5-[2-(N-hydroxy-carbamimidoyl)ethyl]pyrimidin-2-yl})amino-2-ethyl-6-methoxy-3,4-dihydro-2H-[1,5]naphthyridine-1-carboxylic acid ethyl ester (140 mg) is dissolved in acetonitrile (1 ml), and thereto is added carbodiimidazole (51 mg). The mixture is heated at 60° C. and stirred for 25.5 hours. The reaction solution is cooled to room temperature, and partitioned by adding water and ethyl acetate. The organic layer is washed with saturated brine, then dried over magnesium sulfate, and concentrated under reduced pressure. The resulting residue is purified by column chromatography (silica gel; chloroform:methanol=1:0→19:1) to give (2R,4S)-4-([3,5-bis-(trifluoromethyl)benzyl]-{5-[2-(5-oxo-4,5-dihydro[1,2,4]oxadiazol-3-yl)ethyl]pyrimidin-2-yl})amino-2-ethyl-6-methoxy-3,4-dihydro-2H-[1,5]naphthyridine-1-carboxylic acid ethyl ester (84 mg). MS (m/z): 696 [M+H]$^+$.

Example 299

(2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid ethyl ester (2.0 g), zinc cyanide (352 mg) and tetrakis-(triphenylphosphine)palladium (347 mg) are dissolved in N,N-dimethylformamide (10 ml), and stirred under nitrogen at 100° C. for 4 hours. The reaction solution is partitioned by adding ethyl acetate and water. The organic layer is washed with saturated brine and dried over magnesium sulfate, then concentrated under reduced pressure. The resulting residue is purified by column chromatography (silica gel; hexane:ethyl acetate=9:1→3:1) to give (2R,4S)-4-{[3,5-bis(trifluoromethyl)-benzyl]-(5-cyanopyrimidin-2-yl)}amino-2-ethyl-6-methoxy-3,4-dihydro-2H-[1,5]naphthyridine-1-carboxylic acid ethyl ester (1.69 g). MS (m/z): 609 [M+H]⁺.

Example 300

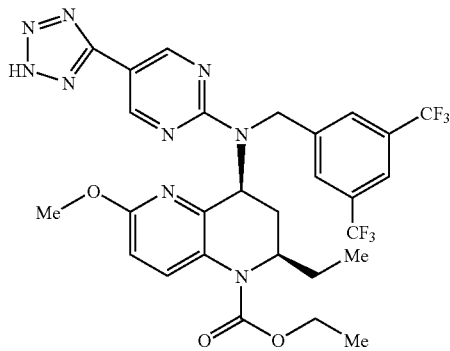

A corresponding starting compound is treated in a similar manner to Example 147 to give the compound of Example 300. MS (m/z): 652 [M+H]⁺

Example 301

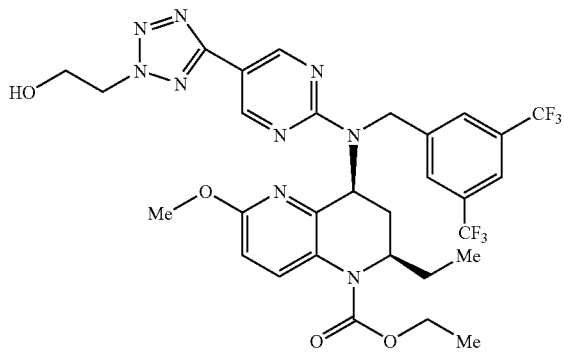

A corresponding starting compound is treated in a similar manner to Example 202 to give the compound of Example 301. MS (m/z): 696 [M+H]⁺

Example 302

Hydroxylamine hydrochloride (285 mg) is dissolved in dimethylsulfoxide (4 ml), and thereto is added triethylamine (0.57 ml). To the reaction solution is added tetrahydrofuran, and the insoluble materials are removed by filtration and the filtrate is evaporated to remove tetrahydrofuran under reduced pressure. To the resulting solution is added (2R,4S)-4-{[3,5-bis(trifluoromethyl)benzyl]-(5-cyanopyrimidin-2-yl)}-amino-2-ethyl-6-methoxy-3,4-dihydro-2H-[1,5]naphthyridine-1-carboxylic acid ethyl ester (500 mg), and the mixture is heated at 75° C. and stirred for 1 hour. The reaction solution is cooled to room temperature, and partitioned by adding water and ethyl acetate. The organic layer is washed with saturated brine and dried over magnesium sulfate, then concentrated under reduced pressure to give (2R,4S)-4-([3,5-bis(trifluoromethyl)benzyl]-{5-(N-hydroxycarbamimidoyl) pyrimidin-2-yl})amino-2-ethyl-6-methoxy-3,4-dihydro-2H-[1,5]naphthyridine-1-carboxylic acid ethyl ester (510 mg). MS (m/z): 642 [M+H]⁺.

Example 303

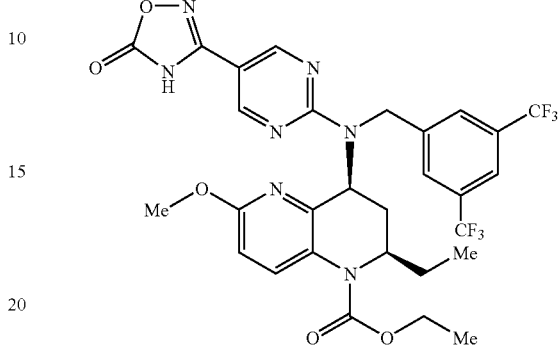

A corresponding starting compound is treated in a similar manner to Example 298 to give the compound of Example 303. MS (m/z): 668 [M+H]⁺

Example 304

(2R,4S)-4-{[3,5-Bis(trifluoromethyl)benzyl]-(5-iodopyrimidin-2-yl)}-amino-2-ethyl-6-methoxy-3,4-dihydro-2H-[1,5]naphthyridine-1-carboxylic acid ethyl ester (250 mg) is dissolved in N,N-dimethylformamide (2 ml), and thereto are added tetrakis(triphenylphosphine)palladium (81 mg), pyridine-3-boronic acid (87 mg) and potassium carbonate (117 mg). The mixture is stirred under nitrogen flow at 100° C. for 2 hours. After allowing to cool to room temperature, to the reaction mixture is added water, and the mixture is extracted with ethyl acetate. The organic layer is washed with saturated brine and dried over magnesium sulfate, then concentrated under reduced pressure. The resulting residue is purified by column chromatography (NH-silica gel; hexane:ethyl acetate=4:1) to give (2R,4S)-4-{[3,5-bis-(trifluoromethyl)benzyl]-[5-(pyridin-3-yl)pyrimidin-2-yl]}amino-2-ethyl-6-methoxy-3,4-dihydro-2H-[1,5]naphthyridine-1-carboxylic acid ethyl ester (96 mg). MS (m/z): 661 [M+H]⁺.

Example 305

(1) (2R,4S)-4-{[3,5-Bis(trifluoromethyl)benzyl]-[5-(pyridin-3-yl)pyrimidin-2-yl]}amino-2-ethyl-6-methoxy-3,4-dihydro-2H-[1,5]naphthyridine-1-carboxylic acid ethyl ester (812 mg) and benzyl bromide (292 μl) are dissolved in acetonitrile (8 ml), and stirred at 50° C. for 6 hours. The reaction solution is concentrated under reduced pressure, and the residue is crystallized and washed with isopropyl ether to give 1-benzyl-3-(2-{[3,5-bis(trifluoromethyl)benzyl]-((2R,4S)-1-ethoxycarbonyl-2-ethyl-6-methoxy-1,2,3,4-tetrahydro-[1,5]naphthyridin-4-yl)}aminopyrimidin-5-yl)pyridinium bromide (1.01 g). MS (m/z): 661 [M+H−PhCH₂Br]⁺.

(2) 1-Benzyl-3-(2-{[3,5-bis(trifluoromethyl)benzyl]-((2R,4S)-1-ethoxy-carbonyl-2-ethyl-6-methoxy-1,2,3,4-tetrahydro-[1,5]naphthyridin-4-yl)}-aminopyrimidin-5-yl) pyridinium bromide (117 mg) is dissolved in methanol (2 ml), and thereto is added sodium tetrahydroborate (11 mg). The mixture is stirred under nitrogen flow at room temperature for 10 minutes. To the reaction solution are added a saturated aqueous sodium hydrogen carbonate solution and ethyl acetate, and the organic layer is washed with saturated brine, and then dried over magnesium sulfate, then concentrated under reduced pressure. The resulting residue is purified by column chromatography (silica gel; hexane:ethyl acetate=4:1→2:1) to give (2R,4S)-4-{[5-(1-benzyl-1,2,5,6-tetrahydropyridin-3-yl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (65 mg). MS (m/z): 755 [M+H]$^+$.

Example 306

(2R,4S)-4-{[5-(1-Benzyl-1,2,5,6-tetrahydropyridin-3-yl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (432 mg) is dissolved in methanol (10 ml), and thereto is added a catalytic amount of 10% palladium-carbon and the mixture is stirred overnight under hydrogen at room temperature. The catalyst (10% palladium-carbon) is removed by filtration, and then the filtrate is concentrated under reduced pressure. The resulting residue is purified by column chromatography (NH-silica gel; hexane:ethyl acetate=1:2→0:1) to give (2R,4S)-4-{[3,5-bis(trifluoromethyl)-benzyl]-[5-(piperidin-3-yl)pyrimidin-2-yl]}amino-2-ethyl-6-methoxy-3,4-dihydro-2H-[1,5]naphthyridine-1-carboxylic acid ethyl ester (177 mg). MS (m/z): 667 [M+H]$^+$.

Example 307

(2R,4S)-4-{[3,5-Bis(trifluoromethyl)benzyl]-[5-(piperidin-3-yl)pyrimidin-2-yl]}amino-2-ethyl-6-methoxy-3,4-dihydro-2H-[1,5]naphthyridine-1-carboxylic acid ethyl ester (143 mg) and triethylamine (45 µl) are dissolved in dichloromethane (2 ml), and thereto is added acetyl chloride (23 µl) at 0° C. and the mixture is stirred at room temperature for 1 hour. To the reaction solution are added a saturated aqueous citric acid solution and dichloromethane. The organic layer is washed with saturated brine and dried over sodium sulfate, and then concentrated under reduced pressure. The resulting residue is purified by column chromatography (silica gel; hexane:ethyl acetate=1:2→0:1) to give (2R,4S)-4-{[5-(1-acetylpiperidin-3-yl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (134 mg). MS (m/z): 709 [M+H]$^+$.

Example 308

(2R,4S)-4-{[3,5-Bis(trifluoromethyl)benzyl]-[5-(pyridin-3-yl)pyrimidin-2-yl]}amino-2-ethyl-6-methoxy-3,4-dihydro-2H-[1,5]naphthyridine-1-carboxylic acid ethyl ester (402 mg) is dissolved in dichloromethane (5 ml), and thereto is added m-chloroperbenzoic acid (210 mg) under ice-cooling and the mixture is stirred at room temperature for 1 hour. To the reaction solution is added a saturated aqueous sodium hydrogen carbonate solution. The organic layer is washed with saturated brine and dried over magnesium sulfate, then concentrated under reduced pressure. The resulting residue is purified by column chromatography (silica gel; chloroform:methanol=1:0→49:1) to give (2R,4S)-4-{[3,5-bis-(trifluoromethyl)benzyl]-[5-(1-oxy-pyridin-3-yl)pyrimidin-2-yl]}amino-2-ethyl-6-methoxy-3,4-dihydro-2H-[1,5]naphthyridine-1-carboxylic acid ethyl ester (361 mg). MS (m/z): 677 [M+H]$^+$.

Example 309

(2R,4S)-4-{[3,5-Bis(trifluoromethyl)benzyl]-[5-(1-oxy-pyridin-3-yl)pyrimidin-2-yl]}amino-2-ethyl-6-methoxy-3,4-dihydro-2H-[1,5]naphthyridine-1-carboxylic acid ethyl ester (272 mg) is dissolved in acetic anhydride (3 ml), and stirred under reflux for 3 days. The reaction solution is cooled to room temperature, and thereto and concentrated under reduced pressure. The resulting residue is dissolved in methanol, and thereto is added concentrated aqueous ammonia solution and the mixture is stirred at room temperature for 1 hour. The reaction solution is concentrated under reduced pressure, and the resulting residue is purified by column chromatography (silica gel; hexane:ethyl acetate=1:2→0:1) to give (2R,4S)-4-{[3,5-bis(trifluoromethyl)benzyl]-[5-(2-hydroxypyridin-3-yl)pyrimidin-2-yl]}amino-2-ethyl-6-methoxy-3,4-dihydro-2H-[1,5]naphthyridine-1-carboxylic acid ethyl ester (150 mg). MS (m/z): 677 [M+H]$^+$.

Example 310

(1) (2R,4S)-4-{[3,5-Bis(trifluoromethyl)benzyl]-(5-iodopyrimidin-2-yl)}-amino-2-ethyl-6-methoxy-3,4-dihydro-2H-[1,5]naphthyridine-1-carboxylic acid ethyl ester (300 mg) is dissolved in N,N-dimethylformamide (2.5 ml), and thereto are added tetrakis(triphenylphosphine)palladium (98 mg), 5-formylpyridine-3-boronic acid pinacol ester (197 mg) and sodium carbonate (108 mg). The mixture is stirred overnight under nitrogen flow at 100° C. After allowing to cool to room temperature, to the reaction mixture is added a saturated aqueous sodium hydrogen carbonate solution, and the mixture is extracted with ethyl acetate. The organic layer is washed with saturated brine and dried over magnesium sulfate, then concentrated under reduced pressure to give (2R,4S)-4-{[3,5-bis(trifluoromethyl)benzyl]-[5-(5-formylpyridin-3-yl)pyrimidin-2-yl]}amino-2-ethyl-6-methoxy-3,4-dihydro-2H-[1,5]naphthyridine-1-carboxylic acid ethyl ester (69 mg). MS (m/z): 689 [M+H]$^+$.

(2) (2R,4S)-4-{[3,5-Bis(trifluoromethyl)benzyl]-[5-(5-formylpyridin-3-yl)pyrimidin-2-yl]}amino-2-ethyl-6-methoxy-3,4-dihydro-2H-[1,5]naphthyridine-1-carboxylic acid ethyl ester (65 mg) is dissolved in tert-butyl alcohol (0.67 ml), and thereto are added water (0.18 ml), 2-methyl-2-butene (44 µl) and monosodium phosphate dihydrate (15 mg), and slowly added sodium chlorite (36 mg) under water-cooling. The mixture is stirred at room temperature for 1 hour. To the reaction mixture is added a 10% aqueous citric acid solution, and the mixture is extracted with ethyl acetate. The organic layer is washed with saturated brine and dried over magnesium sulfate, then concentrated under reduced pressure. The resulting residue is purified by column chromatography (silica gel; chloroform:methanol=19:1→9:1) to give (2R,4S)-4-{[3,5-bis-(trifluoromethyl)benzyl]-[5-(5-carboxypyridin-3-yl)pyrimidin-2-yl]}amino-2-ethyl-6-methoxy-3,4-dihydro-2H-[1,5]naphthyridine-1-carboxylic acid ethyl ester (54 mg). MS (m/z): 705 [M+H]$^+$.

Example 311

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid ethyl ester (100 mg) is dissolved in chloroform (1.5 ml), and thereto is added m-chloroperbenzoic acid (48 mg) and the mixture is stirred at room temperature for 30 minutes. To the reaction mixture is added a saturated aqueous sodium hydrogen carbonate solution, and the mixture is extracted with ethyl acetate. The organic layer is washed with a saturated aqueous sodium hydrogen carbonate solution and saturated brine, and dried over magnesium sulfate. The acidic impurities are removed using a small amount of NH-silica gel, and the organic layer is concentrated under reduced pressure. To the resulting residue are added diethyl ether and isopropyl ether, and the precipitated crystals are removed by filtration to give (2R,4S)-4-{[3,5-bis-(trifluoromethyl)benzyl]-[5-(4-oxy-morpholin-4-yl)pyrimidin-2-yl]}amino-2-ethyl-6-methoxy-3,4-dihydro-2H-[1,5]naphthyridine-1-carboxylic acid ethyl ester (89 mg). MS (m/z): 685 [M+H]$^+$.

Example 312

(1) (2R,4S)-4-{[3,5-Bis(trifluoromethyl)benzyl]-[5-(3-hydroxypropenyl)-pyrimidin-2-yl]}amino-2-ethyl-6-methoxy-3,4-dihydro-2H-[1,5]naphthyridine-1-carboxylic acid ethyl ester (750 mg) is dissolved in chloroform (15 ml), and thereto is added m-chloroperbenzoic acid (303 mg) under ice-cooling. The mixture is stirred at room temperature for 2 hours, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; hexane:ethyl acetate=7:3→2:3) to give (2R,4S)-4-([3,5-bis(trifluoromethyl)benzyl]-{5-[1-(3-chlorobenzoyloxy)-2,3-dihydroxypropyl]pyrimidin-2-yl})amino-2-ethyl-6-methoxy-3,4-dihydro-2H-[1,5]naphthyridine-1-carboxylic acid ethyl ester (677 mg) as a crude product. MS (m/z): 812/814 [M+H]$^+$.
(2) The crude product (360 mg) of (2R,4S)-4-([3,5-bis(trifluoromethyl)-benzyl]-{5-[1-(3-chlorobenzoyloxy)-2,3-dihydroxypropyl]pyrimidin-2-yl})-amino-2-ethyl-6-methoxy-3,4-dihydro-2H-[1,5]naphthyridine-1-carboxylic acid ethyl ester is dissolved in methanol (10 ml), and thereto is added 1N aqueous NaOH solution (5 ml) and the mixture is stirred at room temperature for 30 minutes. The reaction solution is concentrated under reduced pressure, and partitioned by adding ethyl acetate. The organic layer is washed with saturated brine and dried over magnesium sulfate, then concentrated under reduced pressure. The resulting residue is purified by column chromatography (NH-silica gel; chloroform:methanol=1:0→9:1) to give (2R,4S)-4-{[3,5-bis(trifluoromethyl)benzyl]-[5-(1,2,3-trihydroxy)propylpyrimidin-2-yl]}amino-2-ethyl-6-methoxy-3,4-dihydro-2H-[1,5]naphthyridine-1-carboxylic acid ethyl ester (184 mg). MS (m/z): 674 [M+H]$^+$.

Example 313

(2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid ethyl ester (300 mg) is dissolved in 1,4-dioxane (1 ml), and thereto are added cesium carbonate (205 mg), pyrrolidin-2-one (41 μl), 4,5-bis-(diphenylphosphino)-9,9-xanthene (81 mg) and tris(dibenzylideneacetone)-dipalladium (41.5 mg). The mixture is heated at 90° C. and stirred for 15 hours. The reaction solution is cooled to room temperature, and partitioned by adding water and diethyl ether. The organic layer is washed with saturated brine, then dried over magnesium sulfate, and concentrated under reduced pressure. The resulting residue is purified by column chromatography (silica gel; hexane:ethyl acetate=4:1→7:3) to give (2R,4S)-4-{[3,5-bis(trifluoromethyl)benzyl]-[5-(2-oxopyrrolidin-1-yl)pyrimidin-2-yl]}amino-2-ethyl-6-methoxy-3,4-dihydro-2H-[1,5]naphthyridine-1-carboxylic acid ethyl ester (126.6 mg). MS (m/z): 667 [M+H]$^+$.

Example 314

(2R*,4S*)-4-{[3,5-Bis(trifluoromethyl)benzyl]-(5-iodopyrimidin-2-yl)}-amino-2-ethyl-6-methoxy-3,4-dihydro-2H-[1,5]naphthyridine-1-carboxylic acid ethyl ester (300 mg), sodium 3-methoxy-3-oxopropan-1-sulfinate (221 mg) and copper (I) iodide (242 mg) are dissolved in dimethylsulfoxide (2 ml). The mixture is stirred under nitrogen flow at 110° C. for 3 hours. The reaction solution is cooled to room temperature, and thereto are added water and ethyl acetate. After the precipitated insoluble materials are removed by filtration through Celite™, the organic layer is washed with saturated brine, and then dried over magnesium sulfate and concentrated under reduced pressure. The resulting residue is purified by column chromatography (silica gel; hexane:ethyl acetate=4:1→2:1) to give (2R*,4S*)-4-{[3,5-bis(trifluoromethyl)benzyl]-[5-(2-methoxycarbonyl-ethanesulfonyl)pyrimidin-2-yl]}amino-2-ethyl-6-methoxy-3,4-dihydro-2H-[1,5]naphthyridine-1-carboxylic acid ethyl ester (286 mg). MS (m/z): 734 [M+H]$^+$.

Example 315

(2R*,4S*)-4-{[3,5-Bis(trifluoromethyl)benzyl]-[5-(2-methoxycarbonyl-ethanesulfonyl)pyrimidin-2-yl]}amino-2-ethyl-6-methoxy-3,4-dihydro-2H-[1,5]naphthyridine-1-carboxylic acid ethyl ester (141 mg) and 2N aqueous NaOH solution (384 μl) are dissolved in ethanol (3 ml), and the mixture is stirred at 50° C. for 30 minutes. To the reaction solution is added 2N aqueous HCl solution (385 μl), and stirred overnight. To the reaction mixture is added ethyl acetate, and the organic layer is washed with saturated brine and dried over magnesium sulfate, then concentrated under reduced pressure. The resulting residue is purified by column chromatography (silica gel; chloroform:methanol=9:1→4:1) to give (2R*,4S*)-4-{[3,5-bis(trifluoromethyl)benzyl]-(5-sulfopyrimidin-2-yl)}amino-2-ethyl-6-methoxy-3,4-dihydro-2H-[1,5]naphthyridine-1-carboxylic acid ethyl ester (64 mg). MS (m/z): 662 [M−H]$^−$.

Example 316

(1) (2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid ethyl ester (2 g), sodium 3-methoxy-3-oxopropan-1-sulfinate (2.63 g) and copper (I) iodide (2.88 g) are dissolved in dimethylsulfoxide (25 ml), and the mixture is stirred under nitrogen flow at 110° C. for 6 hours. The reaction solution is cooled to room temperature, and thereto are added water and ethyl acetate. After the precipitated insoluble materials are removed by filtration through Celite™, the organic layer is washed with saturated brine and dried over magnesium sulfate, and concentrated under reduced pressure. The resulting residue is purified by column chromatography (silica gel; hexane:ethyl acetate=4:1→2:1) to give (2R,4S)-4-{[3,5-bis(trifluoromethyl)benzyl]-[5-(2-methoxycarbonyl-ethanesulfonyl)pyrimidin-2-yl]}amino-2-ethyl-6-methoxy-3,4-dihydro-2H-[1,5]naphthyridine-1-carboxylic acid ethyl ester (1.92 g). MS (m/z): 734 [M+H]$^+$.
(2) (2R,4S)-4-{[3,5-Bis(trifluoromethyl)benzyl]-[5-(2-methoxycarbonyl-ethanesulfonyl)pyrimidin-2-yl]

}amino-2-ethyl-6-methoxy-3,4-dihydro-2H-[1,5]naph-thyridine-1-carboxylic acid ethyl ester (1.9 g) and 2N aqueous NaOH solution (2.6 ml) are dissolved in ethanol (20 ml), and the mixture is stirred at room temperature for 30 minutes. To the reaction solution are added 2N aqueous HCl solution (2.7 ml) and hydrogen peroxide solution (10 ml), and the mixture is stirred overnight. To the reaction mixture is added chloroform, and the organic layer is washed with saturated brine and dried over magnesium sulfate, then concentrated under reduced pressure. The resulting residue is purified by column chromatography (silica gel; chloroform:methanol=9:1→4:1) to give (2R,4S)-4-{[3,5-bis-(trifluoromethyl)benzyl]-(5-sulfopyrimidin-2-yl)}amino-2-ethyl-6-methoxy-3,4-dihydro-2H-[1,5]naphthyridine-1-carboxylic acid ethyl ester (1.68 g). MS (m/z): 662 [M−H]−.

(3) (2R,4S)-4-{[3,5-Bis(trifluoromethyl)benzyl]-(5-sulfopyrimidin-2-yl)}-amino-2-ethyl-6-methoxy-3,4-dihydro-2H-[1,5]naphthyridine-1-carboxylic acid ethyl ester (200 mg) is dissolved in thionyl chloride (2 ml), and stirred at 120° C. for 2 hours. The reaction solution is cooled to room temperature, and then concentrated under reduced pressure. To the resulting residue is added toluene (2 ml), then added a solution (15 ml) of 0.5M ammonia in 1,4-dioxane under ice-cooling, and the mixture is stirred overnight at room temperature. The reaction solution is concentrated under reduced pressure, and then to the resulting residue are added water and ethyl acetate. The organic layer is washed with saturated brine and dried over magnesium sulfate, then concentrated under reduced pressure. The resulting residue is purified by column chromatography (silica gel; hexane:ethyl acetate=3:1→2:1) to give (2R,4S)-4-{[3,5-bis(trifluoromethyl)-benzyl]-(5-sulfamoylpyrimidin-2-yl)}amino-2-ethyl-6-methoxy-3,4-dihydro-2H-[1,5]naphthyridine-1-carboxylic acid ethyl ester (75 mg). MS (m/z): 663 [M+H]+.

Example 317

(1) (2R,4S)-4-{[3,5-Bis(trifluoromethyl)benzyl]-(5-sulfopyrimidin-2-yl)}-amino-2-ethyl-6-methoxy-3,4-dihydro-2H-[1,5]naphthyridine-1-carboxylic acid ethyl ester (927 mg) is dissolved in thionyl chloride (10 ml), and heated at 100° C. and stirred for 2 hours. The reaction solution is concentrated under reduced pressure and the resulting residue is dissolved in toluene (10 ml). To the mixture are added glycine tert-butyl ester hydrochloride (468 mg) and triethylamine (389 il) under ice-cooling, and the reaction mixture is stirred for 5 hours with allowing to warm gradually from under ice-cooling to room temperature. The reaction mixture is partitioned by adding saturated brine and ethyl acetate. The organic layer is washed with saturated brine and dried over magnesium sulfate, then concentrated under reduced pressure. The resulting residue is purified by column chromatography (silica gel; hexane:ethyl acetate=6:1→2:1) to give (2R,4S)-4-{[3,5-bis(trifluoromethyl)benzyl]-[5-(tert-butoxy-carbonylmethylsulfamoyl) pyrimidin-2-yl]}amino-2-ethyl-6-methoxy-3,4-dihydro-2H-[1,5]naphthyridine-1-carboxylic acid ethyl ester (235 mg). MS (m/z): 777 [M+H]+.

(2) (2R,4S)-4-{[3,5-Bis(trifluoromethyl)benzyl]-[5-(tert-butoxycarbonyl-methylsulfamoyl)pyrimidin-2-yl]}amino-2-ethyl-6-methoxy-3,4-dihydro-2H-[1,5]naphthyridine-1-carboxylic acid ethyl ester (230 mg) is dissolved in ethyl acetate (6 ml), and thereto is added a solution (4 ml) of 4N HCl/ethyl acetate. The mixture is stirred overnight at room temperature, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; chloroform:methanol=1:0→4:1) to give (2R,4S)-4-{[3,5-bis-(trifluoromethyl)benzyl]-(5-carboxymethylsulfamoylpyrimidin-2-yl)}amino-2-ethyl-6-methoxy-3,4-dihydro-2H-[1,5]naphthyridine-1-carboxylic acid ethyl ester (135 mg). MS (m/z): 721 [M+H]+.

Examples 318-319

Corresponding starting compounds are treated in a similar manner to Example 156 (1) to give the compounds listed in Table 33.

TABLE 33

| Example No. | R | R' | Physical properties, etc. |
|---|---|---|---|
| 318 | Br— | ![3-CF3-5-CN-benzyl] | MS (m/z): 619/621 [M + H]+ |
| 319 | Br— | ![3,5-dimethoxybenzyl] | MS (m/z): 586/588 [M + H]+ |

Example 320

(2R,4S)-4-[(5-Bromopyrimidin-2-yl)-(3-cyano-5-trifluoromethyl-benzyl)]amino-2-ethyl-6-methoxy-3,4-dihydro-2H-[1,5]naphthyridine-1-carboxylic acid ethyl ester (300 mg) is dissolved in toluene (4 ml), and thereto are added tris(dibenzylideneacetone)dipalladium (44 mg), sodium tert-butoxide (70 mg), 2-(di-tert-butylphosphino)biphenyl (58 mg) and acetyl piperazine (93 mg). The mixture is stirred at room temperature for 1 hour under nitrogen flow, then heated at 50° C. and stirred for 5.5 hours, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; hexane:ethyl acetate=1:1→0:1) to give (2R,4S)-4-{[5-(4-acetylpiperazin-1-yl)pyrimidin-2-yl]-(3-cyano-5-trifluoromethyl-benzyl)}amino-2-ethyl-6- methoxy-3,4-dihydro-2H-[1,5]naphthyridine-1-carboxylic acid ethyl ester (177 mg). MS (m/z): 667 [M+H]⁺.

Example 321

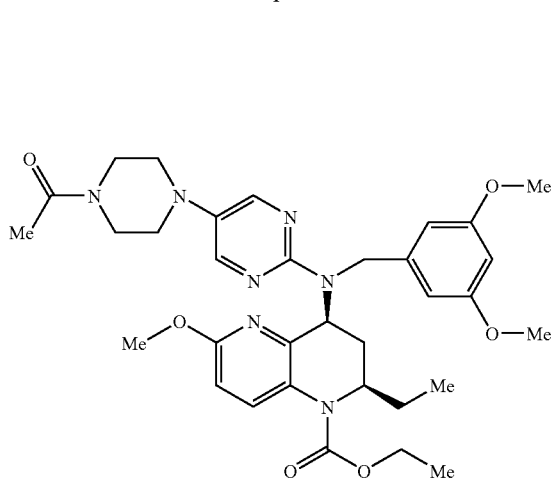

A corresponding starting compound is treated in a similar manner to Example 320 to give the compound of Example 321. MS (m/z): 634 [M+H]⁺

Example 322

(1) (2R,4S)-4-[(5-Bromopyrimidin-2-yl)-(3-cyano-5-trifluoromethyl-benzyl)]amino-2-ethyl-6-methoxy-3,4-dihydro-2H-[1,5]naphthyridine-1-carboxylic acid ethyl ester (3 g) is dissolved in 1,4-dioxane (30 ml), and thereto are added acrylic acid benzyl ester (1.57 g), tris(dibenzylideneacetone)dipalladium (665 mg), dicyclohexylmethylamine (1.42 g) and tri-tert-butylphosphonium tetrafluoroborate (420 mg). The mixture is stirred at room temperature for 3 days under nitrogen flow, and partitioned by adding aqueous citric acid solution and ethyl acetate. The organic layer is washed with saturated brine and dried over magnesium sulfate, then concentrated under reduced pressure. The resulting residue is purified by column chromatography (silica gel; hexane:ethyl acetate=9:1→7:3→3:2) to give (2R,4S)-4-{[5-(2-benzyloxycarbonylvinyl)pyrimidin-2-yl]-(3-cyano-5-trifluoromethylbenzyl)}amino-2-ethyl-6-methoxy-3,4-dihydro-2H-[1,5]naphthyridine-1-carboxylic acid ethyl ester (1.82 g). MS (m/z): 701 [M+H]⁺.

(2) (2R,4S)-4-{[5-(2-Benzyloxycarbonylvinyl)pyrimidin-2-yl]-(3-cyano-5-trifluoromethylbenzyl)}amino-2-ethyl-6-methoxy-3,4-dihydro-2H-[1,5]naphthyridine-1-carboxylic acid ethyl ester (800 mg) is dissolved in a mixture of tetrahydrofuran (16 ml) and methanol (4 ml), and thereto is added 10% palladium-carbon (230 mg). The mixture is stirred for 9 hours under hydrogen. The reaction solution is filtered, and then the filtrate is concentrated under reduced pressure. The resulting residue is purified by column chromatography (silica gel; chloroform:methanol=1:0→9:1) to give (2R,4S)-4-{[5-(2-carboxyethyl)pyrimidin-2-yl]-(3-cyano-5-trifluoromethyl-benzyl)}amino-2-ethyl-6-methoxy-3,4-dihydro-2H-[1,5]naphthyridine-1-carboxylic acid ethyl ester (317 mg). MS (m/z): 613 [M+H]⁺.

Example 323

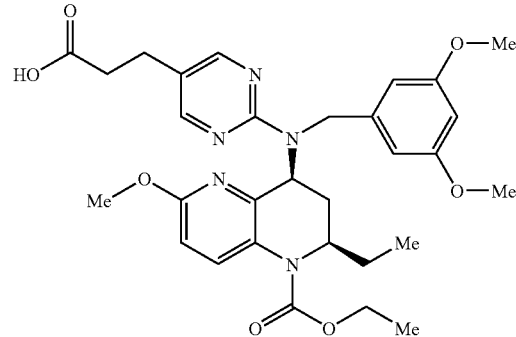

A corresponding starting compound is treated in a similar manner to Example 322 to give the compound of Example 323. MS (m/z): 580 [M+H]⁺

Examples 324-325

Corresponding starting compounds are treated in a similar manner to Example 143 to give the compounds listed in Table 34.

TABLE 34

| Example No. | R | R' | Physical properties, etc. |
|---|---|---|---|
| 324 | HO~~~ | 3-CF₃, 5-CN benzyl | MS (m/z): 599 [M + H]⁺ |
| 325 | HO~~~ | 3-OMe, 5-OMe benzyl | MS (m/z): 566 [M + H]⁺ |

Example 326

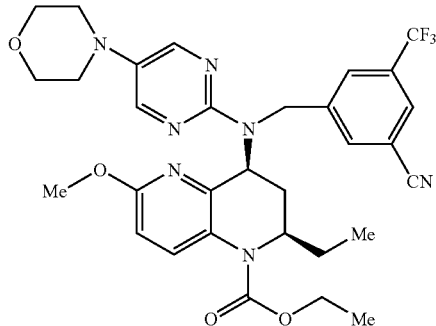

A corresponding starting compound is treated in a similar manner to Example 156 (2) to give the compound of Example 326. MS (m/z): 626 [M+H]+

Example 327

(2R,4S)-4-{(3-Cyano-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid ethyl ester (315 mg) is dissolved in methanol (9 ml), and thereto is added 1N aqueous NaOH solution (1 ml). The mixture is stirred at room temperature for 1 day, and partitioned by adding 1N HCl and ethyl acetate. The organic layer is washed with saturated brine and dried over magnesium sulfate, then concentrated under reduced pressure. The resulting residue is purified by column chromatography (silica gel; hexane:ethyl acetate=7:3→3:7→0:1) to give (2R,4S)-2-ethyl-6-methoxy-4-{(3-methoxycarbonyl-5-trifluoromethylbenzyl)-[5-(morpholin-4-yl)pyrimidin-2-yl]}amino-3,4-dihydro-2H-[1,5]naphthyridine-1-carboxylic acid ethyl ester (54 mg). MS (m/z): 659 [M+H]+.

Example 328

(2R,4S)-2-Ethyl-6-methoxy-4-{(3-methoxycarbonyl-5-trifluoromethylbenzyl)-[5-(morpholin-4-yl)pyrimidin-2-yl]}amino-3,4-dihydro-2H-[1,5]naphthyridine-1-carboxylic acid ethyl ester (86 mg) is dissolved in methanol (9 ml) and N,N-dimethylformamide (1 ml), and thereto is added 1N aqueous NaOH solution (3 ml). The mixture is stirred at room temperature for 1.5 hours, and partitioned by adding 1N HCl and ethyl acetate. The organic layer is washed with saturated brine, then dried over magnesium sulfate, and concentrated under reduced pressure. The resulting residue is purified by thin layer silica gel chromatography (chloroform:methanol=9:1) to give (2R,4S)-4-{(3-carboxy-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid ethyl ester (25 mg). MS (m/z): 645 [M+H]+.

Example 329

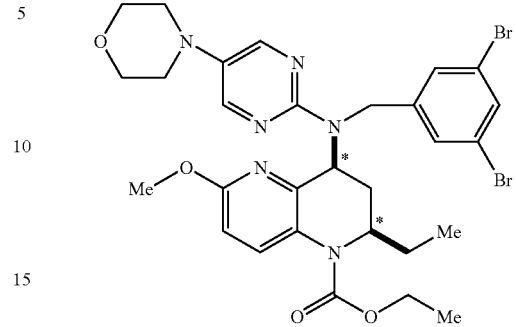

A corresponding starting compound is treated in a similar manner to Example 177 (2) to give the compound of Example 329. MS (m/z): 689/691 [M+H]+

Example 330

(2R*,4S*)-4-{(3,5-Dibromobenzyl)-[5-(morpholin-4-yl)pyrimidin-2-yl]}amino-2-ethyl-6-methoxy-3,4-dihydro-2H-[1,5]naphthyridine-1-carboxylic acid ethyl ester (200 mg) is dissolved in N,N-dimethylformamide (4 ml), and thereto are added zinc cyanide (75 mg), a catalytic amount of tetrakis(triphenylphosphine)palladium. The mixture is heated at 110° C. and stirred for 2 hours under nitrogen flow. The reaction solution is cooled to room temperature, and partitioned by adding a saturated aqueous sodium hydrogen carbonate solution and ethyl acetate. The organic layer is washed with saturated brine and dried over magnesium sulfate, then concentrated under reduced pressure. The resulting residue is purified by column chromatography (silica gel; hexane:ethyl acetate=7:3→1:1) to give (2R*,4S*)-4-{(3,5-dicyanobenzyl)-[5-(morpholin-4-yl)pyrimidin-2-yl]}amino-2-ethyl-6-methoxy-3,4-dihydro-2H-[1,5]naphthyridine-1-carboxylic acid ethyl ester (134 mg). MS (m/z): 583 [M+H]+.

Example 331

(1) (2R,4S)-4-[(5-Bromopyrimidin-2-yl)-(3-cyano-5-trifluoromethyl-benzyl)]amino-2-ethyl-6-methoxy-3,4-dihydro-2H-[1,5]naphthyridine-1-carboxylic acid ethyl ester (300 mg), isonipecotic acid ethyl ester (109 μl), sodium tert-butoxide (70 mg) and 2-(di-tert-butylphosphino)biphenyl (58 mg) are dissolved in toluene (5 ml), and thereto is added tris-(dibenzylideneacetone)dipalladium (44 mg). The mixture is stirred overnight under nitrogen at room temperature, and partitioned by adding ethyl acetate and saturated brine to the reaction solution. The organic layer is washed with saturated brine, then dried over magnesium sulfate, and concentrated under reduced pressure. The residue is purified by column chromatography (silica gel; hexane:ethyl acetate=9:1→3:2) to give (2R,4S)-4-{(3-cyano-5-trifluoromethylbenzyl)-[5-(4-ethoxycarbonylpiperidin-1-yl)pyrimidin-2-yl]}amino-2-ethyl-6-methoxy-3,4-dihydro-2H-[1,5]naphthyridine-1-carboxylic acid ethyl ester (125 mg). MS (m/z): 696 [M+H]+.

(2) (2R,4S)-4-{(3-Cyano-5-trifluoromethylbenzyl)-[5-(4-ethoxycarbonyl-piperidin-1-yl)pyrimidin-2-yl]}amino-2- ethyl-6-methoxy-3,4-dihydro-2H-[1,5]naphthyridine-1-carboxylic acid ethyl ester (120 mg) is treated in a similar manner to Example 36 to give (2R,4S)-4-{[5-(4-carboxypiperidin-1-yl)pyrimidin-2-yl]-(3-cyano-5-trifluoromethylbenzyl)}amino-2-ethyl-6-methoxy-3,4-dihydro-2H-[1,5]naphthyridine-1-carboxylic acid ethyl ester (65 mg). MS (m/z): 668 [M+H]$^+$.

Example 332

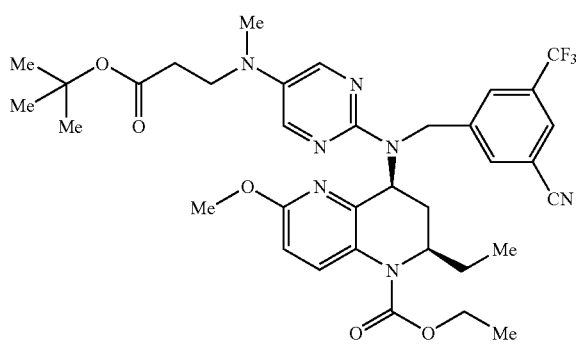

A corresponding starting compound is treated in a similar manner to Example 224 (1) to give the compound of Example 332. MS (m/z): 698 [M+H]$^+$ Example 333

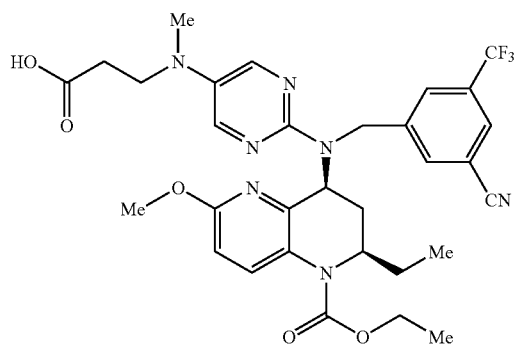

A corresponding starting compound is treated in a similar manner to Example 224 (2) to give the compound of Example 333. MS (m/z): 642 [M+H]$^+$ Example 334

(1) (2R,4S)-4-[(5-Bromopyrimidin-2-yl)-(3-cyano-5-trifluoromethyl-benzyl)]amino-2-ethyl-6-methoxy-3,4-dihydro-2H-[1,5]naphthyridine-1-carboxylic acid ethyl ester (10 g) is treated in a similar manner to Example 4 to give (2R,4S)-4-[(3-cyano-5-trifluoromethylbenzyl)-(5-iodopyrimidin-2-yl)]amino-2-ethyl-6-methoxy-3,4-dihydro-2H-[1,5]naphthyridine-1-carboxylic acid ethyl ester (8.18 g). MS (m/z): 667 [M+H]$^+$.

(2) (2R,4S)-4-[(3-Cyano-5-trifluoromethylbenzyl)-(5-iodopyrimidin-2-yl)]amino-2-ethyl-6-methoxy-3,4-dihydro-2H-[1,5]naphthyridine-1-carboxylic acid ethyl ester (300 mg) is dissolved in N,N-dimethylformamide (2.5 ml), and thereto are added tetrakis(triphenylphosphine)palladium (104 mg), pyrimidin-5-boronic acid (112 mg) and sodium carbonate (114 mg). The mixture is stirred at 100° C. for 4 hours under nitrogen flow. After allowing to cool to room temperature, to the reaction mixture is added water. The mixture is extracted with ethyl acetate, and the organic layer is washed with saturated brine and dried over magnesium sulfate, then concentrated under reduced pressure. The resulting residue is purified by column chromatography (NH-silica gel; hexane:ethyl acetate=2:1) to give (2R,4S)-4-[([5,5']bipyrimidinyl-2-yl)-(3-cyano-5-trifluoromethylbenzyl)]-amino-2-ethyl-6-methoxy-3,4-dihydro-2H-[1,5]naphthyridine-1-carboxylic acid ethyl ester (116 mg). MS (m/z): 619 [M+H]$^+$.

Example 335

(2R,4S)-4-{[3,5-Bis(trifluoromethyl)benzyl]-[5-(morpholin-4-yl)-pyrimidin-2-yl]}amino-2-ethyl-6-trifluoromethanesulfonyloxy-3,4-dihydro-2H-[1,5]naphthyridine-1-carboxylic acid ethyl ester (100 mg) is dissolved in dimethylsulfoxide (2 ml), and thereto is added a 2M solution (300 μl) of dimethylamine in tetrahydrofuran under ice-cooling. The mixture is stirred at 40° C. for 72 hours in a closed vessel, and partitioned by adding water and ethyl acetate to the reaction solution. The organic layer is washed with saturated brine and dried over magnesium sulfate, then concentrated under reduced pressure. The resulting residue is purified by column chromatography (silica gel; hexane:ethyl acetate=4:1→2:1) to give (2R,4S)-4-{[3,5-bis(trifluoromethyl)benzyl]-[5-(morpholin-4-yl)pyrimidin-2-yl]}amino-6-dimethylamino-2-ethyl-3,4-dihydro-2H-[1,5]naphthyridine-1-carboxylic acid ethyl ester (78 mg). MS (m/z): 682 [M+H]$^+$.

Example 336

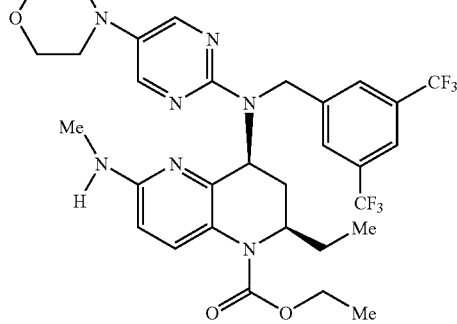

A corresponding starting compound is treated in a similar manner to Example 335 to give the compound of Example 336. MS (m/z): 668 [M+H]$^+$ Example 337

(1) To a suspension of (2R,4S)-4-{[5-(4-acetylpiperazin-1-yl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (3.45 g), sodium iodide (4.6 g) and acetonitrile (50 ml) is added dropwise trimethylsilyl chloride (3.8 ml) at 80° C. After dropwise addition, the reaction solution is cooled to room temperature, and thereto are added saturated aqueous sodium thiosulfate solution and ethyl acetate. The organic layer is washed with saturated brine and dried over magnesium sulfate, then concentrated under reduced pressure. The resulting residue is purified by column chromatography (silica gel; chloroform:methanol=49:1→19:1) to give (2R, 4S)-4-{[5-(4-acetylpiperazin-1-yl)pyrimidin-2-yl]-[3,5-bis(trifluoromethyl)benzyl]}amino-2-ethyl-6-hydroxy-3,4-dihydro-2H-[1,5]naphthyridine-1-carboxylic acid ethyl ester (3.09 g). MS (m/z): 696 [M+H]$^+$.

(2) (2R,4S)-4-{[5-(4-Acetylpiperazin-1-yl)pyrimidin-2-yl]-[3,5-bis(trifluoromethyl)benzyl]}amino-2-ethyl-6-hydroxy-3,4-dihydro-2H-[1,5]naphthyridine-1-carboxylic acid ethyl ester (3.05 g) and pyridine (1.06 ml) are dissolved in methylene chloride (20 ml), and thereto is added dropwise trifluoromethanesulfonic anhydride (885 µl) under ice-cooling. The mixture is stirred at the same temperature for 4 hours, and thereto is added an aqueous citric acid solution. The organic layer is washed with a saturated aqueous sodium. hydrogen carbonate solution, followed by saturated brine, and then dried over magnesium sulfate, then concentrated under reduced pressure. The resulting residue is purified by column chromatography (silica gel; hexane:ethyl acetate=1:2→0:1) to give (2R,4S)-4-{[5-(4-acetylpiperazin-1-yl)pyrimidin-2-yl]-[3,5-bis(trifluoromethyl)-benzyl]}amino-2-ethyl-6-trifluoromethanesulfonyloxy-3,4-dihydro-2H-[1,5]naphthyridine-1-carboxylic acid ethyl ester (2.39 g). MS (m/z): 828 [M+H]$^+$.

(3) (2R,4S)-4-{[5-(4-Acetylpiperazin-1-yl)pyrimidin-2-yl]-[3,5-bis-(trifluoromethyl)benzyl]}amino-2-ethyl-6-trifluoromethanesulfonyloxy-3,4-dihydro-2H-[1,5]naphthyridine-1-carboxylic acid ethyl ester (200 mg) is dissolved in dimethylsulfoxide (4 ml), and thereto is added a 2M solution of dimethylamine in tetrahydrofuran (1.2 ml) under ice-cooling. The mixture is stirred at 40° C. for 48 hours in a closed vessel. To the reaction solution are added water and ethyl acetate, and then the organic layer is washed with saturated brine and dried over magnesium sulfate, then concentrated under reduced pressure. The resulting residue is purified by column chromatography (silica gel; hexane:ethyl acetate=1:2→0:1) to give (2R, 4S)-4-{[5-(4-acetylpiperazin-1-yl)pyrimidin-2-yl]-[3,5-bis(trifluoromethyl)-benzyl]}amino-6-dimethylamino-2-ethyl-3,4-dihydro-2H-[1,5]naphthyridine-1-carboxylic acid ethyl ester (163 mg). MS (m/z): 723 [M+H]$^+$.

Example 338

(2R,4S)-4-{[5-(4-Acetylpiperazin-1-yl)pyrimidin-2-yl]-[3,5-bis-(trifluoromethyl)benzyl]}amino-2-ethyl-6-trifluoromethanesulfonyloxy-3,4-dihydro-2H-[1,5]naphthyridine-1-carboxylic acid ethyl ester (250 mg), palladium acetate (34 mg), 1,1'-bis(diphenylphosphino)ferrocene (84 mg) and triethylamine (126 µl) are dissolved in N,N-dimethylformamide (2 ml), and thereto is added formic acid (28 µl). The mixture is stirred at 60° C. for 1 hour under nitrogen flow. To the reaction solution are added water and ethyl acetate, and then the organic layer is washed with saturated brine and dried over magnesium sulfate, then concentrated under reduced pressure. The resulting residue is purified by column chromatography (NH-silica gel; hexane:ethyl acetate=1:2→0:1) to give (2R,4S)-4-{[5-(4-acetylpiperazin-1-yl)pyrimidin-2-yl]-[3,5-bis(trifluoromethyl)benzyl]}amino-2-ethyl-3,4-dihydro-2H-[1,5]naphthyridine-1-carboxylic acid ethyl ester (195 mg). MS (m/z): 680 [M+H]$^+$.

Example 339

(2R,4S)-4-{[5-(4-Acetylpiperazin-1-yl)pyrimidin-2-yl]-[3,5-bis-(trifluoromethyl)benzyl]}amino-2-ethyl-6-trifluoromethanesulfonyloxy-3,4-dihydro-2H-[1,5]naphthyridine-1-carboxylic acid ethyl ester (200 mg) is dissolved in 1,4-dioxane (2 ml), and thereto are added dropwise a catalytic amount of tetrakis(triphenylphosphine)palladium, silver carbonate and copper (I) chloride, and a 1M solution (362 µl) of trimethylaluminum in hexane under nitrogen flow. The mixture is stirred at 60° C. for 1 hour. The reaction solution is cooled to room temperature, and thereto are added water and ethyl acetate. The organic layer is washed with saturated brine and dried over magnesium sulfate, then concentrated under reduced pressure. The resulting residue is purified by column chromatography (NH-silica gel; hexane:ethyl acetate=1:2→0:1) to give (2R,4S)-4-{[5-(4-acetylpiperazin-1-yl)pyrimidin-2-yl]-[3,5-bis(trifluoromethyl)benzyl]}amino-2-ethyl-6-methyl-3,4-dihydro-2H-[1,5]naphthyridine-1-carboxylic acid ethyl ester (142 mg). MS (m/z): 694 [M+H]$^+$.

Example 340

(2R,4S)-4-{[5-(4-Acetylpiperazin-1-yl)pyrimidin-2-yl]-[3,5-bis-(trifluoromethyl)benzyl]}amino-2-ethyl-6-trifluoromethanesulfonyloxy-3,4-dihydro-2H-[1,5]naphthyridine-1-carboxylic acid ethyl ester (200 mg), a catalytic amount of tetrakis(triphenylphosphine)palladium, zinc cyanide (37 mg) are dissolved in N,N-dimethylformamide (2 ml), and the mixture is stirred at 100° C. for 6 hours under nitrogen flow. The reaction solution is cooled to room temperature, and thereto are added water and ethyl acetate. The mixture is washed with saturated brine and dried over magnesium sulfate, then concentrated under reduced pressure. The resulting residue is purified by column chromatography (silica gel; hexane:ethyl acetate=3:7→0:1) to give (2R,4S)-4-{[5-(4-acetylpiperazin-1-yl)pyrimidin-2-yl]-[3,5-bis(trifluoromethyl)benzyl]}amino-6-cyano-2-ethyl-3,4-dihydro-2H-[1,5] naphthyridine-1-carboxylic acid ethyl ester (149 mg). MS (m/z): 705 [M+H]$^+$.

Example 341

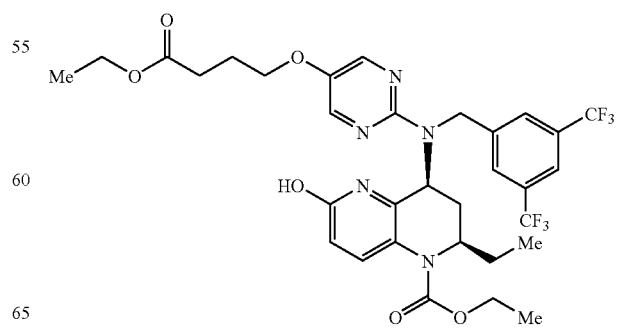

A corresponding starting compound is treated in a similar manner to Example 337 (1) to give the compound of Example 341. MS (m/z): 700 [M+H]⁺

Example 342

(1) (2R,4S)-4-{[3,5-Bis(trifluoromethyl)benzyl]-[5-(3-ethoxycarbonyl-propoxy)pyrimidin-2-yl]}amino-2-ethyl-6-hydroxy-3,4-dihydro-2H-[1,5]naphthyridine-1-carboxylic acid ethyl ester (1.5 g) and pyridine (519 µl) are dissolved in methylene chloride (10 ml), and thereto is added trifluoromethanesulfonic anhydride (432 µl) under ice-cooling under nitrogen. The mixture is stirred for 1 hour, and partitioned by adding methylene chloride and a saturated aqueous citric acid solution to the reaction solution. The organic layer is washed with a saturated aqueous sodium hydrogen carbonate solution and saturated brine, and dried over magnesium sulfate, then concentrated under reduced pressure. The resulting residue is purified by column chromatography (silica gel; hexane:ethyl acetate=9:1→3:2) to give (2R,4S)-4-{[3,5-bis(trifluoromethyl)benzyl]-[5-(3-ethoxycarbonylpropoxy)pyrimidin-2-yl]}amino-2-ethyl-6-trifluoromethanesulfonyloxy-3,4-dihydro-2H-[1,5]naphthyridine-1-carboxylic acid ethyl ester (1.56 g). MS (m/z): 832 [M+H]⁺.

(2) (2R,4S)-4-{[3,5-Bis(trifluoromethyl)benzyl]-[5-(3-ethoxycarbonyl-propoxy)pyrimidin-2-yl]}amino-2-ethyl-6-trifluoromethanesulfonyloxy-3,4-dihydro-2H-[1,5]naphthyridine-1-carboxylic acid ethyl ester (1.27 g) is dissolved in N,N-dimethylformamide (10 ml), and thereto are added palladium acetate (34 mg), 1,1'-bis(diphenylphosphino)ferrocene (169 mg), benzyl alcohol (3.16 ml) and triethylamine (2.13 ml). The mixture is purged by carbon monoxide at room temperature for 5 minutes, then is heated at 80° C. and stirred for 1.5 hours under carbon monoxide. The reaction solution is cooled to room temperature, and thereto is added saturated brine. The mixture is extracted with ethyl acetate. The organic layer is washed with saturated brine and dried over magnesium sulfate, then concentrated under reduced pressure. The resulting residue is purified by column chromatography (silica gel; hexane:ethyl acetate=19:1→3:1) to give (2R,4S)-4-{[3,5-bis(trifluoromethyl)benzyl]-[5-(3-ethoxy-carbonylpropoxy)pyrimidin-2-yl]}amino-6-benzyloxycarbonyl-2-ethyl-3,4-dihydro-2H-[1,5]naphthyridine-1-carboxylic acid ethyl ester (520 mg) MS (m/z): 818 [M+H]⁺ and (2R,4S)-4-{[3,5-bis(trifluoromethyl)benzyl]-[5-(3-ethoxycarbonylpropoxy)pyrimidin-2-yl]}amino-2-ethyl-3,4-dihydro-2H-[1,5]naphthyridine-1-carboxylic acid ethyl ester (330 mg) MS (m/z): 684 [M+H]⁺.

Example 343

(1) (2R,4S)-4-{[3,5-Bis(trifluoromethyl)benzyl]-[5-(3-ethoxycarbonyl-propoxy)pyrimidin-2-yl]}amino-6-benzyloxycarbonyl-2-ethyl-3,4-dihydro-2H-[1,5]naphthyridine-1-carboxylic acid ethyl ester (500 mg) is dissolved in ethanol (2 ml), and thereto is added 10% palladium-carbon (50 mg). The mixture is stirred at room temperature for 1.5 hours under hydrogen. Palladium-carbon is removed by filtration, and the filtrate is concentrated under reduced pressure. The resulting residue is purified by column chromatography (silica gel; hexane:ethyl acetate=4:1→:7) to give (2R,4S)-4-{[3,5-bis(trifluoromethyl)benzyl]-[5-(3-ethoxycarbonylpropoxy)pyrimidin-2-yl]}amino-2-ethyl-3,4-dihydro-2H-[1,5]naphthyridine-1,6-dicarboxylic acid 1-ethyl ester (323 mg). MS (m/z): 728 [M+H]⁺.

(2) A mixture of (2R,4S)-4-{[3,5-bis(trifluoromethyl)benzyl]-[5-(3-ethoxycarbonylpropoxy)pyrimidin-2-yl]}amino-2-ethyl-3,4-dihydro-2H-[1,5]naphthyridine-1,6-dicarboxylic acid 1-ethyl ester (300 mg) and bis(2-methoxyethyl)aminosulfur trifluoride (1.6 ml) is stirred overnight at 80° C. The reaction solution is cooled to room temperature, and thereto is added ethyl acetate for dilution. The mixture is poured into a saturated aqueous sodium hydrogen carbonate solution. The organic layer is washed with 1N HCl and saturated brine, and dried over magnesium sulfate, then concentrated under reduced pressure. The resulting residue is purified by thin layer silica gel chromatography (hexane:ethyl acetate=2:1) to give (2R,4S)-4-{[3,5-bis(trifluoromethyl)benzyl]-[5-(3-ethoxycarbonylpropoxy)-pyrimidin-2-yl]}amino-2-ethyl-6-trifluoromethyl-3,4-dihydro-2H-[1,5]naphthyridine-1-carboxylic acid ethyl ester (77 mg) MS (m/z): 752 [M+H]⁺, and (2R,4S)-6-[bis(2-methoxyethyl)carbamoyl]-4-{[3,5-bis-(trifluoromethyl)benzyl]-[5-(3-ethoxycarbonylpropoxy)pyrimidin-2-yl]}-amino-2-ethyl-3,4-dihydro-2H-[1,5]naphthyridine-1-carboxylic acid ethyl ester (184 mg) MS (m/z): 843 [M+H]⁺.

Examples 344-346

Corresponding starting compounds are treated in a similar manner to Example 36 to give the compounds listed in Table 35.

TABLE 35

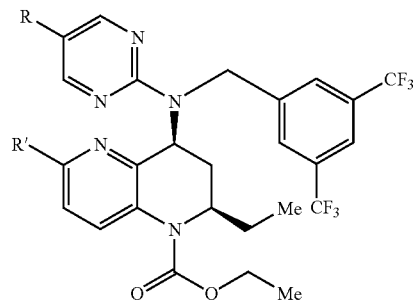

| Example No. | R | R' | Physical properties, etc. |
|---|---|---|---|
| 344 | HO-C(=O)-CH₂CH₂CH₂-O-CH₃ | F₃C— | MS (m/z): 724 [M + H]⁺ |
| 345 | HO-C(=O)-CH₂CH₂CH₂-O-CH₂CH₂-N(C(=O)-)-CH₂CH₂-O-Me with MeO- | | MS (m/z): 815 [M + H]⁺ |
| 346 | HO-C(=O)-CH₂CH₂CH₂-O-CH₃ | H— | MS (m/z): 656 [M + H]⁺ |

Example 347

(1) To an aqueous solution (650 ml) of sodium azide (101.4 g) is added dropwise a solution (390 ml) of acrylic acid chloride (117.7 ml) in toluene under ice-cooling, and the mixture is stirred at the same temperature for 1 hour. Then the ice-water bath is removed and the mixture is stirred until cooling to room temperature. The solution of the reaction mixture is washed with a saturated aqueous sodium hydrogen carbonate solution and dried over magnesium sulfate. The resulting solution in toluene is added dropwise into a mixture of (R)-1-phenylethyl alcohol (173 ml), pyridine (52.6 ml) and hydroquinone (7.90 g) which is warmed to 85° C., and the mixture is stirred at the same temperature for 1 hour. The reaction mixture is cooled to room temperature. The mixture is washed with a saturated aqueous sodium hydrogen carbonate solution and saturated brine, and dried over magnesium sulfate, then concentrated under reduced pressure. The resulting residue is purified by column chromatography (silica gel; hexane:ethyl acetate=10:1→19:1) to give vinylcarbamic acid (R)-1-phenylethyl ester (167.3 g). MS (m/z): 191[M]$^+$.

(2) {[1-(Benzotriazol-1-yl)propyl]-(6-methoxypyridin-3-yl)}amine (212.5 g), vinylcarbamic acid (R)-1-phenylethyl ester (143.4 g) and p-toluenesulfonic acid monohydrate (1.43 g) are dissolved in toluene (2.80 l), and the mixture is stirred at 85° C. for 3 hours. After the mixture is allowed to stand for cooling to room temperature, the reaction solution is washed with a saturated aqueous sodium hydrogen carbonate solution, water and saturated brine. The organic layer is dried over magnesium sulfate, and then concentrated under reduced pressure. The resulting residue is purified by column chromatography (silica gel; hexane:ethyl acetate=4:1). To the residue is added hexane-ethyl acetate (9:1), and the precipitated crystals are removed by filtration. To the resulting mixture of diastereomers is added ether and the mixture is stirred, and the precipitated crystals are removed by filtration. To the resulting crystals are added a mixture of hexane-ethyl acetate (4:1) and the mixture is stirred. The resulting crystals are removed by filtration to give (2R,4S)-2-ethyl-6-methoxy-1,2,3,4-tetrahydro-[1,5]naphthyridin-4-yl)carbamic acid (R)-1-phenylethyl ester (38.7 g). MS (m/z): 356 [M+H]$^+$.

(3) ((2R,4S)-2-Ethyl-6-methoxy-1,2,3,4-tetrahydro-[1,5]naphthyridin-4-yl)carbamic acid (R)-1-phenylethyl ester (200 mg) is dissolved in tetrahydrofuran (3 ml), and thereto is added di-tert-butyl dicarbonate (395 mg). The mixture is stirred overnight at 70° C. After the mixture is allowed to stand for cooling to room temperature, to the reaction solution is added a saturated aqueous sodium hydrogen carbonate solution and the mixture is extracted with ethyl acetate. The organic layer is washed with saturated brine and dried over magnesium sulfate, then concentrated under reduced pressure. The resulting residue is purified by column chromatography (silica gel; hexane:ethyl acetate=6:1→4:1) to give (2R,4S)-2-ethyl-6-methoxy-4-((R)-1-phenylethoxycarbonyl)amino-3,4-dihydro-2H-[1,5]naphthyridine-1-carboxylic acid tert-butyl ester (270 mg). MS (m/z): 456 [M+H]$^+$.

(4) (2R,4S)-2-Ethyl-6-methoxy-4-((R)-1-phenylethoxycarbonyl)amino-3,4-dihydro-2H-[1,5]naphthyridine-1-carboxylic acid tert-butyl ester (39.10 g) is dissolved in methanol (550 ml), and thereto is added 10% palladium-carbon (20.0 g). The mixture is stirred at room temperature for 2 hours under hydrogen flow. The reaction mixture is filtered and the filtrate is concentrated under reduced pressure. The resulting residue is purified by column chromatography (silica gel; hexane:ethyl acetate=1:1→chloroform:methanol=9:1) to give (2R,4S)-4-amino-2-ethyl-6-methoxy-3,4-dihydro-2H-[1,5]naphthyridine-1-carboxylic acid tert-butyl ester (24.87 g). MS (m/z): 308 [M+H]$^+$.

(5) (2R,4S)-4-Amino-2-ethyl-6-methoxy-3,4-dihydro-2H-[1,5]naphthyridine-1-carboxylic acid tert-butyl ester (24.80 g) is dissolved in 1,4-dioxane (450 ml), and thereto are added 5-bromo-2-chloropyrimidine (39.01 g) and N,N-diisopropylethylamine (35.1 ml). The mixture is stirred overnight at 80° C. After the mixture is allowed to stand for cooling to room temperature, the mixture is concentrated under reduced pressure. The resulting residue is purified by column chromatography (silica gel; hexane:ethyl acetate=6:1) to give (2R,4S)-4-(5-bromopyrimidin-2-yl)-amino-2-ethyl-6-methoxy-3,4-dihydro-2H-[1,5]naphthyridine-1-carboxylic acid tert-butyl ester (27.48 g). MS (m/z): 466/464 [M+H]$^+$.

(6) (2R,4S)-4-(5-Bromopyrimidin-2-yl)amino-2-ethyl-6-methoxy-3,4-dihydro-2H-[1,5]naphthyridine-1-carboxylic acid tert-butyl ester (20.00 g) is dissolved in N,N-dimethylformamide (150 ml), and thereto is added sodium hydride (62.7%, 2.46 g) under ice-cooling. The mixture is stirred at the same temperature for 30 minutes. Subsequently, 3,5-bis(trifluoromethyl)benzyl bromide (11.8 ml) is added to the mixture, and the mixture is stirred at room temperature for 1 hour. After the reaction solution is neutralized by adding 10% aqueous citric acid solution, the mixture is extracted with ethyl acetate. The organic layer is washed with saturated brine, then dried over magnesium sulfate, and concentrated under reduced pressure. To the resulting residue are added ether and hexane. The precipitated crystals are removed by filtration to give (2R,4S)-4-{[3,5-bis(trifluoromethyl)benzyl]-(5-bromopyrimidin-2-yl)}amino-2-ethyl-6-methoxy-3,4-dihydro-2H-[1,5]naphthyridine-1-carboxylic acid tert-butyl ester (28.13 g). MS (m/z): 692/690 [M+H]$^+$.

(7) (2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid tert-butyl ester (6.00 g) is dissolved in toluene (60 ml), and thereto are added tris(dibenzylideneacetone)dipalladium (796 mg), 2-(di-tert-butyl-phosphino)biphenyl (1.04 g), morpholine (1.52 ml) and sodium tert-butoxide (1.67 g). The mixture is stirred at room temperature for 7 hours under nitrogen flow. After the reaction mixture is neutralized by adding 10% aqueous citric acid solution, the mixture is extracted with ethyl acetate. The organic layer is washed with water and saturated brine, and dried over magnesium sulfate, then concentrated under reduced pressure. The resulting residue is purified by column chromatography (silica gel; hexane:ethyl acetate=4:1) to give (2R,4S)-4-{[3,5-bis(trifluoromethyl)-benzyl]-[5-(morpholin-4-yl)pyrimidin-2-yl]}amino-2-ethyl-6-methoxy-3,4-dihydro-2H-[1,5]naphthyridine-1-carboxylic acid tert-butyl ester (5.37 g).
MS (m/z): 697 [M+H]$^+$.

(8) (2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid tert-butyl ester (5.36 g) is dissolved in 1,4-dioxane (15 ml), and thereto is added a solution (40 ml) of 4N HCl/1,4-dioxane under water-cooling. The mixture is stirred at room temperature for 3 hours. After the reaction mixture is neutralized by adding a saturated aqueous sodium hydrogen carbonate solution, the mixture is extracted with ethyl acetate. The organic layer is washed with saturated brine and dried over magnesium sulfate, then concentrated under reduced pressure to give (2R,4S)-4-{[3,5-bis(trifluoromethyl)benzyl]-[5-(morpholin-4-yl)pyrimidin-2-yl]}amino-2-ethyl-6-methoxy-1,2,3,4-tetrahydro-[1,5]naphthyridine (4.48 g). MS (m/z): 597 [M+H]$^+$.

(9) (2R,4S)-4-{[3,5-Bis(trifluoromethyl)benzyl]-[5-(morpholin-4-yl)-pyrimidin-2-yl]}amino-2-ethyl-6-methoxy-1,2,3,4-tetrahydro-[1,5]naphthyridine (233 mg) is dissolved in methylene chloride (2 ml), and thereto is added triethylamine (65 μl), then added triphosgene (46 mg) under water-cooling. The mixture is stirred at the same temperature for 30 minutes. To the reaction mixture is added water and the mixture is extracted with ethyl acetate. The organic layer is washed with saturated brine and dried over magnesium sulfate, then concentrated under reduced pressure. To the resulting residue are added tetrahydrofuran (2 ml), ethylene glycol (1.0 ml), triethylamine (0.40 ml) and dimethylaminopyridine (10 mg), and the mixture is stirred at room temperature for 5 days. To the reaction mixture is added water, and the mixture is extracted with ethyl acetate. The organic layer is washed with saturated brine and dried over magnesium sulfate, then concentrated under reduced pressure. The resulting residue is purified by column chromatography (silica gel; hexane:ethyl acetate=1:2) to give (2R,4S)-4-{[3,5-bis(trifluoromethyl)-benzyl]-[5-(morpholin-4-yl)pyrimidin-2-yl]}amino-2-ethyl-6-methoxy-3,4-dihydro-2H-[1,5]naphthyridine-1-carboxylic acid 2-hydroxyethyl ester (192 mg). MS (m/z): 685 [M+H]$^+$.

Examples 348-353

Corresponding starting compounds are treated in a similar manner to Example 347 (9) to give the compounds listed in Table 36.

TABLE 36

| Example No. | R | R' | Physical properties, etc. |
|---|---|---|---|
| 348 | 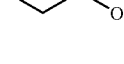 |  | MS (m/z): 699 [M + H]$^+$ |
| 349 |  | 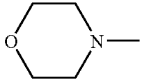 | MS (m/z): 695 [M + H]$^+$ |
| 350 | 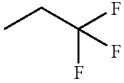 | 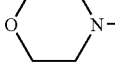 | MS (m/z): 723 [M + H]$^+$ |
| 351 | 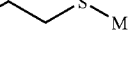 | 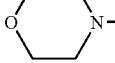 | MS (m/z): 715 [M + H]$^+$ |
| 352 | 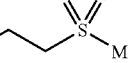 | 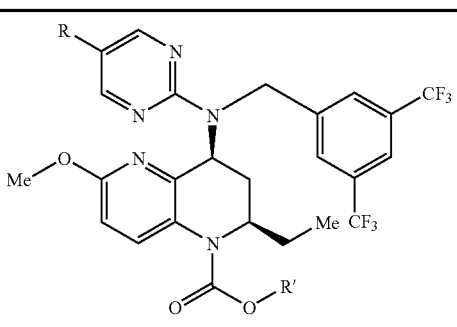 | MS (m/z): 747 [M + H]$^+$ |

TABLE 36-continued

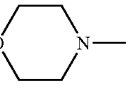

| Example No. | R | R' | Physical properties, etc. |
|---|---|---|---|
| 353 | 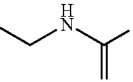 |  | MS (m/z): 726 [M + H]$^+$ |

Example 354

(1) (2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid tert-butyl ester (3.00 g) is dissolved in 1,4-dioxane (25 ml), and thereto are added tris(dibenzylideneacetone)dipalladium (596 mg), tri-tert-butylphosphine-tetrafluoroborate complex (378 mg), methyl acrylate (0.78 ml) and N,N-dicyclohexylmethylamine (1.27 g). The mixture is stirred at 40° C. for 7 hours under nitrogen flow. To the reaction mixture is added 10% aqueous citric acid solution, and then the mixture is extracted with ethyl acetate. The organic layer is washed with water and saturated brine, and dried over magnesium sulfate, then concentrated under reduced pressure. The resulting residue is purified by column chromatography (silica gel; hexane:ethyl acetate=4:1) to give (2R,4S)-4-{[3,5-bis-(trifluoromethyl)benzyl]-[5-(2-methoxycarbonylvinyl)pyrimidin-2-yl]}amino-2-ethyl-6-methoxy-3,4-dihydro-2H-[1,5]naphthyridine-1-carboxylic acid tert-butyl ester (2.93 g). MS (m/z): 696 [M+H]$^+$.

(2) (2R,4S)-4-{[3,5-Bis(trifluoromethyl)benzyl]-[5-(2-methoxycarbonyl-vinyl)pyrimidin-2-yl]}amino-2-ethyl-6-methoxy-3,4-dihydro-2H-[1,5]naphthyridine-1-carboxylic acid tert-butyl ester (2.92 g) is dissolved in methanol (60 ml), and thereto is added 10% palladium-carbon (3.00 g). The mixture is stirred at room temperature for 2 hours under hydrogen flow. The reaction mixture is filtered and the filtrate is concentrated under reduced pressure. The resulting residue is purified by column chromatography (silica gel; hexane:ethyl acetate=8:1→6:1) to give (2R,4S)-4-{[3,5-bis(trifluoromethyl)benzyl]-[5-(2-methoxycarbonylethyl)pyrimidin-2-yl]}amino-2-ethyl-6-methoxy-3,4-dihydro-2H-[1,5]naphthyridine-1-carboxylic acid tert-butyl ester (2.19 g). MS (m/z): 698 [M+H]$^+$.

(3) (2R,4S)-4-{[3,5-Bis(trifluoromethyl)benzyl]-[5-(2-methoxycarbonyl-ethyl)pyrimidin-2-yl]}amino-2-ethyl-6-methoxy-3,4-dihydro-2H-[1,5]naphthyridine-1-carboxylic acid tert-butyl ester (2.18 g) is dissolved in 1,4-dioxane (5 ml), and thereto is added a solution (10 ml) of 4N HCl in 1,4-dioxane. The mixture is stirred at room temperature for 1.5 hours. After the reaction solution is neutralized by adding a saturated aqueous sodium hydrogen carbonate solution, the mixture is extracted with ethyl acetate. The organic layer is washed with saturated brine and dried over magnesium sulfate, then concentrated under reduced pressure to give (2R,4S)-4-{[3,5-bis(trifluoromethyl)benzyl]-[5-(2-methoxycarbonylethyl)-pyrimidin-2-yl]}amino-2-ethyl-6-methoxy-1,2,3,4-tetrahydro-[1,5]naphthyridine (1.90 g). MS (m/z): 598 [M+H]$^+$.

(4)  (2R,4S)-4-{[3,5-Bis(trifluoromethyl)benzyl]-[5-(2-methoxycarbonyl-ethyl)pyrimidin-2-yl]}amino-2-ethyl-6-methoxy-1,2,3,4-tetrahydro-[1,5]naphthyridine (220 mg) is dissolved in methylene chloride (1.5 ml), and thereto is added triethylamine (62 μl), then added triphosgene (44 mg) under water-cooling. The mixture is stirred at the same temperature for 30 minutes. To the reaction mixture is added water, and the mixture is extracted with ethyl acetate. The organic layer is washed with saturated brine and dried over magnesium sulfate, then concentrated under reduced pressure. To the resulting residue are added tetrahydrofuran (2.5 ml), ethylene glycol (1.0 ml), triethylamine (0.40 ml) and dimethylaminopyridine (10 mg), the mixture is stirred overnight at room temperature under nitrogen flow. To the reaction mixture is added water, and the mixture is extracted with ethyl acetate. The organic layer is washed with saturated brine and dried over magnesium sulfate, then concentrated under reduced pressure. The resulting residue is purified by column chromatography (silica gel; hexane:ethyl acetate=1:2) to give (2R,4S)-4-{[3,5-bis-(trifluoromethyl)benzyl]-[5-(2-methoxycarbonylethyl)pyrimidin-2-yl]}amino-2-ethyl-6-methoxy-3,4-dihydro-2H-[1,5]naphthyridine-1-carboxylic acid 2-hydroxyethyl ester (145 mg). MS (m/z): 686 [M+H]$^+$.

(5)  (2R,4S)-4-{[3,5-Bis(trifluoromethyl)benzyl]-[5-(2-methoxycarbonyl-ethyl)pyrimidin-2-yl]}amino-2-ethyl-6-methoxy-3,4-dihydro-2H-[1,5]naphthyridine-1-carboxylic acid 2-hydroxyethyl ester (141 mg) is dissolved in 1,4-dioxane (3 ml), and thereto is added 1N aqueous NaOH solution (1 ml). The mixture is stirred at room temperature for 1 hour. After the reaction solution is acidified by adding 10% aqueous citric acid solution, the mixture is extracted with ethyl acetate. The organic layer is washed with saturated brine and dried over magnesium sulfate, then concentrated under reduced pressure to give (2R,4S)-4-{[3,5-bis-(trifluoromethyl)benzyl]-[5-(2-carboxyethyl)pyrimidin-2-yl]}amino-2-ethyl-6-methoxy-3,4-dihydro-2H-[1,5]naphthyridine-1-carboxylic acid 2-hydroxyethyl ester (138 mg). MS (m/z): 672 [M+H]$^+$.

Examples 355-357

Corresponding starting compounds are treated in a similar manner to Example 354 (4)-(5) to give the compounds listed in Table 37.

TABLE 37

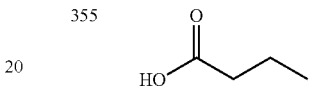

| Example No. | R | R' | Physical properties, etc. |
|---|---|---|---|
| 355 | 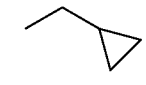 | 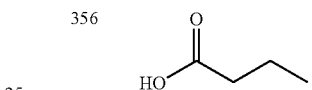 | MS (m/z): 682 [M + H]$^+$ |
| 356 | 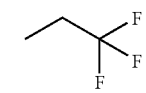 | 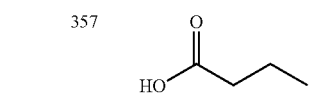 | MS (m/z): 710 [M + H]$^+$ |
| 357 | 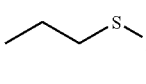 | (structure with S-Me) | MS (m/z): 702 [M + H]$^+$ |

Example 358

(1)  (2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid tert-butyl ester (4.00 g) is dissolved in toluene (40 ml), and thereto are added tris(dibenzylideneacetone)dipalladium (530 mg), 2-(di-tert-butyl-phosphino)biphenyl (691 mg), 4-ethoxycarbonylpiperidine (1.37 g) and sodium tert-butoxide (835 mg). The mixture is stirred overnight at room temperature under nitrogen flow. After the reaction mixture is neutralized by adding 10% aqueous citric acid solution, the mixture is extracted with ethyl acetate. The organic layer is washed with saturated brine and dried over magnesium sulfate, then concentrated under reduced pressure. The resulting residue is purified by column chromatography (NH-silica gel; hexane:ethyl acetate=9:1→6:1) to give (2R,4S)-4-{[3,5-bis(trifluoromethyl)-benzyl]-[5-(4-ethoxycarbonylpiperidin-1-yl)pyrimidin-2-yl]}amino-2-ethyl-6-methoxy-3,4-dihydro-2H-[1,5]naphthyridine-1-carboxylic acid tert-butyl ester (2.16 g). MS (m/z): 767 [M+H]$^+$.

(2)  (2R,4S)-4-{[3,5-Bis(trifluoromethyl)benzyl]-[5-(4-ethoxycarbonyl-piperidin-1-yl)pyrimidin-2-yl]}amino-2-ethyl-6-methoxy-3,4-dihydro-2H-[1,5]naphthyridine-1-carboxylic acid tert-butyl ester (2.03 g) is dissolved in 1,4-dioxane (6 ml), and thereto is added a solution (15 ml) of 4N HCl in 1,4-dioxane. The mixture is stirred at room temperature for 1 hour. After the reaction mixture is neutralized by adding a saturated aqueous sodium hydrogen carbonate solution, the mixture is extracted with ethyl acetate. The organic layer is washed with saturated brine and dried over magnesium sulfate, then concentrated under reduced pressure to give (2R,4S)-4-{[3,5-bis(trifluoromethyl)benzyl]-[5-(4-ethoxycarbonylpiperidin-1-yl)pyrimidin-2-yl]}amino-2-ethyl-6-methoxy-1,2,3,4-tetrahydro-[1,5]naphthyridine (1.79 g). MS (m/z): 667 [M+H]⁺.

(3) (2R,4S)-4-{[3,5-Bis(trifluoromethyl)benzyl]-[5-(4-ethoxycarbonyl-piperidin-1-yl)pyrimidin-2-yl]}amino-2-ethyl-6-methoxy-1,2,3,4-tetrahydro-[1,5]naphthyridine (130 mg) is dissolved in methylene chloride (2 ml), and thereto is added pyridine (47 μl), then added dropwise propyl chloroformate (77 μl) under ice-cooling. The mixture is stirred at the same temperature for 2 hours under nitrogen flow. To the reaction mixture is added a saturated aqueous sodium hydrogen carbonate solution, and the mixture is extracted with ethyl acetate. The organic layer is washed with saturated brine and dried over magnesium sulfate, then concentrated under reduced pressure. The resulting residue is dissolved in ethanol (1 ml), and thereto is added 2M aqueous NaOH solution (1 ml). The mixture is stirred at 50° C. for 1 hour. After 10% aqueous citric acid solution is added to the reaction mixture, the mixture is extracted with ethyl acetate. The organic layer is washed with saturated brine and dried over magnesium sulfate, then concentrated under reduced pressure. The resulting residue is purified column chromatography (silica gel; chloroform:methanol=19:1) to give (2R,4S)-4-{[3,5-bis(trifluoromethyl)benzyl]-[5-(4-carboxypiperidin-1-yl)pyrimidin-2-yl]}amino-2-ethyl-6-methoxy-3,4-dihydro-2H-[1,5]naphthyridine-1-carboxylic acid propyl ester (115 mg). MS (m/z): 725 [M+H]⁺.

Example 359

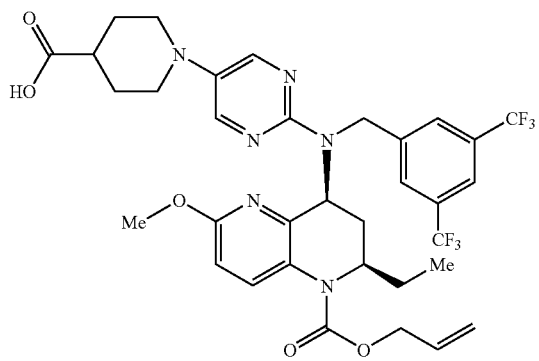

A corresponding starting compound is treated in a similar manner to Example 358 to give the compound of Example 359. MS (m/z): 723 [M+H]⁺

Example 360

(2R,4S)-4-{[3,5-Bis(trifluoromethyl)benzyl]-[5-(4-ethoxycarbonyl-piperidin-1-yl)pyrimidin-2-yl]}amino-2-ethyl-6-methoxy-3,4-dihydro-2H-[1,5]naphthyridine-1-carboxylic acid tert-butyl ester (120 mg) is dissolved in 1,4-dioxane (1 ml), and thereto is added 1M aqueous NaOH solution (1 ml). The mixture is stirred at 50° C. for 1 hour. After 10% aqueous citric acid solution is added to the reaction mixture, the mixture is extracted with ethyl acetate. The organic layer is washed with saturated brine and dried over magnesium sulfate, then concentrated under reduced pressure. The resulting residue is purified by column chromatography (silica gel; chloroform:methanol=19:1) to give (2R,4S)-4-{[3,5-bis(trifluoromethyl)-benzyl]-[5-(4-carboxypiperidin-1-yl)pyrimidin-2-yl]}amino-2-ethyl-6-methoxy-3,4-dihydro-2H-[1,5]naphthyridine-1-carboxylic acid tert-butyl ester (77 mg). MS (m/z): 739 [M+H]⁺.

Examples 361-364

Corresponding starting compounds are treated in a similar manner to Example 354 (4)-(5) to give the compounds listed in Table 38.

TABLE 38

| Example No. | R | R' | Physical properties, etc. |
|---|---|---|---|
| 361 | HO-C(O)-piperidin-N- | -CH₂CH₂CH₂F | MS (m/z): 729 [M + H]⁺ |
| 362 | HO-C(O)-piperidin-N- | -CH(Me)CH₂Me (isobutyl) | MS (m/z): 725 [M + H]⁺ |
| 363 | HO-C(O)-piperidin-N- | -CH₂CH₂CF₂F | MS (m/z): 765 [M + H]⁺ |
| 364 | HO-C(O)-piperidin-N- | -CH₂-cyclobutyl | MS (m/z): 737 [M + H]⁺ |

Example 365

(1) (2R,4S)-4-{[3,5-Bis(trifluoromethyl)benzyl]-[5-(morpholin-4-yl)-pyrimidin-2-yl]}amino-2-ethyl-6-methoxy-1,2,3,4-tetrahydro-[1,5]naphthyridine (100 mg) is dissolved in methylene chloride (1.0 ml), and thereto is added triethylamine (28 μl), then added triphosgene (20 mg) under water-cooling. The mixture is stirred at the same temperature for 5 minutes under nitrogen flow. The reaction mixture is concentrated under reduced pressure, and to the resulting residue are added methylene chloride (1.5 ml), triethylamine (28 μl) and 2-aminoethanol (24 μl). The mixture is stirred overnight at room temperature under nitrogen flow. To the reaction mixture is added saturated brine, and the mixture is extracted with ethyl acetate. The organic layer is washed with saturated brine and dried over magnesium sulfate, then concentrated under reduced pressure. The resulting residue is purified by column chromatography (silica gel; chloroform:methanol=1:0→19:1) to give (2R,4S)-4-{[3,5-bis-(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid (2-hydroxyethyl)amide (97 mg). MS (m/z): 684 [M+H]$^+$.

Example 366

(2R,4S)-4-{[3,5-Bis(trifluoromethyl)benzyl]-[5-(morpholin-4-yl)-pyrimidin-2-yl]}amino-2-ethyl-6-methoxy-1,2,3,4-tetrahydro-[1,5]naphthyridine (150 mg) is dissolved in toluene (2.0 ml), and thereto is added 2-chloroethyl isocyanate (40 mg). The mixture is stirred at 60° C. for 9 hours under nitrogen flow. To the reaction mixture is added a saturated aqueous sodium hydrogen carbonate solution, the mixture is extracted with ethyl acetate. The organic layer is washed with saturated brine and dried over magnesium sulfate, then concentrated under reduced pressure. The resulting residue is purified by column chromatography (silica gel; hexane:ethyl acetate=2:1→1:9) to give (2R,4S)-4-{[3,5-bis(trifluoromethyl)-benzyl]-[5-(morpholin-4-yl)pyrimidin-2-yl]}amino-2-ethyl-6-methoxy-3,4-dihydro-2H-[1,5]naphthyridine-1-carboxylic acid (2-chloroethyl)amide (160 mg). MS (m/z): 702/704 [M+H]$^+$.

Example 367

(2R,4S)-4-{[3,5-Bis(trifluoromethyl)benzyl]-[5-(morpholin-4-yl)-pyrimidin-2-yl]}amino-2-ethyl-6-methoxy-1,2,3,4-tetrahydro-[1,5]naphthyridine (250 mg) is dissolved in methylene chloride (2.0 ml), and thereto is added triethylamine (118 µl), then added triphosgene (50 mg) under water-cooling. The mixture is stirred at the same temperature for 30 minutes under nitrogen flow. To the reaction mixture is added water, and the mixture is extracted with ethyl acetate. The organic layer is washed with saturated brine and dried over magnesium sulfate, then concentrated under reduced pressure. The resulting residue is dissolved in a mixture of tetrahydrofuran (2.5 ml) and N,N-dimethylformamide (1 ml), and thereto are added O-methylhydroxylamine hydrochloride (70 mg) and triethylamine (230 µl). The mixture is stirred at room temperature for 4 days under nitrogen flow. To the reaction mixture is added water, and the mixture is extracted with ethyl acetate. The organic layer is washed with saturated brine and dried over magnesium sulfate, then concentrated under reduced pressure. The resulting residue is purified by column chromatography (silica gel; hexane:ethyl acetate=2:1→chloroform:methanol=19:1) to give (2R,4S)-4-{[3,5-bis-(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid methoxyamide (57 mg). MS (m/z): 670 [M+H]$^+$.

Example 368

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid (2-chloroethyl)amide (147 mg) is dissolved in acetonitrile (2.0 ml), and thereto is added 40% alumina-supported potassium fluoride (121 mg). The mixture is stirred overnight at 50° C. The reaction mixture is filtered through Celite™, and the filtered insoluble materials are washed with ethyl acetate. The filtrate and the washing are combined, and concentrated under reduced pressure. The resulting residue is purified by column chromatography (silica gel; hexane:ethyl acetate=1:1 chloroform:methanol=19:1) to give (2R,4S)-4-{[3,5-bis(trifluoromethyl)benzyl]-[5-(morpholin-4-yl)pyrimidin-2-yl]}amino-1-(4,5-dihydroxazol-2-yl)-2-ethyl-6-methoxy-3,4-dihydro-2H-[1,5]naphthyridine (51 mg). MS (m/z): 666 [M+H]$^+$.

Example 369

(1) (2R,4S)-4-{[3,5-Bis(trifluoromethyl)benzyl]-[5-(morpholin-4-yl)pyrimidin-2-yl]}amino-2-ethyl-6-methoxy-1,2,3,4-tetrahydro-[1,5]naphthyridine (250 mg) is dissolved in methylene chloride (2.0 ml), and thereto is added triethylamine (118 µl), then added triphosgene (50 mg) under water-cooling. The mixture is stirred at the same temperature for 30 minutes under nitrogen flow. To the reaction mixture is added water, and the mixture is extracted with ethyl acetate. The organic layer is washed with saturated brine and dried over magnesium sulfate, then concentrated under reduced pressure. The resulting residue is dissolved in a mixture of tetrahydrofuran (2.5 ml) and N,N-dimethylformamide (1 ml), and thereto are added O-tert-butyl-L-serine methyl ester hydrochloride (178 mg) and triethylamine (230 µl). The mixture is stirred at room temperature for 4 days under nitrogen flow. To the reaction mixture is added water, and the mixture is extracted with ethyl acetate. The organic layer is washed with saturated brine and dried over magnesium sulfate, then concentrated under reduced pressure. The resulting residue is purified by column chromatography (silica gel; hexane:ethyl acetate=2:1) to give (2R,4S)-4-{[3,5-bis(trifluoromethyl)benzyl]-[5-(morpholin-4-yl)-pyrimidin-2-yl]}amino-2-ethyl-6-methoxy-3,4-dihydro-2H-[1,5]naphthyridine-1-carboxylic acid ((S)-2-tert-butoxy-1-methoxycarbonyl-ethyl)amide (309 mg). MS (m/z): 798 [M+H]$^+$.

(2) To (2R,4S)-4-{[3,5-bis(trifluoromethyl)benzyl]-[5-(morpholin-4-yl)-pyrimidin-2-yl]}amino-2-ethyl-6-methoxy-3,4-dihydro-2H-[1,5]naphthyridine-1-carboxylic acid ((S)-2-tert-butoxy-1-methoxycarbonyl-ethyl)amide (298 mg) is added a solution (5 ml) of 4N HCl in 1,4-dioxane. The mixture is stirred at room temperature for 5 hours. After the reaction mixture is neutralized by adding a saturated aqueous sodium hydrogen carbonate solution, the mixture is extracted with ethyl acetate. The organic layer is washed with saturated brine and dried over magnesium sulfate, then concentrated under reduced pressure. The resulting residue is purified by column chromatography (silica gel; hexane:ethyl acetate=1:1→0:1) to give (2R,4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid ((S)-2-hydroxy-1-methoxycarbonyl-ethyl)amide (237 mg). MS (m/z): 742 [M+H]$^+$.

(3) (2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid ((S)-2-hydroxy-1-methoxycarbonyl-ethyl)amide (214 mg) is dissolved in methylene chloride (3.0 ml), and thereto is added pyridine (28 µl), then added trifluoromethanesulfonic anhydride (58 µl) at −20° C. The mixture is stirred at the same temperature for 40 minutes under nitrogen flow. To the reaction mixture is added a saturated aqueous sodium hydrogen carbonate solution, the mixture is extracted with ethyl acetate. The organic layer is washed with saturated brine and dried over magnesium sulfate, then concentrated under reduced pressure. The resulting residue is purified by column chromatography (silica gel; hexane:ethyl acetate=1:1→1:9) to give (2R,4S)-4-{[3,5-bis(trifluoromethyl)benzyl]-[5-(morpholin-4-yl)pyrimidin-2-yl]}amino-2-ethyl-6-methoxy-1-((S)-4-methoxycarbonyl-4,5-dihydroxazol-2-yl)-3,4-dihydro-2H-[1,5] naphthyridine (172 mg). MS (m/z): 724 [M+H]⁺.

(4) (2R,4S)-4-{[3,5-Bis(trifluoromethyl)benzyl]-[5-(morpholin-4-yl)-pyrimidin-2-yl]}amino-2-ethyl-6-methoxy-1-((S)-4-methoxycarbonyl-4,5-dihydroxazol-2-yl)-3,4-dihydro-2H-[1,5]naphthyridine (85 mg) is dissolved in tetrahydrofuran (2.0 ml), and thereto is slowly added a 1M solution (0.4 ml) of diisobutylaluminum hydride in tetrahydrofuran under ice-cooling. The mixture is stirred at the same temperature for 30 minutes under nitrogen flow. To the reaction mixture is added saturated brine, and the mixture is stirred at room temperature for 1 hour, and then extracted with ethyl acetate. The organic layer is washed with saturated brine and dried over magnesium sulfate, then concentrated under reduced pressure. The resulting residue is purified by column chromatography (silica gel; chloroform:methanol=19:1) to give (2R,4S)-4-{[3,5-bis(trifluoromethyl)-benzyl]-[5-(morpholin-4-yl)pyrimidin-2-yl]}amino-2-ethyl-1-((R)-4-hydroxymethyl-4,5-dihydroxazol-2-yl)-6-methoxy-3,4-dihydro-2H-[1,5] naphthyridine (61 mg). MS (m/z): 696 [M+H]⁺.

Example 370

(1) (2R,4S)-4-{[3,5-Bis(trifluoromethyl)benzyl]-[5-(morpholin-4-yl)pyrimidin-2-yl]}amino-2-ethyl-6-methoxy-1,2,3,4-tetrahydro-[1,5]naphthyridine (200 mg) is dissolved in methylene chloride (1.5 ml), and thereto is added pyridine (54 µl), then added chloroacetyl chloride (40 µl) under water-cooling. The mixture is stirred at room temperature for 1 hour under nitrogen flow. To the reaction mixture is added a saturated aqueous sodium hydrogen carbonate solution, and the mixture is extracted with ethyl acetate. The organic layer is washed with saturated brine and dried over magnesium sulfate, then concentrated under reduced pressure. The resulting residue is purified by column chromatography (silica gel; hexane:ethyl acetate=2:1→1:1) to give (2R,4S)-4-{[3,5-bis(trifluoromethyl)-benzyl]-[5-(morpholin-4-yl)pyrimidin-2-yl]}amino-1-chloroacetyl-2-ethyl-6-methoxy-3,4-dihydro-2H-[1,5]naphthyridine (156 mg). MS (m/z): 675/673 [M+H]⁺.

(2) (2R,4S)-4-{[3,5-Bis(trifluoromethyl)benzyl]-[5-(morpholin-4-yl)-pyrimidin-2-yl]}amino-1-chloroacetyl-2-ethyl-6-methoxy-3,4-dihydro-2H-[1,5]naphthyridine (80 mg) is dissolved in N,N-dimethylformamide (1.5 ml), and thereto are added morpholine (52 µl) and potassium carbonate (49 mg). The mixture is stirred at room temperature for 3 hours. To the reaction mixture is added saturated brine, and the mixture is extracted with ethyl acetate. The organic layer is washed with saturated brine and dried over magnesium sulfate, then concentrated under reduced pressure. The resulting residue is purified by column chromatography (silica gel; chloroform:methanol=1:0→19:1) to give (2R,4S)-4-{[3,5-bis-(trifluoromethyl)benzyl]-[5-(morpholin-4-yl)pyrimidin-2-yl]}amino-2-ethyl-6-methoxy-1-(morpholin-4-yl)acetyl-3,4-dihydro-2H-[1,5]naphthyridine (60 mg). MS (m/z): 724 [M+H]⁺.

Example 371

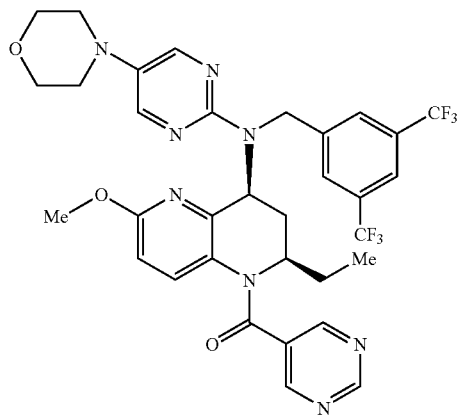

A corresponding starting compound is treated in a similar manner to Example 370 (1) to give the compound of Example 371. MS (m/z): 703 [M+H]⁺

Example 372

(2R,4S)-4-{[3,5-Bis(trifluoromethyl)benzyl]-[5-(morpholin-4-yl)pyrimidin-2-yl]}amino-2-ethyl-6-methoxy-1,2,3,4-tetrahydro-[1,5]naphthyridine (300 mg) is dissolved in N,N-dimethylformamide (3 ml), and thereto is added sodium hydride (62.7%, 21 mg) under ice-cooling, then after 1 hour added ethyl iodoacetate (71 µl). The mixture is stirred at room temperature for 24 hours. The reaction solution is partitioned by adding water and ethyl acetate. The organic layer is washed with saturated brine, then dried over magnesium sulfate and concentrated under reduced pressure. The resulting residue is purified by NH-column chromatography (silica gel; hexane:ethyl acetate=9:1→4:1) to give (2R,4S)-4-{[3,5-bis(trifluoromethyl)benzyl]-[5-(morpholin-4-yl)pyrimidin-2-yl]}amino-1-ethoxycarbonylmethyl-2-ethyl-6-methoxy-3,4-dihydro-2H-[1,5]naphthyridine (107 mg). MS (m/z): 683 [M+H]⁺.

Example 373

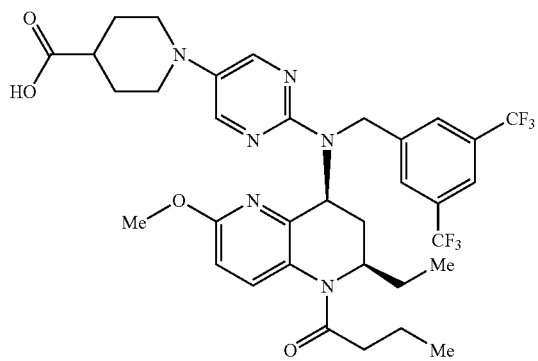

A corresponding starting compound is treated in a similar manner to Example 370 (1) and Example 36 to give the compound of Example 373.

MS (m/z): 709 [M+H]⁺

Example 374

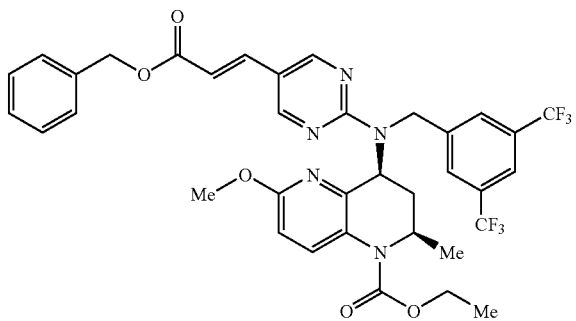

A corresponding starting compound is treated in a similar manner to Example 322 (1) to give the compound of Example 374. MS (m/z): 730 [M+H]⁺

Example 375

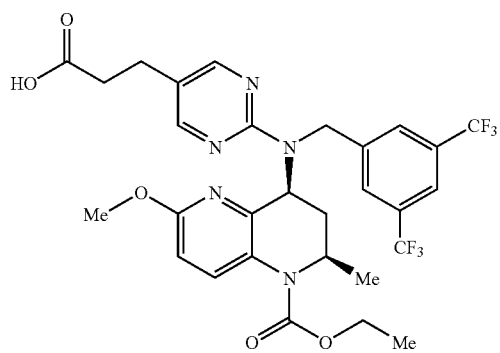

A corresponding starting compound is treated in a similar manner to Example 322 (2) to give the compound of Example 375. MS (m/z): 642 [M+H]⁺

Example 376

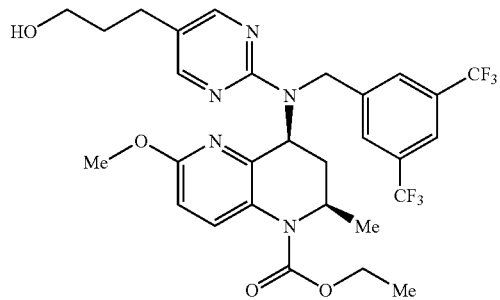

A corresponding starting compound is treated in a similar manner to Example 143 to give the compound of Example 376. MS (m/z): 628 [M+H]⁺

Example 377

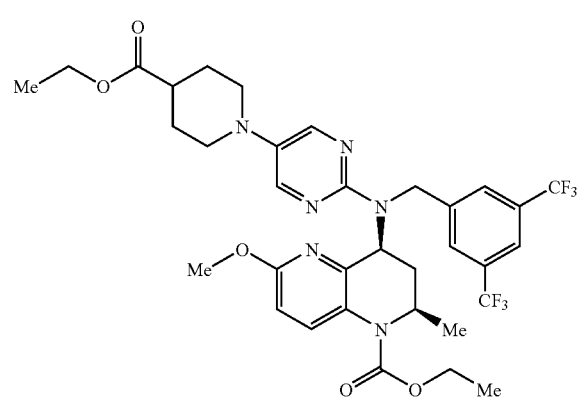

A corresponding starting compound is treated in a similar manner to Example 15 to give the compound of Example 377. MS (m/z): 725 [M+H]⁺

Example 378

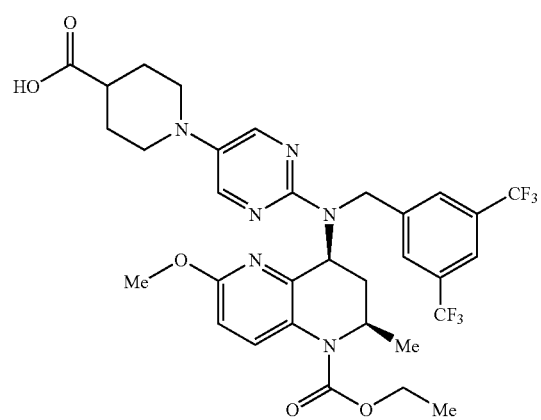

A corresponding starting compound is treated in a similar manner to Example 36 to give the compound of Example 378. MS (m/z): 697 [M+H]+

Example 379

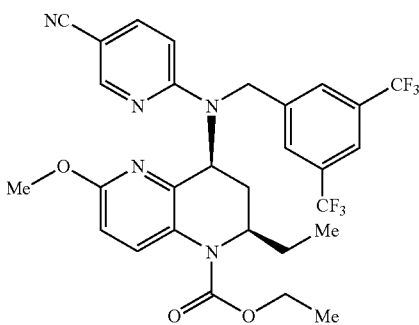

A corresponding starting compound is treated in a similar manner to Example 200 to give the compound of Example 379. MS (m/z): 608 [M+H]+

Example 380

(2R,4S)-4-{[3,5-Bis(trifluoromethyl)benzyl]-[5-cyanopyridin-2-yl]}-amino-2-ethyl-6-methoxy-3,4-dihydro-2H-[1,5]naphthyridine-1-carboxylic acid ethyl ester (300 mg), hydroxylammonium chloride (170 mg) and triethylamine (340 µl) are dissolved in ethanol (2 ml), and the mixture is stirred under reflux for 2 hours. The reaction solution is cooled to room temperature, and thereto are added water and ethyl acetate. The organic layer is washed with saturated brine, then dried over magnesium sulfate, and then concentrated under reduced pressure to give (2R,4S)-4-{[3,5-bis(trifluoromethyl)benzyl]-[5-(N-hydroxycarbamimidoyl)pyridin-2-yl]}-amino-2-ethyl-6-methoxy-3,4-dihydro-2H-[1,5]naphthyridine-1-carboxylic acid ethyl ester (360 mg). MS (m/z): 641 [M+H]+.

Example 381

(2R,4S)-4-{[3,5-Bis(trifluoromethyl)benzyl]-[5-(N-hydroxy-carbamimidoyl)pyridin-2-yl]}amino-2-ethyl-6-methoxy-3,4-dihydro-2H-[1,5]naphthyridine-1-carboxylic acid ethyl ester (193 mg) and triethylamine (126 µl) are dissolved in dichloromethane (3 ml), and thereto is added triphosgene (268 mg) at 0° C. The mixture is stirred at room temperature for 30 minutes. To the reaction solution are added water and dichloromethane, and the organic layer is washed with saturated brine. Then the organic layer is dried over sodium sulfate, and then concentrated under reduced pressure. The resulting residue is purified by column chromatography (silica gel; chloroform:methanol=1:0→97:3) to give (2R,4S)-4-{[3,5-bis(trifluoromethyl)benzyl]-[5-(5-oxo-4,5-dihydro-[1,2,4]oxadiazol-3-yl)pyridin-2-yl]}amino-2-ethyl-6-methoxy-3,4-dihydro-2H-[1,5]naphthyridine-1-carboxylic acid ethyl ester (33 mg). MS (m/z): 667 [M+H]+.

Example 382

(2R,4S)-4-{[3,5-Bis(trifluoromethyl)benzyl]-[5-bromopyridin-2-yl]}-amino-2-ethyl-6-methoxy-3,4-dihydro-2H-[1,5]naphthyridine-1-carboxylic acid ethyl ester (276 mg), tris(dibenzylideneacetone)dipalladium (76 mg), sodium tert-butoxide (80 mg), 2-(di-tert-butylphosphino)biphenyl (50 mg) and ethyl isonipecotate (131 mg) are dissolved in toluene (3 ml), and the mixture is stirred at room temperature for 22 hours under nitrogen flow. To the reaction solution are added water and ethyl acetate. The organic layer is washed with saturated brine and dried over magnesium sulfate, then concentrated under reduced pressure. The resulting residue is purified by column chromatography (silica gel; hexane:ethyl acetate=9:1→4:1) to give (2R,4S)-4-{[3,5-bis(trifluoromethyl)benzyl]-(4-ethoxy-carbonyl-3,4,5,6-tetrahydro-2H-[1,3']bipyridinyl-6'-yl)}amino-2-ethyl-6-methoxy-3,4-dihydro-2H-[1,5]naphthyridine-1-carboxylic acid ethyl ester (109 mg). MS (m/z): 738 [M+H]+.

Example 383

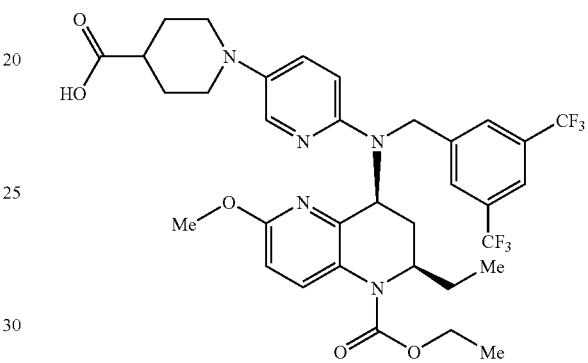

A corresponding starting compound is treated in a similar manner to Example 36 to give the compound of Example 383. MS (m/z): 710 [M+H]+

Example 384

(1) (2R,4S)-4-Amino-2-ethyl-6-methoxy-3,4-dihydro-2H-[1,5]naphthyridine-1-carboxylic acid ethyl ester (10 g) is dissolved in toluene (100 ml), and thereto are added 2-bromopyridine (6.8 ml), tris-(dibenzylideneacetone)dipalladium (328 mg), 2-dicyclohexylphosphino-2'-(N,N-dimethylamino)biphenyl (282 mg) and sodium tert-butoxide (6.9 g). The mixture is stirred at room temperature for 3.5 hours under nitrogen, then heated at 80° C. and stirred for 4 hours. The reaction solution is cooled to room temperature, and partitioned by adding water and ethyl acetate. The organic layer is washed with saturated brine, then dried over magnesium sulfate, and concentrated under reduced pressure. The resulting residue is purified by column chromatography (silica gel; hexane:ethyl acetate=9:1→7:3) to give a crude (6.4 g) of (2R,4S)-2-ethyl-6-methoxy-4-(pyridin-2-yl)amino-3,4-dihydro-2H-[1,5]naphthyridine-1-carboxylic acid ethyl ester. MS (m/z): 357 [M+H]+.

(2) The crude (6.3 g) of (2R,4S)-2-ethyl-6-methoxy-4-(pyridin-2-yl)-amino-3,4-dihydro-2H-[1,5]naphthyridine-1-carboxylic acid ethyl ester is dissolved in methylene chloride (80 ml), and thereto is added N-bromosuccinimide (3.15 g). The mixture is stirred at room temperature for 15 minutes. The reaction solution is concentrated under reduced pressure. The resulting residue is purified by column chromatography (silica gel; hexane:ethyl acetate=9:1→4:1) to give (2R,4S)-2-ethyl-6-methoxy-4-(5-bromopyridin-2-yl)amino-3,4-dihydro-2H-[1,5] naphthyridine-1-carboxylic acid ethyl ester (5.0 g). MS (m/z): 435/437 [M+H]+.

(3) (2R,4S)-2-Ethyl-6-methoxy-4-(5-bromopyridin-2-yl)amino-3,4-dihydro-2H-[1,5]naphthyridine-1-carboxylic acid ethyl ester (3 g) is dissolved in N,N-dimethylformamide (20 ml), and thereto is added sodium hydride (62.7%, 580 mg) under ice-cooling. The mixture is stirred for 30 minutes, and then to the mixture is added 3,5-bis(trifluoromethyl)benzyl bromide (3.2 ml). The mixture is stirred at room temperature for 24 hours, and partitioned by adding water and ethyl acetate under ice-cooling. The organic layer is washed with saturated brine, then dried over magnesium sulfate and concentrated under reduced pressure. The resulting residue is purified by column chromatography (silica gel; hexane:ethyl acetate=9:1→4:1) to give (2R,4S)-4-{[3,5-bis(trifluoromethyl)benzyl]-(5-bromopyridin-2-yl)}amino-2-ethyl-6-methoxy-3,4-dihydro-2H-[1,5]naphthyridine-1-carboxylic acid ethyl ester (1.7 g). MS (m/z): 661/663 [M+H]$^+$.

(4) (2R,4S)-4-{[3,5-Bis(trifluoromethyl)benzyl]-(5-bromopyridin-2-yl)}-amino-2-ethyl-6-methoxy-3,4-dihydro-2H-[1,5]naphthyridine-1-carboxylic acid ethyl ester (1.7 g) is dissolved in toluene (15 ml), and thereto are added morpholine (0.45 ml), tris(dibenzylideneacetone)dipalladium (238 mg), 2-(di-tert-butylphosphino)biphenyl (152 mg) and sodium tert-butoxide (494 mg). The mixture is stirred at room temperature for 85 minutes under nitrogen, then heated at 80° C. and stirred for 3.5 hours. The reaction solution is cooled to room temperature, and partitioned by adding water and ethyl acetate. The organic layer is washed with saturated brine, then dried over magnesium sulfate and concentrated under reduced pressure. The resulting residue is purified by column chromatography (silica gel; hexane:ethyl acetate=9:1→7:3) to give (2R,4S)-4-{[3,5-bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid ethyl ester (1.26 g). MS (m/z): 668 [M+H]$^+$.

(5) (2R,4S)-4-{[3,5-Bis(trifluoromethyl)benzyl]-[5-(morpholin-4-yl)-pyridin-2-yl]}amino-2-ethyl-6-methoxy-3,4-dihydro-2H-[1,5]naphthyridine-1-carboxylic acid ethyl ester (1.25 g) and sodium iodide (1.68 g) are dissolved in acetonitrile (15 ml). Then the mixture is heated at 80° C. and thereto is added dropwise trimethylsilyl chloride (1.4 ml) under nitrogen, and the mixture is stirred for 19.5 hours. The reaction solution is cooled to room temperature, and partitioned by adding water and ethyl acetate. The organic layer is washed with saturated brine, then dried over magnesium sulfate and concentrated under reduced pressure. The resulting residue is purified by column chromatography (silica gel; hexane:ethyl acetate=1:1→0:1) to give (2R,4S)-4-{[3,5-bis(trifluoromethyl)benzyl]-[5-(morpholin-4-yl)pyridin-2-yl]}amino-2-ethyl-6-hydroxy-3,4-dihydro-2H-[1,5]naphthyridine-1-carboxylic acid ethyl ester (642 mg). MS (m/z): 654 [M+H]$^+$.

(6) (2R,4S)-4-{[3,5-Bis(trifluoromethyl)benzyl]-[5-(morpholin-4-yl)-pyridin-2-yl]}amino-2-ethyl-6-hydroxy-3,4-dihydro-2H-[1,5]naphthyridine-1-carboxylic acid ethyl ester (585 mg) is dissolved in methylene chloride (5 ml), and thereto are added pyridine (218 µl) and trifluoromethanesulfonic anhydride (180 µl) under nitrogen under ice-cooling. The reaction solution is stirred for 75 minutes, and partitioned by adding a saturated aqueous citric acid solution and ethyl acetate. The organic layer is washed with water and saturated brine, then dried over magnesium sulfate and concentrated under reduced pressure. The resulting residue is purified by column chromatography (silica gel; hexane:ethyl acetate=9:1→4:1) to give (2R,4S)-4-{[3,5-bis(trifluoromethyl)benzyl]-[5-(morpholin-4-yl)pyridin-2-yl]}-amino-2-ethyl-6-trifluoromethanesulfonyloxy-3,4-dihydro-2H-[1,5]naphthyridine-1-carboxylic acid ethyl ester (657 mg). MS (m/z): 786 [M+H]$^+$ (7) (2R,4S)-4-{[3,5-Bis(trifluoromethyl)benzyl]-[5-(morpholin-4-yl)-pyridin-2-yl]}amino-2-ethyl-6-trifluoromethanesulfonyloxy-3,4-dihydro-2H-[1,5]naphthyridine-1-carboxylic acid ethyl ester (650 mg) is dissolved in dimethylsulfoxide (20 ml), and thereto are added triethylamine (1 ml) and a 2M solution (20 ml) of methylamine in tetrahydrofuran. The mixture is heated at 100° C. and stirred for 5 hours in a sealed tube under nitrogen. The reaction solution is cooled to room temperature, and partitioned by adding water and ethyl acetate. The organic layer is washed with saturated brine and dried over sodium sulfate, and concentrated under reduced pressure. The resulting residue is purified by column chromatography (NH-silica gel; hexane:ethyl acetate=9:1→7:3) to give (2R,4S)-4-{[3,5-bis(trifluoromethyl)benzyl]-[5-(morpholin-4-yl)pyridin-2-yl]}amino-2-ethyl-6-methylamino-3,4-dihydro-2H-[1,5]naphthyridine-1-carboxylic acid ethyl ester (45 mg). MS (m/z): 667 [M+H]$^+$ Example 385

(1) (2R,4S)-4-Amino-2-ethyl-6-methoxy-3,4-dihydro-2H-[1,5]naphthyridine-1-carboxylic acid ethyl ester (2 g), 2-chlorooxazole-4-carboxylic acid ethyl ester (3.77 g) and diisopropylethylamine (2.5 ml) are dissolved in 1,4-dioxane (15 ml), and the mixture is stirred for 9 hours under reflux. The reaction solution is cooled to room temperature, and thereto are added water and ethyl acetate. The organic layer is washed with saturated brine and dried over magnesium sulfate, then concentrated under reduced pressure. The resulting residue is purified by column chromatography (silica gel; hexane:ethyl acetate=4:1→2:1) to give (2R,4S)-4-(4-ethoxycarbonyloxazol-2-yl)amino-2-ethyl-6-methoxy-3,4-dihydro-2H-[1,5]naphthyridine-1-carboxylic acid ethyl ester (2.85 g). MS (m/z): 419 [M+H]$^+$.

(2) (2R,4S)-4-(4-Ethoxycarbonyloxazol-2-yl)amino-2-ethyl-6-methoxy-3,4-dihydro-2H-[1,5]naphthyridine-1-carboxylic acid ethyl ester (2.75 g) is dissolved in N,N-dimethylformamide (30 ml), and thereto is added sodium hydride (62.7%, 315 mg) under ice-cooling. The mixture is stirred at room temperature for 30 minutes. To the mixture is added 3,5-bis-(trifluoromethyl)benzyl bromide (1.8 ml) under ice-cooling, and the mixture is stirred overnight at room temperature. To the reaction solution are added water and ethyl acetate. The organic layer is washed with saturated brine and dried over magnesium sulfate, then concentrated under reduced pressure. The resulting residue is purified by column chromatography (silica gel; hexane:ethyl acetate=4:1→3:1) to give (2R,4S)-4-{[3,5-bis(trifluoromethyl)benzyl]-(4-ethoxycarbonyloxazol-2-yl)}amino-2-ethyl-6-methoxy-3,4-dihydro-2H-[1,5]naphthyridine-1-carboxylic acid ethyl ester (3.53 g). MS (m/z): 645 [M+H]$^+$.

Example 386

(2R,4S)-4-{[3,5-Bis(trifluoromethyl)benzyl]-(4-ethoxycarbonyloxazol-2-yl)}amino-2-ethyl-6-methoxy-3,4-dihydro-2H-[1,5]naphthyridine-1-carboxylic acid ethyl ester (200 mg) and lithium hydroxide monohydrate (78 mg) are dissolved in a mixture of methanol (3 ml) and water (500 µl), and the mixture is stirred at room temperature for 2 hours. The reaction solution is acidified by adding 2N aqueous HCl solution, then added ethyl acetate. The organic layer is washed with saturated brine and dried over magnesium sulfate, then concentrated under reduced pressure to give (2R,4S)-4-{[3,5-bis(trifluoromethyl)benzyl]-(4-carboxyoxazol-2-yl)}amino-2-ethyl-6-methoxy-3,4-dihydro-2H-[1,5]naphthyridine-1-carboxylic acid ethyl ester (190 mg). MS (m/z): 617 [M+H]$^+$.

Example 387

(2R,4S)-4-{[3,5-Bis(trifluoromethyl)benzyl]-(4-carboxyoxazol-2-yl)}-amino-2-ethyl-6-methoxy-3,4-dihydro-2H-[1,5]naphthyridine-1-carboxylic acid ethyl ester (200 mg) and 1-hydroxybenzotriazole hydrate (53 mg) are dissolved in N,N-dimethylformamide (3 ml), and thereto is added 1-ethyl-3-(3-dimethylaminopropyl)carbodiimide hydrochloride (311 mg). The mixture is stirred at room temperature for 30 minutes. To the mixture is added concentrated ammonia water (3 ml) under ice-cooling, and the mixture is stirred at room temperature for 3 hours. To the reaction mixture are added water and ethyl acetate. The organic layer is washed with saturated brine, and then dried over magnesium sulfate and concentrated under reduced pressure to give (2R,4S)-4-{[3,5-bis(trifluoromethyl)benzyl]-(4-carbamoyloxazol-2-yl)}amino-2-ethyl-6-methoxy-3,4-dihydro-2H-[1,5]naphthyridine-1-carboxylic acid ethyl ester (200 mg). MS (m/z): 616 [M+H]$^+$.

Example 388

(1) (2R,4S)-4-Amino-2-ethyl-6-methoxy-3,4-dihydro-2H-[1,5]naphthyridine-1-carboxylic acid ethyl ester (3.0 g) is dissolved in 1,2-dichloroethane (50 ml), and thereto is added 3,5-bis(trifluoromethyl)-benzaldehyde (1.9 ml). The mixture is stirred at room temperature for 1 hour, then added 95% sodium triacetoxyborohydride (4.6 g). The mixture is stirred for 17 hours, and partitioned by adding water and diethyl ether. The organic layer is washed with saturated brine, and then dried over magnesium sulfate and concentrated under reduced pressure. The resulting residue is purified by column chromatography (silica gel; hexane:ethyl acetate=9:1→7:3) to give (2R,4S)-4-[3,5-bis(trifluoromethyl)-benzyl]amino-2-ethyl-6-methoxy-3,4-dihydro-2H-[1,5]naphthyridine-1-carboxylic acid ethyl ester (4.92 g). MS (m/z): 506 [M+H]$^+$.

(2) (2R,4S)-4-[3,5-Bis(trifluoromethyl)benzyl]amino-2-ethyl-6-methoxy-3,4-dihydro-2H-[1,5]naphthyridine-1-carboxylic acid ethyl ester (4.9 g) is dissolved in ethanol (30 ml), and thereto are added sodium bicarbonate (2.5 g) and cyanogen bromide (1.1 g). The mixture is stirred at room temperature for 16 hours, and partitioned by adding water and diethyl ether. The organic layer is washed with saturated brine, and then dried over magnesium sulfate and concentrated under reduced pressure. The resulting residue is purified by column chromatography (silica gel; hexane:ethyl acetate=9:1→13:7) to give (2R,4S)-4-{[3,5-bis-(trifluoromethyl)benzyl]-cyano}amino-2-ethyl-6-methoxy-3,4-dihydro-2H-[1,5]naphthyridine-1-carboxylic acid ethyl ester (4.35 g). MS (m/z): 531 [M+H]$^+$.

(3) (2R,4S)-4-{[3,5-Bis(trifluoromethyl)benzyl]-cyano}amino-2-ethyl-6-methoxy-3,4-dihydro-2H-[1,5]naphthyridine-1-carboxylic acid ethyl ester (3 g) is dissolved in N,N-dimethylformamide (30 ml), and thereto are added ammonium chloride (3 g) and sodium azide (3.7 g). The mixture is heated at 100° C. and stirred for 24 hours. The reaction solution is cooled to room temperature, and partitioned by adding water and ethyl acetate. The organic layer is washed with saturated brine, then dried over magnesium sulfate and concentrated under reduced pressure. The resulting residue is purified by column chromatography (silica gel; chloroform:methanol=1:0→19:1), and the eluent is concentrated, followed by recrystallized (hexane:isopropanol) to give (2R,4S)-4-{[3,5-bis(trifluoromethyl)benzyl]-(tetrazol-5-yl)}amino-2-ethyl-6-methoxy-3,4-dihydro-2H-[1,5]naphthyridine-1-carboxylic acid ethyl ester (1.2 g). MS (m/z): 574 [M+H]$^+$.

Example 389

(2R,4S)-4-{[3,5-Bis(trifluoromethyl)benzyl]-(tetrazol-5-yl)}amino-2-ethyl-6-methoxy-3,4-dihydro-2H-[1,5]naphthyridine-1-carboxylic acid ethyl ester (230 mg) is dissolved in tetrahydrofuran (3 ml), and thereto are added 3-hydroxy-2,2-dimethylpropionic acid methyl ester (58 µl), a solution (0.18 ml) of 40% diethyl azodicarboxylate in toluene and triphenylphosphine (121 mg). The mixture is stirred at room temperature for 19 hours, and partitioned by adding water and diethyl ether. The organic layer is washed with saturated brine, then dried over magnesium sulfate and concentrated under reduced pressure. The resulting residue is purified by column chromatography (silica gel; hexane:ethyl acetate=9:1→7:3) to give (2R,4S)-4-{[3,5-bis(trifluoromethyl)benzyl]-[2-(2-methoxycarbonyl-2-methylpropyl)-2H-tetrazol-5-yl]}amino-2-ethyl-6-methoxy-3,4-dihydro-2H-[1,5]naphthyridine-1-carboxylic acid ethyl ester (243 mg). MS (m/z): 688 [M+H]$^+$.

Example 390

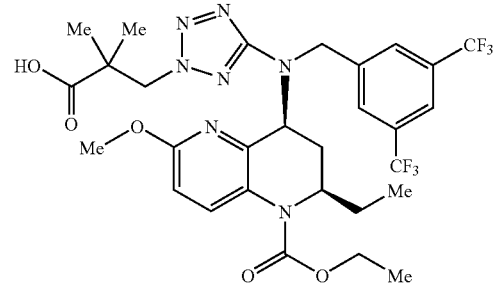

A corresponding starting compound is treated in a similar manner to Example 386 to give the compound of Example 390. MS (m/z): 674 [M+H]$^+$ Example 391

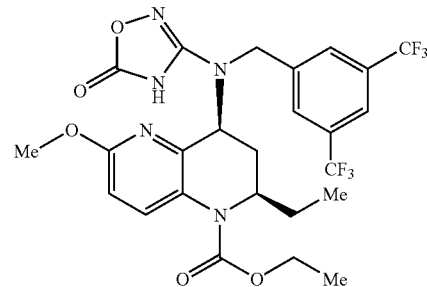

A corresponding starting compound is treated in a similar manner to Example 240 to give the compound of Example 391. MS (m/z): 590 [M+H]$^+$

Example 392

(1) (2R,4S)-4-{(N-Hydroxycarbamimidoyl)-[3,5-bis(trifluoromethyl)-benzyl]}amino-2-ethyl-6-methoxy-3,4-dihydro-2H-[1,5]naphthyridine-1-carboxylic acid ethyl ester (513 mg) and diisopropylethylamine (317 μl) are dissolved in dichloroethane (5 ml), and thereto is added acetoxyacetyl chloride (127 μl) at 0° C. The mixture is stirred overnight at room temperature. To the reaction solution is added a saturated aqueous citric acid solution, and the organic layer is washed with saturated brine and dried over magnesium sulfate, then concentrated under reduced pressure. The resulting residue is purified by column chromatography (silica gel; hexane:ethyl acetate=4:1→1:1) to give (2R,4S)-4-{[(acetyloxyacetyl)amino-(acetyloxyacetyloxy)iminomethyl]-[3,5-bis(trifluoromethyl)benzyl]}amino-2-ethyl-6-methoxy-3,4-dihydro-2H-[1,5]naphthyridine-1-carboxylic acid ethyl ester (330 mg). MS (m/z): 764 [M+H]$^+$.

(2) (2R,4S)-4-{[(Acetyloxyacetyl)amino-(acetyloxyacetyloxy)iminomethyl]-[3,5-bis(trifluoromethyl)benzyl]}amino-2-ethyl-6-methoxy-3,4-dihydro-2H-[1,5]naphthyridine-1-carboxylic acid ethyl ester (320 mg) and potassium carbonate (579 mg) are suspended in ethanol (5 ml), and the mixture is stirred overnight at room temperature. To the reaction solution are added water and ethyl acetate, and the organic layer is washed with saturated brine and then dried over sodium sulfate, then concentrated under reduced pressure. The resulting residue is purified by column chromatography (silica gel; hexane:ethyl acetate=2:1→0:1) to give (2R,4S)-4-{[3,5-bis(trifluoromethyl)benzyl]-(5-hydroxymethyl-[1,2,4]oxadiazol-3-yl)}-amino-2-ethyl-6-methoxy-3,4-dihydro-2H-[1,5]naphthyridine-1-carboxylic acid ethyl ester (52 mg). MS (m/z): 604 [M+H]$^+$.

Example 393

(1) (2R,4S)-4-Amino-2-ethyl-6-methoxy-3,4-dihydro-2H-[1,5]naphthyridine-1-carboxylic acid ethyl ester (5.0 g) is dissolved in 1,4-dioxane (90 ml), and thereto are added triethylamine (7.5 ml) and 4,6-dichloropyrimidine (5.3 g). The mixture is heated at 80° C. and is stirred for 18.5 hours. The reaction solution is cooled to room temperature, and then concentrated under reduced pressure, and partitioned by adding 1N HCl and diethyl ether. The organic layer is washed with water, a saturated aqueous sodium hydrogen carbonate solution, water and saturated brine, then dried over magnesium sulfate and concentrated under reduced pressure. The resulting residue is purified by column chromatography (silica gel; hexane:ethyl acetate=9:1→1:1) to give (2R,4S)-4-(6-chloropyrimidin-4-yl)amino-2-ethyl-6-methoxy-3,4-dihydro-2H-[1,5]naphthyridine-1-carboxylic acid ethyl ester (5.92 g). MS (m/z): 392/394 [M+H]$^+$.

(2) (2R,4S)-4-(6-Chloropyrimidin-4-yl)amino-2-ethyl-6-methoxy-3,4-dihydro-2H-[1,5]naphthyridine-1-carboxylic acid ethyl ester (4.0 g) is dissolved in acetonitrile (50 ml), and thereto is added sodium hydride (62.7%, 428.7 mg) under ice-cooling. The mixture is stirred for 5 minutes, and then thereto is added 3,5-bis(trifluoromethyl)benzyl bromide (2.8 ml). The mixture is stirred at room temperature for 14 hours, and partitioned by adding water and diethyl ether under ice-cooling. The organic layer is washed with saturated brine, then dried over magnesium sulfate and concentrated under reduced pressure. The resulting residue is purified by column chromatography (silica gel; hexane:ethyl acetate=9:1→7:3) to give (2R,4S)-4-{[3,5-bis(trifluoromethyl)benzyl]-(6-chloropyrimidin-4-yl)}amino-2-ethyl-6-methoxy-3,4-dihydro-2H-[1,5]naphthyridine-1-carboxylic acid ethyl ester (5.1 g). MS (m/z): 618/620 [M+H]$^+$.

(3) (2R,4S)-4-{[3,5-Bis(trifluoromethyl)benzyl]-(6-chloropyrimidin-4-yl)}-amino-2-ethyl-6-methoxy-3,4-dihydro-2H-[1,5]naphthyridine-1-carboxylic acid ethyl ester (140 mg) is dissolved in 1,3-dimethyl-2-imidazolidinone (2 ml), and thereto are added diisopropylethylamine (0.4 ml) and 3-methyl-aminopropionic acid tert-butyl ester (150 mg). The mixture is heated at 80° C. and stirred for 56.5 hours. The reaction solution is cooled to room temperature, and partitioned by adding water and diethyl ether. The organic layer is washed with saturated brine, then dried over magnesium sulfate and concentrated under reduced pressure. The resulting residue is purified by column chromatography (silica gel; hexane:ethyl acetate=4:1→3:2) to give (2R,4S)-4-{[3,5-bis(trifluoromethyl)benzyl]-[6-(2-tert-butoxycarbonylethyl)methylaminopyrimidin-4-yl]}amino-2-ethyl-6-methoxy-3,4-dihydro-2H-[1,5]naphthyridine-1-carboxylic acid ethyl ester (113.2 mg). MS (m/z): 741 [M+H]$^+$.

(4) (2R,4S)-4-{[3,5-Bis(trifluoromethyl)benzyl]-[6-(2-tert-butoxy-carbonylethyl)methylaminopyrimidin-4-yl]}amino-2-ethyl-6-methoxy-3,4-dihydro-2H-[1,5]naphthyridine-1-carboxylic acid ethyl ester (100 mg) is dissolved in a 2N solution (2 ml) of HCl/1,4-dioxane, and the mixture is stirred at room temperature for 3 hours. The reaction solution is concentrated under reduced pressure. The resulting residue is purified by column chromatography (silica gel; chloroform:methanol=1:0→9:1) to give (2R,4S)-4-{[3,5-bis(trifluoromethyl)benzyl]-[6-(2-carboxyethyl)methyl-aminopyrimidin-4-yl]}amino-2-ethyl-6-methoxy-3,4-dihydro-2H-[1,5]naphthyridine-1-carboxylic acid ethyl ester (29 mg). MS (m/z): 685 [M+H]$^+$.

Example 394

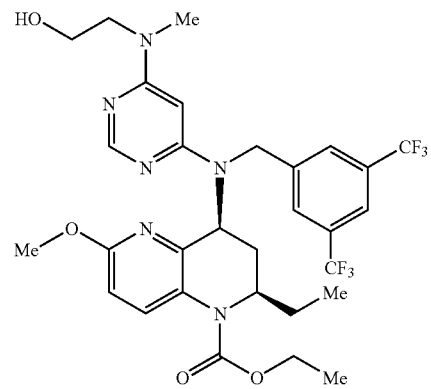

A corresponding starting compound is treated in a similar manner to Example 393 (3) to give the compound of Example 394. MS (m/z): 657 [M+H]$^+$

Example 395

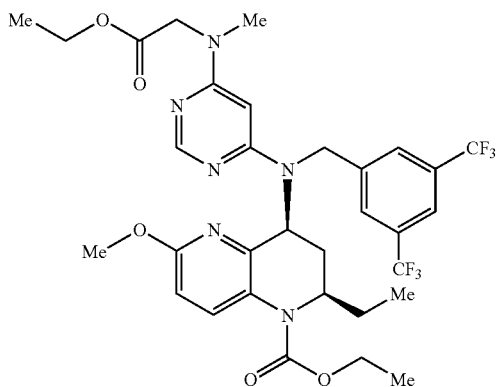

A corresponding starting compound is treated in a similar manner to Example 393 (3) to give the compound of Example 395. MS (m/z): 699 [M+H]+

Example 396

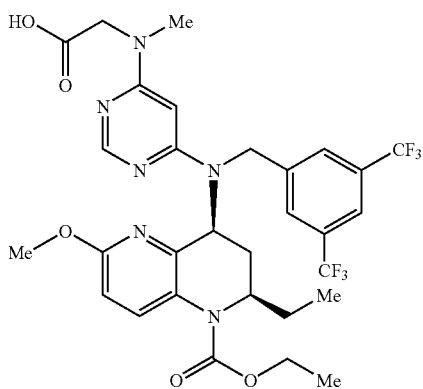

A corresponding starting compound is treated in a similar manner to Example 36 to give the compound of Example 396. MS (m/z): 671 [M+H]+

Example 397

(1) 4-Chloro-2-methylsulfanylpyrimidine-5-carboxylic acid ethyl ester (5 g) is dissolved in ethanol (100 ml), and thereto are added sodium carbonate (11.4 g) and 2-methylaminoethanol (4.6 ml). The mixture is heated at 80° C. and stirred for 3 hours. The reaction solution is cooled to room temperature, then concentrated under reduced pressure, and partitioned by adding water and chloroform. The organic layer is washed with saturated brine, then dried over magnesium sulfate and concentrated under reduced pressure. The resulting residue is purified by column chromatography (silica gel; chloroform:methanol=1:0→19:1) to give 9-methyl-2-methylsulfanyl-8,9-dihydro-7H-pyrimido[4,5-e][1,4]oxazepin-5-one (2.92 g). MS (m/z): 226 [M+H]+.

(2) 9-Methyl-2-methylsulfanyl-8,9-dihydro-7H-pyrimido[4,5-e][1,4]oxazepin-5-one (1 g) is dissolved in tetrahydrofuran (50 ml), and thereto is added meta-chloroperbenzoic acid (1 g) under ice-cooling. The mixture is stirred at room temperature for 20 hours, and partitioned by adding a saturated aqueous sodium hydrogen carbonate solution and chloroform. The organic layer is dried over magnesium sulfate and concentrated under reduced pressure. The resulting residue is purified by column chromatography (silica gel; chloroform:methanol=1:0→9:1) to give 2-methanesulfinyl-9-methyl-8,9-dihydro-7H-pyrimido[4,5-e][1,4]oxazepin-5-one (765 mg). MS (m/z): 242 [M+H]+.

(3) (2R,4S)-4-Amino-2-ethyl-6-methoxy-3,4-dihydro-2H-[1,5]naphthyridine-1-carboxylic acid ethyl ester (931 mg) is dissolved in 1,4-dioxane (30 ml), and thereto are added diisopropylethylamine (2.7 ml) and 2-methanesulfinyl-9-methyl-8,9-dihydro-7H-pyrimido[4,5-e][1,4]oxazepin-5-one (750 mg). The mixture is heated at 80° C. and stirred for 19 hours. The reaction solution is cooled to room temperature and partitioned by adding water and ethyl acetate. The organic layer is washed with saturated brine, then dried over magnesium sulfate and concentrated under reduced pressure. The resulting residue is washed with hexane:ethyl acetate to give a crude material (1.13 g) of (2R,4S)-2-ethyl-6-methoxy-4-(9-methyl-5-oxo-5,7,8,9-tetrahydropyrimido[4,5-e][1,4]oxazepin-2-yl)amino-3,4-dihydro-2H-[1,5]naphthyridine-1-carboxylic acid ethyl ester. MS (m/z): 457 [M+H]+.

(4) The crude material (500 mg) of (2R,4S)-2-Ethyl-6-methoxy-4-(9-methyl-5-oxo-5,7,8,9-tetrahydropyrimido[4,5-e][1,4]oxazepin-2-yl)amino-3,4-dihydro-2H-[1,5]naphthyridine-1-carboxylic acid ethyl ester is dissolved in N,N-dimethylformamide (10 ml), and thereto is added sodium hydride (62.7%, 46 mg) under ice-cooling. The mixture is stirred for 10 minutes, and then thereto is added 3,5-bis(trifluoro)benzyl bromide (0.3 ml). The mixture is stirred at room temperature for 15 hours. The reaction solution is partitioned by adding water and diethyl ether under ice-cooling. The organic layer is washed with saturated brine, then dried over magnesium sulfate and concentrated under reduced pressure. The resulting residue is purified by column chromatography (silica gel; hexane:ethyl acetate=1:1→1:4) to give (2R,4S)-4-{[3,5-bis(trifluoromethyl)-benzyl]-(9-methyl-5-oxo-5,7,8,9-tetrahydropyrimido[4,5-e][1,4]oxazepin-2-yl)}amino-2-ethyl-6-methoxy-3,4-dihydro-2H-[1,5]naphthyridine-1-carboxylic acid ethyl ester (331.3 mg). MS (m/z): 683 [M+H]+.

Example 398

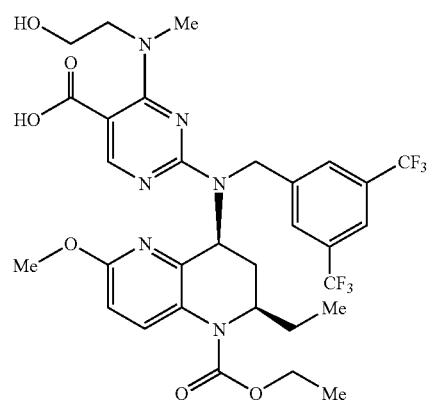

A corresponding starting compound is treated in a similar manner to Example 36 to give the compound of Example 398. MS (m/z): 701 [M+H]+

Example 399

(1) 5-Bromo-2,4-dichloropyrimidine (500 mg) is dissolved in tetrahydrofuran (10 ml), and thereto is added sodium hydride (62.7%, 92.2 mg) under ice-cooling. The mixture is stirred for 10 minutes, and thereto are added benzyl alcohol (236.8 mg) and a few drops of N,N-dimethylformamide. The mixture is stirred at room temperature for 21 hours, and heated at 80° C. and stirred for 3.5 hours. The reaction solution is cooled to room temperature, and partitioned by adding water and diethyl ether. The organic layer is washed with saturated brine, then dried over magnesium sulfate and concentrated under reduced pressure. The resulting residue is purified by column chromatography (silica gel; hexane:ethyl acetate=9:1→4:1) and the eluent is dried under reduced pressure, then the residue is dissolved in 1,4-dioxane (10 ml), and thereto are added (2R,4S)-4-amino-2-ethyl-6-methoxy-3,4-dihydro-2H-[1,5]naphthyridine-1-carboxylic acid ethyl ester (300 mg) and diisopropylethylamine (0.52 ml). The mixture is heated at 80° C. and stirred for 4 hours. The reaction solution is cooled to room temperature, and partitioned by adding water and diethyl ether. The organic layer is washed with saturated brine, then dried over magnesium sulfate and concentrated under reduced pressure. The resulting residue is purified by column chromatography (silica gel; hexane:ethyl acetate=9:1→7:3) and the eluent is dried under reduced pressure, then the residue is dissolved in acetonitrile (6 ml), and thereto is added sodium hydride (62.7%, 23 mg) under ice-cooling. The mixture is stirred for 10 minutes, and then thereto is added 3,5-bis(trifluoro)benzyl bromide (0.15 ml). The mixture is stirred at room temperature for 14.5 hours. The reaction solution is partitioned by adding water and diethyl ether. The organic layer is washed with saturated brine, then dried over magnesium sulfate and concentrated under reduced pressure. The resulting residue is purified by column chromatography (silica gel; hexane:ethyl acetate=9:1→4:1) to give (2R,4S)-4-{(4-benzyloxy-5-bromopyrimidin-2-yl)-[3,5-bis(trifluoromethyl)benzyl]}-amino-2-ethyl-6-methoxy-3,4-dihydro-2H-[1,5]naphthyridine-1-carboxylic acid ethyl ester (45 mg). MS (m/z): 768/770 [M+H]+.

(2) (2R,4S)-4-{(4-Benzyloxy-5-bromopyrimidin-2-yl)-[3,5-bis-(trifluoromethyl)benzyl]}amino-2-ethyl-6-methoxy-3,4-dihydro-2H-[1,5]naphthyridine-1-carboxylic acid ethyl ester (40 mg) is dissolved in toluene (1 ml), and thereto are added morpholine (10.6 µl), tris-(dibenzylideneacetone)dipalladium (11.0 mg), 2-(di-tert-butylphosphino)-biphenyl (14.3 mg) and sodium tert-butoxide (11.6 mg). The mixture is stirred at room temperature for 30 minutes under nitrogen, then heated at 80° C. and stirred for 7 hours. The reaction solution is cooled to room temperature, and partitioned by adding water and diethyl ether. The organic layer is washed with saturated brine, then dried over magnesium sulfate and concentrated under reduced pressure. The resulting residue is purified by NH-column chromatography (silica gel; hexane:ethyl acetate=9:1→3:1) to give (2R,4S)-4-{[4-benzyloxy-5-(morpholin-4-yl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (12.6 mg). MS (m/z): 775 [M+H]+.

(3) (2R,4S)-4-{[4-Benzyloxy-5-(morpholin-4-yl)pyrimidin-2-yl]-[3,5-bis(trifluoromethyl)benzyl]}amino-2-ethyl-6-methoxy-3,4-dihydro-2H-[1,5]naphthyridine-1-carboxylic acid ethyl ester (10 mg) is dissolved in a solution (1 ml) of tetrahydrofuran:methanol=1:1 mixture, and thereto is added 10% palladium-carbon (5 mg). The mixture is stirred at room temperature for 18 hours under hydrogen. The reaction solution is filtered and the filtrate is concentrated under reduced pressure. The resulting residue is purified by column chromatography (silica gel; chloroform:methanol=1:0→9:1) to give (2R,4S)-4-{[3,5-bis(trifluoromethyl)-benzyl]-[4-hydroxy-5-(morpholin-4-yl)pyrimidin-2-yl]}amino-2-ethyl-6-methoxy-3,4-dihydro-2H-[1,5]naphthyridine-1-carboxylic acid ethyl ester (8.3 mg). MS (m/z): 685 [M+H]+.

Example 400

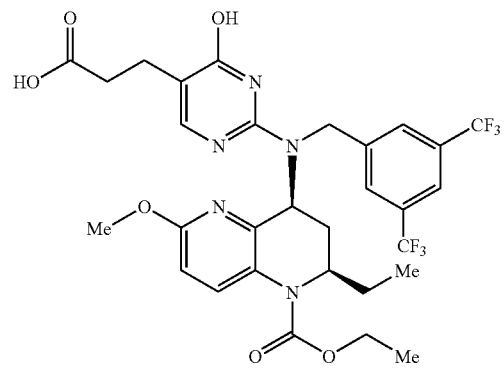

A corresponding starting compound is treated in a similar manner to Example 322 to give the compound of Example 400. MS (m/z): 672 [M+H]+

Example 401

(1) (2R,4S)-4-{[3,5-Bis(trifluoromethyl)benzyl]-[5-(2-carboxyethyl)-4-hydroxypyrimidin-2-yl]}amino-2-ethyl-6-methoxy-3,4-dihydro-2H-[1,5]naphthyridine-1-carboxylic acid ethyl ester (155 mg) is dissolved in tetrahydrofuran (2.5 ml), and thereto are added triethylamine (192 µl) and ethyl chlorocarbonate (132 µl) under ice-cooling. The mixture is stirred at room temperature for 1.5 hours, and then thereto is added sodium borohydride (87.3 mg) under ice-cooling. The mixture is stirred at room temperature for 2 hours. The reaction solution is partitioned by adding water and methylene chloride under ice-cooling. The organic layer is washed with 1N HCl and saturated brine, then dried over magnesium sulfate and concentrated under reduced pressure. The resulting residue is purified by column chromatography (silica gel; chloroform:methanol=1:0→19:1) to give (2R,4S)-4-{[3,5-bis(trifluoromethyl)benzyl]-[4-ethoxy-carbonyloxy-5-(3-hydroxypropoxy)pyrimidin-2-yl]}amino-2-ethyl-6-methoxy-3,4-dihydro-2H-[1,5]naphthyridine-1-carboxylic acid ethyl ester (59 mg). MS (m/z): 730 [M+H]+.

(2) (2R,4S)-4-{[3,5-Bis(trifluoromethyl)benzyl]-[4-ethoxy-carbonyloxy-5-(3-hydroxypropyl)pyrimidin-2-yl]}amino-2-ethyl-6-methoxy-3,4-dihydro-2H-[1,5]naphthyridine-1-carboxylic acid ethyl ester (50 mg) is dissolved in ethanol (1 ml), and thereto is added 5N aqueous NaOH solution (1 ml). The mixture is stirred at room temperature for 2 hours. The reaction solution is partitioned by adding 6N HCl under ice-cooling and concentrated under reduced pressure. The resulting residue is purified by column chromatography (silica gel; hexane:ethyl acetate=7:3→1:1) to give (2R,4S)-4-{[3,5-bis(trifluoromethyl)benzyl]-[4-hydroxy-5-(3-hydroxypropyl)-pyrimidin-2-yl]}amino-2-ethyl-6-methoxy-3,4-dihydro-2H-[1,5]naphthyridine-1-carboxylic acid ethyl ester (24 mg). MS (m/z): 658 [M+H]$^+$.

Example 402

(1) (2R,4S)-4-{(4-Benzyloxy-5-bromopyrimidin-2-yl)-[3,5-bis-(trifluoromethyl)benzyl]}amino-2-ethyl-6-methoxy-3,4-dihydro-2H-[1,5]naphthyridine-1-carboxylic acid ethyl ester (300 mg) is dissolved in toluene (2 ml), and thereto are added 2-methylaminoethanol (73 µl), tris(dibenzylideneacetone)dipalladium (82 mg), 2-(di-tert-butylphosphino)-biphenyl (107 mg) and sodium tert-butoxide (109 mg). The mixture is stirred at room temperature for 30 minutes under nitrogen, then heated at 80° C. and stirred for 17.5 hours. The reaction solution is cooled to room temperature, and thereto are added water and diethyl ether. The organic layer is washed with saturated brine, then dried over magnesium sulfate and concentrated under reduced pressure. The resulting residue is purified by column chromatography (silica gel; hexane:ethyl acetate=9:1→1:1) to give a crude material (130 mg) of (2R,4S)-4-{(4-benzyloxy-pyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester. MS (m/z): 690 [M+H]$^+$.

(2) The crude material (120 mg) of (2R,4S)-4-{(4-benzyloxypyrimidin-2-yl)-[3,5-bis(trifluoromethyl)benzyl]}amino-2-ethyl-6-methoxy-3,4-dihydro-2H-[1,5]naphthyridine-1-carboxylic acid ethyl ester is dissolved in a solution (10 ml) of tetrahydrofuran:methanol=1:1 mixture, and thereto is added 10% palladium-carbon (60 mg). The mixture is stirred at room temperature for 34.5 hours under hydrogen. The reaction solution is filtered and the filtrate is concentrated under reduced pressure. The resulting residue is purified by column chromatography (silica gel; chloroform:methanol=1:0→9:1) to give (2R,4S)-4-{[3,5-bis(trifluoromethyl)-benzyl]-(4-hydroxypyrimidin-2-yl)}amino-2-ethyl-6-methoxy-3,4-dihydro-2H-[1,5]naphthyridine-1-carboxylic acid ethyl ester (72.4 mg). MS (m/z): 600 [M+H]$^+$.

Example 403

(2R,4S)-4-{[3,5-Bis(trifluoromethyl)benzyl]-(4-hydroxypyrimidin-2-yl)}amino-2-ethyl-6-methoxy-3,4-dihydro-2H-[1,5]naphthyridine-1-carboxylic acid ethyl ester (85 mg) is dissolved in acetone (3 ml), and thereto are added potassium carbonate (98.1 mg) and para-toluenesulfonyl chloride (32.4 mg). The mixture is stirred at room temperature for 2 hours. The reaction solution is concentrated under reduced pressure, and partitioned by adding water and diethyl ether. The organic layer is washed with saturated brine, then dried over magnesium sulfate and concentrated under reduced pressure. The resulting residue is dissolved in 1,4-dioxane (3 ml), and thereto are added diisopropylethylamine (0.5 ml) and (2-methoxyethyl)methylamine (15.15 mg). The mixture is heated at 50° C. and stirred for 3 hours, then heated at 100° C. and stirred for 16.5 hours. The reaction solution is cooled to room temperature, and partitioned by adding 1N HCl and diethyl ether. The organic layer is washed with water and saturated brine, then dried over magnesium sulfate and concentrated under reduced pressure. The resulting residue is purified by column chromatography (silica gel; hexane:ethyl acetate=9:1→7:3) to give (2R,4S)-4-([3,5-bis(trifluoromethyl)benzyl]-{4-[(2-methoxyethyl)-methylamino]pyrimidin-2-yl})amino-2-ethyl-6-methoxy-3,4-dihydro-2H-[1,5]naphthyridine-1-carboxylic acid ethyl ester (68 mg). MS (m/z): 671 [M+H]$^+$.

Example 404

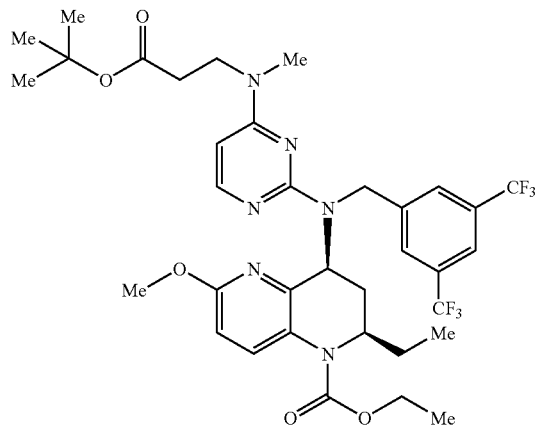

A corresponding starting compound is treated in a similar manner to Example 403 to give the compound of Example 404. MS (m/z): 741 [M+H]$^+$ Example 405

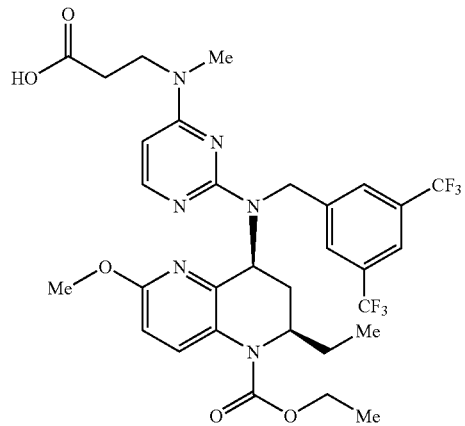

A corresponding starting compound is treated in a similar manner to Example 242 (2) to give the compound of Example 405. MS (m/z): 685 [M+H]$^+$

Example 406

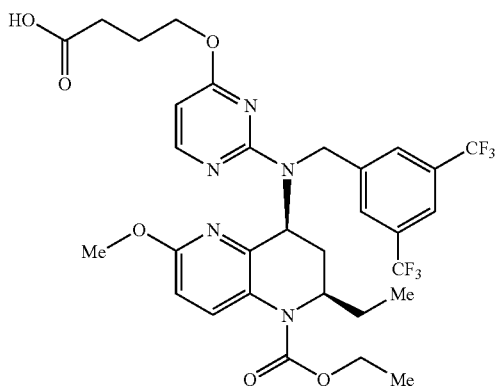

A corresponding starting compound is treated in a similar manner to Example 270 to give the compound of Example 406. MS (m/z): 686 [M+H]$^+$

Example 407

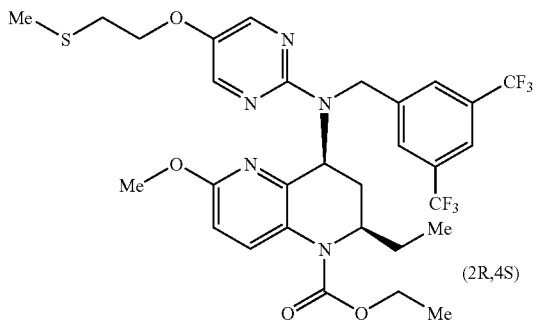

A corresponding starting compound is treated in a similar manner to Example 93 to give the compound of Example 407. MS (m/z): 674 [M+H]$^+$

Example 408

(1) (2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid ethyl ester (10 g) is dissolved in toluene (50 ml), and thereto are added tris(dibenzylideneacetone)dipalladium (1.4 g), 2-(di-tert-butylphosphino)-biphenyl (901 mg), sodium tert-butoxide (3.1 g) and morpholine (2.6 ml). The mixture is stirred at room temperature for 16 hours. The reaction solution is partitioned by adding water and ethyl acetate. The organic layer is washed with saturated brine, then dried over magnesium sulfate and concentrated under reduced pressure. The resulting residue is purified by column chromatography (silica gel; hexane:ethyl acetate=4:1→1:1) to give (2R, 4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid ethyl ester (9.84 g). MS (m/z): 669 [M+H]$^+$.

(2) (2R,4S)-4-{[3,5-Bis(trifluoromethyl)benzyl]-[5-(morpholin-4-yl)-pyrimidin-2-yl]}amino-2-ethyl-6-methoxy-3,4-dihydro-2H-[1,5]naphthyridine-1-carboxylic acid ethyl ester (2.5 g) is dissolved in tetrahydrofuran:ethanol (1:1, 20 ml), and thereto is added sodium hydroxide (1.5 g). The mixture is stirred at 85° C. for 16 hours. The reaction solution is cooled to room temperature, and then partitioned by adding water and diethyl ether. The organic layer is washed with saturated brine, then dried over magnesium sulfate and concentrated under reduced pressure. The resulting residue is purified by column chromatography (NH-silica gel; hexane:ethyl acetate=9:1→7:3) to give (2R,4S)-4-{[3,5-bis(trifluoromethyl)benzyl]-[5-(morpholin-4-yl)pyrimidin-2-yl]}amino-2-ethyl-6-methoxy-1,2,3,4-tetrahydro-[1,5]naphthyridine (1.45 g). MS (m/z): 597 [M+H]$^+$.

(3) (2R,4S)-4-{[3,5-Bis(trifluoromethyl)benzyl]-[5-(morpholin-4-yl)pyrimidin-2-yl]}amino-2-ethyl-6-methoxy-1, 2,3,4-tetrahydro-[1,5]naphthyridine (160 mg) is dissolved in dichloromethane (1.5 ml), and thereto are added triethylamine (93 μl) and triphosgene (62 mg). The mixture is stirred at room temperature for 30 minutes. The reaction solution is concentrated under reduced pressure, and thereto is added diethyl ether. The insoluble materials are removed by filtration and the filtrate is concentrated under reduced pressure. The resulting residue is dissolved in tetrahydrofuran (1.5 ml), and thereto are added 60% sodium hydride (32 mg) and 2,2-difluoro-3-hydroxy-propionic acid ethyl ester (123 mg) under ice-cooling. The mixture is stirred at room temperature for 1.5 hours. The reaction solution is partitioned by adding water and diethyl ether. The organic layer is washed with saturated brine, then dried over magnesium sulfate and concentrated under reduced pressure. The resulting crude product is dissolved in tetrahydrofuran:methanol (1:1, 3 ml), and thereto is added 2N aqueous NaOH solution (0.5 ml). The mixture is stirred at room temperature for 1 hour. To the reaction solution is added 1N—HCl (1.0 ml). The organic layer is washed with saturated brine and dried over magnesium sulfate, then concentrated under reduced pressure. The resulting residue is purified by column chromatography (silica gel; chloroform:methanol=1:0→9:1) to give (2R, 4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 2-carboxy-2,2-difluoroethyl ester (150 mg). MS (m/z): 749 [M+H]$^+$.

Example 409

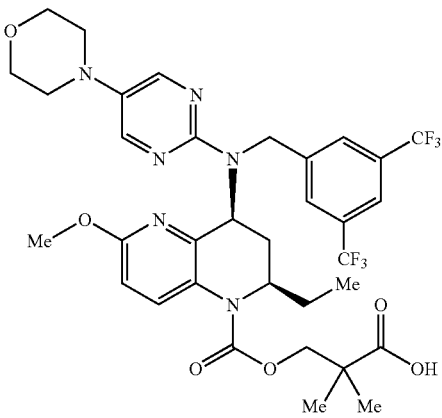

A corresponding starting compound is treated in a similar manner to Example 408 to give the compound of Example 409. MS (m/z): 741 [M+H]⁺

Example 410

(1) (2R,4S)-4-{[3,5-Bis(trifluoromethyl)benzyl]-[5-(morpholin-4-yl)-pyrimidin-2-yl]}amino-2-ethyl-6-methoxy-1,2,3,4-tetrahydro-[1,5]naphthyridine (290 mg) is dissolved in dichloromethane (1.5 ml), and thereto are added triethylamine (203 ml) and triphosgene (145 mg). The mixture is stirred at room temperature for 15 minutes. The reaction solution is concentrated under reduced pressure, and then the insoluble materials are removed by filtration using tetrahydrofuran and the filtrate is concentrated under reduced pressure. The resulting residue is dissolved in tetrahydrofuran (1.5 ml), and thereto are added 60% sodium hydride (20 mg) and 3-hydroxy-propionic acid tert-butyl ester (72 μl) under ice-cooling. The mixture is stirred at room temperature for 1.5 hours. The reaction solution is partitioned by adding water and ethyl acetate. The organic layer is washed with saturated brine, then dried over magnesium sulfate and concentrated under reduced pressure. The resulting residue is purified by column chromatography (silica gel; hexane:ethyl acetate=4:1→1:1) to give (2R,4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 2-tert-butoxycarbonylethyl ester (180 mg). MS (m/z): 769 [M+H]⁺.

(2) To (2R,4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 2-tert-butoxycarbonylethyl ester (165 mg) is added 4N HCl-ethyl acetate solution (2 mL), and the mixture is stirred for 1.5 hours. The reaction solution is concentrated and the resulting residue is partitioned by adding water and ethyl acetate. The organic layer is washed with saturated brine, then dried over magnesium sulfate and concentrated under reduced pressure. The resulting residue is purified by column chromatography (silica gel; chloroform:methanol=1:0→9:1) to give (2R,4S)-4-{[3,5-bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 2-carboxyethyl ester (145 mg). MS (m/z): 713 [M+H]⁺.

Example 411

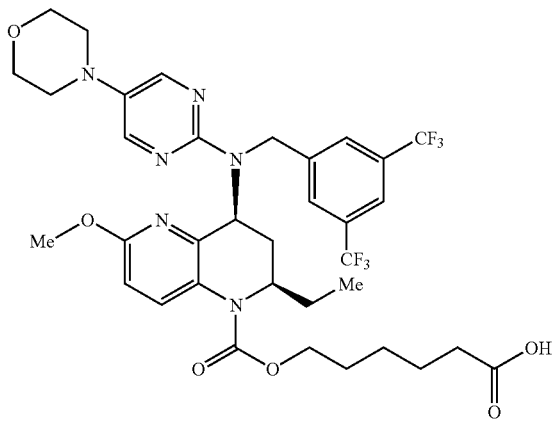

Corresponding starting compound is treated in a similar manner to Example 408 to give the compound of Example 411. MS(m/z): 755[M+H]⁺.

Example 412

(1) (2R,4S)-4-{[3,5-Bis(trifluoromethyl)benzyl]-(5-bromopyrimidin-2-yl)}amino-2-ethyl-6-methoxy-3,4-dihydro-2H-[1,5]naphthyridine-1-carboxylic acid tert-butyl ester (1.0 g) is dissolved in toluene (5 ml), and thereto are added tris(dibenzylideneacetone)dipalladium (133 mg), 2-(di-tert-butylphosphino)biphenyl (173 mg), sodium tert-butoxide (279 mg) and 2N-dimethylamine tetrahydrofuran (2.18 ml). The mixture is stirred at room temperature for 19 hours, and partitioned by adding water and ethyl acetate. The organic layer is washed with saturated brine, dried over magnesium sulfate, and concentrated under reduced pressure. The resulting residue is purified by column chromatography (silica gel; hexane:ethyl acetate=9:1→7:3) to give (2R,4S)-4-{[3,5-bis(trifluoromethyl)-benzyl]-(5-dimethylaminopyrimidin-2-yl)}amino-2-ethyl-6-methoxy-3,4-dihydro-2H-[1,5]naphthyridine-1-carboxylic acid tert-butyl ester (234 mg). MS(m/z): 655[M+H]⁺.

(2) (2R,4S)-4-{[3,5-Bis(trifluoromethyl)benzyl]-(5-dimethylamino-pyrimidin-2-yl)}amino-2-ethyl-6-methoxy-3,4-dihydro-2H-[1,5]-naphthyridine-1-carboxylic acid tert-butyl ester (225 mg) is dissolved in 4N—HCl/ethyl acetate (1 ml) and stirred at room temperature for 2 hours. The reaction solution is partitioned by adding a saturated aqueous sodium bicarbonate and ethyl acetate. The organic layer is washed with saturated brine, dried over magnesium sulfate, and concentrated under reduced pressure. The resulting residue is purified by column chromatography (silica gel; hexane:ethyl acetate=88:12→7:3) to give (2R,4S)-4-{[3,5-bis(trifluoromethyl)benzyl]-(5-dimethylaminopyrimidin-2-yl)}amino-2-ethyl-6-methoxy-3,4-dihydro-2H-[1,5]naphthyridine (180 mg). MS(m/z): 555 [M+H]⁺.

(3) (2R,4S)-4-{[3,5-Bis(trifluoromethyl)benzyl]-(5-dimethylamino-pyrimidin-2-yl)}amino-2-ethyl-6-methoxy-3,4-dihydro-2H-[1,5]-naphthyridine (185 mg) and triethylamine (116 μl) are dissolved in methylene chloride (1.5 ml). To the mixture is added triphosgene (79 mg) under ice-cooling, and the mixture is stirred at the same temperature for 30 minutes. The reaction solution is concentrated under reduce pressure and partitioned by adding a saturated aqueous sodium bicarbonate and ethyl acetate. The organic layer is washed with saturated brine, dried over magnesium sulfate, and concentrated under reduced pressure. The resulting residue is dissolved in tetrahydrofuran (1.5 ml), and thereto are added 3-hydroxy-2,2-dimethylpropionic acid methyl ester (132 mg) and sodium hydride (60%, 20 mg) under ice-cooling. The mixture is stirred at room temperature for 30 minutes and partitioned by adding saturated brine and ethyl acetate. The organic layer is washed with saturated brine, dried over magnesium sulfate, and concentrated under reduced pressure. The resulting residue is purified by column chromatography (silica gel; hexane:ethyl acetate=88:12→72:28) to give (2R,4S)-4-{[3,5-bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 2-methoxycarbonyl-2-methylpropyl ester (218 mg). MS(m/z):713[M+H]⁺.

(4) (2R,4S)-4-{[3,5-Bis(trifluoromethyl)benzyl]-(5-dimethylamino-pyrimidin-2-yl)}amino-2-ethyl-6-methoxy-3,4-dihydro-2H-[1,5]-naphthyridine-1-carboxylic acid 2-methoxycarbonyl-2-methylpropyl ester (210 mg) is dissolved in ethanol (2 ml), and thereto is added 2N aqueous sodium hydroxide (0.443 ml), and the mixture is stirred overnight at room temperature. After the reaction solution is acidified slightly by adding 10% aqueous citric acid solution, the mixture is extracted with ethyl acetate. The organic layer is washed with saturated brine, dried over magnesium sulfate, and concentrated under reduced pressure. The resulting residue is purified by column chromatography (silica gel; chloroform:methanol=1:0→97:3) to give (2R,4S)-4-{[3,5-bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 2-carboxy-2-methylpropyl ester (133 mg). MS(m/z): 699 [M+H]+.

Example 413

(1) (2R,4S)-4-{[3,5-Bis(trifluoromethyl)benzyl]-(5-bromopyrimidin-2-yl)}amino-2-ethyl-6-methoxy-3,4-dihydro-2H-[1,5]naphthyridine-1-carboxylic acid tert-butyl ester (7.17 g) is dissolved in 4N HCl/dioxane solution (45 ml). The mixture is stirred at room temperature for an hour. The reaction solution is concentrated under reduced pressure and partitioned by adding a saturated aqueous sodium bicarbonate and chloroform. The organic layer is washed with saturated brine, dried over magnesium sulfate, and concentrated under reduced pressure to give (2R,4S)-4-{[3,5-bis(trifluoromethyl)benzyl]-(5-bromopyrimidin-2-yl)}amino-2-ethyl-6-methoxy-3,4-dihydro-2H-[1,5]naphthyridine (6.2 g). MS(m/z): 590/592[M+H]+.

(2) (2R,4S)-4-{[3,5-Bis(trifluoromethyl)benzyl]-(5-bromopyrimidin-2-yl)}amino-2-ethyl-6-methoxy-3,4-dihydro-2H-[1,5]naphthyridine (4.0 g) and triethylamine (2.36 ml) are dissolved in methylene chloride (30 ml). To the mixture is added triphosgene (1.61 g) under ice-cooling, and the mixture is stirred at the same temperature for 30 minutes. The reaction solution is concentrated under reduce pressure and partitioned by adding a saturated aqueous sodium bicarbonate and ethyl acetate. The organic layer is washed with saturated brine, dried over magnesium sulfate, and concentrated under reduced pressure. The resulting residue is dissolved in tetrahydrofuran (30 ml), and thereto are added 3-hydroxy-2,2-dimethylpropionic acid methyl ester (2.61 g) and sodium hydride (60%, 407 mg) under ice-cooling followed by stirring at room temperature for 30 minutes. The reaction solution is partitioned by adding saturated brine and ethyl acetate. The organic layer is washed with saturated brine, dried over magnesium sulfate, and concentrated under reduced pressure. The resulting residue is purified by column chromatography (silica gel; hexane:ethyl acetate=99:1→85:15) to give (2R,4S)-4-{[3,5-bis(trifluoromethyl)benzyl]-(5-bromopyrimidin-2-yl)}amino-2-ethyl-6-methoxy-3,4-dihydro-2H-[1,5]naphthyridine-1-carboxylic acid 2-methoxycarbonyl-2-methylpropyl ester (5.1 g). MS(m/z):748/750 [M+H]+.

(3) (2R,4S)-4-{[3,5-Bis(trifluoromethyl)benzyl]-(5-bromopyrimidin-2-yl)}amino-2-ethyl-6-methoxy-3,4-dihydro-2H-[1,5]naphthyridine-1-carboxylic acid 2-methoxycarbonyl-2-methylpropyl ester (2.5 g) is dissolved in dimethylsulfoxide (20 ml), and thereto are added [1,1'-bis(diphenyl-phosphino)ferrocene]dichloropalladium complex with dichloromethane (1:1, 546 mg), potassium acetate (983 mg) and bis(pinacolato)diboron (1.7 g). The mixture is heated to 80° C. under nitrogen and stirred for an hour. The reaction solution is cooled to room temperature and partitioned by adding water and ethyl acetate. The organic layer is washed with saturated brine, dried over magnesium sulfate, and concentrated under reduced pressure. The resulting residue is dissolved in tetrahydrofuran (20 ml), then thereto is added 30% hydrogen peroxide solution (20 ml) under ice-cooling, and the mixture is stirred at room temperature for an hour. After adding saturated aqueous sodium thiosulfate solution, the reaction solution is partitioned by adding ethyl acetate. The organic layer is washed with saturated brine, dried over magnesium sulfate, and concentrated under reduced pressure. The resulting residue is purified by column chromatography (silica gel; hexane:ethyl acetate=82:18→7:3) to give (2R,4S)-4-{[3,5-bis(trifluoromethyl)benzyl]-(5-hydroxypyrimidin-2-yl)}amino-2-ethyl-6-methoxy-3,4-dihydro-2H-[1,5]naphthyridine-1-carboxylic acid 2-methoxycarbonyl-2-methylpropyl ester (1.83 g). MS(m/z):686[M+H]+.

(4) (2R,4S)-4-{[3,5-Bis(trifluoromethyl)benzyl]-(5-hydroxypyrimidin-2-yl)}amino-2-ethyl-6-methoxy-3,4-dihydro-2H-[1,5]naphthyridine-1-carboxylic acid 2-methoxycarbonyl-2-methylpropyl ester (300 mg), 4-bromobutyronitrile (82 mg) and potassium carbonate (121 mg) are added to N,N-dimethylformamide (1 ml), and the mixture is stirred at 50° C. for 2 hours. The reaction solution is partitioned by adding saturated brine and ethyl acetate. The organic layer is washed with water and saturated brine, dried over magnesium sulfate, and concentrated under reduced pressure. The resulting residue is purified by column chromatography (silica gel; hexane:ethyl acetate=88:12→7:3) to give (2R,4S)-4-{[3,5-bis(trifluoro-methyl)benzyl]-[5-(3-cyanopropoxy)pyrimidin-2-yl]}amino-2-ethyl-6-methoxy-3,4-dihydro-2H-[1,5]naphthyridine-1-carboxylic acid 2-methoxycarbonyl-2-methylpropyl ester (315 mg). MS(m/z):753[M+H]+.

(5) (2R,4S)-4-{[3,5-Bis(trifluoromethyl)benzyl]-[5-(3-cyanopropoxy)-pyrimidin-2-yl]}amino-2-ethyl-6-methoxy-3,4-dihydro-2H-[1,5]-naphthyridine-1-carboxylic acid 2-methoxycarbonyl-2-methylpropyl ester (210 mg) is dissolved in ethanol (5 ml), and thereto is added 2N aqueous sodium hydroxide (0.598 ml). The mixture is stirred at room temperature for 2 hours. After the reaction solution is acidified slightly by adding 10% aqueous citric acid solution, the mixture is extracted with ethyl acetate. The organic layer is washed with saturated brine, dried over magnesium sulfate, and concentrated under reduced pressure. The resulting residue is purified by column chromatography (silica gel; chloroform:methanol=1:0→98:2) to give (2R,4S)-4-{[3,5-bis(trifluoromethyl)benzyl]-[5-(3-cyanopropoxy)pyrimidin-2-yl]}amino-2-ethyl-6-methoxy-3,4-dihydro-2H-[1,5]naphthyridine-1-carboxylic acid 2-carboxy-2-methylpropyl ester (154 mg). MS(m/z): 739[M+H]+.

Example 414

(1) (2R,4S)-4-{[3,5-Bis(trifluoromethyl)benzyl]-(5-hydroxypyrimidin-2-yl)}amino-2-ethyl-6-methoxy-3,4-dihydro-2H-[1,5]naphthyridine-1-carboxylic acid 2-methoxycarbonyl-2-methylpropyl ester (300 mg), triphenylphosphine (230 mg), 2-methoxyethanol (69 µl) are dissolved in tetrahydrofuran (5 ml), and thereto is added 40% diethylazodicarboxylate solution in toluene (399 µl). The mixture is stirred at room temperature for 2 hours. The reaction solution is partitioned by adding water and ethyl acetate. The organic layer is washed with water and saturated brine, dried over magnesium sulfate, and concentrated under reduced pressure. The resulting residue is purified by column chromatography (silica gel; hexane: ethyl acetate=92:8→77:23) to give (2R,4S)-4-{[3,5-bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 2-methoxycarbonyl-2-methylpropyl ester (146 mg). MS(m/z): 744[M+H]$^+$.

(2) (2R,4S)-4-{[3,5-Bis(trifluoromethyl)benzyl]-[5-(2-methoxyethoxy)-pyrimidin-2-yl]}amino-2-ethyl-6-methoxy-3,4-dihydro-2H-[1,5]naphthyridine-1-carboxylic acid 2-methoxycarbonyl-2-methylpropyl ester (142 mg) is dissolved in ethanol (1.5 ml) and thereto is added 2N aqueous sodium hydroxide (0.286 ml). The mixture is stirred at room temperature for 2 hours. After the reaction solution is acidified slightly by adding 10% aqueous citric acid solution, the mixture is extracted with ethyl acetate. The organic layer is washed with saturated brine, dried over magnesium sulfate, and concentrated under reduced pressure. The resulting residue is purified by column chromatography (silica gel; chloroform:methanol=1:0→98:2) to give (2R,4S)-4-{[3,5-bis(trifluoro-methyl)benzyl]-[5-(2-methoxyethoxy)pyrimidin-2-yl]}amino-2-ethyl-6-methoxy-3,4-dihydro-2H-[1,5]naphthyridine-1-carboxylic acid 2-carboxy-2-methylpropyl ester (90 mg). MS(m/z): 730[M+H]$^+$.

Reference Example 1

2-(Benzyloxy)ethanol (0.75 ml) is dissolved in N,N-dimethylformamide (3 ml), and added dropwise to a solution of sodium hydride (400 mg) in N,N-dimethylformamide under ice-cooling. The mixture is stirred for 40 minutes. To the reaction solution is added chloroacetic acid (500 mg) under ice-cooling, and the mixture is stirred at room temperature for 1 day. To the reaction solution is added ice-water, and the mixture is extracted with ethyl acetate. To the aqueous layer is added 6N HCl, and the solution is adjusted to pH 2 and extracted with ethyl acetate. The organic layer is washed with saturated brine and dried over magnesium sulfate, then concentrated under reduced pressure to give 2-(benzyloxy)ethoxy acetic acid (895 mg). MS (m/z): 211 [M+H]$^+$.

Reference Example 2

(1) 5-Bromo-2-chloropyrimidine (5 g) is dissolved in 1,4-dioxane (100 ml), and thereto are added diisopropylethylamine (0.81 ml) and morpholine (4.5 ml). The mixture is heated at 60° C. under nitrogen flow and stirred for 4 hours. To the mixture is added distilled water, and the mixture is extracted with ether. The organic layer is washed with saturated brine and dried over magnesium sulfate, then concentrated under reduced pressure. The resulting residue is purified by column chromatography (silica gel; hexane: ethyl acetate=19:1→9:1) to give 4-(5-bromopyrimidin-2-yl)morpholine (6.74 g). MS (m/z): 244/246 [M+H]$^+$.

(2) 4-(5-Bromopyrimidin-2-yl)morpholine (3 g) is dissolved in 1,4-dioxane (60 ml), and thereto are added copper iodide (700 mg), sodium iodide (22 g), N,N'-dimethylethan-1,2-diamine (0.8 ml). The mixture is heated at 110° C. and stirred for 6 days. To the mixture is added distilled water, and the mixture is extracted with ether. The organic layer is washed with saturated brine and dried over magnesium sulfate, then concentrated under reduced pressure. The resulting residue is purified by column chromatography (silica gel), eluted with hexane:ethyl acetate (19:1→7:3) as an elution solvent, to give 4-(5-iodopyrimidin-2-yl)-morpholine (2.33 g). MS (m/z): 292 [M+H]$^+$.

Reference Example 3

(S)-1-Phenylethyl alcohol (1.0 g) and 1,1'-carbonyldiimidazole (1.33 g) are dissolved in tetrahydrofuran (20 ml), and the mixture is stirred at 80° C. for 2 hours. To the reaction solution are added (2R*,4S*)-4-amino-2-ethyl-6-methoxy-3,4-dihydro-2H-[1,5]naphthyridine-1-carboxylic acid ethyl ester (1.91 g) and triethylamine (1.14 ml), and the mixture is heated to reflux for 3 days. The reaction solution is partitioned by adding ethyl acetate and a saturated aqueous sodium bicarbonate solution, and then the organic layer is washed with saturated brine and dried over magnesium sulfate, then concentrated under reduced pressure. The residue is purified by column chromatography (silica gel; hexane:ethyl acetate=90:10→70:30). The resulting mixture of diastereomers is recrystallized from hexane to give (2R,4S)-2-ethyl-6-methoxy-4-((S)-1-phenylethoxycarbonylamino)-3,4-dihydro-2H-[1,5]naphthyridine-1-carboxylic acid ethyl ester (345 mg). The physical property data are the same as the compound obtained in Example 2 (3).

Reference Example 4

(1) To an aqueous solution (1000 ml) of sodium azide (157.6 g) is added dropwise a solution (605 ml) of acrylyl chloride (182.4 ml) in toluene under ice-cooling. The mixture is stirred at the same temperature for 3 hours. To the mixture is added a saturated aqueous sodium bicarbonate solution, and the organic layer is washed with saturated brine and dried over magnesium sulfate. The resulting solution in toluene is added dropwise into a mixture of (S)-1-phenylethyl alcohol (268 ml), pyridine (81.5 ml) and hydroquinone (12.21 g) which is warmed to 85° C., and the mixture is stirred at the same temperature for 2 hours. To the mixture is added a saturated aqueous sodium bicarbonate solution, and the organic layer is washed with saturated brine and dried over sodium sulfate, then concentrated under reduced pressure. The resulting residue is purified by column chromatography (silica gel; hexane:ethyl acetate=10:1→8:1) to give vinylcarbamic acid (S)-1-phenylethyl ester (240.2 g). MS (m/z): 191 [M]$^+$.

(2) {[1-(Benzotriazol-1-yl)propyl]-(6-methoxypyridin-3-yl)}amine (218 g), vinylcarbamic acid (S)-1-phenylethyl ester (147.1 g) and p-toluenesulfonic acid monohydrate (1.47 g) are dissolved in toluene (2.88 1), and the mixture is stirred overnight at 85° C. After the mixture is allowed to stand for cooling to room temperature, to the mixture are added a saturated aqueous sodium bicarbonate solution and ethyl acetate. The organic layer is washed with saturated brine and dried over magnesium sulfate, then concentrated under reduced pressure. The resulting residue is purified by column chromatography (silica gel; hexane: ethyl acetate=3:1→1:1). To the resulting mixture of diastereomers is added hexane-ethyl acetate (4:1). The mixture is allowed to stand and the precipitated crystals are collected by filtration to give (2S,4R)-(2-ethyl-6-methoxy-1,2,3,4-tetrahydro-[1,5]naphthyridin-4-yl)carbamic acid (S)-1-phenylethyl ester (69.0 g). MS (m/z): 356 [M+H]$^+$.

The filtrate is concentrated under reduced pressure to use in the following process (3).

(3) The concentrate (194.7 g) obtained in (2) described above and pyridine (183 ml) are dissolved in methylene chloride (1.65 ). To the mixture is added dropwise a solution (540 ml) of ethyl chloroformate (180 ml) in methylene chloride under ice-cooling, and the mixture is stirred at the same temperature for 2 hours. The reaction solution is washed with 10% aqueous citric acid solution and saturated brine, then dried over sodium sulfate and concentrated under reduced pressure. The resulting residue is purified by column chromatography (silica gel; hexane:ethyl acetate=4:1), and the resulting compound is recrystallized from hexane (350 ml) to give (2R,4S)-2-ethyl-6-methoxy-4-((S)-1-phenylethoxy-carbonylamino)-3,4-dihydro-2H-[1,5]naphthyridine-1-carboxylic acid ethyl ester (133 g). The physical property data are the same as the compound obtained in Example 2 (3).

Reference Example 5 tert-Butyl acrylate (4.4 ml) is dissolved in methanol (5 ml), and thereto is added 2-methoxyethylamine (3.1 ml). The mixture is stirred at room temperature for 3 hours. The reaction solution is concentrated under reduced pressure. The resulting residue is purified by distillation under reduced pressure to give tert-butyl 3-(2-methoxyethylamino)-propionate (4.61 g). Boiling point 98.0-102.0° C. (5.8 mmHg), MS (m/z): 204 [M+H]$^+$.

Reference Example 6

(2R,4S)-4-{[3,5-Bis(trifluoromethyl)benzyl]-(5-bromopyrimidin-2-yl)}-amino-2-ethyl-6-methoxy-3,4-dihydro-2H-[1,5]naphthyridine-1-carboxylic acid ethyl ester (8.0 g), [1,1'-bis(diphenylphosphino)ferrocene]-dichloropalladium (265 mg), potassium acetate (3.56 g) and bis(pinacolato)-diboron (4.6 g) are dissolved in dimethylsulfoxide (50 ml), and the mixture is heated at 80° C. under nitrogen and stirred for 1 hour. After the reaction solution is cooled to room temperature, the mixture is partitioned by adding water and ethyl acetate. The organic layer is washed with saturated brine and dried over magnesium sulfate, then concentrated under reduced pressure. The resulting residue is dissolved in tetrahydrofuran (80 ml), and thereto is added dropwise 30% hydrogen peroxide solution (80 ml) under ice-cooling. After 1 hour, to the mixture is added a saturated aqueous sodium thiosulfate solution under ice-cooling to decompose excessive hydrogen peroxide. The mixture is partitioned by adding water and ethyl acetate. The organic layer is washed with saturated brine and dried over magnesium sulfate, then concentrated under reduced pressure. The resulting residue is purified by column chromatography (silica gel; hexane:ethyl acetate=19:1→3:1) to give (2R,4S)-4-{[3,5-bis(trifluoromethyl)benzyl]-(5-hydroxypyrimidin-2-yl)}amino-2-ethyl-6-methoxy-3,4-dihydro-2H-[1,5]naphthyridine-1-carboxylic acid ethyl ester (4.41 g). The physical property data are the same as the compound obtained in Example 83.

The invention claimed is:
1. A compound of formula (I)

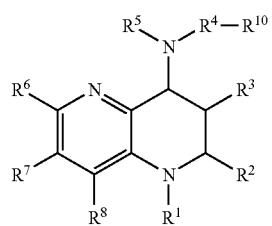

wherein $R^1$ is a hydrogen atom; an alkoxycarbonyl group optionally substituted by 1 to 5 substituents selected independently from hydroxy group, carboxyl group, alkoxy group alkylsulfonyl group, amino group, morpholinyl group and pyrimidinyl group; a carbamoyl group optionally substituted by alkoxy group; a dihydrooxazolyl group optionally substituted by a substituent selected from alkyl group and hydroxyalkyl group; mono- or di-alkylcarbamoyl group optionally substituted by a substituent selected from hydroxy group, carboxyl group, alkoxy group, amino group, mono- or di-alkylamino group, morpholinyl group, and pyridyl group; a morpholinylcarbonyl group; a piperazinylcarbonyl group optionally substituted by alkyl group; a pyrrolidinylcarbonyl group optionally substituted by carboxyl group; or a piperidinylcarbonyl group optionally substituted by carboxyl group;

$R^2$ is an alkyl group;

$R^3$ is a hydrogen atom;

$R^4$ is an alkylene group;

$R^5$ is a heterocyclic group selected from a pyrimidinyl group or a pyridyl group, wherein said heterocyclic group is optionally substituted by 1 to 4 substituents selected from the following groups:

halogen atom;
oxo group;
hydroxy group;
cyano group;
nitro group;
carboxyl group;
sulfo group;
alkyl group optionally substituted by a group selected from halogen atom, cyano group, hydroxy group, carboxyl group, alkoxycarbonyl group, mono- or di-alkylcarbamoyl group, alkoxy group (said alkoxy group is optionally substituted by hydroxy, alkoxy or phenyl group), alkanoyl group, alkanoyloxy group, alkylthio group, alkylsulfonyl group, alkylsulfinyl group, amino group, mono- or di-alkylamino group optionally substituted by alkoxy group, mono- or di-alkylsulfamoylamino group, mono- or di-alkylureido group optionally substituted by morpholinyl group, oxiranyl group, dioxolanyl group optionally substituted by alkyl group, pyrrolidinyl group (said pyrrolidinyl group is optionally substituted by alkoxycarbonyl or carboxyl group), piperidinyl group, piperazinyl group optionally substituted by alkyl group, hexahydroazepinyl group, morpholinyl group, and piperidinyloxy group optionally substituted by alkyl group;
alkenyl group optionally substituted by a group selected from cyano group, hydroxy group, carboxyl group, benzyloxycarbonyl group and tetrazolyl group;
alkoxy group optionally substituted by a group selected from hydroxy group, carboxyl group, alkoxycarbonyl group, phenyl group (said phenyl group is optionally substituted by alkoxy group), alkoxy group (said alkoxy group is optionally substituted by hydroxy group), alkanoyl group, alkylthio group, alkylsulfonyl group, alkylsulfinyl group, mono- or di-alkylamino group, dioxolanyl group optionally substituted by alkyl group, pyrrolidinyl group (said pyrrolidinyl group is optionally substituted by oxo group), morpholinyl group, mono- or di-alkylcarbamoyl group optionally substituted by hydroxy group, pyrimidinyl group, pyridyl group and morpholinylcarbonyl group;
alkoxycarbonyl group optionally substituted by phenyl group;
carbamoyl group;
mono- or di-alkylcarbamoyl group optionally substituted by a group selected from carboxyl group, morpholinyl group, and alkoxy group;

hydroxycarbamimidoyl group;
alkylthio group optionally substituted by a group selected from hydroxy group, carboxyl group and mono- or di-alkylcarbamoyl group;
alkylsulfinyl group;
alkylsulfonyl group optionally substituted by a group selected from hydroxy group, carboxyl group, alkoxycarbonyl group and mono- or di-alkylcarbamoyl group;
amino group;
mono- or di-alkylamino group optionally substituted by a group selected from hydroxy group, carboxyl group, alkoxycarbonyl group, alkoxy group, mono- or di-alkylamino group and morpholinyl group;
alkanoylamino group optionally substituted by a group selected from hydroxy group, alkoxy group, and amino group;
mono- or di-alkylcarbamoylamino group optionally substituted by alkoxy group;
morpholinylcarbonylamino group;
sulfamoyl group;
mono- or di-alkylsulfamoyl group;
alkanoyl group optionally substituted by a group selected from hydroxy group, carboxyl group, alkoxycarbonyl group, alkoxy group, mono- or di-alkylamino group and morpholinyl group;
or
a group selected from the following groups:

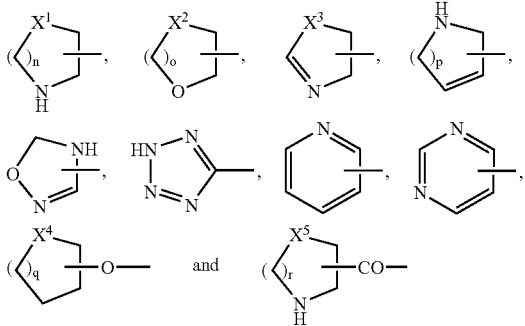

wherein $X^1$ and $X^3$ are independently $CH_2$, NH, O, S, SO or $SO_2$; $X^2$ and $X^5$ are independently $CH_2$, O, S, SO or $SO_2$; $X^4$ is NH, O, S, SO or $SO_2$; and n, o, p, q and r are independently an integer of 1 to 4, wherein each group of the above formula is optionally substituted by a substituent(s) selected from the following groups:
carboxyl group, hydroxy group, cyano group, oxo group, alkyl group, hydroxyalkyl group, alkoxycarbonylalkyl group, carboxyalkyl group, morpholinylalkyl group, phenylalkyl group, alkanoyl group, hydroxyalkanoyl group, alkoxyalkanoyl group, alkoxy group, phenylalkoxy group, alkoxycarbonyl group, benzyloxycarbonyl group, mono- or di-alkylamino group, mono- or di-alkylcarbamoyl group, mono- or di-alkylsulfamoyl group, alkylsulfonyl group, and tetrazolyl group;
$R^6$, $R^7$ and $R^8$ are independently a hydrogen atom, a halogen atom, a hydroxy group, a nitro group, a cyano group, an alkyl group, an alkoxy group, or a mono- or di-alkylamino group, wherein said alkyl, alkoxy, and mono- or di-alkylamino groups are optionally substituted by 1 to 6 substituents selected independently from halogen atom, hydroxy group, alkoxy group, alkylthio group, amino group, nitro group, cyano group, oxo group, carboxyl group, alkoxycarbonyl group and mono- or di-alkylamino group; or
$R^6$ and $R^7$, or $R^7$ and $R^8$ may combine at the ends to form an alkylene group which alkylene group optionally contains 1 to 3 heteroatoms selected independently from nitrogen, sulfur and oxygen atoms;
$R^{10}$ is an aromatic monocyclic ring optionally containing 1 to 3 heteroatoms selected independently from oxygen, sulfur and nitrogen atoms;
wherein the monocyclic aromatic ring is optionally substituted by 1 to 4 substituents selected independently from halogen atom, carboxyl group, alkoxycarbonyl group, carbamoyl group, mono- or di-alkylcarbamoyl group, alkyl group, alkoxy group, hydroxy group, nitro group, cyano group, amino group, mono- or di-alkylamino group, alkanoyl group, alkylthio group, tetrazolyl group and dihydrooxazolyl group, wherein the alkyl, alkoxy, mono- or di-alkylamino, mono- or di-alkylcarbamoyl, alkanoyl and alkylthio groups are optionally substituted by a substituent(s) selected independently from halogen atom, and hydroxy, alkoxy, morpholinyl, piperidinyl, pyrrolidinyl, piperazinyl, alkylpiperazinyl and alkanoylpiperazinyl groups;
or a pharmaceutically acceptable salt thereof.

2. The compound of claim 1, wherein in $R^{10}$, the aromatic monocyclic ring optionally containing 1 to 3 heteroatoms selected independently from oxygen, sulfur and nitrogen atoms is a phenyl group, a pyridyl group, a pyrimidinyl group, a furyl group or a thienyl group.

3. The compound of claim 2, wherein $R^1$ is a hydrogen atom; an alkoxycarbonyl group optionally substituted by 1 to 5 substituents selected independently from hydroxy group, carboxyl group, alkoxy group, alkylsulfonyl group, amino group, morpholinyl group, and pyrimidinyl group; dihydrooxazolyl group optionally substituted by a substituent selected from alkyl group, and hydroxyalkyl group; or a mono- or di-alkylcarbamoyl group optionally substituted by a substituent selected independently from hydroxy group, carboxyl group, alkoxy group, amino group, mono- or di-alkylamino group, morpholinyl group, and pyridyl group;
$R^2$ is an alkyl group;
$R^3$ is a hydrogen atom;
$R^4$ is an alkylene group;
$R^5$ is a heterocyclic group selected from pyrimidinyl group, and pyridyl group wherein said heterocyclic group is substituted by 1 to 4 substituents selected from the following groups:
halogen atom,
hydroxy group;
oxo group;
cyano group;
carboxyl group;
sulfo group;
alkyl group optionally substituted by a group selected from halogen atom, cyano group, hydroxy group, carboxyl group, alkoxy group optionally substituted by hydroxy or alkoxy group, alkoxycarbonyl group, mono- or di-alkylcarbamoyl group, mono- or di-alkylamino group optionally substituted by alkoxy group, pyrrolidinyl group optionally substituted by carboxyl or alkoxycarbonyl group, piperidinyl group, piperazinyl group optionally substituted by alkyl group, morpholinyl group, alkanoyloxy group and alkylsulfonyl group;
alkenyl group optionally substituted by a group selected from cyano group, hydroxy group, carboxyl group, benzyloxycarbonyl group, and tetrazolyl group;

alkoxy group optionally substituted by a group selected from hydroxy group, carboxyl group, alkoxycarbonyl group, mono- or di-alkylcarbamoyl group optionally substituted by hydroxy group, alkoxy group (said alkoxy group is optionally substituted by hydroxy group), alkylthio group, alkylsulfonyl group, alkylsulfinyl group, mono- or di-alkylamino group, morpholinyl group, pyrrolidinyl group (said pyrrolidinyl group is optionally substituted by oxo group), pyrimidinyl group, pyridyl group, dioxolanyl group optionally substituted by alkyl group, and morpholinylcarbonyl group;

alkoxycarbonyl group optionally substituted by phenyl group;

carbamoyl group;

mono- or di-alkylcarbamoyl group optionally substituted by a group selected from morpholinyl group, carboxyl group, and alkoxy group;

hydroxycarbamimidoyl group;

alkylthio group optionally substituted by a group selected from hydroxy group, carboxyl group and mono- or di-alkylcarbamoyl group;

alkylsulfonyl group optionally substituted by a group selected from hydroxy group, alkoxycarbonyl group and mono- or di-alkylcarbamoyl group;

amino group;

mono- or di-alkylamino group optionally substituted by a group selected from hydroxy group, carboxyl group, alkoxycarbonyl group, alkoxy group, mono- or di-alkylamino group and morpholinyl group;

alkanoylamino group optionally substituted by a group selected from hydroxy group, alkoxy group, and amino group;

mono- or di-alkylureido group optionally substituted by alkoxy group;

morpholinylcarbonylamino group;

morpholinyl group optionally substituted by a group selected from oxo group and carboxyl group;

piperazinyl group optionally substituted by a group selected from cyano group, alkyl group, hydroxyalkyl group, alkoxycarbonylalkyl group, carboxyalkyl group, alkanoyl group, alkoxyalkanoyl group, benzyloxycarbonyl group, mono- or di-alkylcarbamoyl group, mono- or di-alkylsulfamoyl group, alkylsulfonyl group, tetrazolyl group, and dihydrooxadiazolyl group optionally substituted by oxo group;

piperidinyl group optionally substituted by a group selected from carboxyl group, hydroxy group, alkyl group optionally substituted by hydroxy or carboxyl group, alkoxy group optionally substituted by phenyl group, alkoxycarbonyl group, oxo group and alkanoyl group;

pyrrolidinyl group optionally substituted by a group selected from carboxyl group, alkoxycarbonyl group, oxo group, and mono- or di-alkylamino group;

pyrrolinyl group optionally substituted by oxo group;

hexahydrodiazepinyl group optionally substituted by alkanoyl group;

imidazolidinyl group optionally substituted by oxo group;

pyridyl group optionally substituted by carboxyl group, hydroxy group, alkanoyl group, alkyl group or hydroxyalkyl group (said pyridyl group is optionally further oxidized);

tetrazolyl group optionally substituted by alkyl group or hydroxyalkyl group;

dihydrooxadiazolyl group optionally substituted by oxo group;

dihydroimidazolyl group;

dihydrooxazolyl group;

oxazolidinyl group optionally substituted by oxo group;

tetrahydropyridyl group optionally substituted by benzyl group;

pyrimidinyl group;

piperidinyloxy group optionally substituted by alkyl group or carboxyl group;

pyrrolidinyloxy group optionally substituted by a group selected from alkyl group, carboxyl group, alkoxycarbonyl group and alkanoyl group;

tetrahydropyranyloxy group;

tetrahydrofuranyloxy group;

optionally oxidized thianyloxy group;

morpholinylcarbonyl group;

piperazinylcarbonyl group optionally substituted by a group selected from alkanoyl group and alkyl group;

pyrrolidinylcarbonyl group optionally substituted by carboxyl group or alkoxycarbonyl group; and piperidinylcarbonyl group optionally substituted by carboxyl group or alkoxycarbonyl group;

$R^6$ and $R^7$ are independently a hydrogen atom, an alkyl group optionally substituted by halogen atom, an alkoxy group optionally substituted by halogen atom, a hydroxy group, a cyano group, or a mono- or di-alkylamino group; or $R^6$ and $R^7$ may combine at the ends to form an alkylenedioxy group;

$R^8$ is a hydrogen atom;

$R^{10}$ is a phenyl or pyridyl group, which phenyl or pyridyl group is optionally substituted by 1 to 4 substituents selected from halogen atom, alkoxycarbonyl group, alkyl group optionally substituted by halogen atom, alkoxy group optionally substitute by halogen atom, hydroxy group, cyano group, amino group, mono- or di-alkylamino group and alkylthio group.

4. The compound of claim 3, wherein $R^1$ is an alkoxycarbonyl group optionally substituted by 1 to 5 substituents selected independently from hydroxy group, carboxyl group, and alkoxy group; or a dihydrooxazolyl group optionally substituted by hydroxyalkyl group;

$R^5$ is a pyrimidinyl or pyridyl group, which group is substituted by 1 to 4 substituents selected from the following groups:

halogen atom;

hydroxy group;

cyano group;

carboxyl group;

alkyl group optionally substituted by a group selected from halogen atom, cyano group, hydroxy group, carboxyl group, alkoxy group optionally substituted by hydroxy or alkoxy group, alkoxycarbonyl group, mono- or di-alkylcarbamoyl group, mono- or di-alkylamino group optionally substituted by alkoxy, pyrrolidinyl group optionally substituted by carboxyl or alkoxycarbonyl group, piperidinyl group, piperazinyl group optionally substituted by alkyl group, morpholinyl group, alkanoyloxy group and alkylsulfonyl group;

alkenyl group optionally substituted by a group selected from cyano group, hydroxy group and carboxyl group;

alkoxy group optionally substituted by a group selected from hydroxy group, carboxyl group, alkoxycarbonyl group, mono- or di-alkylcarbamoyl group optionally substituted by hydroxy group, alkoxy group (said alkoxy group is optionally substituted by hydroxy group), alkylthio group, alkylsulfonyl group, alkylsulfonyl group, mono- or di-alkylamino group, morpholinyl group, pyrrolidinyl group (said pyrrolidinyl group is optionally substituted by oxo group), pyrimidinyl group, pyridyl group, dioxolanyl group optionally substituted by alkyl group, and morpholinylcarbonyl group;
mono- or di-alkylcarbamoyl group optionally substituted by a group selected from morpholinyl group, carboxyl group and alkoxy group;
hydroxycarbamimidoyl group;
alkylthio group optionally substituted by a group selected from hydroxy group, carboxyl group and mono- or di-alkylcarbamoyl group;
amino group;
mono- or di-alkylamino group optionally substituted by a group selected from hydroxy group, carboxyl group, alkoxycarbonyl group, alkoxy group, and morpholinyl group;
alkanoylamino group optionally substituted by a group selected from hydroxy group, alkoxy group and amino group;
mono- or di-alkylureido group optionally substituted by alkoxy group;
morpholinylcarbonylamino group;
morpholinyl group optionally substituted by oxo group;
piperazinyl group optionally substituted by a group selected from cyano group, alkyl group, hydroxyalkyl group, alkoxycarbonylalkyl group, carboxyalkyl group, alkanoyl group, alkoxyalkanoyl group, mono- or di-alkylcarbamoyl group, mono- or di-alkylsulfamoyl group and alkylsulfonyl group;
piperidinyl group optionally substituted by a group selected from carboxyl group, hydroxy group, alkyl group optionally substituted by hydroxy or carboxyl group, alkoxy group, alkoxycarbonyl group, oxo group and alkanoyl group;
pyrrolidinyl group optionally substituted by a group selected from oxo group, carboxyl group, alkoxycarbonyl group and mono- or di-alkylamino group;
hexahydrodiazepinyl group optionally substituted by alkanoyl group;
pyridyl group optionally substituted by hydroxy group, carboxyl group, alkyl group or hydroxyalkyl group (said pyridyl group is optionally further oxidized);
tetrazolyl group optionally substituted by alkyl group or hydroxyalkyl group;
dihydrooxadiazolyl group optionally substituted by oxo group;
oxazolidinyl group optionally substituted by oxo group;
tetrahydropyridyl group optionally substituted by benzyl group;
pyrimidinyl group;
piperidinyloxy group optionally substituted by alkyl group or carboxyl group;
pyrrolidinyloxy group optionally substituted by a group selected from alkyl group and alkanoyl group;
tetrahydropyranyloxy group;
tetrahydrofuranyloxy group; and
optionally oxidized thianyloxy group;
$R^{10}$ is a phenyl or pyridyl group, which phenyl or pyridyl group is optionally substituted by 1 to 4 substituents selected from halogen atom, alkyl group optionally substituted by halogen atom, alkoxy group, hydroxy group, cyano group, amino group and mono- or di-alkylamino group.

5. The compound of claim 1, wherein $R^1$ is a hydrogen atom; an alkoxycarbonyl group optionally substituted by 1 to 5 substituents selected independently from hydroxy group, carboxyl group, alkoxy group, alkylsulfonyl group, amino group, morpholinyl group, and pyrimidinyl group; dihydrooxazolyl group optionally substituted by 1 to 2 substituents selected independently from alkyl group and hydroxyalkyl group; or a mono- or di-alkylcarbamoyl group optionally substituted by 1 to 5 substituents selected independently from hydroxy group, carboxyl group, alkoxy group, amino group, mono- or di-alkylamino group, morpholinyl group, and pyridyl group;
$R^2$ is an alkyl group;
$R^3$ is a hydrogen atom;
$R^4$ is an alkylene group;
wherein $R^5$ is a group of the formula:

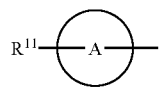

wherein Ring A is a pyrimidinyl or pyridyl group; and
$R^{11}$ is a group selected from the following groups:
halogen atom,
hydroxy group;
oxo group;
cyano group;
carboxyl group;
sulfo group;
alkyl group optionally substituted by a group selected from halogen atom, cyano group, hydroxy group, carboxyl group, alkoxy group optionally substituted by hydroxy or alkoxy group, alkoxycarbonyl group, mono- or di-alkylcarbamoyl group, mono- or di-alkylamino group optionally substituted by alkoxy pyrrolidinyl group optionally substituted by carboxyl or alkoxycarbonyl group, piperidinyl group piperazinyl group optionally substituted by alkyl group, morpholinyl group, alkanoyloxy group and alkylsulfonyl group;
alkenyl group optionally substituted by a group selected from cyano group, hydroxy group, carboxyl group, benzyloxycarbonyl group and tetrazolyl group;
alkoxy group optionally substituted by a group selected from hydroxy group, carboxyl group, alkoxycarbonyl group, mono- or di-alkylcarbamoyl group optionally substituted by hydroxy group, alkoxy group (said alkoxy group is optionally substituted by hydroxy group), alkylthio group, alkylsulfonyl group, alkylsulfinyl group, mono- or di-alkylamino group, morpholinyl group, pyrrolidinyl group (said pyrrolidinyl group is optionally substituted by oxo group), pyrimidinyl group, pyridyl group, dioxolanyl group optionally substituted by alkyl group and morpholinylcarbonyl group;
alkoxycarbonyl group optionally substituted by phenyl group;
carbamoyl group;
mono- or di-alkylcarbamoyl group optionally substituted by a group selected from morpholinyl group, carboxyl group, and alkoxy group;
hydroxycarbamimidoyl group;
alkylthio group optionally substituted by a group selected from hydroxy group, carboxyl group and mono- or di-alkylcarbamoyl group;
alkylsulfonyl group optionally substituted by a group selected from hydroxy group, alkoxycarbonyl group and mono- or di-alkylcarbamoyl group;
amino group;
mono- or di-alkylamino group optionally substituted by a group selected from hydroxy group, carboxyl group, alkoxycarbonyl group, alkoxy group, mono- or di-alkylamino group and morpholinyl group;
alkanoylamino group optionally substituted by a group selected from hydroxy group, alkoxy group, and amino group;
mono- or di-alkylureido group optionally substituted by alkoxy group;
morpholinylcarbonylamino group;
morpholinyl group optionally substituted by a group selected from oxo group and carboxyl group;
piperazinyl group optionally substituted by a group selected from cyano group, alkyl group, hydroxyalkyl group, alkoxycarbonylalkyl group, carboxyalkyl group, alkanoyl group, alkoxyalkanoyl group, benzyloxycarbonyl group, mono- or di-alkylcarbamoyl group, mono- or di-alkylsulfamoyl group, alkylsulfonyl group, tetrazolyl group, and dihydrooxadiazolyl group optionally substituted by oxo group;
piperidinyl group optionally substituted by a group selected from carboxyl group, hydroxy group, alkyl group optionally substituted by hydroxy or carboxyl group, alkoxy group optionally substituted by phenyl group, alkoxycarbonyl group, oxo group, and alkanoyl group;
pyrrolidinyl group optionally substituted by a group selected from carboxyl group, alkoxycarbonyl group, oxo group, and mono- or di-alkylamino group;
pyrrolinyl group optionally substituted by oxo group;
hexahydrodiazepinyl group optionally substituted by alkanoyl group;
imidazolidinyl group optionally substituted by oxo group;
pyridyl group optionally substituted by carboxyl group, hydroxy group, alkanoyl group, alkyl group or hydroxyalkyl group (said pyridyl group is optionally further oxidized);
tetrazolyl group optionally substituted by a group selected from alkyl group and hydroxyalkyl group;
dihydrooxadiazolyl group optionally substituted by oxo group;
dihydroimidazolyl group;
dihydrooxazolyl group;
oxazolidinyl group optionally substituted by oxo group;
tetrahydropyridyl group optionally substituted by benzyl group;
pyrimidinyl group;
piperidinyloxy group optionally substituted by alkyl group or carboxyl group;
pyrrolidinyloxy group optionally substituted by a group selected from alkyl group, carboxyl group, alkoxycarbonyl group and alkanoyl group;
tetrahydropyranyloxy group;
tetrahydrofuranyloxy group;
optionally oxidized thianyloxy group;
morpholinylcarbonyl group;
piperazinylcarbonyl group optionally substituted by a group selected from alkanoyl group and alkyl group;
pyrrolidinylcarbonyl group optionally substituted by carboxyl group or alkoxycarbonyl group; and
piperidinylcarbonyl group optionally substituted by carboxyl group or alkoxycarbonyl group;
$R^6$ and $R^7$ are independently a hydrogen atom, an alkyl group optionally substituted by halogen atom, an alkoxy group optionally substituted by halogen atom, a hydroxy group, a cyano group, or a mono- or di-alkylamino group; or
$R^6$ and $R^7$ may combine at the ends to form an alkylenedioxy group;

$R^8$ is a hydrogen atom; and
$R^{10}$ is a phenyl or pyridyl group, which phenyl or pyridyl group is optionally substituted by 1 to 4 substituents selected from halogen atom, alkoxycarbonyl group, alkyl group optionally substituted by halogen atom, alkoxy group optionally substituted by halogen atom, hydroxy group, cyano group, amino group, mono- or di-alkylamino group and alkylthio group.

6. The compound of claim 5, wherein $R^{11}$ is a group selected from the groups:
alkyl group optionally substituted by a group selected from carboxyl group, hydroxyalkoxy group, mono- or di-alkylamino group optionally substituted by alkoxy group, amino group, mono- or di-alkylcarbamoyl group and morpholinyl group:
alkenyl group optionally substituted by hydroxy group, carboxyl group or cyano group;
alkoxy group optionally substituted by a group selected from hydroxy group, carboxyl group, alkoxycarbonyl group, mono- or di-alkylcarbamoyl group optionally substituted by hydroxy group, hydroxyalkoxy group, alkylsulfonyl group, alkylsulfinyl group, mono- or di-alkylamino group, morpholinyl group, oxopyrrolidinyl group, pyridyl group and morpholinylcarbonyl group;
carbamoyl group;
alkylthio group optionally substituted by hydroxy group or mono- or di-alkylcarbamoyl group;
mono- or di-alkylamino group optionally substituted by hydroxy group, carboxyl group or alkoxy group;
alkanoylamino group optionally substituted by hydroxy group or alkoxy group;
mono- or di-alkylureido group optionally substituted by alkoxy group;
morpholinyl group;
piperazinyl group optionally substituted by a group selected from alkyl group, hydroxyalkyl group, alkoxycarbonylalkyl group, carboxyalkyl group, alkanoyl group and mono- or di-alkylcarbamoyl group;
piperidinyl group optionally substituted by a group selected from carboxyl group, alkoxycarbonyl group, hydroxy group, hydroxyalkyl group, carboxyalkyl group and oxo group;
pyrrolidinyl group optionally substituted by a group selected from carboxyl group and mono-or di-alkylamino group;
pyridyl group that is substituted by hydroxyalkyl group or oxidized;
tetrazolyl group optionally substituted by alkyl group or hydroxyalkyl group;
oxodihydrooxadiazolyl group;
pyrimidinyl group;
pyrrolidinyloxy group optionally substituted by alkanoyl group; and
optionally oxidized thianyloxy group;
$R^6$ is a hydrogen atom, an alkyl group optionally substituted by halogen atom, an alkoxy group, a cyano group, or a mono- or di-alkylamino group; and
$R^{10}$ is a phenyl group which is substituted by 1 to 3 substituents selected from halogen atom, alkyl group optionally substituted by halogen atom, alkoxy group and cyano group.

7. The compound of claim 6, wherein $R^1$ is an alkoxycarbonyl group optionally substituted by 1 to 5 substituents selected independently from hydroxy group, carboxyl group, and alkoxy group; or a dihydrooxazolyl group optionally substituted by hydroxyalkyl group;

$R^{11}$ is a group selected from the groups:
alkyl group optionally substituted by carboxyl group, alkoxycarbonyl group or hydroxy group, carboxyalkenyl group;
alkoxy group optionally substituted by a group selected from hydroxy group, carboxyl group, alkoxycarbonyl group, carbamoyl group, mono- or di-alkylcarbamoyl group, mono-or di-alkylcarbamoyl group substituted by hydroxy group, hydroxyalkoxy group, alkylsulfonyl group, alkylsulfinyl group, mono- or di-alkylamino group and oxopyrrolidinyl group;
mono- or di-alkylamino group optionally substituted by carboxyl group;
alkanoylamino group optionally substituted by hydroxy group or alkoxy group;
morpholinyl group;
piperazinyl group optionally substituted by a group selected from alkyl group, alkanoyl group and mono- or di-alkylcarbamoyl group;
piperidinyl group optionally substituted by carboxyl group, alkoxycarbonyl group, hydroxy group, carboxyalkyl group or hydroxyalkyl group;
pyrrolidinyl group optionally substituted by mono- or di-alkylamino group;
pyridyl group that is substituted by hydroxyalkyl group or oxidized;
tetrazolyl group optionally substituted by hydroxyalkyl group;
pyrimidinyl group;
pyrrolidinyloxy group optionally substituted by alkyl group or alkanoyl group; and
optionally oxidized thianyloxy group; and
$R^{10}$ is a phenyl group which is substituted by 1 to 3 substituents selected from alkyl group optionally substituted by halogen atom, alkoxy group and cyano group.

8. The compound of claim 7, wherein $R^1$ is an alkoxycarbonyl group optionally substituted by 1 or 5 substituents selected independently from carboxyl group, and hydroxy group;
$R^{11}$ is an alkyl group optionally substituted by carboxyl group; a carboxyalkenyl group; an alkoxy group optionally substituted by a group selected from hydroxy group, carboxyl group, alkylthio group and alkylsulfonyl group; an mono- or di-alkylamino group optionally substituted by carboxyl group; a hydroxyalkanoylamino group; a morpholinyl group; a piperazinyl group optionally substituted by alkyl group or alkanoyl group; or a piperidinyl group optionally substituted by carboxyl group or hydroxy group;
$R^6$ is an alkyl group optionally substituted by halogen atom, an alkoxy group or a mono- or di-alkylamino group; and
$R^7$ is a hydrogen atom.

9. The compound of claim 8, wherein $R^1$ is an ethoxycarbonyl group, or a hydroxyethoxycarbonyl group; $R^2$ is an ethyl group; $R^{10}$ is a phenyl group substituted by 1 to 2 substituents selected from cyano group and trifluoromethyl group; and $R^6$ is a methoxy group or a trifluoromethyl group.

10. The compound of claim 8, wherein $R^1$ is a carboxy $(C_{2-10}$alkoxy)carbonyl group or an alkoxycarbonyl $(C_{2-10}$alkoxy) carbonyl group; $R^2$ is an ethyl group; $R^{10}$ is a phenyl group substituted by 1 to 2 substituents selected from cyano group and trifluoromethyl group; and $R^6$ is a methoxy group or a trifluoromethyl group.

11. The compound of claim 1, wherein the compound is selected from the following compounds:

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid ethyl ester;

(2R*,4S*)-4-{[3,5-Bis(trifluoromethy)benzyl]-[5-(4-hydroxymethylpyperidine-1-yl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-methylpiperadin-1-yl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-acetylpiperadin)-1-yl)pyrimidin-2-yl]}amino-2-ethyl-6-methoxy-3,4-dihydro-2H-[1,5]naphthyridine-1-carboxylic acid ethyl ester;

(2R*,4S*)-4-{[3,5-Bis(trifluoromethyl)benzyl]-[5-(hydroxyacetylamino)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[(5-(2-methylsulfonylethoxy)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2,3-dihydroxypropoxy)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2-carboxyvinyl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2-carboxyethyl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid ethyl ester;

(2R,4S)-4[3,5-Bis(trifluoromethyl)benzyl]-(5-{[methyl-(2-carboxyethyl)]amino}pyrimidin-2-yl)]amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-carboxypyperidin-1-yl)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-carboxypyperidin-1-yl)pyridin-2-yl ]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(2-carboxyethoxy)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(3-carboxypropoxy)pyrimidin-2-yl]}amino-2-ethyl-6-methoxy-3,4-dihydro-2H-[1,5]naphthyridine-1-carboxylic acid ethyl ester;

(2R,4S)-4-{[3,5-Bis(trifluoromethyl)benzyl]-[5-(4-carboxybutoxy)pyrimidin-2-yl]}amino-2-ethyl-6-methoxy-3,4-dihydro-2H-[1,5]naphthyridine-1-carboxylic acid ethyl ester;

(2R,4S)-4-{[5-(2-Carboxyethyl)pyrimidin-2-yl)]-(3-cyano-5-trifluoromethylbenzyl)}amino-2-ethyl-6-methoxy-3,4-dihydro-2H-[1,5]naphthyridine-1-carboxylic acid ethyl ester;

(2R,4S)-4-[(3-Cyano-5-trifluoromethylbenzyl)-(5-{[methyl-(2-carboxyethyl)]-amino}pyrimidin-2-yl)]amino-2-ethyl-6-methoxy-3,4-dihydro-2H-[1,5]naphthyridine-1-carboxylic acid ethyl ester;

(2R,4S)-4-{[5-(4-Acetylpiperadin-1-yl)pyrimidin-2-yl)]-[3,5-bis(trifluoromethyl)benzyl]}amino-6-dimethylamino-2-ethyl-3,4-dihydro-2H-[1,5]naphthyridine-1-carboxylic acid ethyl ester;

(2R,4S)-4-{[5-(4-Acetylpiperadin-1-yl)pyrimidin-2-yl]-[3,5-bis(trifluoromethyl)benzyl]}amino-2-ethyl-6-methyl-3,4-dihydro-2H-[1,5]naphthyridine-1-carboxylic acid ethyl ester;

(2R,4S)-4-{[3,5-Bis(trifluoromethyl)benzyl]-[5-(3-carboxypropoxy)pyrimidin-2-yl]}amino-2-ethyl-6-trifluoromethyl-3,4-dihydro-2H-[1,5]naphthyridine-1-carboxylic acid ethyl ester;

(2R,4S)-4-{[3,5-Bis(trifluoromethyl)benzyl]-[5-(2-carboxyethyl)pyrimidin-2-yl]}amino-2-ethyl-6-methoxy-3,4-dihydro-2H-[1,5]naphthyridine-1-carboxylic acid 2,2,2-trifluoroethyl ester;

(2R,4S)-4-{[3,5-Bis(trifluoromethyl)benzyl]-[5-(4-carboxypyperidin-1-yl)pyrimidin-2-yl]}amino-2-ethyl-6-methoxy-3,4-dihydro-2H-[1,5]naphthyridine-1-carboxylic acid tert-butyl ester;

(2R,4S)-4-{[3,5-Bis(trifluoromethyl)benzyl]-[5-(4-carboxypyperidin-1-yl)pyrimidin-2-yl]}amino-2-ethyl-6-methoxy-3,4-dihydro-2H-[1,5]naphthyridine-1-carboxylic acid 2-fluoroethyl ester;

(2R,4S)-4-{[3,5-Bis(trifluoromethyl)benzyl]-[5-(4-carboxypyperidin-1-yl)pyrimidin-2-yl]}amino-2-ethyl-6-methoxy-3,4-dihydro-2H-[1,5]naphthyridine-1-carboxylic acid 1-methylethyl ester;

(2R,4S)-4-{[3,5-Bis(trifluoromethyl)benzyl]-[5-(morpholin-4-yl)pyrimidin-2-yl]}amino-1-((R)-4-hydroxymethyl-4,5-dihydrooxazol-2-yl)-2-ethyl-6-methoxy-3,4-dihydro-2H-[1,5]naphthyridine;

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 2-carboxy-2-methylpropyl ester; or (2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 5-carboxypentyl ester or a pharmaceutically acceptable salt thereof.

12. The compound of claim 1, wherein the compound is selected from the following group:

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 2-carboxyethyl ester;

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 3-carboxypropyl ester;

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-[1,5]naphthyridine-1-carboxylic acid 4-carboxybutyl ester;

(2R,4S)-4-{[3,5-Bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid 2-carboxyethyl ester;

(2R,4S)-4-{[3,5-Bis(trifluoromethyl)benzyl]-[5-(2-hydroxyethoxy)pyrimidin-2-yl]}amino-2-ethyl-6-methoxy-3,4-dihydro-2H-[4 1,5]naphthyridine-1-carboxylic acid 3-carboxypropyl ester;

(2R,4S)-4{-[3,5-Bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid 4-carboxybutyl ester;

(2R,4S)-4-{[3,5-Bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(2-hydroxyethoxy)pyrimidin-2-yl]}amino-2-ethyl-6-methoxy-3,4-dihydro-2H-[1,5]naphthyridine-1-carboxylic acid 5-carboxypentyl ester;

(2R,4S)-4-{[3,5-Bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 2-carboxyethyl ester;

(2R,4S)-4-{[3,5-Bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 3-carboxypropyl ester;

(2R,4S)-4-{[3,5-Bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 4-carboxybutyl ester;

(2R,4S)-4-{[3,5-Bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(2-methoxyethoxy)pyrimidin-2-yl]}amino-2-ethyl-6-methoxy-3,4-dihydro-2H-[1,5]naphthyridine-1-carboxylic acid 5-carboxypentyl ester;

(2R,4S)-4-{[3,5-Bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 2-carboxyethyl ester;

(2R,4S)-4-{[3,5-Bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 3-carboxypropyl ester;

(2R,4S)-4-{[3,5-Bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 4-carboxybutyl ester;

(2R,4S)-4-{[3,5-Bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 2-carboxy-2-methylpropyl ester;

(2R,4S)-4-{[3,5-Bis(trifluoromethyl)benzyl]-(5-dimethylaminopyrimidin-2-yl)}amino-2-ethyl-6-methoxy-3,4-dihydro-2H-[1,5]naphthyridine-1-carboxylic acid 5-carboxypentyl ester;

(2R,4S)-4-{(3-Cyano-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid 2-carboxyethyl ester;

(2R,4S)-4-{(3-Cyano-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid 3-carboxypropyl ester;

(2R,4S)-4-{(3-Cyano-5-trifluoromethylbenzyl)-[5-(moipholin-4-yl)pyrimidin-2-yl]}amino-2-ethyl-6-methoxy-3,4-dihydro-2H-[1,5]naphthyridine-1-carboxylic acid 4-carboxybutyl ester;

(2R,4S)-4-{(3-Cyano-5-trifluorornethylbenzyl[5-(morpholin-4-yl)pyrimidin-2-yl]}amino-2-ethyl-6-methoxy-3,4-dihydro-2H-[1,5]naphthyridine-1-carboxylic acid 2-carboxy-2-methylpropyl ester;

(2R,4S)-4-{(3-Cyano-5-trifluoromethylbenzyl)-[5-(morpholin-4-yl)pyrimidin-2-yl]}amino-2-ethyl-6-methoxy-3,4-dihydro-2H-[1,5]naphthyridine-1-carboxylic acid 5-carboxypentyl ester;

(2R,4S)-4-{[3,5-Bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid 2-carboxyethyl ester;

(2R,4S)-4-{[3,5-Bis(tifluoromethyl)benzyl]-[5-(morpholin-4-yl)pyridin-2-yl]}amino-2-ethyl-6-methoxy-3,4-dihydro-2H-[1,5]naphthyridine-1-carboxylic acid 3-carboxypropyl ester;

(2R,4S)-4-{[3,5-Bis(trifluoromethyl)benzyl]-[5-(moipholin-4-yl)pyridin-2-yl]}amino-2-ethyl-6-methoxy-3,4-dihydro-2H-[1,5]naphthyridine-1-carboxylic acid 4-carboxybutyl ester;

(2R,4S)-4-{[3,5-Bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(morpholin-4-yl)pyridin-2-yl]}amino-2-ethyl-6-methoxy-3,4-dihydro-2H-[1,5]naphthyridine-1-carboxylic acid 5-carboxypentyl ester;

(2R,4S)-4-{[3,5-Bis(trifluoromethyl)benzyl]-[5-(2-methoxyethoxy)pyridin-2-yl]}amino-2-ethyl-6-methoxy-3,4-dihydro-2H-[1,5]naphthyridine-1-carboxylic acid 3-carboxypropyl ester;

(2R,4S)-4-{[3,5-Bis(trifluoromethyl)benzyl]-[5-(2-methoxyethoxy)pridin-2-yl]}amino-2-ethyl-6-methoxy-3,4-dihydro-2H-[1,5]naphthyridine-1-carboxylic acid 4-carboxybutyl ester;

(2R,4S)-4-{[3,5-Bis(trifluoromethyl)benzyl]-[5-(2-methoxyethoxy)pyridin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(2-methoxyethoxy)pyridin-2-yl]}amino-2-ethyl-6-methoxy-3,4-dihydro-2H-[1,5]naphthyridine-1-carboxylic acid 5-carboxypentyl ester;

(2R,4S)-4-{(3-Cyano-5-trifluoromethylbenzyl)-[5-(morpholin-4-yl)pyridin-2-yl]}amino-2-ethyl-6-methoxy-3,4-dihydro-2H-[1,5]naphthyridine-1-carboxylic acid 2-carboxy-2-methylpropyl ester;

(2R,4S)-4-{[3,5-Bis(trilluoromethyl)benzyl]-[5-(morpholin-4-yl)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-[1,5]naphthyridine-1-carboxylic acid 3-carboxypropyl ester;

(2R,4S)-4-{[3,5-Bis(trifluoromethyl)benzyl]-[5-(morpholin-4-yl)pyrimidin-2-yl])}amino-2-ethyl-6-trifluoromethyl-3,4-dihydro-2H-[1,5]naphthyridine-1-carboxylic acid 4-carboxybutyl ester;

(2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-[1,5]naphthyridine-1-carboxylic acid 5-carboxypentyl ester;

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 3-carboxypropyl ester;

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 4-carboxybutyl ester;

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-[1,5]naphthyridine-1-carboxylic acid 5-carboxypentyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-[1,5]naphthyridine-1-carboxylic acid 3-carboxypropyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-[1,5]naphthyridine-1-carboxylic acid 4-carboxybutyl ester;

(2R,4S)-4-{[3,5-Bis(trifluoromethyl)benzyl]-[5-(2-methoxyethoxy)pyrimidin-2-yl]}amino-2-ethyl-6-tifluoromethyl-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-[1,5]naphthyridine-1-carboxylic acid 5-carboxypentyl ester;

(2R,4S)-4-{[3,5-Bis(trifluoromethyl)benzyl]-(5-dimethylaminopyrimidin-2-yl) }amino-2-ethyl-6-trifluoromethyl-3,4-dihydro-2H-[1,5]naphthyridine-1-carboxylic acid 3-carboxypropyl ester;

(2R,4S)-4-{[3,5-Bis(trifluoromethyl)benzyl]-(5-dimethylaminopyrimidin-2-yl)}amino-2-ethyl-6-trifluoromethyl-3,4-dihydro-2H-[1,5]naphthyridine-1-carboxylic acid 4-carboxybutyl ester;

(2R,4S)-4-{[3,5-Bis(trifluoromethyl)benzyl]-(5-dimethylaminopyrimidin-2-yl)}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-Bis(trifluoromethyl)benzyl]-(5-dimethylaminopyrimidin-2-yl)}amino-2-ethyl-6-trifluoromethyl-3,4-dihydro-2H-[1,5]naphthyridine-1-carboxylic acid 5-carboxypentyl ester;

(2R,4S)-4-{(3-Cyano-5-trifluoromethylbenzyl)-[5-(morpholin-4-yl)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{(3-Cyano-5-trifluoromethylbenzyl)-[5-(morpholin-4-yl)pyrimidin-2-yl]}amino-2-ethyl-6-trifluoromethyl-3,4-dihydro-2H-[1,5]naphthyridine-1-carboxylic acid 3-carboxypropyl ester;

(2R,4S)-4-{(3-Cyano-5-trifluoromethylbenzyl)-[5-(morpholin-4-yl)pyrimidin-2-yl)]}amino-2-ethyl-6-trifluoromethyl-3,4-dihydro-2H-[1,5]naphthyridine-1-carboxylic acid 4-carboxybutyl ester;

(2R,4S)-4-{(3-Cyano-5-trifluoromethylbenzyl)-[5-(morpholin-4-yl) pyrimidin -2-yl)]}amino-2-ethyl-6-trifluoromethyl-3,4-dihydro-2H-[1,5]naphthyridine-1-carboxylic acid 2-carboxy-2-methylpropyl ester;

(2R,4S)-4-{(3-Cyano-5-trifluoromethylbenzyl)-[5-(morpholin-4-yl)pyrimidin-2-yl]}amino-2-ethyl-6-trifluoromethyl-3,4-dihydro-2H-[1,5]naphithyridine-1-carboxylic acid 5-carboxypentyl ester;

(2R,4S)-4-{[3,5-Bis(trifluoromethyl)benzyl]-[5-(morpholin-4-yl)pyridin-2-yl]}amino-6-ethyl-6-trifluoromethyl-3,4-dihydro-2H-[1,5]naphthyridine-1-carboxylic acid 2-carboxyethyl ester;

(2R,4S)-4-{[3,5-Bis(trifluoromethyl)benzyl]-[5-(morpholin-4-yl)pyridin-2-yl]}amino-6-ethyl-6-trifluoromethyl-3,4-dihydro-2H-[1,5]naphthyridine-1-carboxylic acid 3-carboxypropyl ester;

(2R,4S)-4-{[3,5-Bis(trifluoromethyl)benzyl]-[5-(morpholin-4-yl)pyridin-2-yl]}amino-6-ethyl-6-trifluoromethyl-3,4-dihydro-2H-[1,5]naphthyridine-1-carboxylic acid 4-carboxybutyl ester;

(2R,4S)-4-{([3,5-Bis(trifluoromethyl)benzyl]-[5-(molpholin-4-yl)pyridin-2-yl]}amino-6-ethyl-6-trifluoromethyl-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(morpholin-4-yl)pyridin-2-yl]}amino-6-ethyl-6-trifluoromethyl-3,4-dihydro-2H-[1,5]naphthyridine-1-carboxylic acid 5-carboxypentyl ester;

(2R,4S)-4-{[(3-Cyano-5-trifluoromethylbenzyl) ]-[5-(morpholin-4-yl)pyridin-2-yl]}amino-2-ethyl-6-trifluoromethyl-3,4-dihydro-2H-[1,5]naphthyridine-1-carboxylic acid 4-carboxybutyl ester; or (2R,4S)-4-{(3-Cyano-5-trifluoromethylbenzyl)-[5-(morpholin-4-yl)pyridin-2-yl]}amino-6-ethyl-6-trifluoromethyl-3,4-dihydro-2H-[1,5]naphthyridine-1-carboxylic acid 2-carboxy-2-methylpropyl ester;

or a pharmaceutically acceptable salt thereof.

13. The compound of claim 1, wherein the compound is selected from the following group:

(2R,4S)-4-{[3,5-Bis(trifluoromethyl)benzyl]-[5-(3-hydroxypropoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-([3,5-Bis(trifluoromethyl)benzyl]-{5-[2-hydroxyethoxy)ethoxy]pyrimidin -2-yl})amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(2,3-dihydroxypropoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{[3,5-Bis(trifluoromethyl)benzyl]-[5-(3-hydroxypropoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-([3,5-Bis(trifluoromethyl)benzyl]-{5-[2(2-hydroxyethoxy)ethoxy]pyrimidin-2-yl})amino-2-ethyl-6-trifluoromethyl-3,4-dihydro-2H-[1,5]naphthyridine-1-carboxylic acid 2-carboxyethyl ester;

(2R,4S)-4-{[3,5-Bis(trifluoromethyl)benzyl]-[5-(2,3-dihydroxypropoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{(3-Cyano-5-trifluoromethylbenzyl)-[5-(2-hydroxyethoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-[1,5]naphthyridine-1-carboxylic acid 2-carboxy-2-methylpropyl ester;

(2R,4S)-4-{(3-Cyano-5-trifluoromethylbenzyl)-[5-(2-hydroxyethoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-[1,5]naphthyridine-1-carboxylic acid 2-carboxyethyl ester;

(2R,4S)-4[(3-Cyano-5-trifluoromethylbenzyl)-(5-dimethylaminopyrimidin-2-yl)]amino-2-ethyl-6-trifluoromethyl-3,4-dihydro-2H-[1,5]naphthyridine-1-carboxylic acid 2-carboxyethyl ester;

(2R,4S)-4-([3,5-Bis(trifluoromethyl)benzyl]-{5-[(ethylmethyl)amino]pyrimidin-2-yl}) amino-2-ethyl-6-trifluoromethyl-3,4-dihydro-2H-[1,5]naphthyridine-1-carboxylic acid2-carboxyethyl ester;

(2R,4S)-4-{[3,5-Bis(trifluoromethyl)benzyl]-(5-diethylaminopyrimidin-2-yl)}amino-2-ethyl-6-trifluoromethyl-3,4-dihydro-2H-[1,5]naphthyridine-1-carboxylic acid 2-carboxyethyl ester;

(2R,4S)-4-([3,5-Bis(trifluoromethyl)benzyl]-{5-[(ethylmethyl)amino]pyrimidin-2-yl}) amino-2-ethyl-6-trifluoromethyl-3,4-dihydro-2H-[1,5]naphthyridine-1-carboxylic acid 2-carboxy-2-methylpropyl ester; and (2R,4S)-4-{[3,5-Bis(trifluoromethyl)benzyl]-(5-diethylaminopyrimidin-2-yl)}amino-2-ethyl-6-trifluoromethyl-3,4-dihydro-2H-[1,5]naphthyridine-1-carboxylic acid 2-carboxy-2-methylpropyl ester;

or a pharmaceutically acceptable salt thereof.

14. A process for preparing a tetrahydronaphthyridine derivative of the formula (I):

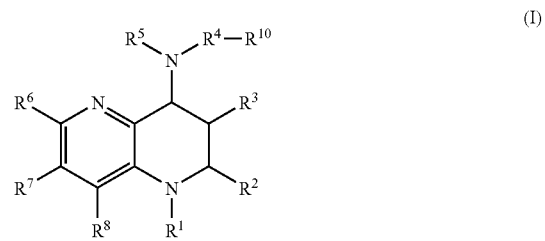

(I)

wherein the symbols $R^1, R^2, R^3, R^4, R^5, R^6, R^7, R^8$ and $R^{10}$ have the same meaning as defined in claim 1, which comprises condensing a compound of the formula (II):

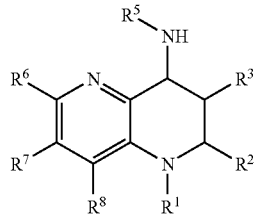 (II)

wherein each symbol has the same meaning as defined above with a compound of the formula (III):

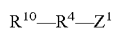 (III)

wherein $Z^1$ is a leaving group and the other symbols have the same meaning as defined above.

15. A compound of the formula (II):

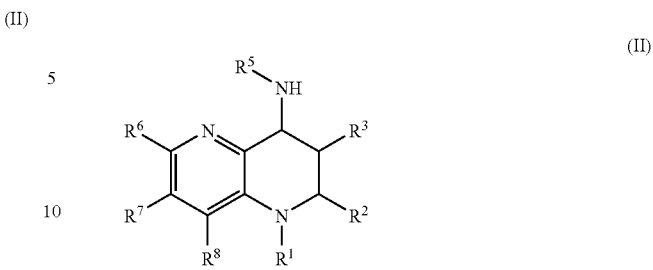 (II)

wherein the symbols $R^1, R^2, R^3, R^4, R^5, R^6, R^7, R^8$ have the same meaning as defined in claim 1, or a salt thereof.

16. A pharmaceutical composition, which comprises as an active ingredient a compound according to claim 1, or a pharmaceutically acceptable salt thereof.

* * * * *